US012780840B2

(12) United States Patent
Mccartney et al.

(10) Patent No.: US 12,780,840 B2
(45) Date of Patent: Nov. 3, 2026

(54) MODULATORS OF CYSTIC FIBROSIS TRANSMEMBRANE CONDUCTANCE REGULATOR

(71) Applicant: VERTEX PHARMACEUTICALS INCORPORATED, Boston, MA (US)

(72) Inventors: Jason Mccartney, Cardiff by the Sea, CA (US); Alexander Russell Abela, Escondido, CA (US); Sunny Abraham, San Diego, CA (US); Corey Don Anderson, Brighton, MA (US); Vijayalaksmi Arumugam, San Marcos, CA (US); Jaclyn Chau, San Diego, CA (US); Jeremy Clemens, San Diego, CA (US); Thomas Cleveland, San Marcos, CA (US); Timothy A. Dwight, Quincy, MA (US); Bryan A. Frieman, La Jolla, CA (US); Peter Grootenhuis, Del Mar, CA (US); Sara Sabina Hadida Ruah, La Jolla, CA (US); Yoshihiro Ishihara, San Diego, CA (US); Mark Thomas Miller, Rancho Santa Fe, CA (US); Alina Silina, Needham, MA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 734 days.

(21) Appl. No.: 18/030,537

(22) PCT Filed: Oct. 6, 2021

(86) PCT No.: PCT/US2021/053862

§ 371 (c)(1),
(2) Date: Apr. 6, 2023

(87) PCT Pub. No.: WO2022/076626

PCT Pub. Date: Apr. 14, 2022

(65) Prior Publication Data

US 2023/0416275 A1 Dec. 28, 2023

Related U.S. Application Data

(60) Provisional application No. 63/088,639, filed on Oct. 7, 2020.

(51) Int. Cl.

| | |
|---|---|
| ***C07D 515/18*** | (2006.01) |
| ***A61K 45/06*** | (2006.01) |
| ***C07D 515/08*** | (2006.01) |
| ***C07D 515/22*** | (2006.01) |

(52) U.S. Cl.

CPC ............ *C07D 515/18* (2013.01); *A61K 45/06* (2013.01); *C07D 515/08* (2013.01); *C07D 515/22* (2013.01); *C07B 2200/09* (2013.01)

(58) Field of Classification Search

CPC ................ C07D 515/18; C07D 515/08; C07D 515/22; A61K 45/06

See application file for complete search history.

(56) References Cited

U.S. PATENT DOCUMENTS

| | | | |
|---|---|---|---|
| 7,332,612 | B2 | 2/2008 | Dolitzky et al. |
| 8,586,615 | B2 | 11/2013 | Hadida-Ruah et al. |
| 8,865,902 | B2 | 10/2014 | Morgan |
| 8,883,206 | B2 | 11/2014 | Dokou et al. |
| 9,181,192 | B2 | 11/2015 | Morgan |
| 9,512,079 | B2 | 12/2016 | Morgan |

(Continued)

FOREIGN PATENT DOCUMENTS

| | | | |
|---|---|---|---|
| CL | 2019002734 | A1 | 1/2020 |
| CL | 2020000856 | A1 | 8/2020 |

(Continued)

OTHER PUBLICATIONS

"Symdeko in Cystic Fibrosis Patients", ClinicalTrials.gov, Apr. 23, 2018 (Apr. 23, 2018), XP055661778, Retrieved from the Internet: URL:https://clinicaltrials.gov/ct2/show/record/NCT03506061 [retrieved on Jan. 24, 2020].

Bastin, Richard J., et al., "Salt selection and optimization procedures for pharmaceutical new chemical entities," Org. Pro. Res. Dev. 2000, 4(5), 427-435.

Borhade, Sanjay R., et al., "Synthesis of Novel Aryl and Heteroaryl Acyl Sulfonimidamides via Pd-Catalyzed Carbonylation Using a Nongaseous Precursor," Organic Letters, 2013, vol. 15, No. 5, pp. 1056-1059, received Jan. 8, 2013, XP055374206A, ©2013 American Chemical Society, ISSN: 1523-7060, DOI:10.1021/0 4/00049m, published on web Feb. 13, 2013.

(Continued)

*Primary Examiner* — Brandon J Fetterolf

(74) *Attorney, Agent, or Firm* — Finnegan, Henderson, Farabow, Garrett & Dunner, LLP

(57) ABSTRACT

This disclosure provides modulators of Cystic Fibrosis Transmembrane Conductance Regulator (CFTR) having core structure (I), pharmaceutical compositions containing at least one such modulator, methods of treatment of cystic fibrosis using such modulators and pharmaceutical compositions, combination pharmaceutical compositions and combination therapies, and processes and intermediates for making such modulators.

(I)

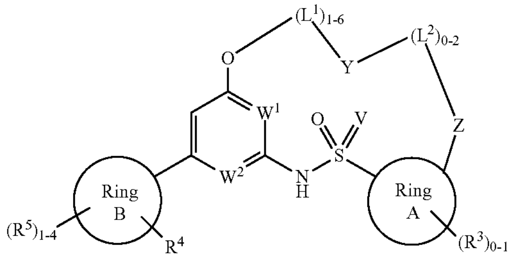

17 Claims, No Drawings

(56) References Cited

U.S. PATENT DOCUMENTS

| | | | |
|---|---|---|---|
| 9,663,508 | B2 | 5/2017 | Bregman et al. |
| 9,782,408 | B2 | 10/2017 | Miller et al. |
| 9,981,910 | B2 | 5/2018 | Altenbach et al. |
| 10,047,053 | B2 | 8/2018 | Morgan |
| 10,118,916 | B2 | 11/2018 | Altenbach et al. |
| 10,131,670 | B2 | 11/2018 | Strohbach et al. |
| 10,138,227 | B2 | 11/2018 | Altenbach et al. |
| 10,208,053 | B2 | 2/2019 | Strohbach et al. |
| 10,258,624 | B2 | 4/2019 | Miller et al. |
| 10,479,766 | B2 | 11/2019 | Morgan |
| 10,570,115 | B2 | 2/2020 | Alcacio et al. |
| 10,654,829 | B2 | 5/2020 | Dhamankar et al. |
| 10,675,277 | B2 | 6/2020 | Kárpáti et al. |
| 10,738,030 | B2 | 8/2020 | Bear et al. |
| 10,758,534 | B2 | 9/2020 | Miller |
| 10,759,721 | B2 | 9/2020 | Morgan et al. |
| 10,793,547 | B2 | 10/2020 | Abela et al. |
| 10,894,773 | B2 | 1/2021 | Morgan et al. |
| 11,066,417 | B2 | 7/2021 | Clemens et al. |
| 11,179,367 | B2 | 11/2021 | Chu et al. |
| 11,584,761 | B2 | 2/2023 | Angell et al. |
| 11,591,350 | B2 | 2/2023 | Anderson et al. |
| 11,708,331 | B2 | 7/2023 | Lemercier Lewandowski et al. |
| 11,866,450 | B2 | 1/2024 | Clemens |
| 11,873,300 | B2 | 1/2024 | Shi et al. |
| 12,186,306 | B2 | 1/2025 | Borek et al. |
| 12,319,693 | B2 | 6/2025 | Shi et al. |
| 12,421,251 | B2 * | 9/2025 | Abela et al. |
| 2013/0317000 | A1 | 11/2013 | Chowdhury et al. |
| 2013/0317001 | A1 | 11/2013 | Andrez et al. |
| 2018/0099932 | A1 | 4/2018 | Altenbach et al. |
| 2018/0125838 | A1 | 5/2018 | Uttamsingh |
| 2018/0141954 | A1 | 5/2018 | Strohbach et al. |
| 2018/0170938 | A1 | 6/2018 | Strohbach et al. |
| 2018/0244611 | A1 | 8/2018 | Altenbach et al. |
| 2018/0244640 | A1 | 8/2018 | Altenbach et al. |
| 2019/0077784 | A1 | 3/2019 | Altenbach et al. |
| 2019/0153000 | A1 | 5/2019 | Munoz et al. |
| 2022/0041621 | A1 | 2/2022 | Clemens et al. |
| 2022/0047564 | A1 | 2/2022 | Altshuler et al. |
| 2022/0106331 | A1 | 4/2022 | Clemens et al. |
| 2022/0127247 | A1 | 4/2022 | Azimioara et al. |
| 2022/0184049 | A1 | 6/2022 | Borek et al. |
| 2022/0313698 | A1 | 10/2022 | Abela et al. |
| 2022/0372047 | A1 | 11/2022 | Abela et al. |
| 2023/0374038 | A1 | 11/2023 | McCartney et al. |
| 2023/0382925 | A1 | 11/2023 | MCartney et al. |
| 2024/0261286 | A1 | 8/2024 | Wörwag et al. |
| 2025/0221971 | A1 * | 7/2025 | Borek et al. |

FOREIGN PATENT DOCUMENTS

| | | | |
|---|---|---|---|
| CN | 103833630 | | 6/2014 |
| CO | 12038470 | | 3/2012 |
| EP | 3424534 | B1 | 5/2018 |
| JP | 2011-518836 | A | 6/2011 |
| JP | 2014-526500 | A | 10/2014 |
| NC | 2018/0000413 | | 1/2018 |
| NC | 2018/0012171 | | 11/2018 |
| TW | I410423 | B | 10/2013 |
| TW | 201811766 | A | 1/2018 |
| WO | WO 2005/049018 | A1 | 6/2005 |
| WO | WO 2005/075435 | A1 | 8/2005 |
| WO | WO 2006/002421 | A2 | 1/2006 |
| WO | WO 2007/021982 | A2 | 2/2007 |
| WO | WO 2007/053641 | A2 | 5/2007 |
| WO | WO 2007/075946 | A1 | 7/2007 |
| WO | WO 2007/079139 | A2 | 7/2007 |
| WO | WO 2007/087066 | A2 | 8/2007 |
| WO | WO 2007/117715 | A2 | 10/2007 |
| WO | WO 2007/134279 | A2 | 11/2007 |
| WO | WO 2008/127399 | A2 | 10/2008 |
| WO | WO 2009/006315 | A1 | 1/2009 |
| WO | WO 2009/038683 | A2 | 3/2009 |
| WO | WO 2009/073757 | A1 | 6/2009 |
| WO | WO 2009/076142 | A2 | 6/2009 |
| WO | WO 2009/108657 | A2 | 9/2009 |
| WO | WO 2010/019239 | A2 | 2/2010 |
| WO | WO 2010/048526 | A2 | 4/2010 |
| WO | WO 2010/053471 | A1 | 5/2010 |
| WO | WO 2010/054138 | A2 | 5/2010 |
| WO | WO 2010/108162 | A1 | 9/2010 |
| WO | WO 2011/019413 | A1 | 2/2011 |
| WO | WO 2011/029059 | A1 | 3/2011 |
| WO | WO 2011/072241 | A1 | 6/2011 |
| WO | WO 2011/116397 | A1 | 9/2011 |
| WO | WO 2011/119984 | A1 | 9/2011 |
| WO | WO 2011/127241 | A2 | 10/2011 |
| WO | WO 2011/127290 | A2 | 10/2011 |
| WO | WO 2011/133751 | A2 | 10/2011 |
| WO | WO 2011/133951 | A1 | 10/2011 |
| WO | WO 2012/027247 | A2 | 3/2012 |
| WO | WO 2012/027731 | A2 | 3/2012 |
| WO | WO 2012/158885 | A1 | 11/2012 |
| WO | WO 2012/170061 | A1 | 12/2012 |
| WO | WO 2013/038386 | A1 | 3/2013 |
| WO | WO 2013/070961 | A1 | 5/2013 |
| WO | WO 2013/112804 | A1 | 8/2013 |
| WO | WO 2013/130669 | A1 | 9/2013 |
| WO | WO 2013/158121 | A1 | 10/2013 |
| WO | WO 2013/185112 | A1 | 12/2013 |
| WO | WO 2014/014841 | A1 | 1/2014 |
| WO | WO 2014/071122 | A1 | 5/2014 |
| WO | WO 2014/078842 | A1 | 5/2014 |
| WO | WO 2015/073231 | A1 | 7/2015 |
| WO | WO 2015/138934 | A1 | 9/2015 |
| WO | WO 2015/160787 | A1 | 10/2015 |
| WO | WO 2016/057572 | A1 | 4/2016 |
| WO | WO 2016/057730 | A1 | 4/2016 |
| WO | WO 2016/081556 | A1 | 5/2016 |
| WO | WO 2016/160945 | A1 | 10/2016 |
| WO | WO 2017/009804 | A1 | 1/2017 |
| WO | WO 2017/053455 | A1 | 3/2017 |
| WO | WO 2017/053711 | A2 | 3/2017 |
| WO | WO 2017/172802 | A1 | 10/2017 |
| WO | WO 2017/173274 | A1 | 10/2017 |
| WO | WO 2017/177124 | A1 | 10/2017 |
| WO | WO 2017/187321 | A1 | 11/2017 |
| WO | WO 2017/208115 | A1 | 12/2017 |
| WO | WO 2017/223188 | A1 | 12/2017 |
| WO | WO 2018/064632 | A1 | 4/2018 |
| WO | WO 2018/080591 | A1 | 5/2018 |
| WO | WO 2018/081377 | A1 | 5/2018 |
| WO | WO 2018/081378 | A1 | 5/2018 |
| WO | WO 2018/081381 | A1 | 5/2018 |
| WO | WO 2018/107100 | A1 | 6/2018 |
| WO | WO 2018/116185 | A1 | 6/2018 |
| WO | WO 2018/127130 | A1 | 7/2018 |
| WO | WO 2018/183367 | A1 | 10/2018 |
| WO | WO 2018/183964 | A1 | 10/2018 |
| WO | WO 2018/201126 | A1 | 11/2018 |
| WO | WO 2018/227049 | A1 | 12/2018 |
| WO | WO 2019/010092 | A1 | 1/2019 |
| WO | WO 2019/014352 | A1 | 1/2019 |
| WO | WO 2019/018353 | A1 | 1/2019 |
| WO | WO 2019/018395 | A1 | 1/2019 |
| WO | WO 2019/028228 | A1 | 2/2019 |
| WO | WO 2019/071078 | A1 | 4/2019 |
| WO | WO 2019/079760 | A1 | 4/2019 |
| WO | WO 2019/109021 | A1 | 6/2019 |
| WO | WO 2019/113089 | A1 | 6/2019 |
| WO | WO 2019/113476 | A2 | 6/2019 |
| WO | WO 2019/152940 | A1 | 8/2019 |
| WO | WO 2019/161078 | A1 | 8/2019 |
| WO | WO 2019/191620 | A1 | 10/2019 |
| WO | WO 2019/195739 | A1 | 10/2019 |
| WO | WO 2019/200246 | A1 | 10/2019 |
| WO | WO 2020/102346 | A1 | 5/2020 |
| WO | WO 2020/128925 | A1 | 6/2020 |
| WO | WO 2020/206080 | A1 | 10/2020 |
| WO | WO 2020/214921 | A1 | 10/2020 |
| WO | WO 2020/242935 | A1 | 12/2020 |
| WO | WO 2021/030552 | A1 | 2/2021 |
| WO | WO 2021/030554 | A1 | 2/2021 |

(56) References Cited

FOREIGN PATENT DOCUMENTS

| | | | |
|---|---|---|---|
| WO | WO 2021/030555 | A1 | 2/2021 |
| WO | WO 2021/030556 | A1 | 2/2021 |
| WO | WO 2021/097054 | A1 | 5/2021 |
| WO | WO 2022/032068 | A1 | 2/2022 |
| WO | WO 2022/036060 | A1 | 2/2022 |
| WO | WO 2022/076618 | A1 | 4/2022 |
| WO | WO 2022/076620 | A1 | 4/2022 |
| WO | WO 2022/076621 | A1 | 4/2022 |
| WO | WO 2022/076622 | A2 | 4/2022 |
| WO | WO 2022/076624 | A1 | 4/2022 |
| WO | WO 2022/076625 | A1 | 4/2022 |
| WO | WO 2022/076626 | A1 | 4/2022 |
| WO | WO 2022/076627 | A1 | 4/2022 |
| WO | WO 2022/076628 | A1 | 4/2022 |
| WO | WO 2022/076629 | A1 | 4/2022 |
| WO | WO 2022/125826 | A1 | 6/2022 |
| WO | WO 2023/196429 | A1 | 10/2023 |
| WO | WO 2025/166342 | A1 | 8/2025 |
| WO | WO 2025/171098 | A1 | 8/2025 |

OTHER PUBLICATIONS

Cherepakha, Artem Yu., et al. (2018), "Hetaryl Bromides Bearing the SO2F Group—Versatile Substrates for Palladium-Catalyzed C—C Coupling Reactions," Eur J Org Chem, 47: 6682-6692.

Clinical Trials US: "A Phase 2 Study to Evaluate Efficacy and Safety of VX-561 in Subjects Aged 18 Years and Older With Cystic Fibrosis," ClinicalTrials.gov, Apr. 11, 2019 (Apr. 11, 2019), XP055903562, Retrieved from the Internet: URL:https://clinicaltrials.gov/ct2/show/NCT03911713 [retrieved on Mar. 21, 2022].

Clinical Trials US: "A Study to Evaluate the Safety and Efficacy of VX-121 Combination Therapy in Subjects with Cystic Fibrosis," ClinicalTrials.gov, Apr. 30, 2019 (Apr. 30, 2019), XP55903330, Retrieved from the Internet: URL:https://clinicaltrials.gov/ct2/show/NCT03912233 [retrieved on Mar. 21, 2022].

Donaldson, S.H. et al. (2017) "Tezacaftor/Ivacaftor in Subjects with Cystic Fibrosis and F508del/F508del-CFTR or F508del/G551D-CFTR", *Am. J. Respir. Crit. Care Med.*, 197(2): 214-224.

Eu Clinical Trials Register: "A phase 1/2 study of VX-121 in healthy subjects and in subjects with cystic fibrosis", May 3, 2019 (May 3, 2019). XP055903414, Retrieved from the Internet: URL:https://www.clinicaltrialsregister.eu/ctr-search/trial/2018-000126-55/NL [retrieved on Mar. 21, 2022].

International Patent Application No. PCT/US2021/053862: International Search Report and Written Opinion, mailed Dec. 22, 2021 (12 pages).

Newkome, George R., et al. (1979), "Nicotinic Acid Crown Ethers. Synthesis, Reactions, and Complexation of Nicotinonitrile Macrocycles," J Org Chem, 44(15): 2639-2697.

Nishida, Haruyuki, et al. (2017), "Exploration of pyrrole derivatives to find an effective potassium competitive acid blocker with moderately long-lasting suppression of gastric acid secretion," Bioorg Med Chem, 25(13): 3447-3460.

Notice of Allowance and Fee(s) Due for U.S. Appl. No. 16/992,441, mailed Aug. 25, 2023.

Prashantha, Gunaga, et al. (2017), "Selective IKur Inhibitors for the Potential Treatment of Atrial Fibrillation: Optimization of the Phenyl Quinazoline Series Leading to Clinical Candidate 5 [5-Phenyl-4-(pyridin-2-ylmethylamino)quinazolin-2-yl]pyridine-3-sulfonamide," J Med Chem, 60(9): 3795-3803.

Rewcastle, Gordon W., et al. (1996), "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," J Med Chem, 39(9): 1823-1835.

U.S. Appl. No. 18/493,667, filed Oct. 24, 2023, by Shi et al.

Davies, J.C. et al. (2018), "VX-659-Tezacaftor-Ivacaftor in Patients with Cystic Fibrosis and One or Two Phe508del Alleles," The New England Journal of Medicine, 379, 17, 1599-1611.

Harbeson, Scott L., et al. "Altering Metabolic Profiles of Drugs by Precision Deuteration 2: Discovery of a Deuterated Analog of Ivacaftor with Differentiated Pharmacokinetics for Clinical Development." The Journal of Pharmacology and Experimental Therapeutics, 2017, 362, 2, 359-367.

Hoppe, Jordana, et al. Vanzacaftor-tezacaftor-deutivacaftor for children aged 6-11 years with cystic fibrosis (RIDGELINE Trial VX21-121-105): an analysis from a sing-arm, phase 3 trial. www.thelancet.com/respiratory, vol. 13. Mar. 2025.

Keating, D. et al., "VX-445-Tezacaftor-Ivacaftor in Patients with Cystic Fibrosis and One or Two Phe508del Alleles," The New England Journal of Medicine, 2018, 379, 17, 1612-1620.

Matsuoka, Masakuni, Base & Application of Polymorphic Crystals, popular edition, 1st printing, CMC Publishing Co.,Ltd., Oct. 22, 2010, pp. 105-117, pp. 181-191.

Morissette et al., "High-throughput crystallization: polymorphs, salts, co-crystals and solvates of pharmaceutical solids," Advanced Drug Delivery Reviews, 2004, 56, 275-300.

Taylor-Cousar, Jennifer L. Taylor-Cousar, et al. "Tezacaftor-Ivacaftor in Patients with Cystic Fibrosis Homozygous for Phe508del". The New England Journal of Medicine, 2017, 377, 21, 2017.

Uluer, Ahmet, et al., Safety and efficacy of vanzacaftor-tezacaftor-deutivacaftor in adults with cystic fibrosis: randomised, double-blind, controlled, phase 2 trials, www.thelancet.com/respiratory vol. 11 Jun. 2023.

2021 Vertex to Initiate Phase 3 Development Program for New Once-Daily Triple Combination Regimen in People with Cystic Fibrosis.

2024 Vertex Announces Positive Results for Pivotal Trials of Vanzacaftor, Tezacaftor, Deutivacaftor, Next-in-Class Triple Combination Treatment for Cystic Fibrosis.

Wang, Xueqing, et al. "Discovery of 4-[(2R,4R)-4-({1-(2,2-Difluoro-1,3-benzodioxol-5-yl)cyclopropyl} carbonyl)amino]-7-(difluoromethoxy)-3,4-dihydro-2H-chromen-2-yl)benzoic Acid (ABBV/GLPG-2222), a Potent Cystic Fibrosis Transmembrane Conductance Regulator (CFTR) Corrector for the Treatment of Cystic Fibrosis." Journal of Medicinal Chemistry, 2018, 61, 1436-1449.

* cited by examiner

MODULATORS OF CYSTIC FIBROSIS TRANSMEMBRANE CONDUCTANCE REGULATOR

This application claims the benefit of priority of U.S. Provisional Application No. 63/088,639, filed Oct. 7, 2020, the contents of which are incorporated by reference herein in their entirety.

The disclosure relates to modulators of Cystic Fibrosis Transmembrane Conductance Regulator (CFTR), pharmaceutical compositions containing the modulators, methods of treatment of CFTR mediated diseases, including cystic fibrosis, using such modulators and pharmaceutical compositions, combination therapies and combination pharmaceutical compositions employing such modulators, and processes and intermediates for making such modulators.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to increased mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 432 of these identified mutations, with sufficient evidence to define 352 mutations as disease causing. The most prevalent disease-causing mutation is a deletion of phenylalanine at position 508 of the CFTR amino acid sequence and is commonly referred to as the F508del mutation. This mutation occurs in many of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease-causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

A number of CFTR modulating compounds have recently been identified. However, compounds that can treat or reduce the severity of cystic fibrosis and other CFTR mediated diseases, and particularly the more severe forms of these diseases, are still needed.

One aspect of the disclosure provides novel compounds, including compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing.

Formula I encompasses compounds falling within the following structure:

(I)

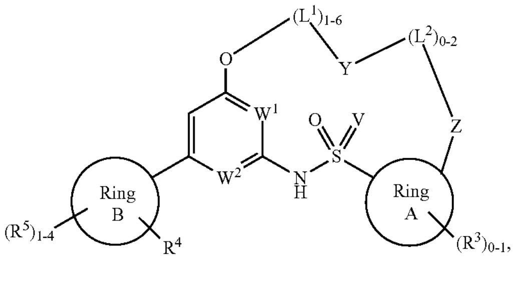

and includes tautomers of those compounds, deuterated derivatives of any of the compounds and tautomers, and pharmaceutically acceptable salts of any of the foregoing, wherein:

Ring A is selected from:
- $C_6$-$C_{10}$ aryl,
- $C_3$-$C_{10}$ cycloalkyl,
- 3- to 10-membered heterocyclyl, and
- 5- to 10-membered heteroaryl;

Ring B is selected from:
- $C_6$-$C_{10}$ aryl,
- $C_3$-$C_{10}$ cycloalkyl,
- 3- to 10-membered heterocyclyl, and
- 5- to 10-membered heteroaryl;

V is selected from O and NH;

$W^1$ is selected from N and CH;

$W^2$ is selected from N and CH, provided that at least one of $W^1$ and $W^2$ is N;

Y is selected from O and $C(R^{YC})_2$.

Z is selected from O, $NR^{ZN}$, and $C(R^{ZC})_2$, provided that when Y is O and $L^2$ is absent, Z is $C(R^{ZC})_2$;

each $L^1$ is independently selected from $C(R^{L1})_2$ and

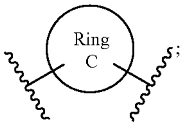

;

each $L^2$ is independently selected from $C(R^{L2})_2$;

Ring C is selected from $C_6$-$C_{10}$ aryl optionally substituted with 1-3 groups independently selected from:
- halogen,
- $C_1$-$C_6$ alkyl, and
- $N(R^N)_2$;

each $R^3$ is independently selected from:
- halogen,
- $C_1$-$C_6$ alkyl,
- $C_1$-$C_6$ alkoxy,
- $C_3$-$C_{10}$ cycloalkyl,
- $C_6$-$C_{10}$ aryl optionally substituted with 1-3 groups independently selected from $C_1$-$C_6$ alkyl, and
- 3- to 10-membered heterocyclyl;

$R^4$ is selected from hydrogen and $C_1$-$C_6$ alkyl;

each $R^5$ is independently selected from:
- hydrogen,
- halogen,
- hydroxyl,
- $N(R^N)_2$,
- SO-Me,
- —CH═C$(R^{LC})_2$, wherein both $R^{LC}$ are taken together to form a $C_3$-$C_{10}$ cycloalkyl,
- $C_1$-$C_6$ alkyl optionally substituted with 1-3 groups independently selected from:
  - hydroxyl,
  - $C_1$-$C_6$ alkoxy optionally substituted with 1-3 groups independently selected from $C_1$-$C_6$ alkoxy and $C_6$-$C_{10}$ aryl,
  - $C_3$-$C_{10}$ cycloalkyl,
  - —$(O)_{0-1}$—($C_6$-$C_{10}$ aryl) optionally substituted with 1-3 groups independently selected from $C_1$-$C_6$ alkyl and $C_1$-$C_6$ alkoxy,
  - 3- to 10-membered heterocyclyl, and
  - $N(R^N)_2$,
- $C_1$-$C_6$ alkoxy optionally substituted with 1-3 groups independently selected from:
  - halogen,
  - $C_6$-$C_{10}$ aryl, and
  - $C_3$-$C_{10}$ cycloalkyl optionally substituted with 1-3 groups independently selected from $C_1$-$C_6$ fluoroalkyl,
- $C_1$-$C_6$ fluoroalkyl,
- $C_3$-$C_{10}$ cycloalkyl,
- $C_6$-$C_{10}$ aryl, and
- 3- to 10-membered heterocyclyl;

$R^{ZN}$ is selected from:
- hydrogen,
- $C_1$-$C_9$ alkyl optionally substituted with 1-3 groups independently selected from:
  - hydroxyl,
  - oxo,
  - cyano,
  - $C_1$-$C_6$ alkoxy optionally substituted with 1-3 groups independently selected from halogen and $C_1$-$C_6$ alkoxy,
  - $N(R^N)_2$,
  - $SO_2Me$,
  - $C_3$-$C_{10}$ cycloalkyl optionally substituted with 1-3 groups independently selected from:
    - hydroxyl,
    - $C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
    - $C_1$-$C_6$ fluoroalkyl,
    - $C_1$-$C_6$ alkoxy,
    - COOH,
    - $N(R^N)_2$,
    - $C_6$-$C_{10}$ aryl, and
    - 3- to 10-membered heterocyclyl optionally substituted with 1-3 groups independently selected from oxo and $C_1$-$C_6$ alkyl,
  - $C_6$-$C_{10}$ aryl optionally substituted with 1-3 groups independently selected from:
    - halogen,
    - hydroxyl,
    - cyano,
    - $SiMe_3$,
    - $SO_2Me$,
    - $SF_5$,
    - $N(R^N)_2$,
    - $P(O)Me_2$,
    - —$(O)_{0-1}$—($C_3$-$C_{10}$ cycloalkyl) optionally substituted with 1-3 groups independently selected from $C_1$-$C_6$ fluoroalkyl,
    - $C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
    - $C_1$-$C_6$ alkoxy optionally substituted with 1-3 groups independently selected from hydroxyl, oxo, $N(R^N)_2$, and $C_6$-$C_{10}$ aryl,
    - $C_1$-$C_6$ fluoroalkyl,
    - 3- to 10-membered heterocyclyl optionally substituted with 1-3 groups independently selected from $C_1$-$C_6$ alkyl,
    - —$(O)_{0-1}$—($C_6$-$C_{10}$ aryl), and
    - —$(O)_{0-1}$-(5- to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
  - 3- to 10-membered heterocyclyl optionally substituted with 1-4 groups independently selected from:
    - hydroxyl,
    - oxo,
    - $N(R^N)_2$,
    - $C_1$-$C_6$ alkyl optionally substituted with 1-3 groups independently selected from oxo and $C_1$-$C_6$ alkoxy,
    - $C_1$-$C_6$ alkoxy,
    - $C_1$-$C_6$ fluoroalkyl,
    - $C_6$-$C_{10}$ aryl optionally substituted with 1-3 groups independently selected from halogen, and
    - 5- to 10-membered heteroaryl, and 5- to 10-membered heteroaryl optionally substituted with 1-3 groups independently selected from:
hydroxyl,
cyano,
oxo,
halogen,
$B(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3 —$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
—$(O)_{0-1}$—($C_6$-$C_{10}$ aryl),
—$(O)_{0-1}$-(3- to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, and 3- to 10-membered heterocyclyl (optionally substituted with 1-3 groups independently selected from $C_1$-$C_6$ fluoroalkyl), and
5- to 10-membered heteroaryl optionally substituted with 1-4 groups independently selected from $C_1$-$C_6$ alkyl and $C_3$-$C_{10}$ cycloalkyl,
$C_1$-$C_6$ fluoroalkyl,
$C_3$-$C_{10}$ cycloalkyl optionally substituted with 1-3 groups independently selected from:
hydroxyl,
oxo,
halogen,
cyano,
$N(R^N)_2$,
$C_1$-$C_6$ alkyl optionally substituted with 1-3 groups independently selected from:
hydroxyl,
oxo,
$N(R^N)_2$,
$C_1$-$C_6$ alkoxy, and
$C_6$-$C_{10}$ aryl,
$C_1$-$C_6$ alkoxy optionally substituted with 1-3 groups independently selected from halogen, oxo, $C_6$-$C_{10}$ aryl, and $N(R^N)_2$,
halogen,
$C_3$-$C_{10}$ cycloalkyl,
3- to 10-member heterocyclyl optionally substituted with 1-3 groups independently selected from $C_1$-$C_6$ alkyl, and
5- to 10-membered heteroaryl optionally substituted with 1-3 groups independently selected from:
hydroxyl,
cyano,
oxo,
halogen,
$N(R^N)_2$,
$C_1$-$C_6$ alkyl optionally substituted with 1-3 groups independently selected from hydroxyl, oxo, $C_1$-$C_6$ alkoxy, and $N(R^N)_2$,
$C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
$C_6$-$C_{10}$ aryl, and
3- to 10-membered heterocyclyl optionally substituted with 1-3 groups independently selected from $C_1$-$C_6$ alkyl,
$C_6$-$C_{10}$ aryl,
3- to 10-membered heterocyclyl optionally substituted with 1-3 groups independently selected from:
oxo,
$C_1$-$C_6$ alkyl optionally substituted with 1-3 groups independently selected from:
oxo,
hydroxyl,
$N(R^N)_2$,
$C_1$-$C_6$ alkoxy optionally substituted with 1-3 groups independently selected from halogen and $C_6$-$C_{10}$ aryl, and
—$(O)_{0-1}$—($C_3$-$C_{10}$ cycloalkyl),
$C_1$-$C_6$ fluoroalkyl,
$C_3$-$C_{10}$ cycloalkyl optionally substituted with 1-3 groups independently selected from halogen, and
3- to 10-membered heterocyclyl,
5- to 10-membered heteroaryl optionally substituted with 1-3 groups independently selected from:
halogen,
$C_1$-$C_6$ alkyl optionally substituted with 1-3 groups independently selected from oxo, $C_1$-$C_6$ alkoxy, and $N(R^N)_2$, and
3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and
$R^F$,
each $R^{YC}$ and $R^{ZC}$ is independently selected from:
hydrogen,
$C_1$-$C_6$ alkyl optionally substituted with 1-3 groups independently selected from $C_6$-$C_{10}$ aryl (optionally substituted with 1-3 groups independently selected from $C_1$-$C_6$ alkyl),
$C_6$-$C_{10}$ aryl optionally substituted with 1-3 groups independently selected from $C_1$-$C_6$ alkyl, and
$R^F$;
or two $R^{YC}$ are taken together to form an oxo group;
or two $R^{ZC}$ are taken together to form an oxo group;
each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from:
halogen,
hydroxyl,
oxo,
$N(R^N)_2$,
$C_1$-$C_6$ alkoxy optionally substituted with 1-3 groups independently selected from $C_6$-$C_{10}$ aryl,
$C_3$-$C_{10}$ cycloalkyl optionally substituted with 1-3 groups independently selected from halogen and $C_1$-$C_6$ fluoroalkyl, $C_6$-$C_{10}$ aryl optionally substituted with 1-3 groups independently selected from $C_1$-$C_6$ alkyl, and
3- to 10-membered heterocyclyl optionally substituted with 1-3 groups independently selected from $C_1$-$C_6$ alkyl (optionally substituted with 1-3 groups independently selected from hydroxyl and oxo),
$C_3$-$C_{10}$ cycloalkyl,
$C_6$-$C_{10}$ aryl optionally substituted with 1-4 groups independently selected from:
halogen,
cyano,
$SiMe_3$,
$POMe_2$,
$C_1$-$C_7$ alkyl optionally substituted with 1-3 groups independently selected from:
hydroxyl,
oxo,
cyano,
$SiMe_3$,
$N(R^N)_2$, and
$C_3$-$C_{10}$ cycloalkyl optionally substituted with 1-3 groups independently selected from $C_1$-$C_6$ fluoroalkyl,
$C_1$-$C_6$ alkoxy optionally substituted with 1-3 groups independently selected from:
$C_3$-$C_{10}$ cycloalkyl optionally substituted with 1-3 groups independently selected from $C_1$-$C_6$ fluoroalkyl, and
$C_1$-$C_6$ alkoxy,
$C_1$-$C_6$ fluoroalkyl,
$C_3$-$C_{10}$ cycloalkyl optionally substituted with 1-3 groups independently selected from $C_1$-$C_6$ alkyl and $C_1$-$C_6$ fluoroalkyl,
$C_6$-$C_{10}$ aryl,
3- to 10-membered heterocyclyl optionally substituted with 1-3 groups independently selected from $C_1$-$C_6$ alkyl, and
5- to 10-membered heteroaryl,
3- to 10-membered heterocyclyl optionally substituted with 1-3 groups independently selected from:
$C_1$-$C_6$ alkyl optionally substituted with 1-3 groups independently selected from:
oxo, and
$C_1$-$C_6$ alkoxy,
5- to 10-membered heteroaryl optionally substituted with 1-3 groups independently selected from:
$C_1$-$C_6$ alkyl optionally substituted with 1-3 groups independently selected from:
$C_3$-$C_{10}$ cycloalkyl optionally substituted with 1-3 groups independently selected from $C_1$-$C_6$ fluoroalkyl, and
$C_6$-$C_{10}$ aryl optionally substituted with 1-3 groups independently selected from $C_1$-$C_6$ alkyl, and
$R^F$;
or two $R^{L1}$ on the same carbon atom are taken together to form an oxo group;
each $R^{L2}$ is independently selected from hydrogen and $R^F$;
or two $R^{L2}$ on the same carbon atom are taken together to form an oxo group;
each $R^N$ is independently selected from:
hydrogen,
$C_1$-$C_8$ alkyl optionally substituted with 1-3 groups independently selected from:
oxo,
halogen,
hydroxyl,
$NH_2$,
NHMe,
$NMe_2$,
$C_1$-$C_6$ alkoxy optionally substituted with 1-3 groups independently selected from $C_6$-$C_{10}$ aryl,
—$(O)_{0-1}$—($C_3$-$C_{10}$ cycloalkyl),
$C_6$-$C_{10}$ aryl optionally substituted with 1-3 groups independently selected from halogen and $C_1$-$C_6$ alkyl,
3- to 14-membered heterocyclyl optionally substituted with 1-4 groups independently selected from oxo and $C_1$-$C_6$ alkyl, and
5- to 14-membered heteroaryl optionally substituted with 1-4 groups independently selected from oxo and $C_1$-$C_6$ alkyl,
$C_3$-$C_{10}$ cycloalkyl optionally substituted with 1-3 groups independently selected from:
hydroxyl,
$NH_2$,
NHMe, and
$C_1$-$C_6$ alkyl optionally substituted with 1-3 groups independently selected from hydroxyl, and
$C_6$-$C_{10}$ aryl, and
3- to 10-membered heterocyclyl;
or two $R^N$ on the same nitrogen atom are taken together with the nitrogen to which they are bonded to form a 3- to 10-membered heterocyclyl optionally substituted with 1-3 groups selected from:
hydroxyl,
oxo,
cyano,
$C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl,
$C_1$-$C_6$ alkoxy, and
$C_1$-$C_6$ fluoroalkyl;
or one $R^4$ and one $R^{L1}$ are taken together to form a $C_6$-$C_8$ alkylene;
when $R^F$ is present, two $R^F$ taken together with the atoms to which they are bonded form a group selected from:
$C_3$-$C_{10}$ cycloalkyl optionally substituted with 1-3 groups independently selected from $C_1$-$C_6$ alkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl,
3- to 11-membered heterocyclyl optionally substituted with 1-3 groups independently selected from:
oxo,
$N(R^N)_2$,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen and $C_6$-$C_{10}$ aryl, $C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), —$(O)_{0-1}$—($C_1$-$C_6$ fluoroalkyl), and $C_6$-$C_{10}$ aryl (optionally substituted with 1-3 groups independently selected from $C_1$-$C_6$ alkoxy), —$(O)_{0-1}$—($C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl, 3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$, —O-(5- to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and 5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl, $C_3$-$C_{12}$ cycloalkyl optionally substituted with 1-4 groups independently selected from halogen, $C_1$-$C_6$ alkyl, and $C_1$-$C_6$ fluoroalkyl, $C_6$-$C_{10}$ aryl, 3- to 10-membered heterocyclyl, and 5- to 10-membered heteroaryl optionally substituted with 1-3 groups independently selected from $C_1$-$C_6$ alkoxy and $C_1$-$C_6$ fluoroalkyl, and 5- to 12-membered heteroaryl optionally substituted with 1-3 groups independently selected from $C_1$-$C_6$ alkyl and $C_1$-$C_6$ fluoroalkyl.

Formula I also includes compounds of Formula Ia:

(Ia)

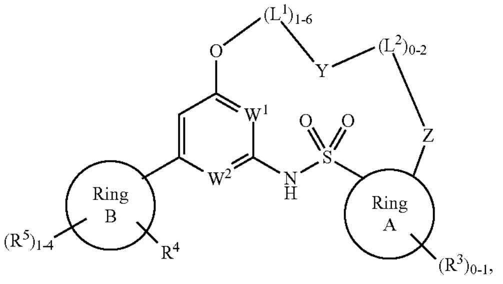

tautomers of those compounds, deuterated derivatives of any of the compounds and tautomers, and pharmaceutically acceptable salts of any of the foregoing, wherein Ring A, Ring B, $W^1$, $W^2$, Y, Z, $L^1$, $L^2$, $R^3$, $R^4$, and $R^5$ are as defined for Formula I.

Formula I also includes compounds of Formula IIa:

(IIa)

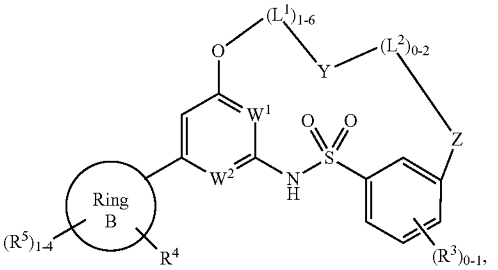

tautomers of those compounds, deuterated derivatives of any of the compounds and tautomers, and pharmaceutically acceptable salts of any of the foregoing, wherein Ring B, $W^1$, $W^2$, Y, Z, $L^1$, $L^2$, $R^3$, $R^4$, and $R^5$ are as defined for Formula I.

Formula I also includes compounds of Formula IIb:

(IIb)

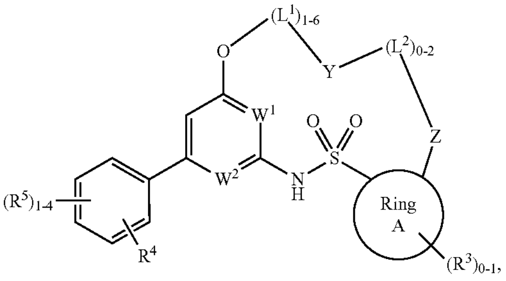

tautomers of those compounds, deuterated derivatives of any of the compounds and tautomers, and pharmaceutically acceptable salts of any of the foregoing, wherein Ring A, $W^1$, $W^2$, Y, Z, $L^1$, $L^2$, $R^3$, $R^4$, and $R^5$ are as defined for Formula I.

Formula I also includes compounds of Formula III:

(III)

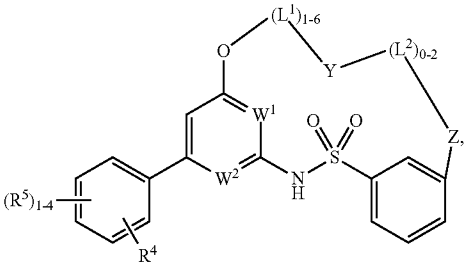

tautomers of those compounds, deuterated derivatives of any of the compounds and tautomers, and pharmaceutically acceptable salts of any of the foregoing, wherein $W^1$, $W^2$, Y, Z, $L^1$, $L^2$, $R^4$, and $R^5$ are as defined for Formula I.

Formula I also includes compounds of Formula IV:

(IV)

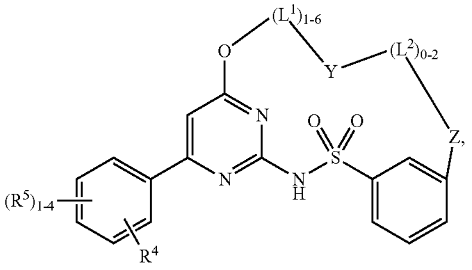

tautomers of those compounds, deuterated derivatives of any of the compounds and tautomers, and pharmaceutically acceptable salts of any of the foregoing, wherein Y, Z, $L^1$, $L^2$, $R^4$, and $R^5$ are as defined for Formula I.

Formula I also includes compounds of Formula Va and Formula Vb:

(Va)

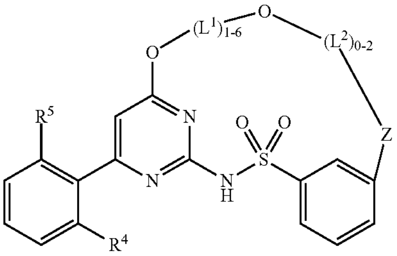

and (Vb)

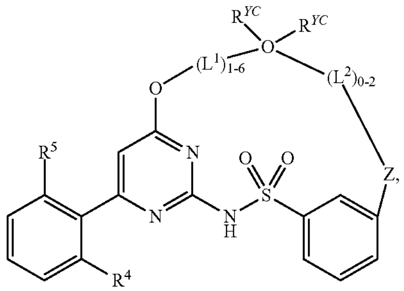

tautomers of those compounds, deuterated derivatives of any of the compounds and tautomers, and pharmaceutically acceptable salts of any of the foregoing, wherein Z, $L^1$, $L^2$, $R^4$, $R^5$, and $R^{YC}$ are as defined for Formula I.

Formula I also includes compounds of Formula V:

(V)

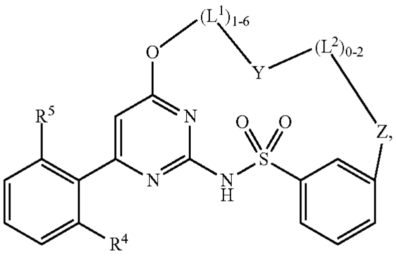

tautomers of those compounds, deuterated derivatives of any of the compounds and tautomers, and pharmaceutically acceptable salts of any of the foregoing, wherein Y, Z, $L^1$, $L^2$, $R^4$, and $R^5$ are as defined for Formula I.

Formula I also includes compounds of Formula VI:

(VI)

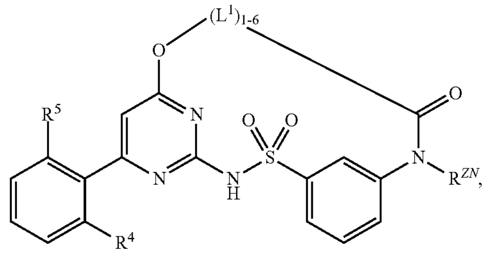

tautomers of those compounds, deuterated derivatives of any of the compounds and tautomers, and pharmaceutically acceptable salts of any of the foregoing, wherein $L^1$, $R^4$, $R^5$, and $R^{ZN}$ are as defined for Formula I.

Another aspect of the disclosure provides pharmaceutical compositions comprising at least one compound chosen from the novel compounds disclosed herein, tautomers thereof, deuterated derivatives those compounds and tautomers, and pharmaceutically acceptable salts of any of the foregoing, and at least one pharmaceutically acceptable carrier, which compositions may further include at least one additional active pharmaceutical ingredient. In some embodiments, the at least one additional active pharmaceutical ingredient is at least one other CFTR modulator. In some embodiments, the at least one other CFTR modulator is selected from CFTR potentiators. In some embodiments, the at least one other CFTR modulator is selected from CFTR correctors. In some embodiments, the at least one other CFTR modulator includes a potentiator and corrector. In some embodiments, the at least one other CFTR modulator is selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

Thus, another aspect of the disclosure provides methods of treating the CFTR-mediated disease cystic fibrosis comprising administering at least one compound chosen from the novel compounds disclosed herein, tautomers thereof, deuterated derivatives of those compounds and tautomers, and pharmaceutically acceptable salts of any of the foregoing, and at least one pharmaceutically acceptable carrier, optionally as part of a pharmaceutical composition comprising at least one additional active pharmaceutical ingredient, to a subject in need thereof. In some embodiments, the at least one additional active pharmaceutical ingredient is at least one other CFTR modulator. In some embodiments, the at least one other CFTR modulator is selected from CFTR potentiators. In some embodiments, the at least one other CFTR modulator is selected from CFTR correctors. In some embodiments, the at least one other CFTR modulator includes a potentiator and corrector. In some embodiments, the at least one other CFTR modulator is selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

In certain embodiments, the pharmaceutical compositions of the disclosure comprise at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing. In some embodiments, compositions comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing may optionally further comprise (a) at least one compound chosen from (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (tezacaftor), 3-(6-(1-(2,2-difluorobenzo[d][1,3]dioxol-5-yl)cyclopropane carboxamido)-3-methylpyridin-2-yl)benzoic acid (lumacaftor) and deuterated derivatives and pharmaceutically acceptable salts of tezacaftor and lumacaftor; and/or (b) at least one compound chosen from N-[2,4-bis(1,1-dimethylethyl)-5-hydroxyphenyl]-1,4-dihydro-4-oxoquinoline-3-carboxamide (ivacaftor), N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide (deutivacaftor), (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

Another aspect of the disclosure provides methods of treating the CFTR-mediated disease, cystic fibrosis, that comprise administering to a patient in need thereof at least one compound chosen from the novel compounds disclosed herein, deuterated derivatives thereof, and pharmaceutically acceptable salts of any of the foregoing, and optionally further administering one or more additional CFTR modulating agents. A further aspect of the disclosure provides the pharmaceutical compositions of the disclosure comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing and, optionally, one or more CFTR modulating agents, for use in therapy or for use in the manufacture of a medicament. In some embodiments, the optional one or more additional CFTR modulating agents are selected from CFTR potentiators. In some embodiments, the one or more additional CFTR modulating agents are selected from CFTR correctors. In some embodiments, the one or more additional CFTR modulating agents are selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

A further aspect of the disclosure provides intermediates and methods for making the compounds and pharmaceutical compositions disclosed herein.

Definitions

"Tezacaftor," as used herein, refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide, which can be depicted with the following structure:

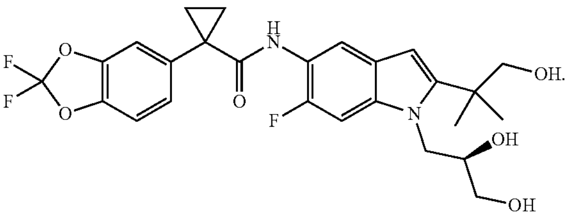 [SMILES: CC(C)(CO)c1cc2cc(NC(=O)C3(c4ccc5c(c4)OC(F)(F)O5)CC3)c(F)cc2n1C[C@@H](O)CO]

Tezacaftor may be in the form of a deuterated derivative or a pharmaceutically acceptable salt, or a pharmaceutically acceptable salt of a deuterated derivative. Tezacaftor and methods of making and using tezacaftor are disclosed in WO 2010/053471, WO 2011/119984, WO 2011/133751, WO 2011/133951, WO 2015/160787, and US 2009/0131492, each of which is incorporated herein by reference.

"Ivacaftor" as used throughout this disclosure refers to N-(2,4-di-tert-butyl-5-hydroxyphenyl)-1,4-dihydro-4-oxo-quinoline-3-carboxamide, which is depicted by the structure:

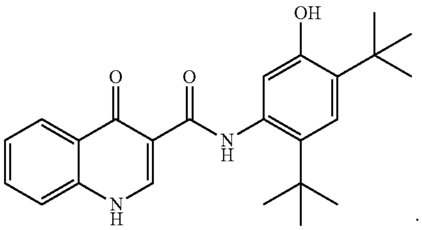 [SMILES: CC(C)(C)c1cc(C(C)(C)C)c(NC(=O)c2c[nH]c3ccccc3c2=O)cc1O]

Ivacaftor may also be in the form of a deuterated derivative, a pharmaceutically acceptable salt, or a pharmaceutically acceptable salt of a deuterated derivative. Ivacaftor and methods of making and using ivacaftor are disclosed in WO 2006/002421, WO 2007/079139, WO 2010/108162, and WO 2010/019239, each of which is incorporated herein by reference.

In some embodiments, a specific deuterated derivative of ivacaftor (deutivacaftor) is employed in the compositions and methods disclosed herein. A chemical name for deutivacaftor is N-(2-(tert-butyl)-5-hydroxy-4-(2-(methyl-d3) propan-2-yl-1,1,1,3,3,3-d6)phenyl)-4-oxo-1,4-dihydroquinoline-3-carboxamide, as depicted by the structure:

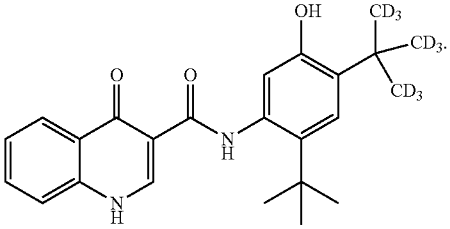 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

Deutivacaftor may be in the form of a further deuterated derivative, a pharmaceutically acceptable salt, or a pharmaceutically acceptable salt of a further deuterated derivative. Deutivacaftor and methods of making and using deutivacaftor are disclosed in WO 2012/158885, WO 2014/078842, and U.S. Pat. No. 8,865,902, each of which is incorporated herein by reference.

"Lumacaftor," as used herein, refers to 3-(6-(1-(2,2-difluorobenzo[d][1,3]dioxol-5-yl)cyclopropanecarboxamido)-3-methylpyridin-2-yl)benzoic acid, which is depicted by the chemical structure:

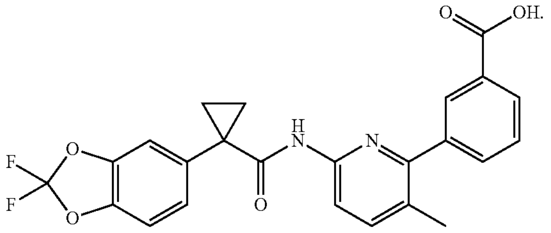 [SMILES: Cc1ccc(NC(=O)C2(c3ccc4c(c3)OC(F)(F)O4)CC2)nc1-c1cccc(C(=O)O)c1]

Lumacaftor may be in the form of a deuterated derivative, a pharmaceutically acceptable salt, or a pharmaceutically acceptable salt of a deuterated derivative. Lumacaftor and methods of making and using lumacaftor are disclosed in WO 2007/056341, WO 2009/073757, and WO 2009/076142, each of which is incorporated herein by reference.

As used herein, the term "alkyl" refers to a saturated or partially saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms) in which one or more adjacent carbon atoms may be interrupted by a double (alkenyl) or triple (alkynyl) bond. Alkyl groups may be substituted or unsubstituted.

As used herein, the term "haloalkyl group" refers to an alkyl group substituted with one or more halogen atoms, e.g., fluoroalkyl, which is an alkyl group substituted with one or more fluorine atoms.

The term "alkoxy," as used herein, refers to an alkyl or cycloalkyl covalently bonded to an oxygen atom. Alkoxy groups may be substituted or unsubstituted.

As used herein, the term "haloalkoxyl group" refers to an alkoxy group substituted with one or more halogen atoms.

As used herein, "cycloalkyl" refers to a cyclic, bicyclic, tricyclic, or polycyclic non-aromatic hydrocarbon groups having 3 to 12 carbons (such as, for example, 3-10 carbons) and may include one or more unsaturated bonds. "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, dispiro[2.0.2.1]heptane, and spiro[2,3]hexane. Cycloalkyl groups may be substituted or unsubstituted.

The term "aryl," as used herein, is a functional group or substituent derived from an aromatic ring and encompasses monocyclic aromatic rings and bicyclic, tricyclic, and fused ring systems wherein at least one ring in the system is aromatic. Non-limiting examples of aryl groups include phenyl, naphthyl, and 1,2,3,4-tetrahydronaphthalenyl.

The term "heteroaryl ring," as used herein, refers to an aromatic ring comprising at least one ring atom that is a heteroatom, such as O, N, or S. Heteroaryl groups encompass monocyclic rings and bicyclic, tricyclic, bridged, fused, and spiro ring systems (including mono spiro and dispiro rings) wherein at least one ring in the system is aromatic. Non-limiting examples of heteroaryl rings include pyridine, quinoline, indole, and indoline.

As used herein, the term "heterocyclyl ring" refers to a non-aromatic hydrocarbon containing 3 to 12 atoms in a ring (such as, for example 3-10 atoms) comprising at least one ring atom that is a heteroatom, such as O, N, or S and may include one or more unsaturated bonds. "Heterocyclyl" rings encompass monocyclic, bicyclic, tricyclic, polycyclic, bridged, fused, and spiro rings, including mono spiro and dispiro rings.

"Substituted," whether preceded by the term "optionally" or not, indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

Non-limiting examples of protecting groups for nitrogen include, for example, t-butyl carbamate (Boc), benzyl (Bn), para-methoxybenzyl (PMB), tetrahydropyranyl (THP), 9-fluorenylmethyl carbamate (Fmoc), benzyl carbamate (Cbz), methyl carbamate, ethyl carbamate, 2,2,2-trichloroethyl carbamate (Troc), 2-trimethylsilylethyl carbamate (Teoc), allyl carbamate (Aloc or Alloc), formamide, acetamide, benzamide, allylamine, trifluoroacetamide, triphenylmethylamine, benzylideneamine, and p-toluenesulfonamide. A comprehensive list of nitrogen protecting groups can be found in Wuts, P. G. M. "Greene's Protective Groups in Organic Synthesis: Fifth Edition," 2014, John Wiley and Sons.

As used herein, "deuterated derivative(s)" refers to a compound having the same chemical structure as a reference compound, with one or more hydrogen atoms replaced by a deuterium atom. In some embodiments, the one or more hydrogens replaced by deuterium are part of an alkyl group. In some embodiments, the one or more hydrogens replaced by deuterium are part of a methyl group.

As used herein, "CFTR" means cystic fibrosis transmembrane conductance regulator.

The terms "CFTR modulator" and "CFTR modulating agent" are used interchangeably herein to refer to a compound that increases the activity of CFTR. The increase in activity resulting from a CFTR modulator includes, but is not limited to, compounds that correct, potentiate, stabilize, and/or amplify CFTR.

The terms "corrector" and "CFTR corrector" are used interchangeably herein to refer to a compound that facilitates the processing and trafficking of CFTR to increase the amount of CFTR at the cell surface. The novel compounds disclosed herein are CFTR correctors. Other correctors may be used in combination therapies with the novel compounds disclosed herein to treat CFTR mediated diseases, such as cystic fibrosis. Such other correctors include, e.g., tezacaftor, lumacaftor, and their deuterated derivatives and pharmaceutically acceptable salts.

The term "potentiator" and "CFTR potentiator" are used interchangeably to refer to a compound that increases the channel activity of CFTR protein located at the cell surface, resulting in enhanced ion transport. Ivacaftor and deutivacaftor disclosed herein are CFTR potentiators. Potentiators may be used in combination with the novel compounds of the disclosure to treat CFTR mediated diseases such as cystic fibrosis. Such potentiators include, e.g., ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and their deuterated derivatives and pharmaceutically acceptable salts.

It will be appreciated that when a description of a combination of compound selected from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and other specified CFTR modulating agents is provided herein, typically, but not necessarily, the combination or treatment regime will include at least one potentiator, such as, e.g., a potentiator selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts thereof. It will also be appreciated that typically, but not necessarily, more than one potentiator would not be used in a combination pharmaceutical composition or therapy. In some embodiments, a combination of at least one compound selected from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and other specified CFTR modulating agents, will also include another CFTR corrector, such as, e.g., a corrector compound selected from tezacaftor, lumacaftor, and deuterated derivatives and pharmaceutically acceptable salts thereof.

The term "at least one compound selected from," as used herein, refers to the selection of one or more of the compounds from a specified group.

A reference to "Compounds 1-124" in this disclosure is intended to represent a reference to each of Compounds 1 through 124 individually or groups of compounds chosen from amongst Compounds 1 through 124.

As used herein, the term "active pharmaceutical ingredient" or "therapeutic agent" ("API") refers to a biologically active compound.

The terms "patient" and "subject" are used interchangeably and refer to an animal, including a human.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement in one or more symptoms of CF or lessening the severity of CF or one or more symptoms of CF in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

It should be understood that references herein to methods of treatment (e.g., methods of treating a CFTR mediated disease or a method of treating cystic fibrosis) using one or more compounds of the disclosure optionally in combination with one or more additional CFTR modulating agents (e.g., a compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, optionally in combination with one or more additional CFTR modulating agents) should also be interpreted as references to:

- one or more compounds (e.g., compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, optionally in combination with one or more additional CFTR modulating agents) for use in methods of treating, e.g., cystic fibrosis, optionally in combination with one or more additional CFTR modulating agents; and/or
- the use of one or more compounds (e.g., a compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, optionally in combination with one or more additional CFTR modulating agents) in the manufacture of a medicament for treating, e.g., cystic fibrosis.

It should be also understood that references herein to methods of treatment (e.g., methods of treating a CFTR mediated disease or a method of treating cystic fibrosis) using a pharmaceutical composition of the disclosure (e.g., a pharmaceutical composition comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing and optionally further comprising one or more additional CFTR modulating agents) should also be interpreted as references to:

- a pharmaceutical composition (e.g., a pharmaceutical composition comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing and optionally further comprising one or more additional CFTR modulating agents) for use in methods of treating, e.g., cystic fibrosis; and/or
- the use of a pharmaceutical composition (e.g., a pharmaceutical composition comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing and optionally further comprising one or more additional CFTR modulating agents) in the manufacture of a medicament for treating, e.g., cystic fibrosis.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately" may refer to an acceptable error for a particular value as determined by one of skill in the art, which depends in part on how the value is measured or determined. In some embodiments, the terms “about” and “approximately” mean within 20%, 15%, 10%, 5%, 4%, 3%, 2%, 1%, or 0.5% of a given value or range.

As used herein, the term “solvent” refers to any liquid in which the product is at least partially soluble (solubility of product >1 g/L).

As used herein, the term “room temperature” or “ambient temperature” means 15° C. to 30° C.

It will be appreciated that certain compounds of this disclosure may exist as separate stereoisomers or enantiomers and/or mixtures of those stereoisomers or enantiomers.

Certain compounds disclosed herein may exist as tautomers and both tautomeric forms are intended, even though only a single tautomeric structure is depicted. For example, a description of Compound X is understood to include its tautomer Compound Y and vice versa, as well as mixtures thereof:

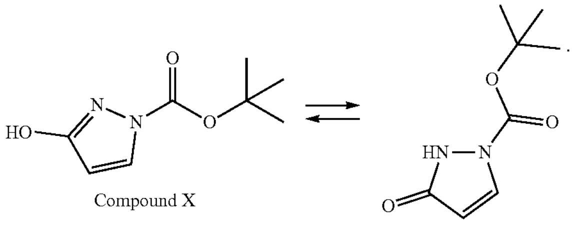

Compound X

Compound Y

As used herein, “minimal function (MF) mutations” refer to CFTR gene mutations associated with minimal CFTR function (little-to-no functioning CFTR protein) and include, for example, mutations associated with severe defects in ability of the CFTR channel to open and close, known as defective channel gating or “gating mutations”; mutations associated with severe defects in the cellular processing of CFTR and its delivery to the cell surface; mutations associated with no (or minimal) CFTR synthesis; and mutations associated with severe defects in channel conductance.

As used herein, the term “pharmaceutically acceptable salt” refers to a salt form of a compound of this disclosure, wherein the salt is nontoxic. Pharmaceutically acceptable salts of the compounds of this disclosure include those derived from suitable inorganic and organic acids and bases. A “free base” form of a compound, for example, does not contain an ionically bonded salt.

The phrase “and deuterated derivatives and pharmaceutically acceptable salts thereof” is used interchangeably with “and deuterated derivatives and pharmaceutically acceptable salts thereof of any of the forgoing” in reference to one or more compounds or formulae of the disclosure. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of “a compound or a pharmaceutically acceptable salt thereof” is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences,* 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}\ alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

Methods of Treatment

Any of the novel compounds disclosed herein, such as for example, compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, can act as a CFTR modulator, i.e., modulating CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the disclosure provides methods of treating, lessening the severity of, or symptomatically treating cystic fibrosis in a patient comprising administering to the patient an effective amount of any of the novel compounds disclosed herein, such as for example, compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, alone or in combination with another active ingredient, such as one or more CFTR modulating agents. In some embodiments, the one (or more) CFTR modulating agent is a corrector. In some embodiments, the one (or more) CFTR modulating agent is a potentiator. In some embodiments, the one (or more) CFTR modulating agents include both a corrector and a potentiator. In some embodiments, the one or more CFTR modulating agents are selected from potentiators: ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing; and correctors: lumacaftor, tezacaftor, and deuterated derivatives and pharmaceutically acceptable salts thereof.

In some embodiments, the patient to be treated has an F508del/minimal function (MF) genotype, F508del/F508del genotype (homozygous for the F508del mutation), F508del/gating genotype, or F508del/residual function (RF) genotype. In some embodiments, the patient is heterozygous and has one F508del mutation. In some embodiments, the patient is homozygous for the N1303K mutation.

In some embodiments, 5 mg to 500 mg of a compound disclosed herein, a tautomer thereof, a deuterated derivatives of the compound and tautomer, or a pharmaceutically acceptable salt of any of the foregoing are administered daily.

In some embodiments, the patient to be treated has at least one F508del mutation in the CFTR gene. In some embodiments, the patient has a CFTR gene mutation that is responsive to a compound, tautomer, deuterated derivative, or pharmaceutically acceptable salt of the disclosure based on in vitro data. In some embodiments, the patient is heterozygous and has an F508del mutation on one allele and a mutation on the other allele selected from Table 2:

TABLE 2

| CFTR Mutations | | | | | |
|---|---|---|---|---|---|
| MF Category | Mutation | | | | |
| Nonsense mutations | Q2X | L218X | Q525X | R792X | E1104X |
| | S4X | Q220X | G542X | E822X | W1145X |
| | W19X | Y275X | G550X | W882X | R1158X |
| | G27X | C276X | Q552X | W846X | R1162X |
| | Q39X | Q290X | R553X | Y849X | S1196X |
| | W57X | G330X | E585X | R851X | W1204X |
| | E60X | W401X | G673X | Q890X | L1254X |
| | R75X | Q414X | Q685X | S912X | S1255X |
| | L88X | S434X | R709X | Y913X | W1282X |
| | E92X | S466X | K710X | Q1042X | Q1313X |
| | Q98X | S489X | Q715X | W1089X | Q1330X |
| | Y122X | Q493X | L732X | Y1092X | E1371X |
| | E193X | W496X | R764X | W1098X | Q1382X |
| | W216X | C524X | R785X | R1102X | Q1411X |
| Canonical splice mutations | 185 + 1G→T | 711 + 5G→A | 1717 − 8G→A | 2622 + 1G→A | 3121 − 1G→A |
| | 296 + 1G→A | 712 − 1G→T | 1717 − 1G→A | 2790 − 1G→C | 3500 − 2A→G |
| | 296 + 1G→T | 1248 + 1G→A | 1811 + 1G→C | 3040G→C | 3600 + 2insT |
| | 405 + 1G→A | 1249 − 1G→A | 1811 + 1.6kbA→G | (G970R) | 3850 − 1G→A |
| | 405 + 3A→C | 1341 + 1G→A | 1811 + 1643G→T | 3120G→A | 4005 + 1G→A |
| | 406 − 1G→A | 1525 − 2A→G | 1812 − 1G→A | 3120 + 1G→A | 4374 + 1G→T |
| | 621 + 1G→T | 1525 − 1G→A | 1898 + 1G→A | 3121 − 2A→G | |
| | 711 + 1G→T | | 1898 + 1G→C | | |
| Small (≤3 nucleotide) insertion/deletion (ins/del) frameshift mutations | 182delT | 1078delT | 1677delTA | 2711delT | 3737delA |
| | 306insA | 1119delA | 1782delA | 2732insA | 3791delC |
| | 306delTAGA | 1138insG | 1824delA | 2869insG | 3821delT |
| | 365-366insT | 1154insTC | 1833delT | 2896insAG | 3876delA |
| | 394delTT | 1161delC | 2043delG | 2942insT | 3878delG |
| | 442delA | 1213delT | 2143delT | 2957delT | 3905insT |
| | 444delA | 1259insA | 2183AA→G[a] | 3007delG | 4016insT |
| | 457TAT→G | 1288insTA | 2184delA | 3028delA | 4021dupT |
| | 541delC | 1343delG | 2184insA | 3171delC | 4022insT |
| | 574delA | 1471delA | 2307insA | 3171insC | 4040delA |

TABLE 2-continued

CFTR Mutations

| MF Category | Mutation | | | | |
|---|---|---|---|---|---|
| | 663delT | 1497delGG | 2347delG | 3271delGG | 4279insA |
| | 849delG | 1548delG | 2585delT | 3349insT | 4326delTC |
| | 935delA | 1609del CA | 2594delGT | 3659delC | |
| Non-small (>3 nucleotide) insertion/deletion (ins/del) frameshift mutations | CFTRdel1 | | CFTdele16-17b | 1461ins4 | |
| | CFTRdele2 | | CFTRdele17a, 17b | 1924del7 | |
| | CFTRdele2, 3 | | CFTRdele17a-18 | 2055del9→A | |
| | CFTRdele2-4 | | CFTRdele19 | 2105-2117del13insAGAAA | |
| | CFTRdele3-10, 14b-16 | | CFTRdele19-21 | 2372del8 | |
| | CFTRdele4-7 | | CFTRdele21 | 2721del11 | |
| | CFTRdele4-11 | | CFTRdele22-24 | 2991del32 | |
| | CFTR 50kbdel | | CFTRdele22, 23 | 3667ins4 | |
| | CFTRdup6b-10 | | 124del23bp | 4010del4 | |
| | CFTRdele11 | | 602del14 | 4209TGTT→AA | |
| | CFTRdele13, 14a | | 852del22 | | |
| | CFTRdele14b-17b | | 991del5 | | |
| Missense mutations that Are not responsive in vitro to TEZ, IVA, or TEZ/IVA and % PI >50% and $SwCl^-$ >86 mmol/L | A46D | V520F | Y569D | N1303K | |
| | G85E | A559T | L1065P | | |
| | R347P | R560T | R1066C | | |
| | L467P | R560S | L1077P | | |
| | I507del | A561E | M1101K | | |

[a]Also known as 2183delAA→G.
CFTR: cystic fibrosis transmembrane conductance regulator;
IVA: ivacaftor.
SwCl: sweat chloride.
TEZ: tezacaftor.
Source: CFTR2.org [Internet]. Baltimore (MD): Clinical and functional translation of CFTR.
The Clinical and Functional Translation of CFTR (CFTR2), US Cystic Fibrosis Foundation, Johns Hopkins University, the Hospital for Sick Children.
Available at: http://www.cftr2.org/. Accessed 15 May 2018.
Notes:
% PI: percentage of F508del-CFTR heterozygous patients in the CFTR2 patient registry who are pancreatic insufficient;
SwCl: mean sweat chloride of F508del-CFTR heterozygous patients in the CFTR2 patient registry.

In some embodiments, the disclosure also is directed to methods of treatment using isotope-labelled compounds of the afore-mentioned compounds, or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$ $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)- and/or carbon-14 ($^{14}C$)-labelled compounds are particularly useful for various types of assays, such as substrate tissue distribution assays, due to relatively simple preparation and excellent detectability. For example, deuterium ($^{2}H$)-labelled ones are therapeutically useful with potential therapeutic advantages over the non-$^{2}H$-labelled compounds. In general, deuterium ($^{2}H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "D."

The concentration of the isotope(s) (e.g., deuterium) incorporated into the isotope-labelled compounds and salts of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Combination Therapies

One aspect disclosed herein provides methods of treating cystic fibrosis and other CFTR mediated diseases using any of the novel compounds disclosed herein, such as, for example, compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, in combination with at least one additional active pharmaceutical ingredient.

In some embodiments, at least one additional active pharmaceutical ingredient is selected from mucolytic agents, bronchodilators, antibiotics, anti-infective agents, and anti-inflammatory agents.

In some embodiments, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In some embodiments, the additional agent is a mucolyte. Exemplary mucolytes useful herein includes Pulmozyme®.

In some embodiments, the additional agent is a bronchodilator. Exemplary bronchodilators include albuterol, metaprotenerol sulfate, pirbuterol acetate, salmeterol, or tetrabuline sulfate.

In some embodiments, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In some embodiments, the additional agent is a nutritional agent. Exemplary nutritional agents include pancrelipase (pancreatic enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In some embodiments, at least one additional active pharmaceutical ingredient is selected from CFTR modulating agents. In some embodiments, the additional active pharmaceutical ingredient is selected from CFTR potentiators. In some embodiments, the potentiator is selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing. In some embodiments, the additional active pharmaceutical ingredient is chosen from CFTR correctors. In some embodiments, the corrector is selected from lumacaftor, tezacaftor, deuterated derivatives of lumacaftor and tezacaftor, and pharmaceutically acceptable salts of any of the foregoing. In some embodiments, the additional active pharmaceutical ingredient includes both a CFTR potentiator and a CFTR corrector.

In some embodiments, the at least one additional active pharmaceutical ingredient is chosen from (a) tezacaftor, lumacaftor, and deuterated derivatives and pharmaceutically acceptable salts thereof; and/or (b) ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing. Thus, in some embodiments, the combination therapies provided herein comprise (a) a compound selected from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing; (b) at least one compound selected from tezacaftor, lumacaftor, and deuterated derivatives and pharmaceutically acceptable salts thereof; or (c) at least one compound selected from ivacaftor, deutivacaftor, and deuterated derivatives and pharmaceutically acceptable salts thereof. In some embodiments, the combination therapies provided herein comprise (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing; (b) at least one compound selected from tezacaftor, lumacaftor, and deuterated derivatives and pharmaceutically acceptable salts thereof; and (c) at least one compound selected from ivacaftor, deutivacaftor, and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from deutivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof and at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof and at least one compound chosen from deutivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from tezacaftor and deuterated derivatives and pharmaceutically acceptable salts thereof and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof and at least one compound chosen from ivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof and at least one compound chosen from deutivacaftor and deuterated derivatives and pharmaceutically acceptable salts thereof. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in combination with at least one compound chosen from lumacaftor and deuterated derivatives and pharmaceutically acceptable salts thereof and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof.

Each of the compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, independently can be administered once daily, twice daily, or three times daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered once daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered twice daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from tezacaftor, lumacaftor, and deuterated derivatives and pharmaceutically acceptable salts thereof are administered once daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from tezacaftor, lumacaftor, and deuterated derivatives and pharmaceutically acceptable salts thereof are administered twice daily.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from ivacaftor, deutivacaftor, and deuterated derivatives and pharmaceutically acceptable salts thereof are administered once daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from ivacaftor, deutivacaftor, and deuterated derivatives and pharmaceutically acceptable salts thereof are administered twice daily.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered once daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered twice daily.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, and (c) at least one compound chosen from ivacaftor, deutivacaftor, and deuterated derivatives and pharmaceutically acceptable salts thereof are administered once daily. In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor and pharmaceutically acceptable salts thereof, and (c) at least one compound chosen from ivacaftor, deutivacaftor, and pharmaceutically acceptable salts thereof are administered twice daily.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from ivacaftor, deutivacaftor, and deuterated derivatives and pharmaceutically acceptable salts thereof, and (c) at least one compound chosen from lumacaftor and deuterated derivatives and pharmaceutically acceptable salts thereof, are administered once daily. In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from ivacaftor, deutivacaftor, and deuterated derivatives and pharmaceutically acceptable salts thereof, and (c) at least one compound chosen from lumacaftor and deuterated derivatives and pharmaceutically acceptable salts thereof, are administered twice daily.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, at least one compound chosen from tezacaftor, lumacaftor, and deuterated derivatives and pharmaceutically acceptable salts thereof, and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered once daily. In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, at least one compound chosen from tezacaftor, lumacaftor, and deuterated derivatives and pharmaceutically acceptable salts thereof, and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered twice daily.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from tezacaftor and deuterated derivatives and pharmaceutically acceptable salts thereof, are administered once daily and (b) at least one compound chosen from ivacaftor and deuterated derivatives and pharmaceutically acceptable salts thereof, is administered twice daily. In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one compound chosen from lumacaftor and deuterated derivatives and pharmaceutically acceptable salts thereof, are administered once daily and (b) at least one compound chosen from ivacaftor and deuterated derivatives and pharmaceutically acceptable salts thereof, are administered twice daily.

Compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and optionally at least one compound selected from tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing can be administered in a single pharmaceutical composition or separate pharmaceutical compositions. Such pharmaceutical compositions can be administered once daily or multiple times daily, such as twice or three times daily. As used herein, the phrase that a given amount of API (e.g., tezacaftor, lumacaftor, ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, or a deuterated derivative or a pharmaceutically acceptable salt thereof) is administered once or twice daily or per day means that said given amount is administered per dosing once or twice daily.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; (b) at least one compound chosen from tezacaftor and deuterated derivatives and pharmaceutically acceptable salts thereof is administered in a second pharmaceutical composition; and (c) at least one compound chosen from ivacaftor and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; (b) at least one compound chosen from tezacaftor and deuterated derivatives and pharmaceutically acceptable salts thereof is administered in a second pharmaceutical composition; (c) at least one compound chosen from deutivacaftor and deuterated derivatives and pharmaceutically acceptable salts thereof is administered in a third pharmaceutical composition.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; at least one compound chosen from tezacaftor and deuterated derivatives and pharmaceutically acceptable salts thereof is administered in a second pharmaceutical composition; at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; (b) at least one compound chosen from ivacaftor, deutivacaftor, and deuterated derivatives and pharmaceutically acceptable salts thereof is administered in a second pharmaceutical composition; (c) at least one compound chosen from lumacaftor and deuterated derivatives and pharmaceutically acceptable salts thereof is administered in a third pharmaceutical composition.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof is administered in a second pharmaceutical composition; at least one compound chosen from lumacaftor and deuterated derivatives and pharmaceutically acceptable salts thereof is administered in a third pharmaceutical composition.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; and (b) at least one compound chosen from tezacaftor and pharmaceutically acceptable salts thereof and at least one compound chosen from ivacaftor, deutivacaftor, and deuterated derivatives and pharmaceutically acceptable salts thereof are administered in a second pharmaceutical composition. In some embodiments, the second pharmaceutical composition comprises a half of a daily dose of ivacaftor or a pharmaceutically acceptable salt thereof, and the other half of said daily dose of ivacaftor or a pharmaceutically acceptable salt thereof is administered in a third pharmaceutical composition.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, is administered in a first pharmaceutical composition; and at least one compound chosen from tezacaftor, lumacaftor, and deuterated derivatives and pharmaceutically acceptable salts thereof and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered in a second pharmaceutical composition.

In some embodiments, (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing; (b) at least one compound chosen from tezacaftor and pharmaceutically acceptable salts thereof and at least one compound chosen from ivacaftor, deutivacaftor, and pharmaceutically acceptable salts thereof are administered in a first pharmaceutical composition. In some embodiments, the first pharmaceutical composition is administered to the patient twice daily. In some embodiments, the first pharmaceutical composition is administered once daily. In some embodiments, the first pharmaceutical composition is administered once daily and a second composition comprising only ivacaftor is administered once daily.

In some embodiments, at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing; at least one compound chosen from tezacaftor and pharmaceutically acceptable salts thereof and at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof are administered in a first pharmaceutical composition. In some embodiments, the first pharmaceutical composition is administered to the patient twice daily. In some embodiments, the first pharmaceutical composition is administered once daily. In some embodiments, the first pharmaceutical composition is administered once daily and a second composition comprising only (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol (or deuterated derivative or pharmaceutically acceptable salt thereof) is administered once daily.

Any suitable pharmaceutical compositions can be used for compounds of Formula I, compounds of any one of Formulae Ia, IIa, IIb, III, IV, V, Va, Vb, and VI, Compounds 1-124, and tautomers thereof, deuterated derivatives of those compounds and tautomers, and pharmaceutically acceptable salts of any of the foregoing, with or without including one or more compounds selected from tezacaftor, ivacaftor, deutivacaftor, lumacaftor, (6R,12R)-17-amino-12-methyl-6,15-bis(trifluoromethyl)-13,19-dioxa-3,4,18-triazatricyclo [12.3.1.12,5]nonadeca-1(18),2,4,14,16-pentaen-6-ol, and deuterated derivatives and pharmaceutically acceptable salts of any of the foregoing. Some exemplary pharmaceutical compositions for tezacaftor and its pharmaceutically acceptable salts can be found in WO 2011/119984 and WO 2014/014841, which are incorporated herein by reference. Some exemplary pharmaceutical compositions for ivacaftor and its pharmaceutically acceptable salts can be found in WO 2007/134279, WO 2010/019239, WO 2011/019413, WO 2012/027731, and WO 2013/130669, and some exemplary pharmaceutical compositions for deutivacaftor and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for lumacaftor and its pharmaceutically acceptable salts can be found in WO 2010/037066, WO 2011/127421, and WO 2014/071122, which are incorporated herein by reference.

Pharmaceutical Compositions

Another aspect of the disclosure provides a pharmaceutical composition comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least one pharmaceutically acceptable carrier.

In some embodiments, the disclosure provides pharmaceutical compositions comprising at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, and at least two additional active pharmaceutical ingredients, one of which is a CFTR corrector and one of which is a CFTR potentiator.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, and (c) at least one pharmaceutically acceptable carrier. In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from lumacaftor and deuterated derivatives and pharmaceutically acceptable salts thereof, and (c) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from ivacaftor, deutivacaftor, and deuterated derivatives and pharmaceutically acceptable salts thereof, and (c) at least one pharmaceutically acceptable carrier. In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof, and (c) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, (c) at least one compound chosen from ivacaftor and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor and deuterated derivatives and pharmaceutically acceptable salts thereof, (c) at least one compound chosen from deutivacaftor and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from ivacaftor, deutivacaftor, and deuterated derivatives and pharmaceutically acceptable salts thereof, (c) at least one compound chosen from lumacaftor and deuterated derivatives and pharmaceutically acceptable salts thereof, and (d) at least one pharmaceutically acceptable carrier.

In some embodiments, the disclosure provides a pharmaceutical composition comprising (a) at least one compound chosen from compounds of Formula I, compounds of any one of Formulae Ia, IIa, IIb, III, IV, V, Va, Vb, and VI, Compounds 1-124, tautomers thereof, deuterated derivatives of those compounds and tautomers, and pharmaceutically acceptable salts of any of the foregoing, (b) at least one compound chosen from tezacaftor, lumacaftor, and deuterated derivatives and pharmaceutically acceptable salts thereof, (c) at least one compound chosen from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts thereof, and (d) at least one pharmaceutically acceptable carrier.

Any pharmaceutical composition disclosed herein may comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, and lubricants.

The pharmaceutical compositions described herein are useful for treating cystic fibrosis and other CFTR mediated diseases.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York disclose various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose, and cellulose acetate), powdered tragacanth, malt, gelatin, talc, excipients (such as cocoa butter and suppository waxes), oils (such as peanut oil, cottonseed oil, safflower oil, sesame oil, olive oil, corn oil, and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

EXEMPLARY EMBODIMENTS

A non-limiting list of embodiments is provided below:

1. A compound of Formula I:

(I)

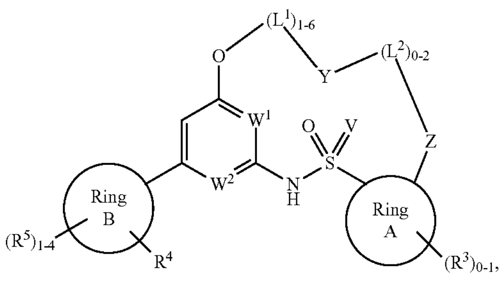

a tautomer thereof, a deuterated derivative of the compound or tautomer, or a pharmaceutically acceptable salt of any of the foregoing, wherein:

Ring A is selected from:
- $C_6$-$C_{10}$ aryl,
- $C_3$-$C_{10}$ cycloalkyl,
- 3- to 10-membered heterocyclyl, and
- 5- to 10-membered heteroaryl;

Ring B is selected from:
- $C_6$-$C_{10}$ aryl,
- $C_3$-$C_{10}$ cycloalkyl,
- 3- to 10-membered heterocyclyl, and
- 5- to 10-membered heteroaryl;

V is selected from O and NH;

$W^1$ is selected from N and CH;

$W^2$ is selected from N and CH, provided that at least one of $W^1$ and $W^2$ is N;

Y is selected from O and $C(R^{YC})_2$;

Z is selected from O, $NR^{ZN}$, and $C(R^{ZC})_2$, provided that when Y is O and $L^2$ is absent, Z is $C(R^{ZC})_2$;

each $L^1$ is independently selected from $C(R^{L1})_2$ and

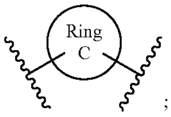

;

each $L^2$ is independently selected from $C(R^{L2})_2$;

Ring C is selected from $C_6$-$C_{10}$ aryl optionally substituted with 1-3 groups independently selected from:
- halogen,
- $C_1$-$C_6$ alkyl, and
- $N(R^N)_2$;

each $R^3$ is independently selected from:
halogen,
$C_1$-$C_6$ alkyl,
$C_1$-$C_6$ alkoxy,
$C_3$-$C_{10}$ cycloalkyl,
$C_6$-$C_{10}$ aryl optionally substituted with 1-3 groups independently selected from $C_1$-$C_6$ alkyl, and
3- to 10-membered heterocyclyl;
$R^4$ is selected from hydrogen and $C_1$-$C_6$ alkyl;
each $R^5$ is independently selected from:
hydrogen,
halogen,
hydroxyl,
$N(R^N)_2$,
—SO-Me,
—CH═C($R^{LC}$)$_2$, wherein both $R^{LC}$ are taken together to form a $C_3$-$C_{10}$ cycloalkyl,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$,
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl,
$C_1$-$C_6$ fluoroalkyl,
$C_3$-$C_{10}$ cycloalkyl,
$C_6$-$C_{10}$ aryl, and
3- to 10-membered heterocyclyl;
$R^{ZN}$ is selected from:
hydrogen,
$C_1$-$C_9$ alkyl optionally substituted with 1-3 groups independently selected from:
hydroxyl,
oxo,
cyano,
$C_1$-$C_6$ alkoxy optionally substituted with 1-3 groups independently selected from halogen and $C_1$-$C_6$ alkoxy,
$N(R^N)_2$,
$SO_2Me$,
$C_3$-$C_{10}$ cycloalkyl optionally substituted with 1-3 groups independently selected from:
hydroxyl,
$C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
$C_1$-$C_6$ fluoroalkyl,
$C_1$-$C_6$ alkoxy,
COOH,
$N(R^N)_2$,
$C_6$-$C_{10}$ aryl, and
3- to 10-membered heterocyclyl optionally substituted with 1-3 groups independently selected from oxo and $C_1$-$C_6$ alkyl,
$C_6$-$C_{10}$ aryl optionally substituted with 1-3 groups independently selected from:
halogen,
hydroxyl,
cyano,
$SiMe_3$,
$SO_2Me$,
$SF_5$,
$N(R^N)_2$,
$P(O)Me_2$,
—$(O)_{0-1}$—($C_3$-$C_{10}$ cycloalkyl) optionally substituted with 1-3 groups independently selected from $C_1$-$C_6$ fluoroalkyl,
$C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
$C_1$-$C_6$ alkoxy optionally substituted with 1-3 groups independently selected from hydroxyl, oxo, $N(R^N)_2$, and $C_6$-$C_{10}$ aryl,
$C_1$-$C_6$ fluoroalkyl,
3- to 10-membered heterocyclyl optionally substituted with 1-3 groups independently selected from $C_1$-$C_6$ alkyl,
—$(O)_{0-1}$—($C_6$-$C_{10}$ aryl), and
—$(O)_{0-1}$-(5- to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
3- to 10-membered heterocyclyl optionally substituted with 1-4 groups independently selected from:
hydroxyl,
oxo,
$N(R^N)_2$,
$C_1$-$C_6$ alkyl optionally substituted with 1-3 groups independently selected from oxo and $C_1$-$C_6$ alkoxy,
$C_1$-$C_6$ alkoxy,
$C_1$-$C_6$ fluoroalkyl,
$C_6$-$C_{10}$ aryl optionally substituted with 1-3 groups independently selected from halogen, and
5- to 10-membered heteroaryl, and
5- to 10-membered heteroaryl optionally substituted with 1-3 groups independently selected from:
hydroxyl,
cyano,
oxo,
halogen,
$B(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3 —$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$—($C_3$-$C_{10}$ cycloalkyl) optionally substituted with 1-3 groups independently selected from $C_1$-$C_6$ alkyl,
—$(O)_{0-1}$—($C_6$-$C_{10}$ aryl),
—$(O)_{0-1}$-(3- to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, and 3- to 10-membered heterocyclyl (optionally substituted with 1-3 groups independently selected from $C_1$-$C_6$ fluoroalkyl), and 5- to 10-membered heteroaryl optionally substituted with 1-4 groups independently selected from $C_1$-$C_6$ alkyl and $C_3$-$C_{10}$ cycloalkyl, $C_1$-$C_6$ fluoroalkyl, $C_3$-$C_{10}$ cycloalkyl optionally substituted with 1-3 groups independently selected from:

hydroxyl, oxo, halogen, cyano, $N(R^N)_2$, $C_1$-$C_6$ alkyl optionally substituted with 1-3 groups independently selected from:

hydroxyl, oxo, $N(R^N)_2$, $C_1$-$C_6$ alkoxy, and $C_6$-$C_{10}$ aryl, $C_1$-$C_6$ alkoxy optionally substituted with 1-3 groups independently selected from halogen, oxo, $C_6$-$C_{10}$ aryl, and $N(R^N)_2$, halogen, $C_3$-$C_{10}$ cycloalkyl, 3- to 10-mememeber heterocyclyl optionally substituted with 1-3 groups independently selected from $C_1$-$C_6$ alkyl, and 5- to 10-membered heteroaryl optionally substituted with 1-3 groups independently selected from:

hydroxyl, cyano, oxo, halogen, $N(R^N)_2$, $C_1$-$C_6$ alkyl optionally substituted with 1-3 groups independently selected from hydroxyl, oxo, $C_1$-$C_6$ alkoxy, and $N(R^N)_2$, $C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl, $C_1$-$C_6$ fluoroalkyl, $-(O)_{0-1}-(C_3$-$C_{10}$ cycloalkyl) optionally substituted with 1-3 groups independently selected from $C_1$-$C_6$ alkyl, $C_6$-$C_{10}$ aryl, and 3- to 10-membered heterocyclyl optionally substituted with 1-3 groups independently selected from $C_1$-$C_6$ alkyl, $C_6$-$C_{10}$ aryl, 3- to 10-membered heterocyclyl optionally substituted with 1-3 groups independently selected from:

oxo, $C_1$-$C_6$ alkyl optionally substituted with 1-3 groups independently selected from:

oxo, hydroxyl, $N(R^N)_2$, $C_1$-$C_6$ alkoxy optionally substituted with 1-3 groups independently selected from halogen and $C_6$-$C_{10}$ aryl, and $-(O)_{0-1}-(C_3$-$C_{10}$ cycloalkyl), $C_1$-$C_6$ fluoroalkyl, $C_3$-$C_{10}$ cycloalkyl optionally substituted with 1-3 groups independently selected from halogen, and 3- to 10-membered heterocyclyl, 5- to 10-membered heteroaryl optionally substituted with 1-3 groups independently selected from:

halogen, $C_1$-$C_6$ alkyl optionally substituted with 1-3 groups independently selected from oxo, $C_1$-$C_6$ alkoxy, and $N(R^N)_2$, and 3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and $R^F$;

each $R^{YC}$ and $R^{ZC}$ is independently selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), $C_6$-$C_{10}$ aryl optionally substituted with 1-3 groups independently selected from $C_1$-$C_6$ alkyl, and $R^F$;

or two $R^{YC}$ are taken together to form an oxo group;

or two $R^{ZC}$ are taken together to form an oxo group;

each $R^{L1}$ is independently selected from:

hydrogen, $N(R^N)_2$, provided that two $N(R^N)_2$ are not bonded to the same carbon, $C_1$-$C_9$ alkyl optionally substituted with 1-3 groups independently selected from:

halogen, hydroxyl, oxo, $N(R^N)_2$, $C_1$-$C_6$ alkoxy optionally substituted with 1-3 groups independently selected from $C_6$-$C_{10}$ aryl, $C_3$-$C_{10}$ cycloalkyl optionally substituted with 1-3 groups independently selected from halogen and $C_1$-$C_6$ fluoroalkyl, $C_6$-$C_{10}$ aryl optionally substituted with 1-3 groups independently selected from $C_1$-$C_6$ alkyl, and 3- to 10-membered heterocyclyl optionally substituted with 1-3 groups independently selected from $C_1$-$C_6$ alkyl (optionally substituted with 1-3 groups independently selected from hydroxyl and oxo), $C_3$-$C_{10}$ cycloalkyl, $C_6$-$C_{10}$ aryl optionally substituted with 1-4 groups independently selected from:

halogen, cyano, $SiMe_3$, $POMe_2$, $C_1$-$C_7$ alkyl optionally substituted with 1-3 groups independently selected from:

hydroxyl, oxo, cyano, $SiMe_3$, $N(R^N)_2$, and $C_3$-$C_{10}$ cycloalkyl optionally substituted with 1-3 groups independently selected from $C_1$-$C_6$ fluoroalkyl, $C_1$-$C_6$ alkoxy optionally substituted with 1-3 groups independently selected from:
$C_3$-$C_{10}$ cycloalkyl optionally substituted with 1-3 groups independently selected from $C_1$-$C_6$ fluoroalkyl, and
$C_1$-$C_6$ alkoxy,
$C_1$-$C_6$ fluoroalkyl,
$C_3$-$C_{10}$ cycloalkyl optionally substituted with 1-3 groups independently selected from $C_1$-$C_6$ alkyl and $C_1$-$C_6$ fluoroalkyl,
$C_6$-$C_{10}$ aryl,
3- to 10-membered heterocyclyl optionally substituted with 1-3 groups independently selected from $C_1$-$C_6$ alkyl, and
5- to 10-membered heteroaryl,
3- to 10-membered heterocyclyl optionally substituted with 1-3 groups independently selected from:
$C_1$-$C_6$ alkyl optionally substituted with 1-3 groups independently selected from:
oxo, and
$C_1$-$C_6$ alkoxy,
5- to 10-membered heteroaryl optionally substituted with 1-3 groups independently selected from:
$C_1$-$C_6$ alkyl optionally substituted with 1-3 groups independently selected from:
$C_3$-$C_{10}$ cycloalkyl optionally substituted with 1-3 groups independently selected from $C_1$-$C_6$ fluoroalkyl, and
$C_6$-$C_{10}$ aryl optionally substituted with 1-3 groups independently selected from $C_1$-$C_6$ alkyl, and
$R^F$;
or two $R^{L1}$ on the same carbon atom are taken together to form an oxo group;
each $R^{L2}$ is independently selected from hydrogen and $R^F$;
or two $R^{L2}$ on the same carbon atom are taken together to form an oxo group;
each $R^N$ is independently selected from:
hydrogen,
$C_1$-$C_8$ alkyl optionally substituted with 1-3 groups independently selected from:
oxo,
halogen,
hydroxyl,
$NH_2$,
NHMe,
$NMe_2$,
$C_1$-$C_6$ alkoxy optionally substituted with 1-3 groups independently selected from $C_6$-$C_{10}$ aryl,
$—(O)_{0-1}—(C_3$-$C_{10}$ cycloalkyl),
$C_6$-$C_{10}$ aryl optionally substituted with 1-3 groups independently selected from halogen and $C_1$-$C_6$ alkyl,
3- to 14-membered heterocyclyl optionally substituted with 1-4 groups independently selected from oxo and $C_1$-$C_6$ alkyl, and
5- to 14-membered heteroaryl optionally substituted with 1-4 groups independently selected from oxo and $C_1$-$C_6$ alkyl,
$C_3$-$C_{10}$ cycloalkyl optionally substituted with 1-3 groups independently selected from:
hydroxyl,
$NH_2$,
NHMe, and
$C_1$-$C_6$ alkyl optionally substituted with 1-3 groups independently selected from hydroxyl,
$C_6$-$C_{10}$ aryl, and
3- to 10-membered heterocyclyl;
or two $R^N$ on the same nitrogen atom are taken together with the nitrogen to which they are bonded to form a 3- to 10-membered heterocyclyl optionally substituted with 1-3 groups selected from:
hydroxyl,
oxo,
cyano,
$C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl,
$C_1$-$C_6$ alkoxy, and
$C_1$-$C_6$ fluoroalkyl;
or one $R^4$ and one $R^{L1}$ are taken together to form a $C_6$-$C_8$ alkylene;
when $R^F$ is present, two $R^F$ taken together with the atoms to which they are bonded form a group selected from:
$C_3$-$C_{10}$ cycloalkyl optionally substituted with 1-3 groups independently selected from $C_1$-$C_6$ alkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl,
3- to 11-membered heterocyclyl optionally substituted with 1-3 groups independently selected from:
oxo,
$N(R^N)_2$,
$C_1$-$C_9$ alkyl optionally substituted with 1-4 groups independently selected from:
oxo,
halogen,
hydroxyl,
$N(R^N)_2$,
$—SO_2—(C_1$-$C_6$ alkyl),
$C_1$-$C_6$ alkoxy optionally substituted with 1-3 groups independently selected from halogen and $C_6$-$C_{10}$ aryl,
$C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), $—(O)_{0-1}—(C_1$-$C_6$ fluoroalkyl), and $C_6$-$C_{10}$ aryl (optionally substituted with 1-3 groups independently selected from $C_1$-$C_6$ alkoxy),
$—(O)_{0-1}—(C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl,
3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$, —O-(5- to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and 5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl, $C_3$-$C_{12}$ cycloalkyl optionally substituted with 1-4 groups independently selected from halogen, $C_1$-$C_6$ alkyl, and $C_1$-$C_6$ fluoroalkyl, $C_6$-$C_{10}$ aryl, 3- to 10-membered heterocyclyl, and 5- to 10-membered heteroaryl optionally substituted with 1-3 groups independently selected from $C_1$-$C_6$ alkoxy and $C_1$-$C_6$ fluoroalkyl, and 5- to 12-membered heteroaryl optionally substituted with 1-3 groups independently selected from $C_1$-$C_6$ alkyl and $C_1$-$C_6$ fluoroalkyl.

2. The compound, tautomer, salt, or deuterated derivative according to embodiment 1, wherein Ring A is selected from $C_6$-$C_{10}$ aryl and 5- to 10-membered heteroaryl.

3. The compound, tautomer, salt, or deuterated derivative according to embodiment 1 or 2, wherein Ring A is selected from phenyl and pyridyl.

4. The compound, tautomer, salt, or deuterated derivative according to any one of embodiments 1 to 3, wherein Ring A is phenyl.

5. The compound, tautomer, salt, or deuterated derivative according to any one of embodiments 1 to 4, wherein Ring B is selected from $C_6$-$C_{10}$ aryl, $C_3$-$C_{10}$ cycloalkyl, and 5- to 10-membered heteroaryl.

6. The compound, tautomer, salt, or deuterated derivative according to any one of embodiments 1 to 5, wherein Ring B is selected from phenyl, naphthyl, cyclohexyl, pyrazoyl, and furanyl.

7. The compound, tautomer, salt, or deuterated derivative according to any one of embodiments 1 to 6, wherein Ring B is phenyl.

8. The compound, tautomer, salt, or deuterated derivative according to any one of embodiments 1 to 7, wherein V is O.

9. The compound, tautomer, salt, or deuterated derivative according to any one of embodiments 1 to 8, wherein $W^1$ is N and $W^2$ is N.

10. The compound, tautomer, salt, or deuterated derivative according to any one of embodiments 1 to 8, wherein $W^1$ is N and $W^2$ is CH.

11. The compound, tautomer, salt, or deuterated derivative according to any one of embodiments 1 to 10, wherein Y is O.

12. The compound, tautomer, salt, or deuterated derivative according to any one of embodiments 1 to 10, wherein Y is $C(R^{YC})_2$.

13. The compound, tautomer, salt, or deuterated derivative according to any one of embodiments 1 to 12, wherein Z is O.

14. The compound, tautomer, salt, or deuterated derivative according to any one of embodiments 1 to 12, wherein Z is $NR^{ZN}$.

15. The compound, tautomer, salt, or deuterated derivative according to any one of embodiments 1 to 12, wherein Z is $C(R^{ZC})_2$.

16. The compound, tautomer, salt, or deuterated derivative according to any one of embodiments 1 to 15, wherein each $L^1$ is $C(R^{L1})_2$.

17. The compound, tautomer, salt, or deuterated derivative according to any one of embodiments 1 to 16, wherein Ring C is phenyl.

18. The compound, tautomer, salt, or deuterated derivative according to any one of embodiments 1 to 17, wherein $R^3$ is absent.

19. The compound, tautomer, salt, or deuterated derivative according to any one of embodiments 1 to 18, wherein $R^4$ is selected from hydrogen and methyl.

20. The compound, tautomer, salt, or deuterated derivative according to any one of embodiments 1 to 19, wherein $R^4$ is methyl.

21. The compound, tautomer, salt, or deuterated derivative according to any one of embodiments 1 to 20, wherein each $R^5$ is independently selected from:

hydrogen, hydroxyl, $N(R^N)_2$, $C_1$-$C_6$ alkyl optionally substituted with 1-3 groups independently selected from:

hydroxyl, $C_1$-$C_6$ alkoxy optionally substituted with 1-3 groups independently selected from $C_1$-$C_6$ alkoxy and $C_6$-$C_{10}$ aryl, $C_3$-$C_{10}$ cycloalkyl, —$(O)_{0-1}$—($C_6$-$C_{10}$ aryl) optionally substituted with 1-3 groups independently selected from $C_1$-$C_6$ alkyl and $C_1$-$C_6$ alkoxy, 3- to 10-membered heterocyclyl, and $N(R^N)_2$, and $C_1$-$C_6$ alkoxy optionally substituted with 1-3 groups independently selected from:

halogen, $C_6$-$C_{10}$ aryl, and $C_3$-$C_{10}$ cycloalkyl optionally substituted with 1-3 groups independently selected from $C_1$-$C_6$ fluoroalkyl.

22. The compound, tautomer, salt, or deuterated derivative according to any one of embodiments 1 to 21, wherein each $R^5$ is independently selected from hydrogen, hydroxyl, $N(R^N)_2$, $C_1$-$C_6$ alkyl, and $C_1$-$C_6$ alkoxy.

23. The compound, tautomer, salt, or deuterated derivative according to any one of embodiments 1 to 22, wherein $R^{ZN}$ is selected from hydrogen and $C_1$-$C_9$ alkyl.

24. The compound, tautomer, salt, or deuterated derivative according to any one of embodiments 1 to 23, wherein $R^{ZN}$ is selected from hydrogen and methyl.

25. The compound, tautomer, salt, or deuterated derivative according to any one of embodiments 1 to 24, wherein each $R^{YC}$ and $R^{ZC}$ is independently selected from:

hydrogen, $C_1$-$C_6$ alkyl optionally substituted with 1-3 groups independently selected from $C_6$-$C_{10}$ aryl, $C_6$-$C_{10}$ aryl, and $R^F$;

or two $R^{YC}$ are taken together to form an oxo group.

26. The compound, tautomer, salt, or deuterated derivative according to any one of embodiments 1 to 25, wherein each $R^{L1}$ is independently selected from:

hydrogen, $N(R^N)_2$, provided that two $N(R^N)_2$ are not bonded to the same carbon, $C_1$-$C_9$ alkyl optionally substituted with 1-3 groups independently selected from $C_6$-$C_{10}$ aryl, $C_6$-$C_{10}$ aryl, and $R^F$.

27. The compound, tautomer, salt, or deuterated derivative according to any one of embodiments 1 to 26, wherein each $R^N$ is independently selected from:

hydrogen, $C_1$-$C_8$ alkyl optionally substituted with 1-3 groups independently selected from:

oxo, $NH_2$,

NHMe, $NMe_2$, and $C_1$-$C_6$ alkoxy, and $C_3$-$C_{10}$ cycloalkyl optionally substituted with 1-3 groups independently selected from $NH_2$ and NHMe, or two $R^N$ on the same nitrogen atom are taken together with the nitrogen to which they are bonded to form a 3- to 10-membered heterocyclyl.

28. The compound, tautomer, salt, or deuterated derivative according to any one of embodiments 1 to 27, wherein when $R^F$ is present, two $R^F$ taken together with the atoms to which they are bonded form a group selected from:

$C_3$-$C_{10}$ cycloalkyl, $C_6$-$C_{10}$ aryl optionally substituted with 1-3 groups independently selected from:

halogen, $C_1$-$C_6$ alkyl, $N(R^N)_2$, and 3- to 10-membered heterocyclyl optionally substituted with 1-3 groups independently selected from hydroxyl, and 3- to 11-membered heterocyclyl optionally substituted with 1-3 groups independently selected from:

oxo, $C_1$-$C_9$ alkyl optionally substituted with 1-4 groups independently selected from:

oxo, halogen, hydroxyl, $N(R^N)_2$,

—$SO_2$—($C_1$-$C_6$ alkyl), $C_1$-$C_6$ alkoxy optionally substituted with 1-3 groups independently selected from halogen, $C_6$-$C_{10}$ aryl, $C_6$-$C_{10}$ aryl, —$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and 3- to 10-membered heterocyclyl, and $C_3$-$C_{12}$ cycloalkyl optionally substituted with 1-4 groups independently selected from $C_1$-$C_6$ alkyl and $C_1$-$C_6$ fluoroalkyl.

29. A compound of Formula Ia:

(Ia)

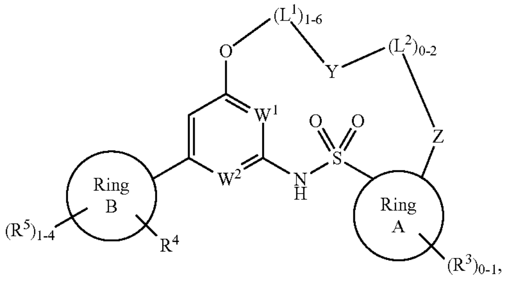

a tautomer thereof, a deuterated derivative of the compound or tautomer, or a pharmaceutically acceptable salt of any of the foregoing, wherein Ring A, Ring B, $W^1$, $W^2$, Y, Z, $L^1$, $L^2$, $R^3$, $R^4$, and $R^5$ are defined as according to embodiment 1.

30. The compound, tautomer, salt, or deuterated derivative according to embodiment 29, wherein Ring A is selected from $C_6$-$C_{10}$ aryl and 5- to 10-membered heteroaryl.

31. The compound, tautomer, salt, or deuterated derivative according to embodiment 29 or 30, wherein Ring A is selected from phenyl and pyridyl.

32. The compound, tautomer, salt, or deuterated derivative according to any one of embodiments 29 to 31, wherein Ring A is phenyl.

33. The compound, tautomer, salt, or deuterated derivative according to any one of embodiments 29 to 32, wherein Ring B is selected from $C_6$-$C_{10}$ aryl, $C_3$-$C_{10}$ cycloalkyl, and 5- to 10-membered heteroaryl.

34. The compound, tautomer, salt, or deuterated derivative according to any one of embodiments 29 to 33, wherein Ring B is selected from phenyl, naphthyl, cyclohexyl, pyrazoyl, and furanyl.

35. The compound, tautomer, salt, or deuterated derivative according to any one of embodiments 29 to 34, wherein Ring B is phenyl.

36. The compound, tautomer, salt, or deuterated derivative according to any one of embodiments 29 to 35, wherein $W^1$ is N and $W^2$ is N.

37. The compound, tautomer, salt, or deuterated derivative according to any one of embodiments 29 to 35, wherein $W^1$ is N and $W^2$ is CH.

38. The compound, tautomer, salt, or deuterated derivative according to any one of embodiments 29 to 37, wherein Y is O.

39. The compound, tautomer, salt, or deuterated derivative according to any one of embodiments 29 to 37, wherein Y is $C(R^{YC})_2$.

40. The compound, tautomer, salt, or deuterated derivative according to any one of embodiments 29 to 39, wherein Z is O.

41. The compound, tautomer, salt, or deuterated derivative according to any one of embodiments 29 to 39, wherein Z is $NR^{ZN}$.

42. The compound, tautomer, salt, or deuterated derivative according to any one of embodiments 29 to 39, wherein Z is $C(R^{ZC})_2$.

43. The compound, tautomer, salt, or deuterated derivative according to any one of embodiments 29 to 42, wherein each $L^1$ is $C(R^{L1})_2$.

44. The compound, tautomer, salt, or deuterated derivative according to any one of embodiments 29 to 43, wherein Ring C is phenyl.

45. The compound, tautomer, salt, or deuterated derivative according to any one of embodiments 29 to 44, wherein $R^3$ is absent.

46. The compound, tautomer, salt, or deuterated derivative according to any one of embodiments 29 to 45, wherein $R^4$ is selected from hydrogen and methyl.

47. The compound, tautomer, salt, or deuterated derivative according to any one of embodiments 29 to 46, wherein $R^4$ is methyl.

48. The compound, tautomer, salt, or deuterated derivative according to any one of embodiments 29 to 47, wherein each $R^5$ is independently selected from:
hydrogen,
hydroxyl,
$N(R^N)_2$,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$, and
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl.

49. The compound, tautomer, salt, or deuterated derivative according to any one of embodiments 29 to 48, wherein each $R^5$ is independently selected from hydrogen, hydroxyl, $N(R^N)_2$, $C_1$-$C_6$ alkyl, and $C_1$-$C_6$ alkoxy.

50. The compound, tautomer, salt, or deuterated derivative according to any one of embodiments 29 to 49, wherein $R^{ZN}$ is selected from hydrogen and $C_1$-$C_9$ alkyl.

51. The compound, tautomer, salt, or deuterated derivative according to any one of embodiments 29 to 50, wherein $R^{ZN}$ is selected from hydrogen and methyl.

52. The compound, tautomer, salt, or deuterated derivative according to any one of embodiments 29 to 51, wherein each $R^{YC}$ and $R^{ZC}$ is independently selected from:
hydrogen,
$C_1$-$C_6$ alkyl optionally substituted with 1-3 groups independently selected from $C_6$-$C_{10}$ aryl,
$C_6$-$C_{10}$ aryl, and
$R^F$;
or two $R^{YC}$ are taken together to form an oxo group.

53. The compound, tautomer, salt, or deuterated derivative according to any one of embodiments 29 to 52, wherein each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from $C_6$-$C_{10}$ aryl,
$C_6$-$C_{10}$ aryl, and
$R^F$;

54. The compound, tautomer, salt, or deuterated derivative according to any one of embodiments 29 to 53, wherein each $R^N$ is independently selected from:
hydrogen,
$C_1$-$C_8$ alkyl optionally substituted with 1-3 groups independently selected from:
oxo,
$NH_2$,
NHMe,
$NMe_2$, and
$C_1$-$C_6$ alkoxy, and
$C_3$-$C_{10}$ cycloalkyl optionally substituted with 1-3 groups independently selected from $NH_2$ and NHMe,
or two $R^N$ on the same nitrogen atom are taken together with the nitrogen to which they are bonded to form a 3- to 10-membered heterocyclyl.

55. The compound, tautomer, salt, or deuterated derivative according to any one of embodiments 29 to 54, wherein when $R^F$ is present, two $R^F$ taken together with the atoms to which they are bonded form a group selected from:
$C_3$-$C_{10}$ cycloalkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl, and
3- to 11-membered heterocyclyl optionally substituted with 1-3 groups independently selected from:
oxo,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen, $C_6$-$C_{10}$ aryl,
$C_6$-$C_{10}$ aryl,
—$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and
3- to 10-membered heterocyclyl, and
$C_3$-$C_{12}$ cycloalkyl optionally substituted with 1-4 groups independently selected from $C_1$-$C_6$ alkyl and $C_1$-$C_6$ fluoroalkyl.

56. A compound of Formula IIa:

(IIa)

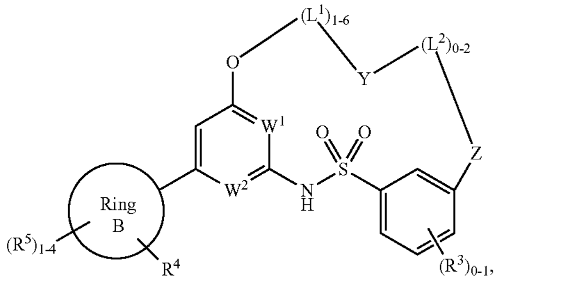

a tautomer thereof, a deuterated derivative of the compound or tautomer, or a pharmaceutically acceptable salt of any of the foregoing, wherein Ring B, $W^1$, $W^2$, Y, Z, $L^1$, $L^2$, $R^3$, $R^4$, and $R^5$ are defined as according to embodiment 1.

57. The compound, tautomer, salt, or deuterated derivative according to embodiment 56, wherein Ring B is selected from $C_6$-$C_{10}$ aryl, $C_3$-$C_{10}$ cycloalkyl, and 5- to 10-membered heteroaryl.

58. The compound, tautomer, salt, or deuterated derivative according to embodiment 56 or 57, wherein Ring B is selected from phenyl, naphthyl, cyclohexyl, pyrazoyl, and furanyl.

59. The compound, tautomer, salt, or deuterated derivative according to any one of embodiments 56 to 58, wherein Ring B is phenyl.

60. The compound, tautomer, salt, or deuterated derivative according to any one of embodiments 56 to 59, wherein $W^1$ is N and $W^2$ is N.

61. The compound, tautomer, salt, or deuterated derivative according to any one of embodiments 56 to 59, wherein $W^1$ is N and $W^2$ is CH.

62. The compound, tautomer, salt, or deuterated derivative according to any one of embodiments 56 to 61, wherein Y is O.

63. The compound, tautomer, salt, or deuterated derivative according to any one of embodiments 56 to 61, wherein Y is $C(R^{YC})_2$.

64. The compound, tautomer, salt, or deuterated derivative according to any one of embodiments 56 to 63, wherein Z is O.

65. The compound, tautomer, salt, or deuterated derivative according to any one of embodiments 56 to 63, wherein Z is $NR^{ZN}$ 66. The compound, tautomer, salt, or deuterated derivative according to any one of embodiments 56 to 63, wherein Z is $C(R^{ZC})_2$.

67. The compound, tautomer, salt, or deuterated derivative according to any one of embodiments 56 to 66, wherein each $L^1$ is $C(R^{L1})_2$.

68. The compound, tautomer, salt, or deuterated derivative according to any one of embodiments 56 to 67, wherein Ring C is phenyl.

69. The compound, tautomer, salt, or deuterated derivative according to any one of embodiments 56 to 68, wherein $R^3$ is absent.

70. The compound, tautomer, salt, or deuterated derivative according to any one of embodiments 56 to 69, wherein $R^4$ is selected from hydrogen and methyl.

71. The compound, tautomer, salt, or deuterated derivative according to any one of embodiments 56 to 70, wherein $R^4$ is methyl.

72. The compound, tautomer, salt, or deuterated derivative according to any one of embodiments 56 to 71, wherein each $R^5$ is independently selected from:
hydrogen,
hydroxyl,
$N(R^N)_2$,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$, and
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl.

73. The compound, tautomer, salt, or deuterated derivative according to any one of embodiments 56 to 72, wherein each $R^5$ is independently selected from hydrogen, hydroxyl, $N(R^N)_2$, $C_1$-$C_6$ alkyl, and $C_1$-$C_6$ alkoxy.

74. The compound, tautomer, salt, or deuterated derivative according to any one of embodiments 56 to 73, wherein $R^{ZN}$ is selected from hydrogen and $C_1$-$C_9$ alkyl.

75. The compound, tautomer, salt, or deuterated derivative according to any one of embodiments 56 to 74, wherein $R^{ZN}$ is selected from hydrogen and methyl.

76. The compound, tautomer, salt, or deuterated derivative according to any one of embodiments 56 to 75, wherein each $R^{YC}$ and $R^{ZC}$ is independently selected from:
hydrogen,
$C_1$-$C_6$ alkyl optionally substituted with 1-3 groups independently selected from $C_6$-$C_{10}$ aryl,
$C_6$-$C_{10}$ aryl, and
$R^F$;
or two $R^{YC}$ are taken together to form an oxo group.

77. The compound, tautomer, salt, or deuterated derivative according to any one of embodiments 56 to 76, wherein each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from $C_6$-$C_{10}$ aryl,
$C_6$-$C_{10}$ aryl, and
$R^F$.

78. The compound, tautomer, salt, or deuterated derivative according to any one of embodiments 56 to 77, wherein each $R^N$ is independently selected from:
hydrogen,
$C_1$-$C_8$ alkyl optionally substituted with 1-3 groups independently selected from:
oxo,
$NH_2$,
NHMe,
$NMe_2$, and
$C_1$-$C_6$ alkoxy, and
$C_3$-$C_{10}$ cycloalkyl optionally substituted with 1-3 groups independently selected from $NH_2$ and NHMe,
or two $R^N$ on the same nitrogen atom are taken together with the nitrogen to which they are bonded to form a 3- to 10-membered heterocyclyl.

79. The compound, tautomer, salt, or deuterated derivative according to any one of embodiments 56 to 78, wherein when $R^F$ is present, two $R^F$ taken together with the atoms to which they are bonded form a group selected from:
$C_3$-$C_{10}$ cycloalkyl, $C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl, and
3- to 11-membered heterocyclyl optionally substituted with 1-3 groups independently selected from:
oxo,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen, $C_6$-$C_{10}$ aryl,
$C_6$-$C_{10}$ aryl,
—$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and
3- to 10-membered heterocyclyl, and
$C_3$-$C_{12}$ cycloalkyl optionally substituted with 1-4 groups independently selected from $C_1$-$C_6$ alkyl and $C_1$-$C_6$ fluoroalkyl.

80. A compound of Formula IIb:

(IIb)

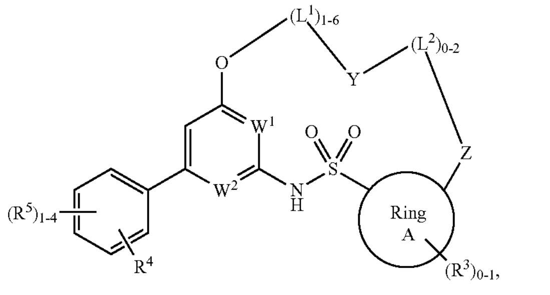

a tautomer thereof, a deuterated derivative of the compound or tautomer, or a pharmaceutically acceptable salt of any of the foregoing, wherein Ring A, $W^1$, $W^2$, Y, Z, $L^1$, $L^2$, $R^3$, $R^4$, and $R^5$ are defined as according to embodiment 1.

81. The compound, tautomer, salt, or deuterated derivative according to embodiment 80, wherein Ring A is selected from $C_6$-$C_{10}$ aryl and 5- to 10-membered heteroaryl.

82. The compound, tautomer, salt, or deuterated derivative according to embodiment 80 or 81, wherein Ring A is selected from phenyl and pyridyl.

83. The compound, tautomer, salt, or deuterated derivative according to any one of embodiments 80 to 82, wherein Ring A is phenyl.

84. The compound, tautomer, salt, or deuterated derivative according to any one of embodiments 80 to 83, wherein $W^1$ is N and $W^2$ is N.

85. The compound, tautomer, salt, or deuterated derivative according to any one of embodiments 80 to 83, wherein $W^1$ is N and $W^2$ is CH.

86. The compound, tautomer, salt, or deuterated derivative according to any one of embodiments 80 to 85, wherein Y is O.

87. The compound, tautomer, salt, or deuterated derivative according to any one of embodiments 80 to 85, wherein Y is $C(R^{YC})_2$.

88. The compound, tautomer, salt, or deuterated derivative according to any one of embodiments 80 to 87, wherein Z is O.

89. The compound, tautomer, salt, or deuterated derivative according to any one of embodiments 80 to 87, wherein Z is $NR^{ZN}$.

90. The compound, tautomer, salt, or deuterated derivative according to any one of embodiments 80 to 87, wherein Z is $C(R^{ZC})_2$.

91. The compound, tautomer, salt, or deuterated derivative according to any one of embodiments 80 to 90, wherein each $L^1$ is $C(R^{L1})_2$.

92. The compound, tautomer, salt, or deuterated derivative according to any one of embodiments 80 to 91, wherein Ring C is phenyl.

93. The compound, tautomer, salt, or deuterated derivative according to any one of embodiments 80 to 92, wherein $R^3$ is absent.

94. The compound, tautomer, salt, or deuterated derivative according to any one of embodiments 80 to 93, wherein $R^4$ is selected from hydrogen and methyl.

95. The compound, tautomer, salt, or deuterated derivative according to any one of embodiments 80 to 94, wherein $R^4$ is methyl.

96. The compound, tautomer, salt, or deuterated derivative according to any one of embodiments 80 to 95, wherein each $R^5$ is independently selected from:
hydrogen,
hydroxyl,
$N(R^N)_2$,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$, and
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl.

97. The compound, tautomer, salt, or deuterated derivative according to any one of embodiments 80 to 96, wherein each $R^5$ is independently selected from hydrogen, hydroxyl, $N(R^N)_2$, $C_1$-$C_6$ alkyl, and $C_1$-$C_6$ alkoxy.

98. The compound, tautomer, salt, or deuterated derivative according to any one of embodiments 80 to 97, wherein $R^{ZN}$ is selected from hydrogen and $C_1$-$C_9$ alkyl.

99. The compound, tautomer, salt, or deuterated derivative according to any one of embodiments 80 to 98, wherein $R^{ZN}$ is selected from hydrogen and methyl.

100. The compound, tautomer, salt, or deuterated derivative according to any one of embodiments 80 to 99, wherein each $R^{YC}$ and $R^{ZC}$ is independently selected from:
hydrogen,
$C_1$-$C_6$ alkyl optionally substituted with 1-3 groups independently selected from $C_6$-$C_{10}$ aryl,
$C_6$-$C_{10}$ aryl, and
$R^F$;
or two $R^{YC}$ are taken together to form an oxo group.

101. The compound, tautomer, salt, or deuterated derivative according to any one of embodiments 80 to 100, wherein each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from $C_6$-$C_{10}$ aryl,
$C_6$-$C_{10}$ aryl, and
$R^F$.

102. The compound, tautomer, salt, or deuterated derivative according to any one of embodiments 80 to 101, wherein each $R^N$ is independently selected from:
hydrogen,
$C_1$-$C_8$ alkyl optionally substituted with 1-3 groups independently selected from:
oxo,
$NH_2$,
NHMe,
$NMe_2$, and
$C_1$-$C_6$ alkoxy, and
$C_3$-$C_{10}$ cycloalkyl optionally substituted with 1-3 groups independently selected from $NH_2$ and NHMe,
or two $R^N$ on the same nitrogen atom are taken together with the nitrogen to which they are bonded to form a 3- to 10-membered heterocyclyl.

103. The compound, tautomer, salt, or deuterated derivative according to any one of embodiments 80 to 102, wherein when $R^F$ is present, two $R^F$ taken together with the atoms to which they are bonded form a group selected from:
$C_3$-$C_{10}$ cycloalkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl, and
3- to 11-membered heterocyclyl optionally substituted with 1-3 groups independently selected from:
oxo,
$C_1$-$C_9$ alkyl optionally substituted with 1-4 groups independently selected from:
oxo,
halogen,
hydroxyl,
$N(R^N)_2$,
$-SO_2-(C_1$-$C_6$ alkyl),
$C_1$-$C_6$ alkoxy optionally substituted with 1-3 groups independently selected from halogen and $C_6$-$C_{10}$ aryl,
$C_6$-$C_{10}$ aryl,
$-(O)_{0-1}-(C_3$-$C_{10}$ cycloalkyl) optionally substituted with 1-4 groups independently selected from $C_1$-$C_6$ alkyl and $C_1$-$C_6$ fluoroalkyl, and
3- to 10-membered heterocyclyl, and
$C_3$-$C_{12}$ cycloalkyl optionally substituted with 1-4 groups independently selected from $C_1$-$C_6$ alkyl and $C_1$-$C_6$ fluoroalkyl.

104. A compound of Formula III:

(III)

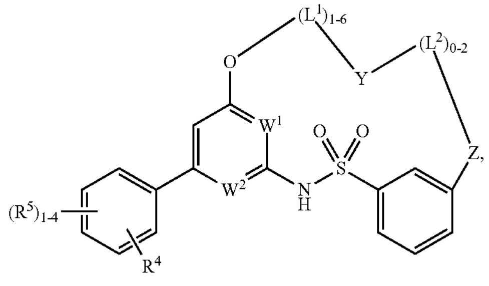

a tautomer thereof, a deuterated derivative of the compound or tautomer, or a pharmaceutically acceptable salt of any of the foregoing, wherein $W^1$, $W^2$, Y, Z, $L^1$, $L^2$, $R^4$, and $R^5$ are defined as according to embodiment 1.

105. The compound, tautomer, salt, or deuterated derivative according to embodiment 104, wherein $W^1$ is N and $W^2$ is N.

106. The compound, tautomer, salt, or deuterated derivative according to embodiment 104, wherein $W^1$ is N and $W^2$ is CH.

107. The compound, tautomer, salt, or deuterated derivative according to any one of embodiments 104 to 106, wherein Y is O.

108. The compound, tautomer, salt, or deuterated derivative according to any one of embodiments 104 to 106, wherein Y is $C(R^{YC})_2$.

109. The compound, tautomer, salt, or deuterated derivative according to any one of embodiments 104 to 108, wherein Z is O.

110. The compound, tautomer, salt, or deuterated derivative according to any one of embodiments 104 to 108, wherein Z is $NR^{ZN}$.

111. The compound, tautomer, salt, or deuterated derivative according to any one of embodiments 104 to 108, wherein Z is $C(R^{ZC})_2$.

112. The compound, tautomer, salt, or deuterated derivative according to any one of embodiments 104 to 111, wherein each $L^1$ is $C(R^{L1})_2$.

113. The compound, tautomer, salt, or deuterated derivative according to any one of embodiments 104 to 112, wherein Ring C is phenyl.

114. The compound, tautomer, salt, or deuterated derivative according to any one of embodiments 104 to 113, wherein $R^4$ is selected from hydrogen and methyl.

115. The compound, tautomer, salt, or deuterated derivative according to any one of embodiments 104 to 114, wherein $R^4$ is methyl.

116. The compound, tautomer, salt, or deuterated derivative according to any one of embodiments 104 to 115, wherein each $R^5$ is independently selected from:
hydrogen,
hydroxyl,
$N(R^N)_2$, $C_1$-$C_6$ alkyl optionally substituted with 1-3 groups independently selected from:

hydroxyl, $C_1$-$C_6$ alkoxy optionally substituted with 1-3 groups independently selected from $C_1$-$C_6$ alkoxy and $C_6$-$C_{10}$ aryl, $C_3$-$C_{10}$ cycloalkyl, —$(O)_{0-1}$—($C_6$-$C_{10}$ aryl) optionally substituted with 1-3 groups independently selected from $C_1$-$C_6$ alkyl and $C_1$-$C_6$ alkoxy, 3- to 10-membered heterocyclyl, and $N(R^N)_2$, and $C_1$-$C_6$ alkoxy optionally substituted with 1-3 groups independently selected from:

halogen, $C_6$-$C_{10}$ aryl, and $C_3$-$C_{10}$ cycloalkyl optionally substituted with 1-3 groups independently selected from $C_1$-$C_6$ fluoroalkyl.

117. The compound, tautomer, salt, or deuterated derivative according to any one of embodiments 104 to 116, wherein each $R^5$ is independently selected from hydrogen, hydroxyl, $N(R^N)_2$, $C_1$-$C_6$ alkyl, and $C_1$-$C_6$ alkoxy.

118. The compound, tautomer, salt, or deuterated derivative according to any one of embodiments 104 to 117, wherein $R^{ZN}$ is selected from hydrogen and $C_1$-$C_9$ alkyl.

119. The compound, tautomer, salt, or deuterated derivative according to any one of embodiments 104 to 118, wherein $R^{ZN}$ is selected from hydrogen and methyl.

120. The compound, tautomer, salt, or deuterated derivative according to any one of embodiments 104 to 119, wherein each $R^{YC}$ and $R^{ZC}$ is independently selected from:

hydrogen, $C_1$-$C_6$ alkyl optionally substituted with 1-3 groups independently selected from $C_6$-$C_{10}$ aryl, $C_6$-$C_{10}$ aryl, and $R^F$;

or two $R^{YC}$ are taken together to form an oxo group.

121. The compound, tautomer, salt, or deuterated derivative according to any one of embodiments 104 to 120, wherein each $R^{L1}$ is independently selected from:

hydrogen, $N(R^N)_2$, provided that two $N(R^N)_2$ are not bonded to the same carbon, $C_1$-$C_9$ alkyl optionally substituted with 1-3 groups independently selected from $C_6$-$C_{10}$ aryl, $C_6$-$C_{10}$ aryl, and $R^F$.

122. The compound, tautomer, salt, or deuterated derivative according to any one of embodiments 104 to 121, wherein each $R^N$ is independently selected from:

hydrogen, $C_1$-$C_8$ alkyl optionally substituted with 1-3 groups independently selected from:

oxo, $NH_2$,

NHMe, $NMe_2$, and $C_1$-$C_6$ alkoxy, and $C_3$-$C_{10}$ cycloalkyl optionally substituted with 1-3 groups independently selected from $NH_2$ and NHMe, or two $R^N$ on the same nitrogen atom are taken together with the nitrogen to which they are bonded to form a 3- to 10-membered heterocyclyl.

123. The compound, tautomer, salt, or deuterated derivative according to any one of embodiments 104 to 122, wherein when $R^F$ is present, two $R^F$ taken together with the atoms to which they are bonded form a group selected from:

$C_3$-$C_{10}$ cycloalkyl, $C_6$-$C_{10}$ aryl optionally substituted with 1-3 groups independently selected from:

halogen, $C_1$-$C_6$ alkyl, $N(R^N)_2$, and 3- to 10-membered heterocyclyl optionally substituted with 1-3 groups independently selected from hydroxyl, and 3- to 11-membered heterocyclyl optionally substituted with 1-3 groups independently selected from:

oxo, $C_1$-$C_9$ alkyl optionally substituted with 1-4 groups independently selected from:

oxo, halogen, hydroxyl, $N(R^N)_2$,

—$SO_2$—($C_1$-$C_6$ alkyl), $C_1$-$C_6$ alkoxy optionally substituted with 1-3 groups independently selected from halogen, $C_6$-$C_{10}$ aryl, $C_6$-$C_{10}$ aryl, —$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and 3- to 10-membered heterocyclyl, and $C_3$-$C_{12}$ cycloalkyl optionally substituted with 1-4 groups independently selected from $C_1$-$C_6$ alkyl and $C_1$-$C_6$ fluoroalkyl.

124. A compound of Formula IV:

(IV)

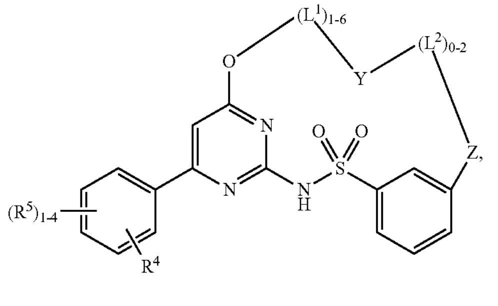

a tautomer thereof, a deuterated derivative of the compound or tautomer, or a pharmaceutically acceptable salt of any of the foregoing, wherein Y, Z, $L^1$, $L^2$, $R^4$, and $R^5$ are defined as according to embodiment 1.

125. The compound, tautomer, salt, or deuterated derivative according to embodiment 124, wherein Y is O.

126. The compound, tautomer, salt, or deuterated derivative according to embodiment 124, wherein Y is $C(R^{YC})_2$.

127. The compound, tautomer, salt, or deuterated derivative according to any one of embodiments 124 to 126, wherein Z is O.

128. The compound, tautomer, salt, or deuterated derivative according to any one of embodiments 124 to 126, wherein Z is $NR^{ZN}$.

129. The compound, tautomer, salt, or deuterated derivative according to any one of embodiments 124 to 126, wherein Z is $C(R^{ZC})_2$.
130. The compound, tautomer, salt, or deuterated derivative according to any one of embodiments 124 to 129, wherein each $L^1$ is $C(R^{L1})_2$.
131. The compound, tautomer, salt, or deuterated derivative according to any one of embodiments 124 to 130, wherein Ring C is phenyl.
132. The compound, tautomer, salt, or deuterated derivative according to any one of embodiments 124 to 131, wherein $R^4$ is selected from hydrogen and methyl.
133. The compound, tautomer, salt, or deuterated derivative according to any one of embodiments 124 to 132, wherein $R^4$ is methyl.
134. The compound, tautomer, salt, or deuterated derivative according to any one of embodiments 124 to 133, wherein each $R^5$ is independently selected from:
hydrogen,
hydroxyl,
$N(R^N)_2$,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$, and
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl.
135. The compound, tautomer, salt, or deuterated derivative according to any one of embodiments 124 to 134, wherein each $R^5$ is independently selected from hydrogen, hydroxyl, $N(R^N)_2$, $C_1$-$C_6$ alkyl, and $C_1$-$C_6$ alkoxy.
136. The compound, tautomer, salt, or deuterated derivative according to any one of embodiments 124 to 135, wherein $R^{ZN}$ is selected from hydrogen and $C_1$-$C_9$ alkyl.
137. The compound, tautomer, salt, or deuterated derivative according to any one of embodiments 124 to 136, wherein $R^{ZN}$ is selected from hydrogen and methyl.
138. The compound, tautomer, salt, or deuterated derivative according to any one of embodiments 124 to 137, wherein each $R^{YC}$ and $R^{ZC}$ is independently selected from:
hydrogen,
$C_1$-$C_6$ alkyl optionally substituted with 1-3 groups independently selected from $C_6$-$C_{10}$ aryl,
$C_6$-$C_{10}$ aryl, and
$R^F$;
or two $R^Y$c are taken together to form an oxo group.
139. The compound, tautomer, salt, or deuterated derivative according to any one of embodiments 124 to 138, wherein each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from $C_6$-$C_{10}$ aryl,
$C_6$-$C_{10}$ aryl, and
$R^F$.

140. The compound, tautomer, salt, or deuterated derivative according to any one of embodiments 124 to 139, wherein each $R^N$ is independently selected from:
hydrogen,
$C_1$-$C_8$ alkyl optionally substituted with 1-3 groups independently selected from:
oxo,
$NH_2$,
NHMe,
$NMe_2$, and
$C_1$-$C_6$ alkoxy, and
$C_3$-$C_{10}$ cycloalkyl optionally substituted with 1-3 groups independently selected from $NH_2$ and NHMe,
or two $R^N$ on the same nitrogen atom are taken together with the nitrogen to which they are bonded to form a 3- to 10-membered heterocyclyl.
141. The compound, tautomer, salt, or deuterated derivative according to any one of embodiments 124 to 140, wherein when $R^F$ is present, two $R^F$ taken together with the atoms to which they are bonded form a group selected from:
$C_3$-$C_{10}$ cycloalkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl, and
3- to 11-membered heterocyclyl optionally substituted with 1-3 groups independently selected from:
oxo,
$C_1$-$C_9$ alkyl optionally substituted with 1-4 groups independently selected from:
oxo,
halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen and $C_6$-$C_{10}$ aryl,
$C_6$-$C_{10}$ aryl,
—$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and
3- to 10-membered heterocyclyl, and
$C_3$-$C_{12}$ cycloalkyl optionally substituted with 1-4 groups independently selected from $C_1$-$C_6$ alkyl and $C_1$-$C_6$ fluoroalkyl.

142. A compound of Formula V:

(V)

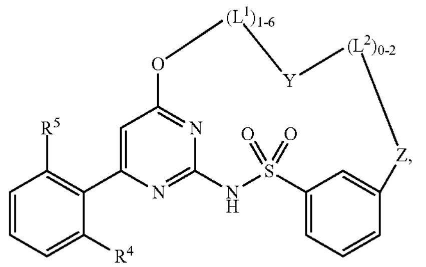

a tautomer thereof, a deuterated derivative of the compound or tautomer, or a pharmaceutically acceptable salt of any of the foregoing, wherein Y, Z, $L^1$, $L^2$, $R^4$, and $R^5$ are defined as according to embodiment 1.

143. The compound, tautomer, salt, or deuterated derivative according to embodiment 142, wherein Y is O.

144. The compound, tautomer, salt, or deuterated derivative according to embodiment 142, wherein Y is $C(R^{YC})_2$.

145. The compound, tautomer, salt, or deuterated derivative according to any one of embodiments 142 to 144, wherein Z is O.

146. The compound, tautomer, salt, or deuterated derivative according to any one of embodiments 142 to 144, wherein Z is $NR^{ZN}$.

147. The compound, tautomer, salt, or deuterated derivative according to any one of embodiments 142 to 144, wherein Z is $C(R^{ZC})_2$.

148. The compound, tautomer, salt, or deuterated derivative according to any one of embodiments 142 to 147, wherein each $L^1$ is $C(R^{L1})_2$.

149. The compound, tautomer, salt, or deuterated derivative according to any one of embodiments 142 to 148, wherein Ring C is phenyl.

150. The compound, tautomer, salt, or deuterated derivative according to any one of embodiments 142 to 149, wherein $R^4$ is selected from hydrogen and methyl.

151. The compound, tautomer, salt, or deuterated derivative according to any one of embodiments 142 to 150, wherein $R^4$ is methyl.

152. The compound, tautomer, salt, or deuterated derivative according to any one of embodiments 142 to 151, wherein each $R^5$ is independently selected from:
hydrogen,
hydroxyl,
$N(R^N)_2$,
$C_1$-$C_6$ alkyl optionally substituted with 1-3 groups independently selected from:
hydroxyl,
$C_1$-$C_6$ alkoxy optionally substituted with 1-3 groups independently selected from $C_1$-$C_6$ alkoxy and $C_6$-$C_{10}$ aryl,
$C_3$-$C_{10}$ cycloalkyl,
—$(O)_{0-1}$—($C_6$-$C_{10}$ aryl) optionally substituted with 1-3 groups independently selected from $C_1$-$C_6$ alkyl and $C_1$-$C_6$ alkoxy,
3- to 10-membered heterocyclyl, and
$N(R^N)_2$, and
$C_1$-$C_6$ alkoxy optionally substituted with 1-3 groups independently selected from:
halogen,
$C_6$-$C_{10}$ aryl, and
$C_3$-$C_{10}$ cycloalkyl optionally substituted with 1-3 groups independently selected from $C_1$-$C_6$ fluoroalkyl.

153. The compound, tautomer, salt, or deuterated derivative according to any one of embodiments 142 to 152, wherein each $R^5$ is independently selected from hydrogen, hydroxyl, $N(R^N)_2$, $C_1$-$C_6$ alkyl, and $C_1$-$C_6$ alkoxy.

154. The compound, tautomer, salt, or deuterated derivative according to any one of embodiments 142 to 153, wherein $R^{ZN}$ is selected from hydrogen and $C_1$-$C_9$ alkyl.

155. The compound, tautomer, salt, or deuterated derivative according to any one of embodiments 142 to 154, wherein $R^{ZN}$ is selected from hydrogen and methyl.

156. The compound, tautomer, salt, or deuterated derivative according to any one of embodiments 142 to 155, wherein each $R^{YC}$ and $R^{ZC}$ is independently selected from:
hydrogen,
$C_1$-$C_6$ alkyl optionally substituted with 1-3 groups independently selected from $C_6$-$C_{10}$ aryl,
$C_6$-$C_{10}$ aryl, and
$R^F$;
or two $R^{YC}$ are taken together to form an oxo group.

157. The compound, tautomer, salt, or deuterated derivative according to any one of embodiments 142 to 156, wherein each $R^{L1}$ is independently selected from:
hydrogen,
$N(R^N)_2$, provided that two $N(R^N)_2$ are not bonded to the same carbon,
$C_1$-$C_9$ alkyl optionally substituted with 1-3 groups independently selected from $C_6$-$C_{10}$ aryl,
$C_6$-$C_{10}$ aryl, and
$R^F$.

158. The compound, tautomer, salt, or deuterated derivative according to any one of embodiments 142 to 157, wherein each $R^N$ is independently selected from:
hydrogen,
$C_1$-$C_8$ alkyl optionally substituted with 1-3 groups independently selected from:
oxo,
$NH_2$,
NHMe,
$NMe_2$, and
$C_1$-$C_6$ alkoxy, and
$C_3$-$C_{10}$ cycloalkyl optionally substituted with 1-3 groups independently selected from $NH_2$ and NHMe,
or two $R^N$ on the same nitrogen atom are taken together with the nitrogen to which they are bonded to form a 3- to 10-membered heterocyclyl.

159. The compound, tautomer, salt, or deuterated derivative according to any one of embodiments 142 to 158, wherein when $R^F$ is present, two $R^F$ taken together with the atoms to which they are bonded form a group selected from:
$C_3$-$C_{10}$ cycloalkyl,
$C_6$-$C_{10}$ aryl optionally substituted with 1-3 groups independently selected from:
halogen,
$C_1$-$C_6$ alkyl,
$N(R^N)_2$, and
3- to 10-membered heterocyclyl optionally substituted with 1-3 groups independently selected from hydroxyl, and
3- to 11-membered heterocyclyl optionally substituted with 1-3 groups independently selected from:

oxo, $C_1$-$C_9$ alkyl optionally substituted with 1-4 groups independently selected from:

oxo, halogen, hydroxyl, $N(R^N)_2$,

—$SO_2$—($C_1$-$C_6$ alkyl), $C_1$-$C_6$ alkoxy optionally substituted with 1-3 groups independently selected from halogen, $C_6$-$C_{10}$ aryl, $C_6$-$C_{10}$ aryl, —$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and 3- to 10-membered heterocyclyl, and $C_3$-$C_{12}$ cycloalkyl optionally substituted with 1-4 groups independently selected from $C_1$-$C_6$ alkyl and $C_1$-$C_6$ fluoroalkyl.

160. A compound of Formula VI:

(VI)

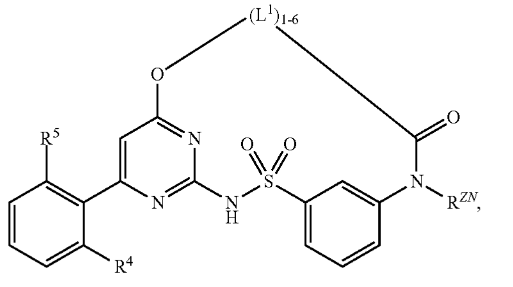

a tautomer thereof, a deuterated derivative of the compound or tautomer, or a pharmaceutically acceptable salt of any of the foregoing, wherein $L^1$, $R^4$, $R^5$, and $R^{ZN}$ are defined as according to embodiment 1.

161. The compound, tautomer, salt, or deuterated derivative according to embodiment 160, wherein each $L^1$ is $C(R^{L1})_2$.

162. The compound, tautomer, salt, or deuterated derivative according to embodiment 160 or 161, wherein Ring C is phenyl.

163. The compound, tautomer, salt, or deuterated derivative according to any one of embodiments 160 to 162, wherein $R^4$ is selected from hydrogen and methyl.

164. The compound, tautomer, salt, or deuterated derivative according to any one of embodiments 160 to 163, wherein $R^4$ is methyl.

165. The compound, tautomer, salt, or deuterated derivative according to any one of embodiments 160 to 164, wherein each $R^5$ is independently selected from:

hydrogen, hydroxyl, $N(R^N)_2$, $C_1$-$C_6$ alkyl optionally substituted with 1-3 groups independently selected from:

hydroxyl, $C_1$-$C_6$ alkoxy optionally substituted with 1-3 groups independently selected from $C_1$-$C_6$ alkoxy and $C_6$-$C_{10}$ aryl, $C_3$-$C_{10}$ cycloalkyl, —$(O)_{0-1}$—($C_6$-$C_{10}$ aryl) optionally substituted with 1-3 groups independently selected from $C_1$-$C_6$ alkyl and $C_1$-$C_6$ alkoxy, 3- to 10-membered heterocyclyl, and $N(R^N)_2$, and $C_1$-$C_6$ alkoxy optionally substituted with 1-3 groups independently selected from:

halogen, $C_6$-$C_{10}$ aryl, and $C_3$-$C_{10}$ cycloalkyl optionally substituted with 1-3 groups independently selected from $C_1$-$C_6$ fluoroalkyl.

166. The compound, tautomer, salt, or deuterated derivative according to any one of embodiments 160 to 165, wherein each $R^5$ is independently selected from hydrogen, hydroxyl, $N(R^N)_2$, $C_1$-$C_6$ alkyl, and $C_1$-$C_6$ alkoxy.

167. The compound, tautomer, salt, or deuterated derivative according to any one of embodiments 160 to 166, wherein $R^{ZN}$ is selected from hydrogen and $C_1$-$C_9$ alkyl.

168. The compound, tautomer, salt, or deuterated derivative according to any one of embodiments 160 to 167, wherein $R^{ZN}$ is selected from hydrogen and methyl.

169. The compound, tautomer, salt, or deuterated derivative according to any one of embodiments 160 to 168, wherein each $R^{L1}$ is independently selected from:

hydrogen, $N(R^N)_2$, provided that two $N(R^N)_2$ are not bonded to the same carbon, $C_1$-$C_9$ alkyl optionally substituted with 1-3 groups independently selected from $C_6$-$C_{10}$ aryl, $C_6$-$C_{10}$ aryl, and $R^F$.

170. The compound, tautomer, salt, or deuterated derivative according to any one of embodiments 160 to 169, wherein each $R^N$ is independently selected from:

hydrogen, $C_1$-$C_8$ alkyl optionally substituted with 1-3 groups independently selected from:

oxo, $NH_2$,

NHMe, $NMe_2$, and $C_1$-$C_6$ alkoxy, and $C_3$-$C_{10}$ cycloalkyl optionally substituted with 1-3 groups independently selected from $NH_2$ and NHMe, or two $R^N$ on the same nitrogen atom are taken together with the nitrogen to which they are bonded to form a 3- to 10-membered heterocyclyl.

171. The compound, tautomer, salt, or deuterated derivative according to any one of embodiments 160 to 170, wherein when $R^F$ is present, two $R^F$ taken together with the atoms to which they are bonded form a group selected from:

$C_3$-$C_{10}$ cycloalkyl, $C_6$-$C_{10}$ aryl optionally substituted with 1-3 groups independently selected from:

halogen, $C_1$-$C_6$ alkyl, $N(R^N)_2$, and 3- to 10-membered heterocyclyl optionally substituted with 1-3 groups independently selected from hydroxyl, and 3- to 11-membered heterocyclyl optionally substituted with 1-3 groups independently selected from:

oxo, $C_1$-$C_9$ alkyl optionally substituted with 1-4 groups independently selected from:

oxo, halogen,
hydroxyl,
$N(R^N)_2$,
—$SO_2$—($C_1$-$C_6$ alkyl),
$C_1$-$C_6$ alkoxy optionally substituted with 1-3 groups independently selected from halogen and $C_6$-$C_{10}$ aryl,
$C_6$-$C_{10}$ aryl,
—$(O)_{0-1}$—($C_3$-$C_{10}$ cycloalkyl) optionally substituted with 1-4 groups independently selected from $C_1$-$C_6$ alkyl and $C_1$-$C_6$ fluoroalkyl, and
3- to 10-membered heterocyclyl, and
$C_3$-$C_{12}$ cycloalkyl optionally substituted with 1-4 groups independently selected from $C_1$-$C_6$ alkyl and $C_1$-$C_6$ fluoroalkyl.

172. The compound, tautomer, deuterated derivative, or pharmaceutically acceptable salt according to any one of embodiments 1 to 171, selected from compounds of any one of Formulae I, Ia, IIa, IIb, III, IV, V, Va, Vb, and VI, tautomers thereof, deuterated derivatives of those compounds and tautomers, and pharmaceutically acceptable salts of any of the foregoing.
173. The compound, tautomer, deuterated derivative, or pharmaceutically acceptable salt according to any one of embodiments 1 to 172, selected from Compounds 1-124 (Table 8), tautomers thereof, deuterated derivatives of those compounds and tautomers, and pharmaceutically acceptable salts of any of the foregoing.
174. A pharmaceutical composition comprising the compound, tautomer, deuterated derivative, or pharmaceutically acceptable salt according to any one of embodiments 1 to 173, and a pharmaceutically acceptable carrier.
175. The pharmaceutical composition of embodiment 174, further comprising one or more additional therapeutic agents.
176. The pharmaceutical composition of embodiment 175, wherein the one or more additional therapeutic agent(s) is selected from mucolytic agents, bronchodilators, antibiotics, anti-infective agents, and anti-inflammatory agents.
177. The pharmaceutical composition of embodiment 175 or embodiment 176, wherein the one or more additional therapeutic agent(s) is an antibiotic selected from tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.
178. The pharmaceutical composition of embodiment 175, wherein the one or more additional therapeutic agent(s) is a CFTR modulator.
179. The pharmaceutical composition of embodiment 178, wherein the CFTR modulator is a potentiator.
180. The pharmaceutical composition of embodiment 178, wherein the CFTR modulator is a corrector.
181. The pharmaceutical composition of embodiment 178, wherein the one or more additional therapeutic agent(s) includes both a CFTR potentiator and a CFTR corrector.
182. The pharmaceutical composition of embodiment 179 or embodiment 181, wherein the CFTR potentiator is selected from ivacaftor, deutivacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.
183. The pharmaceutical composition of embodiment 180 or embodiment 181, wherein the CFTR corrector is selected from tezacaftor and lumacaftor.
184. The pharmaceutical composition of embodiment 152, wherein the composition comprises ivacaftor and tezacaftor.
185. The pharmaceutical composition of embodiment 175, wherein the composition comprises deutivacaftor and tezacaftor.
186. The pharmaceutical composition of embodiment 175, wherein the composition comprises (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and tezacaftor.
187. The pharmaceutical composition of embodiment 175, wherein the composition comprises ivacaftor and lumacaftor.
188. The pharmaceutical composition of embodiment 152, wherein the composition comprises deutivacaftor and lumacaftor.
189. The pharmaceutical composition of embodiment 175, wherein the composition comprises (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and lumacaftor.
190. A method of treating cystic fibrosis comprising administering to a patient in need thereof the compound, tautomer, deuterated derivative, or pharmaceutically acceptable salt according to any one of embodiments 1 to 173, or a pharmaceutical composition according to any one of embodiments 174 to 189.
191. The method of embodiment 190, further comprising administering to the patient one or more additional therapeutic agents prior to, concurrent with, or subsequent to the compound, tautomer, deuterated derivative, or pharmaceutically acceptable salt according to any one of embodiments 1 to 173, or the pharmaceutical composition according to embodiment 174.
192. The method of embodiment 191, wherein the one or more additional therapeutic agents is (are) selected from one or more CFTR modulators.
193. The method of embodiment 192, wherein the one or more CFTR modulator(s) is a potentiator.
194. The method of embodiment 192, wherein the one or more CFTR modulator(s) is a corrector.
195. The method of embodiment 192, wherein the one or more CFTR modulators includes both a CFTR potentiator and a CFTR corrector.
196. The method of embodiment 193 or embodiment 195, wherein the CFTR potentiator is selected from ivacaftor, deutivacaftor, and deuterated derivatives and pharmaceutically acceptable salts of any of the foregoing.
197. The method of embodiment 193 or embodiment 195, wherein the CFTR potentiator is selected from (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol and deuterated derivatives and pharmaceutically acceptable salts of any of the foregoing.
198. The method of embodiment 194 or embodiment 195, wherein the CFTR corrector is selected from tezacaftor, lumacaftor, and deuterated derivatives and pharmaceutically acceptable salts thereof.

199. The method of embodiment 195, comprising administration of ivacaftor and tezacaftor.

200. The method of embodiment 195, comprising administration of deutivacaftor and tezacaftor.

201. The method of embodiment 195, comprising administration of (6R,12R)-17-amino-12-methyl-6,15-bis (trifluoromethyl)-13,19-dioxa-3,4,18-triazatricyclo [12.3.1.12,5]nonadeca-1(18),2,4,14,16-pentaen-6-ol and tezacaftor.

202. The method of embodiment 195, comprising administration of ivacaftor and lumacaftor.

203. The method of embodiment 195, comprising administration of deutivacaftor and lumacaftor.

204. The method of embodiment 195, comprising administration of (6R,12R)-17-amino-12-methyl-6,15-bis (trifluoromethyl)-13,19-dioxa-3,4,18-triazatricyclo [12.3.1.12,5]nonadeca-1(18),2,4,14,16-pentaen-6-ol and lumacaftor.

205. The compound, tautomer, deuterated derivative, or pharmaceutically acceptable salt according to any one of embodiments 1 to 173, or the pharmaceutical composition according to any one of embodiments 174 to 189, for use in the treatment of cystic fibrosis.

206. The compound, tautomer, deuterated derivative, or pharmaceutically acceptable salt according to any one of embodiments 1 to 173, or the pharmaceutical composition according to any one of embodiments 174 to 178, for use in the manufacture of a medicament for the treatment of cystic fibrosis.

207. A compound selected from Compounds 1-124, tautomers thereof, deuterated derivatives of those compounds and tautomers, and pharmaceutically acceptable salts of any of the foregoing.

208. A deuterated derivative of a compound selected from Compounds 1-124.

209. A pharmaceutically acceptable salt of a compound selected from Compounds 1-124.

210. A compound selected from Compounds 1-124.

211. A pharmaceutical composition comprising a compound selected from Compounds 1-124, tautomers thereof, deuterated derivatives of those compounds and tautomers, and pharmaceutically acceptable salts of any of the foregoing and a pharmaceutically acceptable carrier.

212. A pharmaceutical composition comprising a deuterated derivative of a compound selected from Compounds 1-124 and a pharmaceutically acceptable carrier.

213. A pharmaceutical composition comprising a pharmaceutically acceptable salt of a compound selected from Compounds 1-124 and a pharmaceutically acceptable carrier.

214. A pharmaceutical composition comprising a compound selected from Compounds 1-124 and a pharmaceutically acceptable carrier.

215. A pharmaceutical composition comprising (a) a compound selected from Compounds 1-124, tautomers thereof, deuterated derivatives of those compounds and tautomers, and pharmaceutically acceptable salts of any of the foregoing; (b) a CFTR potentiator; and (c) a pharmaceutically acceptable carrier.

216. A pharmaceutical composition composition comprising (a) a deuterated derivative of a compound selected from Compounds 1-124; (b) a CFTR potentiator; and (c) a pharmaceutically acceptable carrier.

217. A pharmaceutical comprising (a) a pharmaceutically acceptable salt of a compound selected from Compounds 1-124; (b) a CFTR potentiator; and (c) a pharmaceutically acceptable carrier.

218. A pharmaceutical composition comprising (a) a compound selected from Compounds 1-124; (b) a CFTR potentiator; and (c) a pharmaceutically acceptable carrier.

219. A pharmaceutical composition comprising (a) a compound selected from Compounds 1-124, tautomers thereof, deuterated derivatives of those compounds and tautomers, and pharmaceutically acceptable salts of any of the foregoing; (b) an additional CFTR corrector; and (c) a pharmaceutically acceptable carrier.

220. A pharmaceutical composition comprising (a) a deuterated derivative of a compound selected from Compounds 1-124; (b) an additional CFTR corrector; and (c) a pharmaceutically acceptable carrier.

221. A pharmaceutical composition comprising (a) a pharmaceutically acceptable salt of a compound selected from Compounds 1-124; (b) an additional CFTR corrector; and (c) a pharmaceutically acceptable carrier.

222. A pharmaceutical composition comprising (a) a compound selected from Compounds 1-124; (b) an additional CFTR corrector; and (c) a pharmaceutically acceptable carrier.

223. A pharmaceutical composition comprising (a) a compound selected from Compounds 1-124, tautomers thereof, deuterated derivatives of those compounds and tautomers, and pharmaceutically acceptable salts of any of the foregoing; (b) an additional CFTR corrector; (c) a CRTR potentiator; and (d) a pharmaceutically acceptable carrier.

224. A pharmaceutical composition comprising (a) a deuterated derivative of a compound selected from Compounds 1-124; (b) an additional CFTR corrector; (c) a CFTR potentiator; and (d) a pharmaceutically acceptable carrier.

225. A pharmaceutical composition comprising (a) a pharmaceutically acceptable salt of a compound selected from Compounds 1-124; (b) an additional CFTR corrector; (c) a CFTR potentiator; and (d) a pharmaceutically acceptable carrier.

226. A pharmaceutical composition comprising (a) a compound selected from Compounds 1-124; (b) an additional CFTR corrector; (c) a CFTR potentiator; and (d) a pharmaceutically acceptable carrier.

227. A compound selected from Compounds 1-124, tautomers thereof, deuterated derivatives of those compounds and tautomers, and pharmaceutically acceptable salts of any of the foregoing for use in a method of treating cystic fibrosis.

228. A deuterated derivative of a compound selected from Compounds 1-124 for use in a method of treating cystic fibrosis.

229. A pharmaceutically acceptable salt of a compound selected from Compounds 1-124 for use in a method of treating cystic fibrosis.

230. A compound selected from Compounds 1-124 for use in a method of treating cystic fibrosis.

231. A pharmaceutical composition comprising a compound selected from Compounds 1-124, tautomers thereof, deuterated derivatives of those compounds and tautomers, and pharmaceutically acceptable salts of any of the foregoing and a pharmaceutically acceptable carrier for use in a method of treating cystic fibrosis.

232. A pharmaceutical composition comprising a deuterated derivative of a compound selected from Compounds 1-124 and a pharmaceutically acceptable carrier for use in a method of treating cystic fibrosis.

233. A pharmaceutical composition comprising a pharmaceutically acceptable salt of a compound selected from Compounds 1-124 and a pharmaceutically acceptable carrier for use in a method of treating cystic fibrosis.

234. A pharmaceutical composition comprising a compound selected from Compounds 1-124 and a pharmaceutically acceptable carrier for use in a method of treating cystic fibrosis.

235. A pharmaceutical composition comprising (a) a compound selected from Compounds 1-124, tautomers thereof, deuterated derivatives of those compounds and tautomers, and pharmaceutically acceptable salts of any of the foregoing; (b) a CFTR potentiator; and (c) a pharmaceutically acceptable carrier for use in a method of treating cystic fibrosis.

236. A pharmaceutical comprising (a) a deuterated derivative of a compound selected from Compounds 1-124; (b) a CFTR potentiator; and (c) a pharmaceutically acceptable carrier for use in a method of treating cystic fibrosis.

237. A pharmaceutical composition comprising (a) a pharmaceutically acceptable salt of a compound selected from Compounds 1-124; (b) a CFTR potentiator; and (c) a pharmaceutically acceptable carrier for use in a method of treating cystic fibrosis.

238. A pharmaceutical composition comprising (a) a compound selected from Compounds 1-124; (b) a CFTR potentiator; and (c) a pharmaceutically acceptable carrier.

239. A pharmaceutical composition comprising (a) a compound selected from Compounds 1-124, tautomers thereof, deuterated derivatives of those compounds and tautomers, and pharmaceutically acceptable salts of any of the foregoing; (b) an additional CFTR corrector; and (c) a pharmaceutically acceptable carrier for use in a method of treating cystic fibrosis.

240. A pharmaceutical composition comprising (a) a deuterated derivative of a compound selected from Compounds 1-124; (b) an additional CFTR corrector; and (c) a pharmaceutically acceptable carrier for use in a method of treating cystic fibrosis.

241. A pharmaceutical composition comprising (a) a pharmaceutically acceptable salt of a compound selected from Compounds 1-124; (b) an additional CFTR corrector; and (c) a pharmaceutically acceptable carrier for use in a method of treating cystic fibrosis.

242. A pharmaceutical composition comprising (a) a compound selected from Compounds 1-124; (b) an additional CFTR corrector; and (c) a pharmaceutically acceptable carrier for use in a method of treating cystic fibrosis.

243. A pharmaceutical composition comprising (a) a compound selected from Compounds 1-124, tautomers thereof, deuterated derivatives of those compounds and tautomers, and pharmaceutically acceptable salts of any of the foregoing; (b) an additional CFTR corrector; (c) a CRTR potentiator; and (d) a pharmaceutically acceptable carrier for use in a method of treating cystic fibrosis.

244. A pharmaceutical composition comprising (a) a deuterated derivative of a compound selected from Compounds 1-124; (b) an additional CFTR corrector; (c) a CFTR potentiator; and (d) a pharmaceutically acceptable carrier for use in a method of treating cystic fibrosis.

245. A pharmaceutical composition comprising (a) a pharmaceutically acceptable salt of a compound selected from Compounds 1-124; (b) an additional CFTR corrector; (c) a CFTR potentiator; and (d) a pharmaceutically acceptable carrier for use in a method of treating cystic fibrosis.

246. A pharmaceutical composition comprising (a) a compound selected from Compounds 1-124; (b) an additional CFTR corrector; (c) a CFTR potentiator; and (d) a pharmaceutically acceptable carrier for use in a method of treating cystic fibrosis.

EXAMPLES

I. Abbreviation List

ACN: Acetonitrile
Boc anhydride ($(Boc)_2O$): Di-tert-butyl dicarbonate
$CDCl_3$: Chloroform-d CDI: Carbonyl diimidazole
CDMT: 2-Chloro-4,6-dimethoxy-1,3,5-triazine
$CH_2Cl_2$: Dichloromethane
$CH_3CN$: Acetonitrile
COMU: (1-Cyano-2-ethoxy-2-oxoethylidenaminooxy)dimethylamino-morpholino-carbenium hexafluorophosphate
Cmpd: Compound
DABCO: 1,4-Diazabicyclo[2.2.2]octane
DBU: 1,8-Diazabicyclo(5.4.0)undec-7-ene
DCE: 1,2-Dichloroethane
DCM: Dichloromethane
DI: Deionized
DIAD: Diisopropyl azodicarboxylate
DIEA: (DIPEA, DiPEA): N,N-diisopropylethylamine
DMA: N,N-Dimethylacetamide
DMAP: 4-Dimethylaminopyridine
DMF: N,N-Dimethylformamide
DMSO: Dimethyl sulfoxide
DMP: Dess-Martin periodinane
EA: Ethyl acetate
EDC: 1-Ethyl-3-(3-dimethylaminopropyl)carbodiimide
ELSD: Evaporative light scattering detector
ESI-MS: Electrospray ionization mass spectrometry
diethylether: Diethyl ether
EtOAc: Ethyl acetate
EtOH: Ethanol
GC: Gas chromatography
Grubbs 1st Generation catalyst: Dichloro(benzylidene)bis(tricyclohexylphosphine)ruthenium(II)
Grubbs 2nd Generation catalyst: [1,3-Bis(2,4,6-trimethylphenyl)imidazolidin-2-ylidene]-dichloro-[(2-isopropoxyphenyl)methylene]ruthenium
HATU: 1-[Bis(dimethylamino)methylene]-1H-1,2,3-triazolo[4,5-b]pyridinium 3-oxid hexafluorophosphate
HPLC: High-performance liquid chromatography
Hoveyda-Grubbs 2nd Generation catalyst: (1,3-Bis-(2,4,6-trimethylphenyl)-2-imidazolidinylidene)dichloro(o-isopropoxyphenylmethylene)ruthenium, Dichloro[1,3-bis(2,4,6-trimethylphenyl)-2-imidazolidinylidene](2-isopropoxyphenylmethylene)ruthenium(II)
IPA: Isopropanol
$KHSO_4$: Potassium bisulfate
LC: Liquid chromatography
LCMS: Liquid chromatography mass spectrometry
LCMS Met.: LCMS method LCMS Rt: LCMS retention time
LDA: Lithium diisopropylamide
LiOH: Lithium hydroxide
MeCN: Acetonitrile
MeOH: Methanol
MeTHF or 2-MeTHF: 2-Methyltetrahydrofuran
$MgSO_4$: Magnesium sulfate
MTBE: Methyl tert-butyl ether
$NaHCO_3$: Sodium bicarbonate
NaOH: Sodium hydroxide
NMP: N-Methyl-2-pyrrolidone
NMM: N-Methylmorpholine
Pd/C: Palladium on carbon
$Pd_2(dba)_3$: Tris(dibenzylideneacetone)dipalladium(0)
$Pd(dppf)Cl_2$: [1,1'-Bis(diphenylphosphino)ferrocene]dichloropalladium(II)
$Pd(OAc)_2$: Palladium(II) acetate
PTFE: Polytetrafluoroethylene
rt, RT: Room temperature
RuPhos: 2-Dicyclohexylphosphino-2',6'-diisopropoxybiphenyl
SFC: Supercritical fluid chromatography
TBAI: Tetrabutylammonium iodide
TEA: Triethylamine
TFA: Trifluoroacetic acid
THF: Tetrahydrofuran
TLC: Thin layer chromatography
TMS: Trimethylsilyl
TMSCl: Trimethylsilyl chloride
T3P: Propanephosphonic acid anhydride
UPLC: Ultra Performance Liquid Chromatography
XANTPHOS: 4,5-Bis(diphenylphosphino)-9,9-dimethylxanthene
XPhos: 2-Dicyclohexylphosphino-2',4',6'-triisopropylbiphenyl

II. General Methods

Reagents and starting materials were obtained by commercial sources unless otherwise stated and were used without purification.

Proton and carbon NMR spectra were acquired on either a Bruker Biospin DRX 400 MHz FTNMR spectrometer operating at a $^{1}H$ and $^{13}C$ resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^{1}H$ using a 45 degree pulse angle, a spectral width of 4800 Hz and 28860 points of acquisition. FID were zero-filled to 32 k points and a line broadening of 0.3 Hz was applied before Fourier transform. $^{19}F$ NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^{1}H$ using a 30 degree pulse angle, a spectral width of 8000 Hz and 128 k points of acquisition. FID were zero-filled to 256 k points and a line broadening of 0.3 Hz was applied before Fourier transform. $^{19}F$ NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Final purity of compounds was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as $[M+1]^+$ species obtained using a single quadrupole mass spectrometer equipped with an electrospray ionization (ESI) source capable of achieving a mass accuracy of 0.1 Da and a minimum resolution of 1000 (no units on resolution) across the detection range. Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30 m×0.25 mm×0.25 μm_df) column, with a 2.0 mL/min flow rate ($H_2$ carrier gas), at an injection temperature of 220° C. and an oven temperature of 120° C., 15 minutes.

III. General UPLC/HPLC/GC Analytical Methods

LC method A: Analytical reverse phase UPLC using an Acquity UPLC BEH Cis column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

LC method B: Reverse phase HPLC using a Kinetex $C_{18}$ column (50×3.0 mm) and a dual gradient run from 5-100% mobile phase B over 6 minutes. Mobile phase A=$H_2O$ (0.1% $CF_3CO_2H$). Mobile phase B=$CH_3CN$ (0.1% $CF_3CO_2H$). Flow rate=1.5 mL/min, injection volume=2 μL, and column temperature=60° C.

LC method C: Kinetex $C_{18}$ 4.6×50 mm 2.6 μm. Temp: 45° C., Flow: 2.0 mL/min, Run Time: 3 min. Mobile phase: Initial 95% water (0.1% formic acid) and 5% acetonitrile (0.1% formic acid) linear gradient to 95% acetonitrile (0.1% formic acid) for 2.0 min then hold at 95% acetonitrile (0.1% formic acid) for 1.0 min.

LC method D: Acquity UPLC BEH $C_{18}$ column (30×2.1 mm, 1.7 μm particle) made by Waters (pn: 186002349), and a dual gradient run from 1-99% mobile phase B over 1.0 minute. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

LC method J: Reverse phase UPLC using an Acquity UPLC BEH $C_{18}$ column (50×2.1 mm, 1.7 μm particle) made by Waters (pn: 186002350), and a dual gradient run from 1-99% mobile phase B over 2.9 minutes. Mobile phase A=$H_2O$ (0.05% $NH_4HCO_2$). Mobile phase B=$CH_3CN$. Flow rate=1.2 mL/min, injection volume=1.5 μL, and column temperature=60° C.

LC method S: Merckmillipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

LC method T: Merckmillipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

LC method W: water Cortex 2.7μ $C_{18}$ (3.0 mm×50 mm), Temp: 55° C.; Flow: 1.2 mL/min; mobile phase: 100% water with 0.1% trifluoroacetic (TFA) acid then 100% acetonitrile with 0.1% TFA acid, grad: 5% to 100% B over 4 min, with stay at 100% B for 0.5 min, equilibration to 5% B over 1.5 min.

Synthesis of Common Intermediates

Example A: Preparation of 3-[[4-Chloro-6-(2,6-dimethylphenyl)pyrimidin-2-yl]sulfamoyl]benzoic Acid

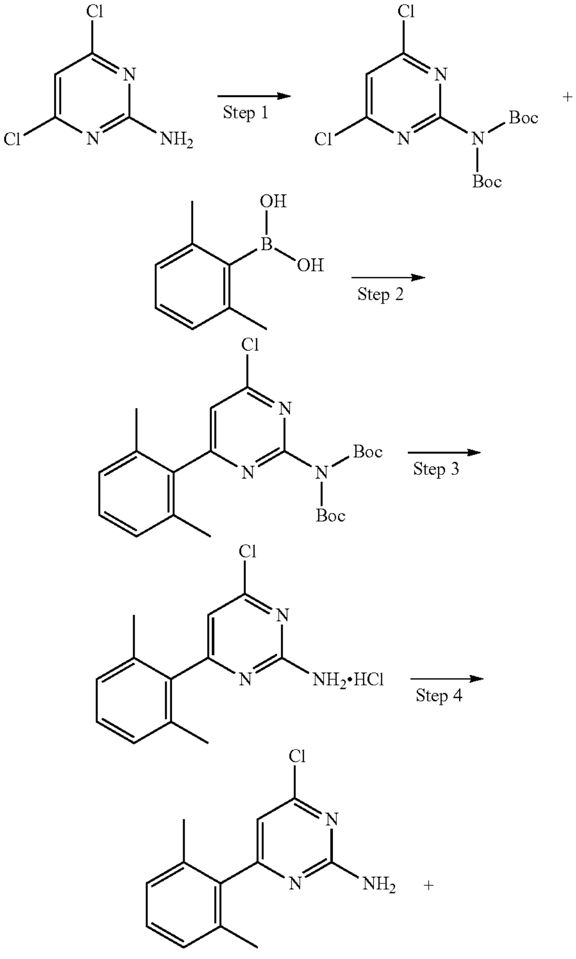

-continued

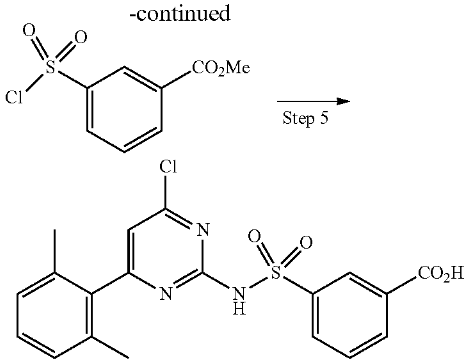

Step 1: tert-Butyl N-tert-butoxycarbonyl-N-(4,6-dichloropyrimidin-2-yl)carbamate

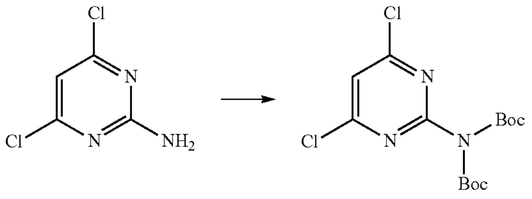 [SMILES: Nc1nc(Cl)cc(Cl)n1 ; CC(C)(C)OC(=O)N(C(=O)OC(C)(C)C)c1nc(Cl)cc(Cl)n1]

To a solution of 4,6-dichloropyrimidin-2-amine (300 g, 1.829 mol) in DCM (2.1 L) was added $(BOC)_2O$ (838 g, 3.840 mol), followed by DMAP (5.6 g, 45.84 mmol). The mixture was stirred at ambient temperature for 6 h. Additional DMAP (5.6 g, 45.84 mmol) was added, and the reaction was continued to stir at ambient temperature for 24 h. The mixture was diluted with water (2.1 L) and the organic phase separated. The organic phase was washed with water (2.1 L), 2.1 L of brine, dried over magnesium sulfate, filtered over Celite, and concentrated in vacuo affording a light orange oil which had a silt in the slurry. The mixture was diluted with ~500 mL of heptane and filtered using an M filter. The precipitate (SM) was washed with 250 mL of heptane. The filtrate was concentrated in vacuo, affording a thick orange oil which was seeded with solid from a previous experiment and crystallized on standing, affording a light orange hard solid. tert-butyl N-tert-butoxycarbonyl-N-(4,6-dichloropyrimidin-2-yl)carbamate (645 g, 97%). $^1H$ NMR (400 MHz, DMSO-$d_6$) δ 8.07 (s, 1H), 1.44 (s, 18H). ESI-MS m/z calc. 363.07526, found 364.1 $(M+1)^+$; Retention time: 2.12 minutes (LC method A).

Step 2: tert-Butyl N-tert-butoxycarbonyl-N-[4-chloro-6-(2,6-dimethylphenyl)pyrimidin-2-yl]carbamate

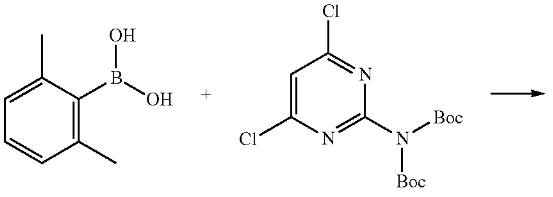

-continued

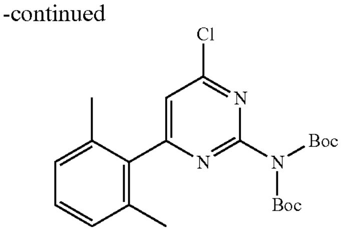

All solvents were degassed prior to use. To a slurry of tert-butyl N-tert-butoxycarbonyl-N-(4,6-dichloropyrimidin-2-yl)carbamate (88 g, 241.6 mmol), (2,6-dimethylphenyl) boronic acid (approximately 36.24 g, 241.6 mmol) and $Cs_2CO_3$ (approximately 196.8 g, 604.0 mmol) in DME (704 mL) and water (176 mL) were added. Pd(dppf)$Cl_2$ (approximately 8.839 g, 12.08 mmol) was added, and the mixture was vigorously stirred under nitrogen at 80° C. (reflux) for 1 hour (no SM remained). The reaction was cooled to ambient temperature and diluted with water (704 mL). The aqueous phase was separated and extracted with EtOAc (704 mL). The organic phase was washed with 700 mL of brine, dried over magnesium sulfate, filtered, and concentrated in vacuo. The crude product was chromatographed on a 1500 g silica gel column eluting with 0-30% EtOAc/hexanes. The product fractions (eluted at 15% EtOAc) were combined and concentrated in vacuo, affording the product as a clear oil which crystallized on standing. tert-butyl N-tert-butoxycarbonyl-N-[4-chloro-6-(2,6-dimethylphenyl)pyrimidin-2-yl] carbamate (81.3 g, 78%). $^1$H NMR (400 MHz, DMSO-$d_6$) δ 7.88 (s, 1H), 7.30 (dd, J=8.2, 7.0 Hz, 1H), 7.21-7.16 (m, 2H), 2.03 (s, 6H), 1.38 (s, 18H). ESI-MS m/z calc. 433.17682, found 434.1 $(M+1)^+$; Retention time: 2.32 minutes (LC method A).

Step 3: 4-Chloro-6-(2,6-dimethylphenyl)pyrimidin-2-amine (Hydrochloride Salt)

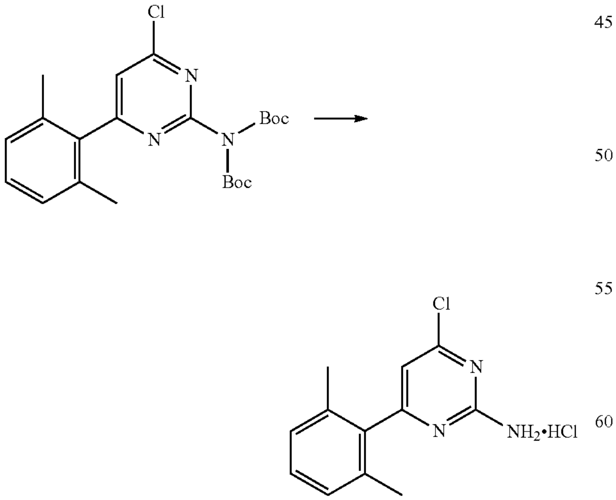

tert-Butyl N-tert-butoxycarbonyl-N-[4-chloro-6-(2,6-dimethylphenyl) pyrimidin-2-yl]carbamate (514.8 g, 915.9 mmol) was dissolved in dichloromethane (4 L). Hydrogen chloride in p-dioxane (1 L, 4 mol) was added and the mixture was stirred overnight at room temperature. The resulting precipitate was collected by vacuum filtration and dried in vacuo to obtain 4-chloro-6-(2,6-dimethylphenyl) pyrimidin-2-amine hydrochloride as a white solid (213.5 g, 82%). $^1$H NMR (250 MHz, DMSO-$d_6$) δ 7.45-6.91 (m, 3H), 6.73 (s, 1H), 2.08 (s, 6H). ESI-MS m/z calc. 233.072, found 234.1 $(M+1)^+$; Retention time: 2.1 minutes (LC Method C).

Step 4: 4-Chloro-6-(2,6-dimethylphenyl)pyrimidin-2-amine

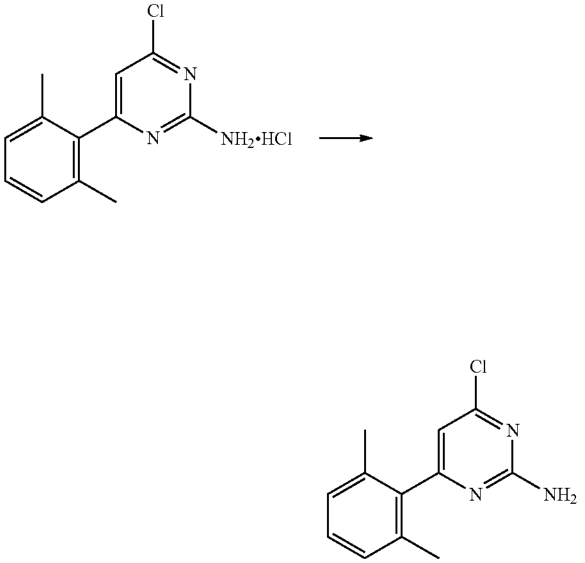

4-Chloro-6-(2,6-dimethylphenyl)pyrimidin-2-amine (hydrochloride salt) (166 g, 614.5 mmol) and 4-chloro-6-(2,6-dimethylphenyl)pyrimidin-2-amine (hydrochloride salt) (30 g, 111.0 mmol) were suspended in DCM (2.5 L), treated with NaOH (725 mL of 1 M, 725.0 mmol) and stirred at room temperature for 1 hour. The mixture was transferred into a separatory funnel and left standing over night. The DCM phase was separated and the aqueous phase with insoluble material was extracted twice more with DCM (2×500 mL). The combined brown DCM phases were stirred over magnesium sulfate and charcoal for 1 hour, filtered and the yellow solution concentrated to a volume of ~500 mL. The solution was diluted with heptane (750 mL) and DCM was removed under reduced pressure at 60° C. to give a cream suspension. It was stirred at room temperature for 1 hour, filtered, washed with cold heptane and dried to give 4-chloro-6-(2,6-dimethylphenyl)pyrimidin-2-amine (157 g, 91%) as a cream solid. $^1$H NMR (400 MHz, DMSO-$d_6$) δ 7.28-7.14 (m, 3H), 7.10 (d, J=7.5 Hz, 2H), 6.63 (s, 1H), 2.06 (s, 6H). ESI-MS m/z calc. 233.07198, found 234.0 $(M+1)^+$; Retention time: 1.45 minutes (LC method A).

Step 5: 3-[[4-Chloro-6-(2,6-dimethylphenyl)pyrimidin-2-yl]sulfamoyl]benzoic Acid

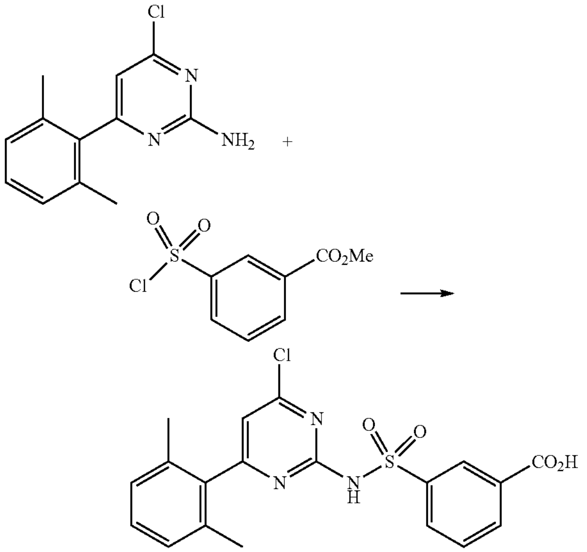

4-Chloro-6-(2,6-dimethylphenyl)pyrimidin-2-amine (235 g, 985.5 mmol) was dissolved in MeTHF (2.3 L) and cooled in an ice bath under stirring and nitrogen. To the cold solution methyl 3-chlorosulfonylbenzoate (347 g, 1.479 mol) was added in one portion (seems slightly endothermic) and to the cold pale-yellow solution a solution of 2-methylbutan-2-ol (lithium salt) (875 mL of 3.1 M, 2.712 mol) (in heptane) was added dropwise over 1.25 hours (exothermic, internal temperature from 0 to 10° C.). The ice bath was removed and the greenish solution was stirred for 4 hours at room temperature. To the greenish solution, cold HCl (2 L of 1.5 M, 3.000 mol) was added, the phases separated and the organic phase was washed once with water (1 L) and once with brine (500 mL). The aqueous phases were back extracted once with MeTHF (350 mL) and the organic phases were combined. This yellow MeTHF solution of methyl 3-[[4-chloro-6-(2,6-dimethylphenyl)pyrimidin-2-yl]sulfamoyl]benzoate (ESI-MS m/z calc. 431.07065, found 432.0 $(M+1)^+$; Retention time: 1.81 minutes) was treated with NaOH (2.3 L of 2 M, 4.600 mol) and stirred at room temperature for 1 hour. The phases were separated and the NaOH phase was washed twice with MeTHF (2×500 mL). The combined organic phases were extracted once with 2 M NaOH (1×250 mL). The combined NaOH phases were combined, stirred in an ice bath, and slowly acidified by addition of HCl (416 mL of 36% w/w, 4.929 mol) while keeping the internal temperature between 10 and 20° C. At the end of the addition (pH ~5-6), the final pH was adjusted to 2-3 by addition of solid citric acid. The formed yellow tacky suspension was stirred at room temperature overnight to give a cream crisp suspension. The solid was collected by filtration, washed with plenty of water, and sucked dry for 3 hours. The solid was dried under reduced pressure with a nitrogen leak at 45-50° C. for 120 hours. 3-[[4-chloro-6-(2,6-dimethylphenyl)pyrimidin-2-yl]sulfamoyl]benzoic acid (395 g, 96%) was isolated as an off-white solid. $^1H$ NMR (400 MHz, DMSO-$d_6$) δ 13.44 (s, 1H), 12.46 (s, 1H), 8.48-8.39 (m, 1H), 8.25-8.15 (m, 1H), 8.15-8.08 (m, 1H), 7.68 (t, J=7.8 Hz, 1H), 7.31 (s, 1H), 7.28-7.18 (m, 1H), 7.10 (d, J=7.6 Hz, 2H), 1.84 (s, 6H). ESI-MS m/z calc. 417.055, found 418.0 $(M+1)^+$; Retention time: 1.56 minutes. (LC method A).

Example B: Preparation of N-[4-chloro-6-(2,6-dimethylphenyl)pyrimidin-2-yl]-3-nitro-benzenesulfonamide Step 1: N-[4-Chloro-6-(2,6-dimethylphenyl)pyrimidin-2-yl]-3-nitro-benzenesulfonamide

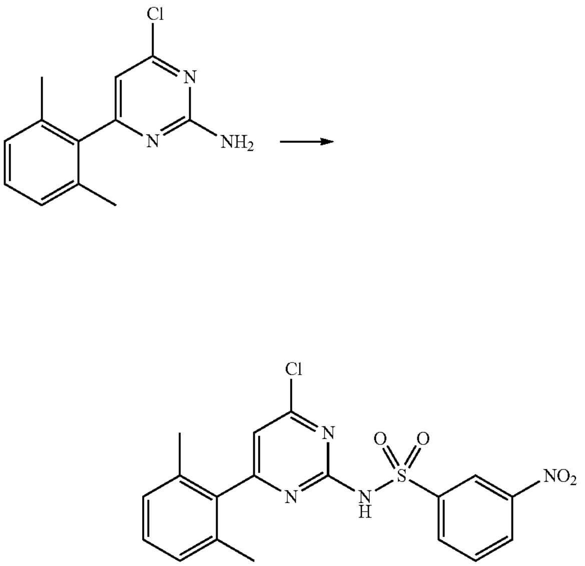

To a suspension of sodium hydride (60% in mineral oil) (4.87 g, 0.122 mol) in anhydrous tetrahydrofuran (30 mL) was added a solution of 4-chloro-6-(2,6-dimethylphenyl)pyrimidin-2-amine (8.13 g, 0.0348 mol) in anhydrous tetrahydrofuran (40 mL) dropwise at 0° C. The reaction mixture was stirred at room temperature for 30 minutes. A solution of 3-nitrobenzenesulfonyl chloride (11.57 g, 52.2 mmol) in anhydrous tetrahydrofuran (40 mL) was added to the reaction mixture dropwise at 0° C. The reaction was stirred at the same temperature for 1 hour. The reaction was quenched with a saturated aqueous solution of sodium bicarbonate (100 mL). The reaction solution was extracted with dichloromethane (3×100 mL). The combined organic layers were washed with water (100 mL), dried over anhydrous sodium sulfate, and then concentrated under vacuum. The residue was purified by silica gel column chromatography using 0 to 10% chloroform-ethyl acetate. The crude product was triturated with a solvent mixture of diethyl ether and hexane (1:5) to furnish N-[4-chloro-6-(2,6-dimethylphenyl)pyrimidin-2-yl]-3-nitro-benzenesulfonamide (5.98 g, 41%) as a white solid. ESI-MS m/z calc. 418.1, found 419.0 (M+1). Retention time: 5.73 minutes. $^1H$ NMR (250 MHz, $CDCl_3$) δ (ppm): 9.01 (s, 1H); 8.43 (t, J=10.5 Hz, 2H); 7.682 (t, J=7.8 Hz, 1H); 7.23 (m, 1H); 7.12 (d, J=7.5 Hz, 2H); 6.95 (s, 1H); 1.99 (s, 6H).

Example C: Preparation of N-[4-(2,6-dimethylphenyl)-6-methylsulfonyl-pyrimidin-2-yl]-3-nitro-benzenesulfonamide

Step 1: N-[4-(2,6-Dimethylphenyl)-6-methylsulfonyl-pyrimidin-2-yl]-3-nitro-benzenesulfonamide

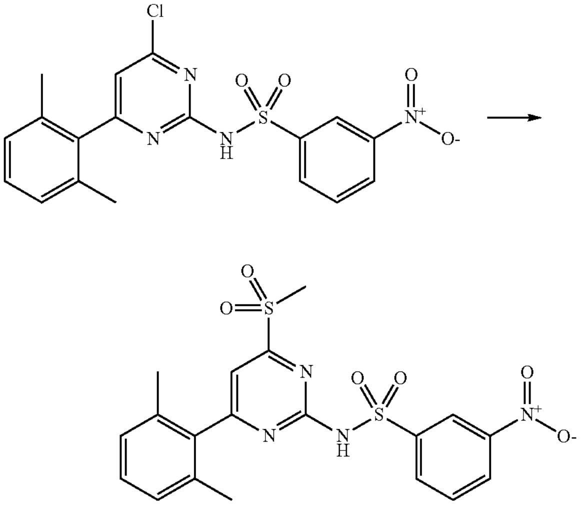 [SMILES: Cc1cccc(C)c1-c1cc(Cl)nc(NS(=O)(=O)c2cccc([N+](=O)[O-])c2)n1 ; Cc1cccc(C)c1-c1cc(S(C)(=O)=O)nc(NS(=O)(=O)c2cccc([N+](=O)[O-])c2)n1]

Stage 1: To a 250 mL round-bottomed flask were added N-[4-chloro-6-(2,6-dimethylphenyl)pyrimidin-2-yl]-3-nitro-benzenesulfonamide (14.14 g, 33.76 mmol), sodium thiomethoxide (5.86 g, 83.61 mmol), and NMP (130 mL). This solution was stirred at 100° C. for 3 h. The reaction mixture was then cooled to room temperature, quenched with 1 N HCl (300 mL), and extracted with ethyl acetate (3×300 mL). The combined organic extracts were washed with water (300 mL), 3% aqueous hydrogen peroxide solution (300 mL), water (300 mL) and saturated aqueous sodium chloride solution (300 mL), then dried over sodium sulfate, filtered, and evaporated in vacuo. This gave an orange foam (16.71 g, 115% crude product yield) that was carried onto the next reaction.

Stage 2: To a 250 mL round-bottomed flask containing the product from Stage 1, DCM (120 mL) was added, followed by m-CPBA (77% pure, 27.22 g, 121.5 mmol). This solution was stirred at room temperature for 90 min. The reaction mixture was quenched by transferring to a 1 L-Erlenmeyer flask containing DCM (400 mL) and solid $Na_2S_2O_3$ (41.15 g, 260.3 mmol). This mixture was stirred at room temperature for 1 h. The reaction mixture was diluted with DCM (300 mL), then washed with water (3×400 mL) and saturated aqueous sodium chloride solution (300 mL). The organic layer was then dried over sodium sulfate, filtered, and evaporated in vacuo. This solid was then partially dissolved in DCM (100 mL) and filtered in vacuo on a Büchner funnel to remove the m-chlorobenzoic acid waste (this was repeated three times). The remaining solution was then purified by silica gel chromatography (330 g of silica, 0 to 60% gradient of ethyl acetate/hexanes) to give N-[4-(2,6-dimethylphenyl)-6-methylsulfonyl-pyrimidin-2-yl]-3-nitro-benzenesulfonamide (5.881 g, 36%). ESI-MS m/z calc. 462.06677, found 463.1 $(M+1)^+$; Retention time: 1.6 minutes; LC method A.

Example D: Preparation of N-[4-methylsulfonyl-6-(o-tolyl)pyrimidin-2-yl]-3-nitro-benzenesulfonamide

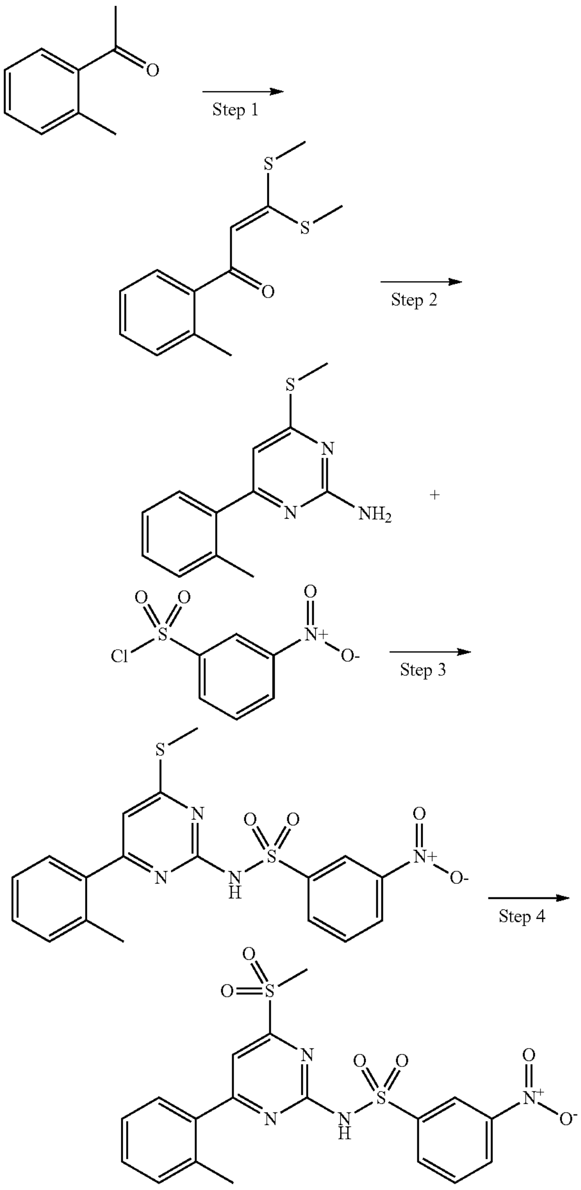

Step 1: 3,3-Bis(methylsulfanyl)-1-(o-tolyl)prop-2-en-1-one

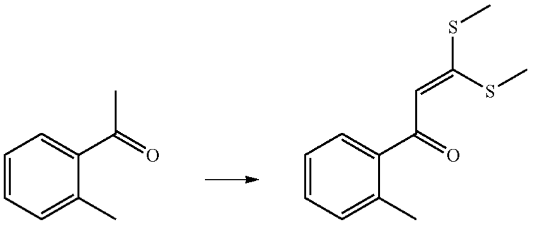

A 1 L round-bottomed flask equipped with a magnetic stir bar was dried with a heat gun under vacuum and purged with nitrogen; to this was added 1-(o-tolyl)ethanone (21.128 g, 157.5 mmol). Dry tetrahydrofuran (500 mL) was added and this solution was cooled to 0° C. 60% NaH (16.101 g, 402.6 mmol) was added in three portions under a blanket of nitrogen, and the reaction mixture was warmed to room temperature over 45 min. The mixture was cooled to 0° C., upon which carbon disulfide (14.0 mL, 232.8 mmol) was added. The solution was then warmed to room temperature over 45 min. The reaction mixture was cooled to 0° C., upon which iodomethane (22.0 mL, 353.4 mmol) was added. The mixture was stirred at 0° C. for 30 min, then warmed to room temperature over 20 h, maintaining a water bath around the flask (CAUTION: hydrogen gas evolution and slight exotherm). The reaction was quenched by a slow transfer onto ice-cold 1 N hydrochloric acid (500 mL). The mixture was extracted with ethyl acetate (3×300 mL). The combined organic extracts was washed with water (300 mL) and saturated aqueous sodium chloride solution (200 mL), then dried over sodium sulfate, filtered, and evaporated in vacuo to give a brown solid, 3,3-bis(methylsulfanyl)-1-(o-tolyl)prop-2-en-1-one (37.0 g, 99%). ESI-MS m/z calc. 238.0486, found 239.0 (M+1)$^+$; Retention time: 0.61 minutes; LC method D.

Step 2: 4-Methylsulfanyl-6-(o-tolyl)pyrimidin-2-amine

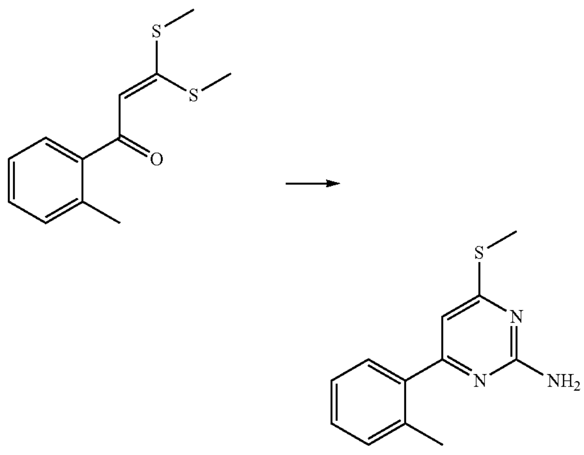

To a 1 L round-bottomed flask equipped with a magnetic stir bar were added 3,3-bis(methylsulfanyl)-1-(o-tolyl)prop-2-en-1-one (37.54 g, 157.5 mmol), dimethylformamide (350 mL), guanidine carbonate (59.56 g, 330.6 mmol) and potassium carbonate (80.23 g, 580.5 mmol), in this order. This slurry was heated at 110° C. for 16 hours then at 100° C. for 20 h. After cooling to room temperature, the flask was opened (CAUTION: stench!) and the contents were quenched by transferring onto cold water (500 mL). This mixture was extracted with ethyl acetate (3×500 mL), then the organic layers were combined and washed with water (2×500 mL) and saturated aqueous sodium chloride solution (500 mL), dried over sodium sulfate, filtered, and evaporated in vacuo. This crude product was purified by silica gel chromatography (330 g of silica, 0 to 30% gradient of ethyl acetate/hexanes) to give a beige solid, 4-methylsulfanyl-6-(o-tolyl)pyrimidin-2-amine (20.43 g, 56%) ESI-MS m/z calc. 231.08302, found 232.0 (M+1)$^+$; Retention time: 0.93 minutes; LC method A.

Step 3: N-[4-Methylsulfanyl-6-(o-tolyl)pyrimidin-2-yl]-3-nitro-benzenesulfonamide

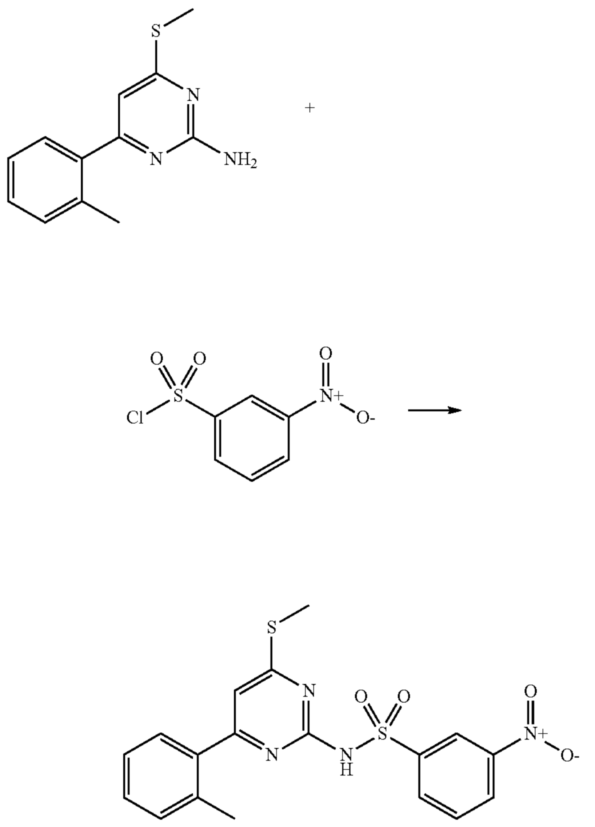

A 250 mL round-bottomed flask equipped with a magnetic stir bar was dried with a heat gun under vacuum and purged with nitrogen; 4-methylsulfanyl-6-(o-tolyl)pyrimidin-2-amine (7.61 g, 32.90 mmol) and dimethylformamide (80 mL) were added, and this solution was cooled to 0° C. 60% NaH (3.20 g, 80.01 mmol) was added in one portion, and the reaction mixture was warmed to room temperature over 15 minutes. The mixture was cooled to 0° C., upon which 3-nitrobenzenesulfonyl chloride (9.31 g, 42.01 mmol) was added in three portions (CAUTION: hydrogen gas evolution). This solution was stirred at room temperature for 80 minutes, then quenched by a slow transfer onto cold 1 N HCl (100 mL). The mixture was extracted with ethyl acetate (3×100 mL). The combined organic extracts were washed with water (2×150 mL) and saturated aqueous sodium chloride solution (150 mL), then dried over sodium sulfate, filtered, and evaporated in vacuo. This crude product was purified by silica gel chromatography (120 g of silica, 0 to 30% gradient of ethyl acetate/hexanes) to give N-[4-methylsulfanyl-6-(o-tolyl)pyrimidin-2-yl]-3-nitro-benzenesulfonamide (2.582 g, 12%) ESI-MS m/z calc. 416.0613, found 417.1 (M+1)$^+$; Retention time: 0.64 minutes; LC method D.

Step 4: N-[4-Methylsulfonyl-6-(o-tolyl)pyrimidin-2-yl]-3-nitro-benzenesulfonamide

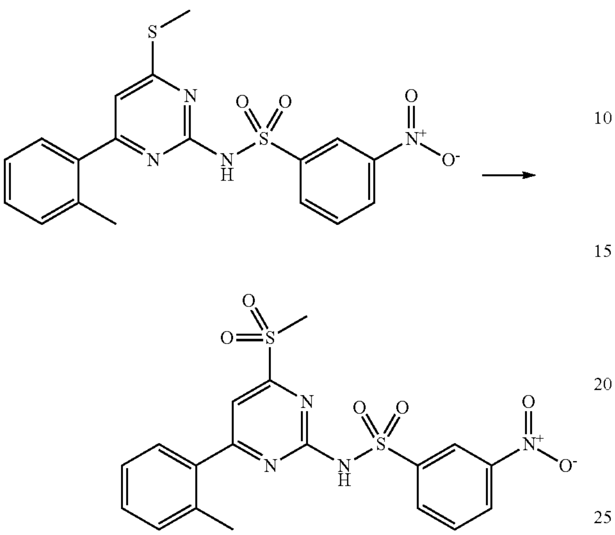

To a 100 mL round-bottomed flask equipped with a magnetic stir bar, N-[4-methylsulfanyl-6-(o-tolyl)pyrimidin-2-yl]-3-nitro-benzenesulfonamide (2.582 g, 4.030 mmol) and dichloromethane (40 mL) were added, followed by 77% m-CPBA (2.151 g, 9.598 mmol). This mixture was stirred at room temperature for 90 minutes, upon which a second addition of 77% m-CPBA (1.035 g, 4.618 mmol) was made. After 1 hour of stirring at room temperature, the reaction mixture was quenched with solid sodium thiosulfate (3.205 g, 20.27 mmol). This mixture was stirred for another 90 minutes at room temperature. The reaction mixture was diluted with dichloromethane (100 mL), then washed with water (100 mL), dried over sodium sulfate, filtered, and evaporated in vacuo. This solid was then partially dissolved in dichloromethane (15 mL) and filtered in vacuo on a Büchner funnel to remove the m-chlorobenzoic acid waste. The remaining solution was then purified by silica gel chromatography (40 g of silica, 0 to 60% gradient of ethyl acetate/hexanes) to give 3 batches of product, which were N-[4-methylsulfonyl-6-(o-tolyl)pyrimidin-2-yl]-3-nitro-benzenesulfonamide (1.7153 g, 79%). $^1H$ NMR (400 MHz, chloroform-d) δ 8.97 (t, J=2.0 Hz, 1H), 8.48-8.41 (m, 2H), 7.75 (s, 1H), 7.71 (t, J=8.1 Hz, 1H), 7.47-7.36 (m, 2H), 7.35-7.28 (m, 2H), 3.27 (s, 3H), 2.44 (s, 3H). ESI-MS m/z calc. 448.05112, found 449.1 $(M+1)^+$; Retention time: 0.6 minutes; LC method D.

Example E: Preparation of 4-(2,6-dimethylphenyl)-6-methylsulfanyl-pyrimidin-2-amine

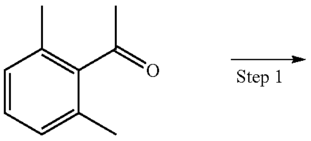

-continued

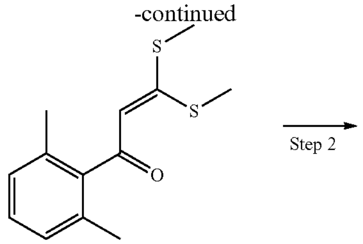

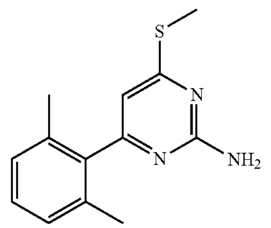

Step 1: 1-(2,6-Dimethylphenyl)-3,3-bis(methylsulfanyl)prop-2-en-1-one

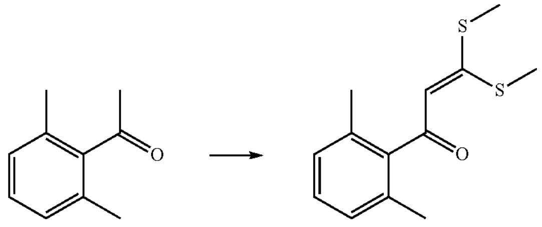 [SMILES: CC(=O)c1c(C)cccc1C ; CSC(=CC(=O)c1c(C)cccc1C)SC]

A 1 L round-bottomed flask equipped with a magnetic stir bar was dried with a heat gun under vacuum and purged with nitrogen; to this was added 1-(2,6-dimethylphenyl)ethanone (20.07 g, 135.4 mmol). Dry tetrahydrofuran (500 mL) was added, and this solution was cooled to 0° C. 95% NaH (7.50 g, 296.9 mmol) was added in three portions under a blanket of nitrogen, and the reaction mixture was warmed to room temperature over 45 minutes. The mixture was cooled to 0° C., upon which carbon disulfide (12.0 mL, 199.5 mmol) was added. The solution was then warmed to room temperature over 45 min. The reaction mixture was cooled to 0° C., upon which iodomethane (20.0 mL, 321.3 mmol) was added. The mixture was stirred at 0° C. for 30 minutes, then warmed to room temperature over 3 h, cooling the flask when necessary (CAUTION: hydrogen gas evolution). The reaction was quenched by a slow transfer onto ice-cold water (500 mL). The mixture was extracted with ethyl acetate (3×300 mL). The combined organic extracts were washed with water (300 mL) and saturated aqueous sodium chloride solution (200 mL), then dried over sodium sulfate, filtered, and evaporated in vacuo. This oil was purified by a short pad of silica gel (150 g of silica, elution with 2 L of 1:1 ethyl acetate/hexanes) to give a brown solid, 1-(2,6-dimethylphenyl)-3,3-bis(methylsulfanyl)prop-2-en-1-one (34.0 g, 100%) ESI-MS m/z calc. 252.06425, found 253.0 $(M+1)^+$; Retention time: 0.63 minutes; LC method D.

Step 2: 4-(2,6-Dimethylphenyl)-6-methylsulfanyl-pyrimidin-2-amine

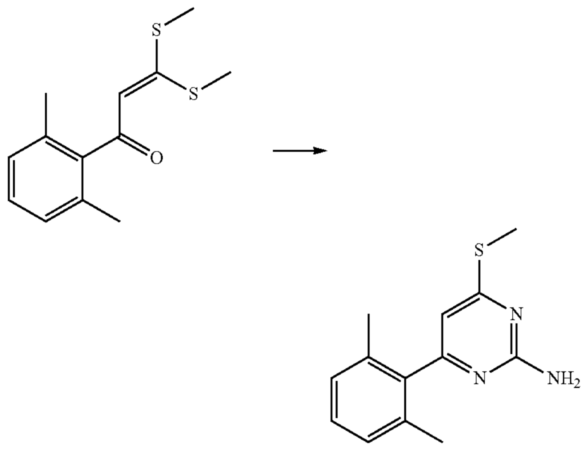

To a 1 L round-bottomed flask equipped with a magnetic stir bar were added 1-(2,6-dimethylphenyl)-3,3-bis(methylsulfanyl)prop-2-en-1-one (34.0 g, 134.7 mmol), dimethylformamide (350 mL), guanidine carbonate (50.0 g, 277.5 mmol) and potassium carbonate (70.0 g, 506.5 mmol), in this order. This slurry was heated at 105° C. for 19 h. After cooling to room temperature, the flask was opened (CAUTION: stench!) and the contents were quenched by transferring onto cold water (500 mL). The product precipitated out of solution, and this solid was collected on a Büchner funnel and dried under vacuum: 4-(2,6-dimethylphenyl)-6-methylsulfanyl-pyrimidin-2-amine (20.117 g, 49%). $^1$H NMR (400 MHz, dimethylsulfoxide-$d_6$) δ 7.16 (dd, J=8.3, 6.7 Hz, 1H), 7.07 (d, J=7.6 Hz, 2H), 6.68 (s, 2H), 6.38 (s, 1H), 2.46 (s, 3H), 2.05 (s, 6H). ESI-MS m/z calc. 245.09866, found 246.0 $(M+1)^+$; Retention time: 0.4 minutes; LC method D.

Example F: Preparation of 2-[1-(trifluoromethyl)cyclopropyl]acetaldehyde

Step 1: 2-[1-(Trifluoromethyl)cyclopropyl]ethanol

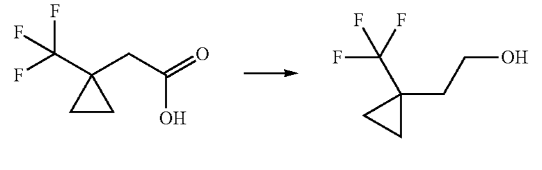 [SMILES: O=C(O)CC1(C(F)(F)F)CC1 ; OCCC1(C(F)(F)F)CC1]

LAH (49.868 g, 1.3139 mol) was added to THF (1700 mL) under nitrogen and the mixture was stirred for 30 minutes before being cooled to 0° C. 2-[1-(trifluoromethyl)cyclopropyl]acetic acid (190.91 g, 1.0107 mol) in THF (500 mL) was added dropwise while controlling the temperature <5° C. The mixture was allowed to warm up to room temperature and stirred for 24 hours. The resulting suspension was cooled to 0° C., water (50 mL) was added very slowly, followed by 15% w/w sodium hydroxide (50 mL) and water (150 mL). The mixture was stirred at 0° C. for 30 minutes, and filtered through Celite pad, the filter cake was washed with THF (2×500 mL). The combined filtrates were evaporated in vacuo to give 2-[1-(trifluoromethyl)cyclopropyl]ethanol (160.27 g, 98%) as amber oil containing ~5% w/w of THF (by NMR). $^1$H NMR (250 MHz, DMSO-$d_6$) δ 4.57 (t, J=5.2 Hz, 1H), 3.55-3.39 (m, 2H), 1.74 (t, J=7.3 Hz, 2H), 1.00-0.58 (m, 4H).

Step 2: 2-[1-(Trifluoromethyl)cyclopropyl]acetaldehyde

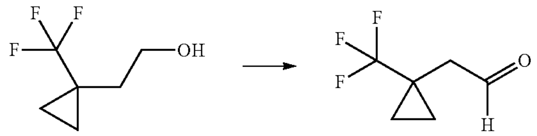 [SMILES: OCCC1(C(F)(F)F)CC1 ; O=CCC1(C(F)(F)F)CC1]

To a solution of 2-[1-(trifluoromethyl)cyclopropyl]ethanol (80 g, 467.1 mmol) in methylene chloride (1.1 L) was stirred at room temperature and treated with Dess-Martin periodinane (250 g, 589.4 mmol) portionwise (exothermic! cooled in ice bath and kept T<15° C.). To the mixture was added water (12 mL, 666.1 mmol) slowly added over 0.5 hour (exothermic during addition up to 33° C., kept between 20 and 33° C. by cooling with cold water) giving a thick suspension. After the addition, the pale-yellow fine suspension was stirred at room temperature for 18 h. The yellow suspension was diluted with diethylether (500 mL) (yellow suspension) and stirred for 30 minutes. The slurry was filtered over Celite and the precipitate washed with 100 mL of Diethylether. diethylether. The organic phase was carefully treated with a saturated aqueous solution of sodium carbonate (500 mL, strong gas evolution, pH ~10 at the end). The three-phase mixture was stirred at room temperature for 1 hour and the solid was removed by filtration (large glass frit). The phases (yellow cloudy diethylether phase, colorless water phase) were separated and the organic phase was washed once more with a saturated aqueous solution of sodium carbonate (250 mL), once with 1M sodium thiosulfate (250 mL) and once with brine (250 mL). The aqueous phases were back extracted once with diethyl ether (150 mL) and the combined organic phases were dried, filtered and evaporated to give 2-[1-(trifluoromethyl)cyclopropyl]acetaldehyde (40 g, 56%) as a yellow liquid.

Example G: Preparation of dispiro[2.0.24.13]heptane-7-carbaldehyde

Step 1: 1-Cyclopropylcyclopropanol

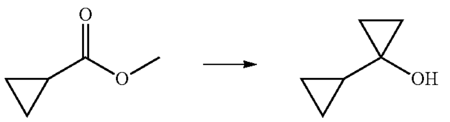

To a solution of methyl cyclopropanecarboxylate (75 g, 749.1 mmol) in ether (450 mL) was added titanium(IV) isopropoxide (55.3 mL, 187.4 mmol). To the mixture was slowly added ethyl magnesium bromide (1.6 L of 1 M, 1.60 mol) over 2 h. The addition is exothermic and controlled with monitoring the addition rate and using a cooling bath. The reaction temperature was kept between 21° C.-26° C. during addition. After addition, the mixture was stirred an additional 2 hours at ambient temperature. Next, the mixture was chilled to −5° C. using an acetone/dry ice bath and slowly quenched with sulfuric acid (970 g of 10% w/w, 990 mmol). The reaction mixture was cooled in a dry ice/acetone bath to keep the reaction vessel below 0° C. during the quench. As the quench progressed, a grey/purple solid formed. Following complete addition of aqueous sulfuric acid, the mixture was stirred at 0° C. for 1 h. The precipitate was filtered through Celite using a medium frit and the precipitate washed with diethyl ether (900 mL). The filtrate was transferred to a separatory funnel and the organic phase was washed with brine (1 L), saturated sodium bicarbonate (1 L) and brine (1 L). The organic phase was dried over magnesium sulfate, filtered over Celite and the solvent was evaporated by rotary evaporation at 100 torr and the water bath set at 20° C. The crude product was stored at −23° C. overnight and used without further purification. The product, 1-cyclopropylcyclopropanol (61 g, 83%) was found to contain ~50% solvent (tetrahydrofuran and $^{i}$PrOH) and used as such in the next step. $^{1}$H NMR (400 MHz, Chloroform-d) δ 1.32 (tt, J=8.2, 5.1 Hz, 1H), 0.71-0.61 (m, 2H), 0.51-0.43 (m, 2H), 0.43-0.33 (m, 2H), 0.23-0.14 (m, 2H).

Step 2: 1-Bromo-1-cyclopropyl-cyclopropane

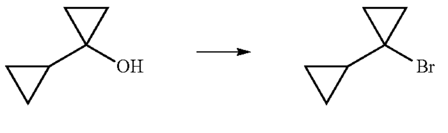 [SMILES: OC1(C2CC2)CC1 ; BrC1(C2CC2)CC1]

A solution of triphenylphosphine (56.1 g, 213.9 mmol) in dichloromethane (200 mL) was cooled to −10° C. A solution of bromine (11.0 mL, 214 mmol) in dichloromethane (40 mL) was added and the reaction was stirred at −10° C. for an additional 15 minutes. The reaction was then cooled to −30° C. and pyridine (3.3 mL, 41 mmol) was added. A solution of 1-cyclopropylcyclopropanol (20.0 g, 204 mmol), pyridine (17.3 mL, 214 mmol) and dichloromethane (100 mL) was added dropwise while maintaining the temperature between −15° C. to −20° C. After 30 minutes, the addition was complete and the reaction was allowed to gradually warm to room temperature. The reaction was then allowed to stir at 40° C. overnight. The reaction was then cooled to room temperature and quenched with water (100 mL). The reaction was then stirred for 10 minutes and the phases were separated. The organic phase was successively washed with 1 M hydrochloric acid (102 mL) then saturated sodium bicarbonate (50 mL), dried over sodium sulfate, filtered and concentrated (30° C./house vacuum ~300 torr) to remove most of the dichloromethane. The crude reaction mixture was flash distilled (40° C./20 torr) to remove further dichloromethane. The solid residue ($Ph_3PO$ and product) was re-heated and distilled (50-60° C./20 torr) to afford 21.5 g (65% yield) of 1-bromo-1-cyclopropyl-cyclopropane as a turbid, colorless liquid. $^{1}$H NMR (400 MHz, Chloroform-d) δ 1.61 (tt, J=8.2, 5.0 Hz, 1H), 1.07-1.02 (m, 2H), 0.78-0.66 (m, 2H), 0.67-0.51 (m, 2H), 0.35-0.21 (m, 2H).

Step 3: Cyclopropylidenecyclopropane

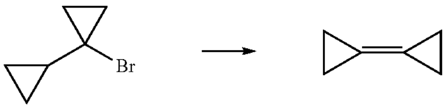 [SMILES: BrC1(C2CC2)CC1 ; C1CC1=C1CC1]

A solution of potassium tert-butoxide (16.7 g, 148.8 mmol) in dimethyl sulfoxide (100 mL) was stirred at room temperature in a 3-neck 250-mL round bottom flask. 1-Bromo-1-cyclopropyl-cyclopropane (20.0 g, 124.2 mmol) was added dropwise and the reaction immediately turned dark and then brown. The reaction was mildly exothermic (maintained temperature between 18° C. to 22° C. using an ice-water bath). After 10 minutes, the addition was completed. The ice-water bath was removed and the reaction was allowed to stir at room temperature. After 90 minutes, the reaction mixture was vacuum distilled using a bulb-to-bulb distillation. The distillation took place from 60° C. to 80° C. between 40 and 100 torr. The distillate slowly collected in the receiver to afford 18.2 g (7.3 g of product as a 42 wt % solution in t-BuOH) of a colorless liquid. The distillate was further washed with water (5×10 mL). Dichloromethane (4 g) was added and the mixture was dried over magnesium sulfate, filtered (washing with 2 additional portions of 3 g of dichloromethane each) to afford 17.30 g (6.9 g product as a 39.6 wt % solution in dichloromethane; 69% yield) as a colorless liquid. $^{1}$H NMR (400 MHz, Chloroform-d) δ 1.19 (s, 8H). The $^{1}$H NMR confirms the presence of dichloromethane and a small amount of tert-butanol.

Step 4: Ethyl dispiro[2.0.2.1]heptane-7-carboxylate

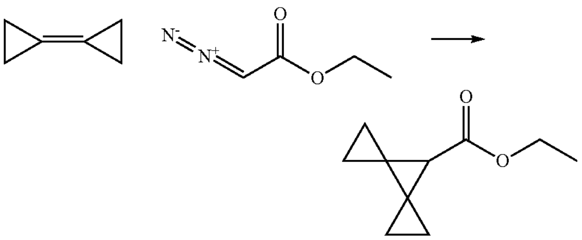

To a solution of cyclopropylidenecyclopropane (49.5 g, 617.8 mmol) in dichloromethane (110 mL) at 0° C. under a nitrogen atmosphere was added rhodium(II) acetate (4.2 g, 9.503 mmol). To the mixture at 0° C. was added ethyl 2-diazoacetate (106.8 mL, 1.016 mol) using a syringe pump set at an addition rate of 0.02 mL/min (1.2 mL/h). The addition was continuous for 89 hr. The crude reaction mixture was filtered through a plug of silica, washing 3× with 150 mL of dichloromethane each. The volatile materials were removed in vacuo affording a crude, dark yellow oil, ethyl dispiro[2.0.2.1]heptane-7-carboxylate (100 g, 97%, contains ~20% dichloromethane, diethyl (E)-but-2-enedioate and diethyl (Z)-but-2-enedioate as contaminants) which was used directly in the next step. $^{1}$H NMR (400 MHz, Chloroform-d) δ 4.13 (q, J=7.1 Hz, 2H), 2.23 (s, 1H), 1.24 (t, J=7.1 Hz, 3H), 1.08-0.93 (m, 4H), 0.90-0.82 (m, 2H), 0.77 (ddd, J=8.2, 5.0, 3.5 Hz, 2H).

Step 5: Dispiro[2.0.2.1]heptan-7-yl methanol

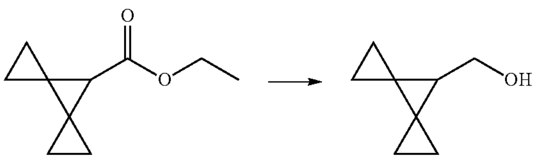

To a slurry of lithium aluminum hydride (7.8 g, 200.2 mmol) in diethyl ether (300 mL) chilled with an ice-water bath was slowly added ethyl dispiro[2.0.2.1]heptane-7-carboxylate (10.77 g, 64.79 mmol). The mixture was allowed to warm to a gentle reflux during the addition and continued to stir at ambient temperature for 1 h. The reaction was chilled with an ice-water bath and slowly quenched with the addition of water (8.0 mL, 440 mmol), followed by sodium hydroxide (8.0 mL of 2 M, 16 mmol) and then water (24.0 mL, 1.33 mol). The light yellow slurry was filtered over Celite and washed 3× with 150 mL of methyl tert-butyl ether. The filtrate was concentrated in vacuo affording 8.87 g of a clear oil, dispiro[2.0.2.1]heptan-7-yl methanol (8.87 g, quantitative yield). $^1H$ NMR (400 MHz, Chloroform-d) δ 3.71 (dd, J=6.7, 5.5 Hz, 2H), 1.76-1.65 (m, 1H), 1.46 (t, J=5.6 Hz, 1H), 0.87 (q, J=1.9 Hz, 4H), 0.72-0.61 (m, 2H), 0.60-0.50 (m, 2H).

Step 6: Dispiro[2.0.24.13]heptane-7-carbaldehyde

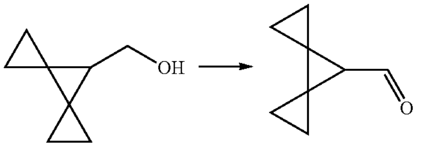 [SMILES: OCC1C2(CC2)C12CC2 ; O=CC1C2(CC2)C12CC2]

To a 20 mL vial was added {dispiro[2.0.2.1]heptan-7-yl}methanol (381 mg, 3.068 mmol), dichloromethane (4 mL), potassium bicarbonate (620 mg, 6.193 mmol), and pyridinium chlorochromate (728 mg, 3.377 mmol) (PCC). The reaction was allowed to stir at rt for 5 hours. The reaction was filtered over Celite and evaporated (300 torr, minimal heating in 40° C. water bath). The reaction mixture was dissolved in diethylether, filtered over Celite, and evaporated at 300 torr (minimal heating in 40° C. water bath) to provide dispiro[2.0.24.13]heptane-7-carbaldehyde (433 mg, 58%) as a pale brown oil. Purity estimated to be around 50%. The crude product was used in the next step without further purification.

Example H: Preparation of 4-chloro-6-(2,6-dimethylphenyl)pyridin-2-amine

Step 1: 4-Chloro-6-(2,6-dimethylphenyl)pyridin-2-amine

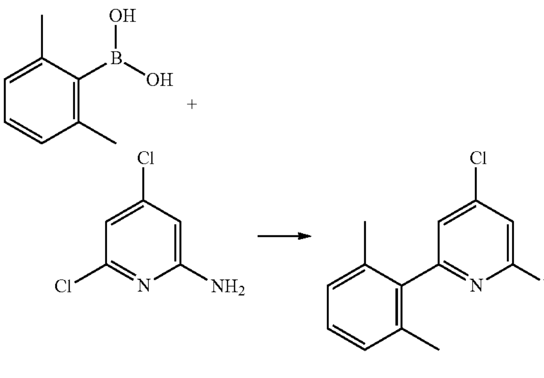

To a stirring solution of (2,6-dimethylphenyl)boronic acid (203 mg, 1.3535 mmol) and 4,6-dichloropyridin-2-amine (217 mg, 1.3312 mmol) in Toluene (7.3 mL) and EtOH (3.7 mL) was added an aqueous solution of Sodium carbonate (2 mL of 2 M, 4.0000 mmol) and the reaction mixture was degassed with nitrogen gas for 10 minutes. Pd(dppf)$Cl_2$ (97 mg, 0.1326 mmol) was then added with degassing continuing for an additional 2 minutes. Then the reaction vial was sealed, and the mixture heated to 100° C. and stirred at that temperature for 22 h. After this time, volatiles were removed under reduced pressure and the residue was extracted with ethyl acetate (3×20 mL). The combined organic layers were washed with brine, dried over anhydrous sodium sulfate, and concentrated under reduced pressure. The crude product was purified by silica gel column chromatography (0-25% EtOAc in Hexanes) to afford 4-chloro-6-(2,6-dimethylphenyl)pyridin-2-amine (147 mg, 46%) as an off-white solid. ESI-MS m/z calc. 232.0767, found 233.1 $(M+1)^+$; Retention time: 2.31 minutes, LC method T.

IV. Synthesis of New Compounds

Example 1: Preparation of Compound 1 and Compound 2

Step 1: tert-Butyl 19-(2,6-dimethylphenyl)-8,15,15-trioxo-2-oxa-$15\lambda^6$-thia-5,9,16,18,21-pentaazatetracyclo[15.3.1.13,7.110,14]tricosa-1(20),10,12,14(22),17(21),18-hexaene-5-carboxylate, Diastereomer 1, Cis, Racemic and tert-butyl 19-(2,6-dimethylphenyl)-8,15,15-trioxo-2-oxa-$15\lambda^6$-thia-5,9,16,18,21-pentaazatetracyclo[15.3.1.13,7.110,14]tricosa-1(20),10,12,14(22),17(21),18-hexaene-5-carboxylate, Diastereomer 2, Trans, Racemic

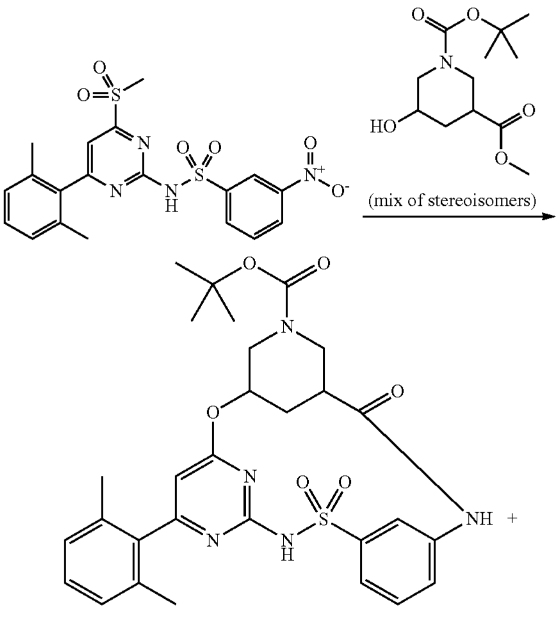

diastereomer 1, cis, racemic

-continued

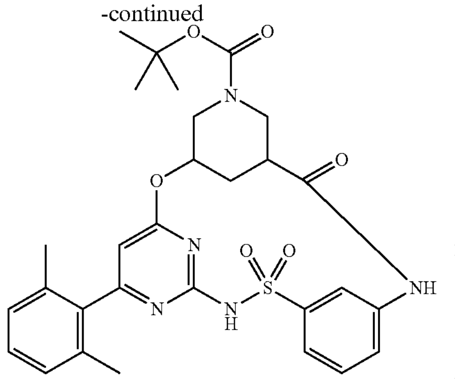

diastereomer 2, trans, racemic

Stage 1: In a 250 mL round-bottomed flask, a solution of O1-tert-butyl O3-methyl 5-hydroxypiperidine-1,3-dicarboxylate (4.565 g, 17.61 mmol) in NMP (120 mL) was cooled to 0° C., treated with 60% NaH (1.802 g, 45.05 mmol) and was warmed to room temperature over 20 minutes. Then, the reaction mixture was cooled to 0° C., N-[4-(2,6-dimethylphenyl)-6-methylsulfonyl-pyrimidin-2-yl]-3-nitro-benzenesulfonamide (5.490 g, 11.28 mmol) was added, and the reaction mixture was warmed to room temperature over 30 minutes. The reaction mixture was then cooled to 0° C., upon which water (40 mL) was added slowly. This mixture was then warmed to room temperature over 3 h. This was then quenched dropwise with 1 N HCl (50 mL) and extracted with ethyl acetate (3×150 mL). The combined organic extracts were washed with water (200 mL) and saturated aqueous sodium chloride solution (200 mL), then dried over sodium sulfate, filtered, and evaporated in vacuo to give a dark brown oil. This crude product was purified by silica gel chromatography (330 g of silica, 0 to 70% gradient of ethyl acetate/hexanes) to give two separable diastereomers of 1-tert-butoxycarbonyl-5-[6-(2,6-dimethylphenyl)-2-[(3-nitrophenyl)sulfonylamino]pyrimidin-4-yl]oxy-piperidine-3-carboxylic acid (MW 627.66; 0.785 g, 1.25 mmol, 11.1% yield of the less polar "diastereomer 1" and 2.743 g, 4.370 mmol, 38.7% yield of the more polar "diastereomer 2".

Stage 2: Each batch of diastereomer was reacted separately in the next reaction.

For "diastereomer 1": In a 100-mL round-bottomed flask equipped with a magnetic stir bar, the product from Stage 1 (0.785 g, 1.25 mmol) was dissolved in EtOH (15 mL). This solution was sparged with a balloon of hydrogen gas for 5 minutes. The cap was briefly removed, and $Pd(OH)_2/C$ (130.8 mg, 0.09314 mmol) was added. This reaction mixture was stirred under hydrogen (2 L, 79.37 mmol) at 60° C. for 2 h, after which it was filtered through Celite and rinsed with methanol (30 mL). This solution was evaporated in vacuo to give 5-[2-[(3-aminophenyl)sulfonylamino]-6-(2,6-dimethylphenyl)pyrimidin-4-yl]oxy-1-tert-butoxycarbonyl-piperidine-3-carboxylic acid (MW 597.68; 0.712 g, 1.19 mmol, 95% yield). Purification was not conducted at this stage.

For "diastereomer 2": In a 20 mL microwave vial equipped with a magnetic stir bar, the product from Stage 1 (2.743 g, 4.370 mmol) was dissolved in EtOH (30 mL). This solution was sparged with a balloon of hydrogen gas for 5 minutes. The cap was briefly removed, and 10% $Pd(OH)_2/C$ (222 mg, 0.1581 mmol) was added. This reaction mixture was stirred under hydrogen (2 L, 79.37 mmol) at 60° C. for 2 h, after which it was filtered through Celite and rinsed with methanol (80 mL). This solution was evaporated in vacuo to give 5-[2-[(3-aminophenyl)sulfonylamino]-6-(2,6-dimethylphenyl)pyrimidin-4-yl]oxy-1-tert-butoxycarbonyl-piperidine-3-carboxylic acid (2.465 g, 4.124 mmol, 94% yield). Purification was not conducted at this stage.

Stage 3: Each batch of diastereomer was reacted separately in the next reaction.

For "diastereomer 1": The product from Stage 2 (0.712 g, 1.19 mmol) was dissolved in DMF (20 mL) and treated with DIPEA (2.0 mL, 11.48 mmol) and $Ph_2P(O)—OC_6F_5$ (1.051 g, 2.735 mmol). This mixture was stirred at room temperature for 20 minutes, after which it was quenched with water (40 mL) and extracted with ethyl acetate (3×50 mL). The combined organic extracts were washed with water (100 mL) and saturated aqueous sodium chloride solution (100 mL), then dried over sodium sulfate, filtered, and evaporated in vacuo. Purification by a silica gel plug (10 g of silica, 400 mL of 2:1 ethyl acetate:hexanes) gave 0.726 g of a 1:1 mixture of pentafluorophenyl ester product and stage 4 product (macrocyclization occurred without heat).

For "diastereomer 2": The product from Stage 2 (2.465 g, 4.124 mmol) was dissolved in DMF (60 mL) and treated with DIPEA (6.0 mL, 34.45 mmol) and $Ph_2P(O)—OC_6F_5$ (3.251 g, 8.461 mmol). This mixture was stirred at room temperature for 20 minutes, after which it was quenched with water (120 mL) and extracted with ethyl acetate (3×150 mL). The combined organic extracts was washed with water (200 mL) and saturated aqueous sodium chloride solution (200 mL), then dried over sodium sulfate, filtered, and evaporated in vacuo. Purification by a silica gel plug (40 g of silica, 300 mL of 1:9 ethyl acetate:hexanes) gave 2.597 g of pentafluorophenyl ester product.

Stage 4: Each batch of diastereomer was reacted separately in the next reaction.

For "diastereomer 1": The product from Stage 3 was dissolved in NMP (30 mL) and stirred at 120° C. for 2 h. This solution was cooled to room temperature, quenched with water (40 mL) and extracted with ethyl acetate (3×50 mL). The combined organic extracts were washed with water (100 mL) and saturated aqueous sodium chloride solution (100 mL), then dried over sodium sulfate, filtered, and evaporated in vacuo. Purification by silica gel chromatography (40 g of silica, 0 to 60% gradient of ethyl acetate/hexanes) gave a white foam, tert-butyl 19-(2,6-dimethylphenyl)-8,15,15-trioxo-2-oxa-15$\lambda^6$-thia-5,9,16,18,21-pentaazatetracyclo[15.3.1.13,7.110,14]tricosa-1(20),10,12,14(22),17(21),18-hexaene-5-carboxylate (0.5184 g, 8%); $^1H$ NMR (400 MHz, dimethylsulfoxide-$d_6$) δ 14.00-11.10 (bs, 1H, $D_2O$ exchangeable), 10.08 (s, 1H, $D_2O$ exchangeable), 8.06 (s, 1H), 7.56-7.41 (m, 2H), 7.34-7.21 (m, 1H), 7.24 (t, J=7.7 Hz, 1H), 7.11 (d, J=7.6 Hz, 2H), 6.37 (s, 1H), 4.97-4.79 (m, 1H), 4.42-4.18 (m, 2H), 3.31-3.21 (m, 1H), 3.08-2.80 (m, 2H), 2.64-2.51 (m, 1H), 2.04 (s, 6H), 1.45 (s, 9H), 1.39-1.26 (m, 1H). ESI-MS m/z calc. 579.21515, found 580.2 $(M+1)^+$; Retention time: 1.67 minutes; LC method A.

For "diastereomer 2": The product from Stage 3 was dissolved in NMP (60 mL) and stirred at 120° C. for 17 h. This solution was cooled to room temperature, quenched with water (60 mL) and extracted with ethyl acetate (3×150 mL). The combined organic extracts were washed with water (300 mL) and saturated aqueous sodium chloride solution (200 mL), then dried over sodium sulfate, filtered, and evaporated in vacuo. Purification by silica gel chromatography (80 g of silica, 0 to 60% gradient of ethyl acetate/hexanes) gave tert-butyl 19-(2,6-dimethylphenyl)-8,15,15-trioxo-2-oxa-15$\lambda^6$-thia-5,9,16,18,21-pentaazatetracyclo[15.3.1.13,7.110,14]tricosa-1(20),10,12,14(22),17(21),18-hexaene-5-carboxylate (0.6436 g, 10%); ESI-MS m/z calc. 579.21515, found 580.3 $(M+1)^+$; Retention time: 1.59 minutes. LC method A.

Step 2: tert-butyl (3R,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (Compound 1), and tert-butyl (3S,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (Compound 2)

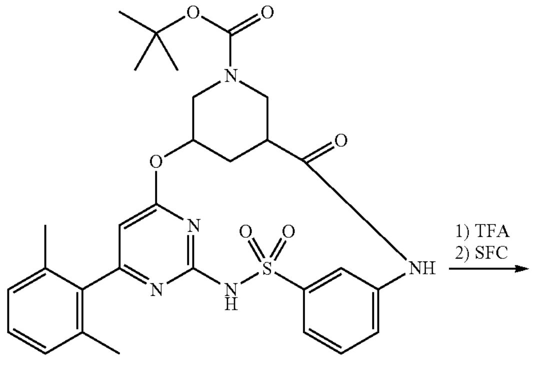

diastereomer 1, cis, racemic

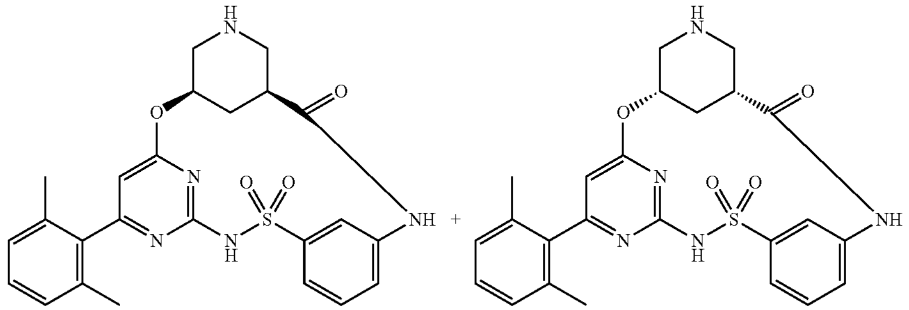

diastereomer 1, Peak 1 diastereomer 1, Peak 2

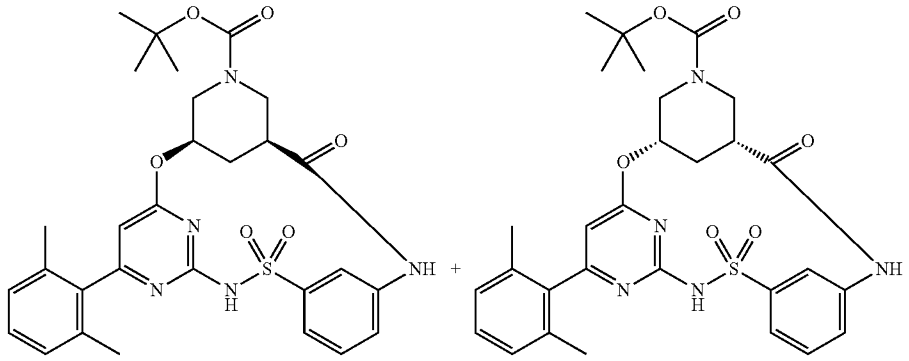

diastereomer 1, Peak 1 diastereomer 1, Peak 2

Stage 1: In a 20 mL vial, "diastereomer 1" of tert-butyl 19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (518.4 mg, 0.8943 mmol) was mixed with DCM (5.0 mL) and TFA (5.0 mL, 64.90 mmol), and this solution was heated at 50° C. for 2 h. The mixture was then cooled to room temperature and evaporated in vacuo to give racemic 19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene (1.6 g of a brown oil, containing leftover solvent).

Stage 2: The product from Stage 1 was dissolved in MeOH (50 mL) to achieve a concentration of ca. 32 mg/mL. Separation of the enantiomers was achieved with an SFC purification method using a ChiralPak OD-H column (250×21.2 mm, 5 μm particle size), with a mobile phase of 40% MeOH (+20 mM $NH_3$)+60% $CO_2$, a flow rate of 70 mL/min, an injection volume of 500 μL, and a pressure of 100 bar. The collected batches were labeled "Peak 1" (169.8 mg) and "Peak 2" (178.4 mg). "Peak 1" was (3R,7S)-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (169.8 mg, 40%) ESI-MS m/z calc. 479.16272, found 480.2 $(M+1)^+$; Retention time: 0.88 minutes; LC method A. "Peak 2" was (3S,7R)-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (178.4 mg, 42%). ESI-MS m/z calc. 479.16272, found 480.2 $(M+1)^+$; Retention time: 0.89 minutes; LC method A.

Stage 3: Both stereoisomers were reacted separately. Only a portion of the products obtained in Stage 2 were used in this stage. In a 20-mL vial, "Peak 1", (3R,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene (53.9 mg, 0.112 mmol) was dissolved in DCM (1.0 mL), to which TEA (50 μL, 0.3587 mmol), Boc anhydride (35.0 mg, 0.1604 mmol) and DMAP (1.0 mg, 0.008185 mmol) were added. This mixture was stirred at room temperature for 5 minutes, after which it was directly purified by silica gel chromatography (4 g of silica, 0 to 90% gradient of ethyl acetate/hexanes) to give "Peak 1", tert-butyl (3R,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (52.9 mg, 10%) ESI-MS m/z calc. 579.21515, found 580.3 $(M+1)^+$; Retention time: 1.68 minutes; LC method A. In a 20-mL vial, "Peak 2", (3S,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene (59.4 mg, 0.124 mmol) was dissolved in DCM (1.0 mL), to which TEA (50 μL, 0.3587 mmol), Boc anhydride (35.0 mg, 0.1604 mmol) and DMAP (1.0 mg, 0.008185 mmol) were added. This mixture was stirred at room temperature for 5 minutes, after which it was directly purified by silica gel chromatography (4 g of silica, 0 to 90% gradient of ethyl acetate/hexanes) to give "Peak 2", tert-butyl (3S,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (59.2 mg, 11%) ESI-MS m/z calc. 579.21515, found 580.3 $(M+1)^+$; Retention time: 1.68 minutes; LC method A.

Example 2: Preparation of Compound 3 and Compound 4

Step 1: tert-Butyl (3R,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(21),10(22),11,13,17,19-hexaene-5-carboxylate (Compound 3), and tert-butyl (3S,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (Compound 4)

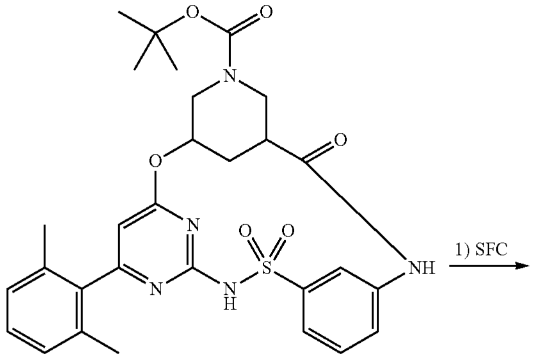

diastereomer 2, trans, racemic

-continued

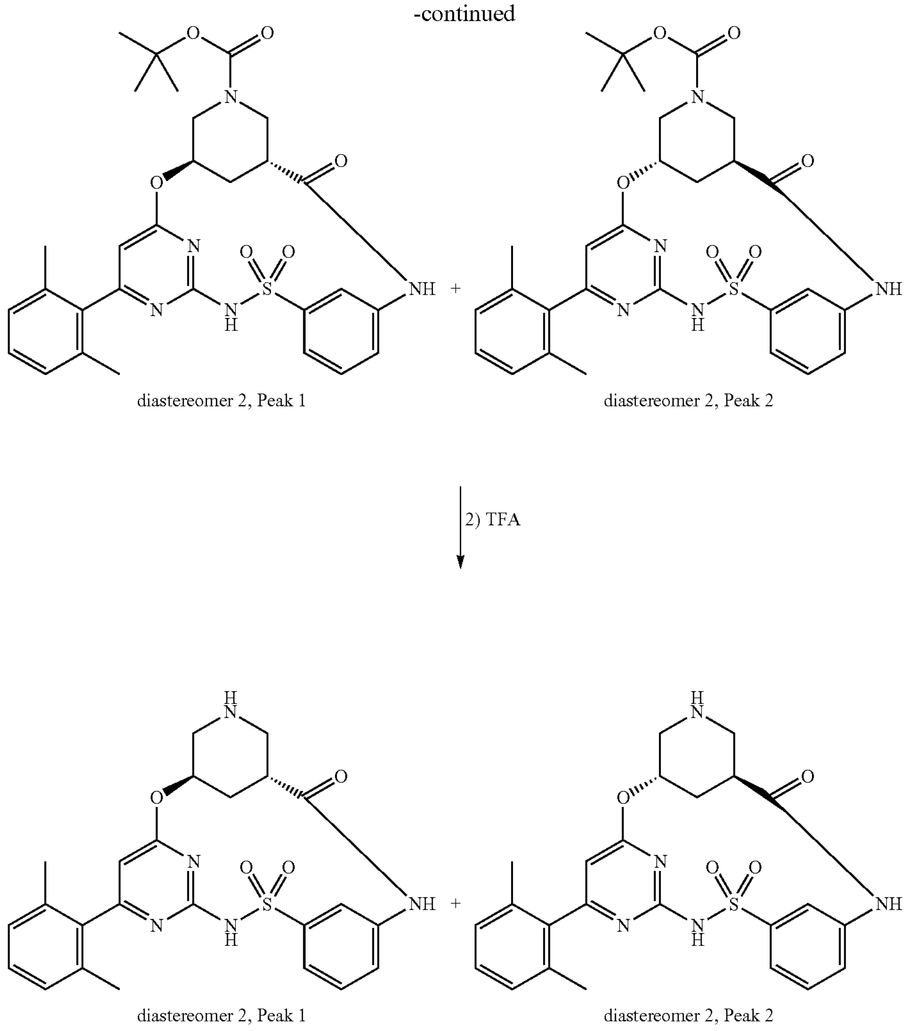

Stage 1: Racemic "diastereomer 2" tert-butyl 19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (643.6 mg, 1.110 mmol) was dissolved in MeOH (20 mL) to achieve a concentration of ca. 32 mg/mL. Separation of the enantiomers was achieved with an SFC purification method using a Regis (R,R)-Whelk-O column (150×2.1 mm, 3 μm particle size), with a mobile phase of 32% MeOH (no modifier)+68% $CO_2$, a flow rate of 70 mL/min, an injection volume of 500 μL, and a pressure of 100 bar. The collected batches were labeled "Peak 1" (169.8 mg) and "Peak 2" (171.6 mg). "Peak 1" was tert-butyl (3R,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(21),10(22),11,13,17,19-hexaene-5-carboxylate (169.8 mg, 26%) ESI-MS m/z calc. 579.21515, found 580.2 $(M+1)^+$; Retention time: 1.6 minutes; LC method A. "Peak 2" was tert-butyl (3S,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(20),10,12,14(22),17(21),18-hexaene-5-carboxylate (171.6 mg, 27%) ESI-MS m/z calc. 579.21515, found 580.2 $(M+1)^+$; Retention time: 1.6 minutes; LC method A. To determine the absolute configurations of these compounds, the (3S,7S) stereoisomer (diastereomer 2, Peak 2) was epimerized at the position alpha to the carbonyl group to give the (3S,7R) stereoisomer (diastereomer 1, Peak 2).

Stage 2: For "Peak 1": tert-butyl (3R,7R)-19-(2,6-dimethylphenyl)-8,15,15-trioxo-2-oxa-15λ$^6$-thia-5,9,16,18,21-pentaazatetracyclo[15.3.1.13,7.110,14]tricosa-1(21),10(22),11,13,17,19-hexaene-5-carboxylate (137.1 mg, 0.2365 mmol) was dissolved in TFA (3.0 mL) and heated at 50° C. for 30 minutes. This solution was cooled to room temperature and evaporated to dryness in vacuo to give (3R,7R)-19-(2,6-dimethylphenyl)-2-oxa-15λ$^6$-thia-5,9,16,18,21-pentaazatetracyclo[15.3.1.13,7.110,14]tricosa-1(21),10(22),11,13,17,19-hexaene-8,15,15-trione (trifluoroacetate salt) (140.4 mg, 21%) ESI-MS m/z calc. 479.16272, found 480.1 $(M+1)^+$; Retention time: 0.82 minutes; LC method A. For "Peak 2": tert-butyl (3S,7S)-19-(2,6-dimethylphenyl)-8,15,15-trioxo-2-oxa-15λ$^6$-thia-5,9,16,18,21-pentaazatetracyclo[15.3.1.13,7.110,14]tricosa-1(21),10(22),11,13,17,19-hexaene-5-carboxylate (140.1 mg, 0.2417 mmol) was dissolved in TFA (3.0 mL) and heated at 50° C. for 30 minutes. This solution was cooled to room temperature and evaporated to dryness in vacuo to give (3S,7S)-19-(2,6-dimethylphenyl)-2-oxa-15λ$^6$-thia-5,9,16,18,21-pentaazatetracyclo[15.3.1.13,7.110,14]tricosa-1(21),10(22),11,13,17,19-hexaene-8,15,15-trione (trifluoroacetate salt) (143.5 mg, 22%) ESI-MS m/z calc. 479.16272, found 480.1 $(M+1)^+$; Retention time: 0.82 minutes; LC method A.

Example 3: Preparation of Compound 5

Step 1: (3S,7R)-5-(3,3-Dimethylbutyl)-19-(2,6-dimethylphenyl)-2-oxa-15$\lambda^6$-thia-5,9,16,18,21-pentaazatetracyclo[15.3.1.13,7.110,14]tricosa-1(20),10,12,14(22),17(21),18-hexaene-8,15,15-trione (Compound 5)

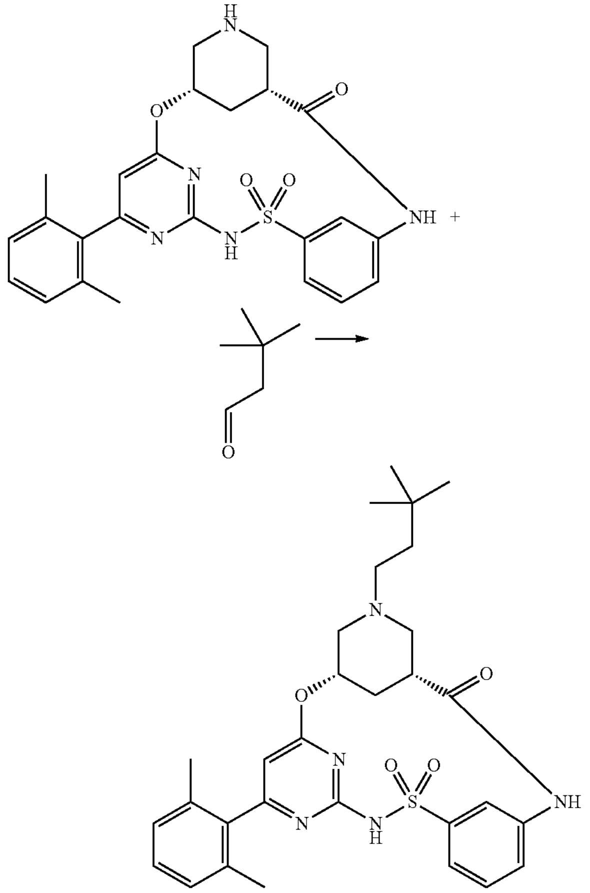

To a 3-mL vial, (3S,7R)-19-(2,6-dimethylphenyl)-2-oxa-15$\lambda^6$-thia-5,9,16,18,21-pentaazatetracyclo[15.3.1.13,7.110,14]tricosa-1(20),10,12,14(22),17(21),18-hexaene-8,15,15-trione (30.0 mg, 0.06256 mmol), acetic acid (800 µL), 3,3-dimethylbutanal (15.1 mg, 0.1508 mmol) and sodium triacetoxyborohydride (35.1 mg, 0.1656 mmol) were added, in this order. After standing at room temperature for 5 minutes, this mixture was diluted with MeOH (200 µL), filtered and purified by reverse phase HPLC (1-70% acetonitrile in water using HCl as a modifier) to give (3S,7R)-5-(3,3-dimethylbutyl)-19-(2,6-dimethylphenyl)-2-oxa-15$\lambda^6$-thia-5,9,16,18,21-pentaazatetracyclo[15.3.1.13,7.110,14]tricosa-1(20),10,12,14(22),17(21),18-hexaene-8,15,15-trione (hydrochloride salt) (19.6 mg, 52%). $^1$H NMR (400 MHz, dimethylsulfoxide-$d_6$) δ 10.71-10.53 (bs, 1H, $D_2O$ exchangeable), 10.37 (s, 1H, $D_2O$ exchangeable), 7.95 (s, 1H), 7.63-7.50 (bs, 2H), 7.39-7.29 (bs, 1H), 7.25 (t, J=7.6 Hz, 1H), 7.13 (d, J=7.6 Hz, 2H), 6.45 (s, 1H), 5.41-5.30 (m, 1H), 3.91-3.60 (m, 3H), 3.33-3.19 (m, 4H), 2.64-2.56 (m, 1H), 2.03 (s, 6H), 1.68 (dhept, J=12.6, 5.7 Hz, 2H), 1.49 (q, J=11.9 Hz, 1H), 0.94 (s, 9H) ESI-MS m/z calc. 563.25665, found 564.3 $(M+1)^+$; Retention time: 1.28 minutes; LC method A.

Example 4: Preparation of Compound 6

Step 1: (3S,7R)-19-(2,6-Dimethylphenyl)-5-({dispiro[2.0.24.13]heptan-7-yl}methyl)-2-oxa-15$\lambda^6$-thia-5,9,16,18,21-pentaazatetracyclo[15.3.1.13,7.110,14]tricosa-1(21),10(22),11,13,17,19-hexaene-8,15,15-trione (Compound 6)

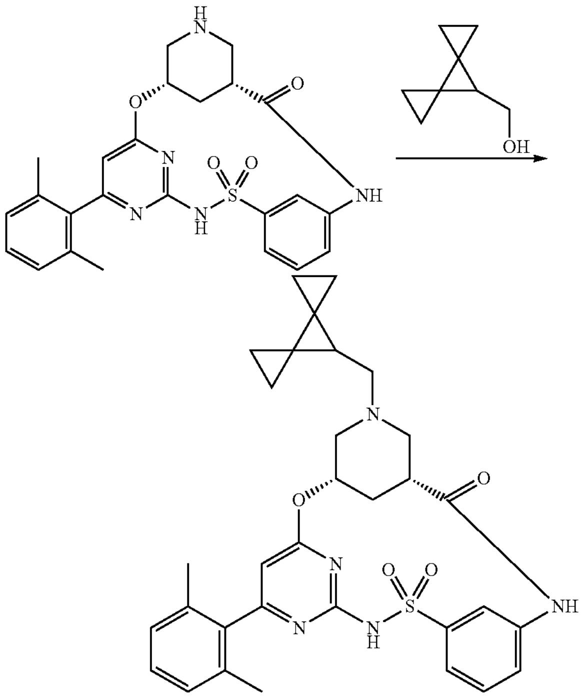

In a 3-mL vial (vial #1), dispiro[2.0.24.13]heptan-7-ylmethanol (18.6 mg, 0.1498 mmol) was treated with a DCM solution of Dess-Martin periodinane (500 µL of 0.3 M, 0.1500 mmol), and this mixture was allowed to stand at room temperature for 30 minutes. Over this time, a white precipitate formed at the bottom of the vial. In another 3-mL vial (vial #2), (3S,7R)-19-(2,6-dimethylphenyl)-2-oxa-15$\lambda^6$-thia-5,9,16,18,21-pentaazatetracyclo[15.3.1.13,7.110,14]tricosa-1(20),10,12,14(22),17(21),18-hexaene-8,15,15-trione (10.2 mg, 0.02127 mmol) was dissolved in acetic acid (600 µL), to which the soluble component of vial #1 was added, followed by sodium triacetoxyborohydride (35 mg, 0.1651 mmol). This reaction mixture was allowed to stand at room temperature for 5 minutes, after which it was filtered and purified by reverse phase HPLC (1-70% acetonitrile in water using HCl as a modifier) to give (3S,7R)-19-(2,6-dimethylphenyl)-5-({dispiro[2.0.24.13]heptan-7-yl}methyl)-2-oxa-15$\lambda^6$-thia-5,9,16,18,21-pentaazatetracyclo[15.3.1.13,7.110,14]tricosa-1(21),10(22),11,13,17,19-hexaene-8,15,15-trione (hydrochloride salt) (4.3 mg, 32%). $^1$H NMR (400 MHz, dimethylsulfoxide-$d_6$) δ 13.25-11.65 (bs, 1H, $D_2O$ exchangeable), 9.96 (s, 1H, $D_2O$ exchangeable), 8.05 (s, 1H), 7.47 (s, 2H), 7.25 (s, 1H), 7.23 (t, J=7.6 Hz, 1H), 7.11 (d, J=7.6 Hz, 2H), 6.34 (s, 1H), 5.12-5.00 (m, 1H), 3.33-3.20 (m, 1H), 3.14-3.00 (m, 2H), 2.58 (d, J=5.9

Hz, 2H), 2.16 (t, J=10.6 Hz, 2H), 2.02 (s, 6H), 1.56 (t, J=5.9 Hz, 1H), 1.08 (q, J=11.6 Hz, 1H), 0.93-0.74 (m, 5H), 0.72-0.64 (m, 2H), 0.58-0.46 (m, 2H) ESI-MS m/z calc. 585.24097, found 586.3 $(M+1)^+$; Retention time: 1.31 minutes; LC method A.

Example 5: Preparation of Compound 7

Step 1: (3S,7R)-19-(2,6-Dimethylphenyl)-5-(2-methoxyethyl)-2-oxa-15λ⁶-thia-5,9,16,18,21-pentaazatetracyclo[15.3.1.13,7.110,14]tricosa-1(21),10(22),11,13,17,19-hexaene-8,15,15-trione (Compound 7)

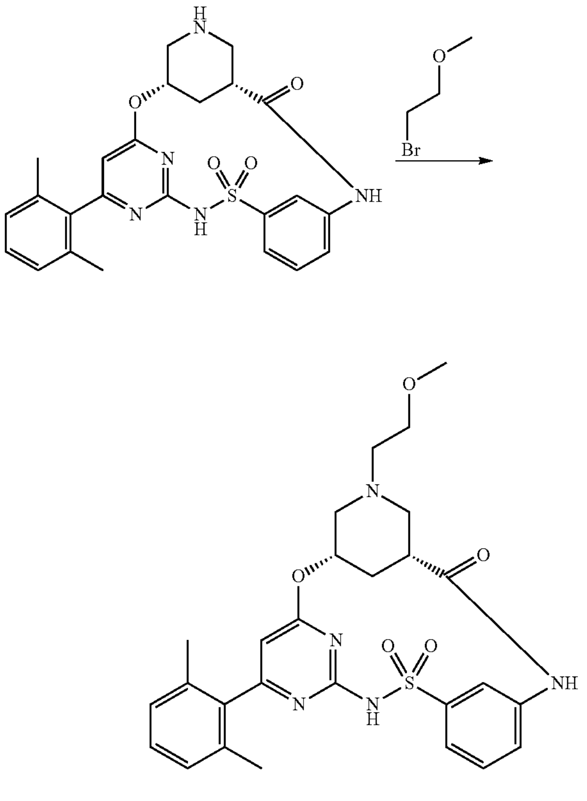

To a 3-mL vial, (3S,7R)-19-(2,6-dimethylphenyl)-2-oxa-15λ⁶-thia-5,9,16,18,21-pentaazatetracyclo[15.3.1.13,7.110,14]tricosa-1(20),10,12,14(22),17(21),18-hexaene-8,15,15-trione (8.8 mg, 0.01835 mmol), potassium carbonate (10.1 mg, 0.07308 mmol), NMP (400 μL), and 1-bromo-2-methoxy-ethane (5.7 mg, 0.04101 mmol) were added, in this order. This mixture was stirred at 70° C. for 21 h. This reaction mixture was then cooled to room temperature, diluted with 1:1 MeOH:DMSO (600 μL), filtered and purified by reverse phase HPLC (1-40% acetonitrile in water using HCl as a modifier) to give (3S,7R)-19-(2,6-dimethylphenyl)-5-(2-methoxyethyl)-2-oxa-15λ⁶-thia-5,9,16,18,21-pentaazatetracyclo[15.3.1.13,7.110,14]tricosa-1(21),10(22),11,13,17,19-hexaene-8,15,15-trione (hydrochloride salt) (1.9 mg, 18%) ESI-MS m/z calc. 537.2046, found 538.3 $(M+1)^+$; Retention time: 0.98 minutes; LC method A.

Example 6: Preparation of Compound 8

Step 1: 3-Methylbutyl (3S,7R)-19-(2,6-dimethylphenyl)-8,15,15-trioxo-2-oxa-15λ⁶-thia-5,9,16,18,21-pentaazatetracyclo[15.3.1.13,7.110,14]tricosa-1(21),10(22),11,13,17,19-hexaene-5-carboxylate (Compound 8)

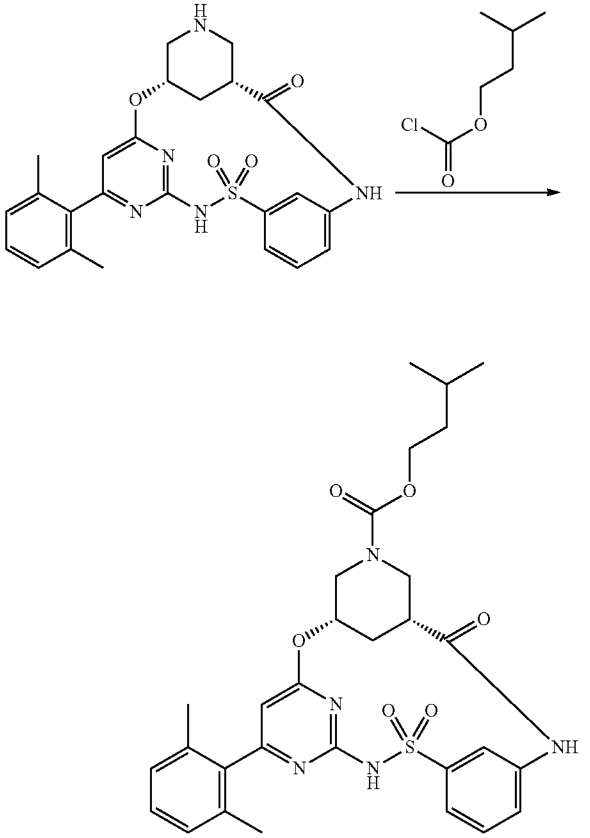

To a 3-mL vial, (3S,7R)-19-(2,6-dimethylphenyl)-2-oxa-15λ⁶-thia-5,9,16,18,21-pentaazatetracyclo[15.3.1.13,7.110,14]tricosa-1(20),10,12,14(22),17(21),18-hexaene-8,15,15-trione (8.0 mg, 0.01668 mmol), DCM (500 μL), TEA (50 μL, 0.3587 mmol) and 3-methylbutyl chloroformate (3.9 mg, 0.02590 mmol) were added in this order. This mixture was stirred at room temperature for 5 minutes, after which it was quenched with MeOH (200 μL), diluted with DMSO (200 μL), filtered and purified by reverse phase HPLC (1-99% acetonitrile in water using HCl as a modifier) to give 3-methylbutyl (3S,7R)-19-(2,6-dimethylphenyl)-8,15,15-trioxo-2-oxa-15λ⁶-thia-5,9,16,18,21-pentaazatetracyclo[15.3.1.13,7.110,14]tricosa-1(21),10(22),11,13,17,19-hexaene-5-carboxylate (3.2 mg, 32%) ESI-MS m/z calc. 593.23083, found 594.3 $(M+1)^+$; Retention time: 1.82 minutes; LC method A.

Example 7: Preparation of Compound 9

Step 1: (3S,7R)-5-Benzyl-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (Compound 9)

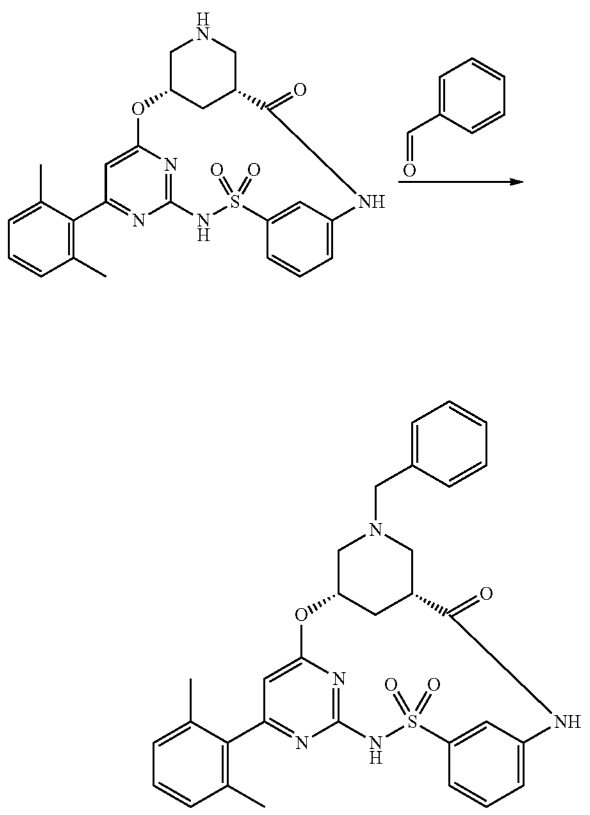

In a 3-mL vial, (3S,7R)-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (8.8 mg, 0.01835 mmol) was dissolved in acetic acid (600 μL), to which benzaldehyde (10 mg, 0.09423 mmol) and sodium triacetoxyborohydride (25 mg, 0.1180 mmol) were added. This reaction mixture was stirred at room temperature for 4 h, then at 50° C. for 16 h. It was then cooled to room temperature, diluted with MeOH (300 μL), filtered and purified by reverse phase HPLC (1-70% acetonitrile in water using HCl as a modifier) to give (3S,7R)-5-benzyl-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (hydrochloride salt) (4.1 mg, 37%); ESI-MS m/z calc. 569.20966, found 570.4 $(M+1)^+$; Retention time: 1.18 minutes; LC method A.

Example 8: Preparation of Compound 10

Step 1: (3S,7R)-5-cyclohexyl-19-(2,6-dimethylphenyl)-2-oxa-15λ$^6$-thia-5,9,16,18,21-pentaazatetracyclo[15.3.1.13,7.110,14]tricosa-1(21),10(22),11,13,17,19-hexaene-8,15,15-trione (Compound 10)

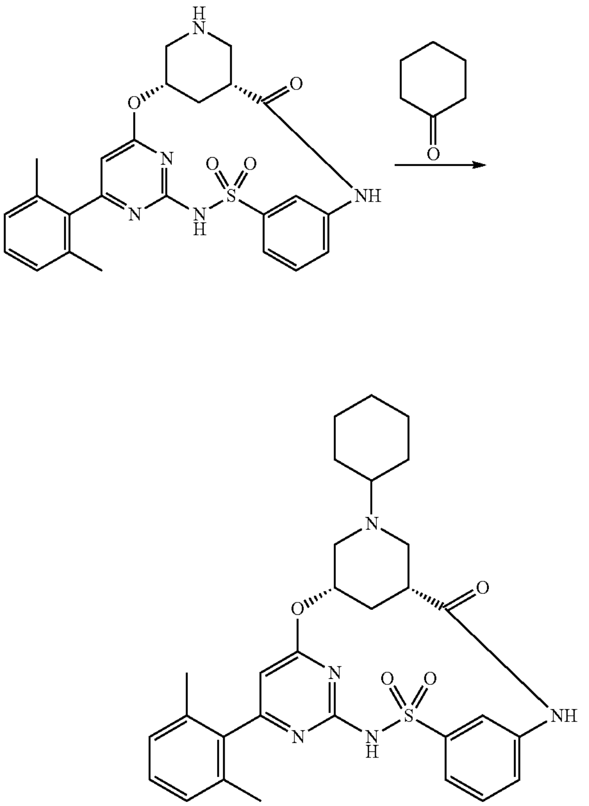

In a 3-mL vial equipped with a pressure-relief cap, (3S,7R)-19-(2,6-dimethylphenyl)-2-oxa-15λ$^6$-thia-5,9,16,18,21-pentaazatetracyclo[15.3.1.13,7.110,14]tricosa-1(20),10,12,14(22),17(21),18-hexaene-8,15,15-trione (12.0 mg, 0.02502 mmol) was mixed with EtOH (600 μL), to which $Ti(OiPr)_4$ (30 μL, 0.1016 mmol), cyclohexanone (10 μL, 0.09649 mmol) and sodium triacetoxyborohydride (30 mg, 0.1415 mmol) were added. This reaction mixture was stirred at room temperature for 2 h, then at 50° C. for 2 h, then at 100° C. for 2 h. It was then cooled to room temperature, diluted with DMSO (300 μL), filtered and purified by reverse phase HPLC (1-70% acetonitrile in water using HCl as a modifier) to give (3S,7R)-5-cyclohexyl-19-(2,6-dimethylphenyl)-2-oxa-15λ$^6$-thia-5,9,16,18,21-pentaazatetracyclo[15.3.1.13,7.110,14]tricosa-1(21),10(22),11,13,17,19-hexaene-8,15,15-trione (hydrochloride salt) (2.9 mg, 19%); ESI-MS m/z calc. 561.24097, found 562.3 $(M+1)^+$; Retention time: 1.19 minutes; LC method A.

Example 9: Preparation of Compound 11

Step 1: (3R,7S)-5-(3,3-Dimethylbutyl)-19-(2,6-dimethylphenyl)-2-oxa-$15\lambda^{6}$-thia-5,9,16,18,21-pentaazatetracyclo[15.3.1.13,7.110,14]tricosa-1(21),10(22),11,13,17,19-hexaene-8,15,15-trione (Compound 11)

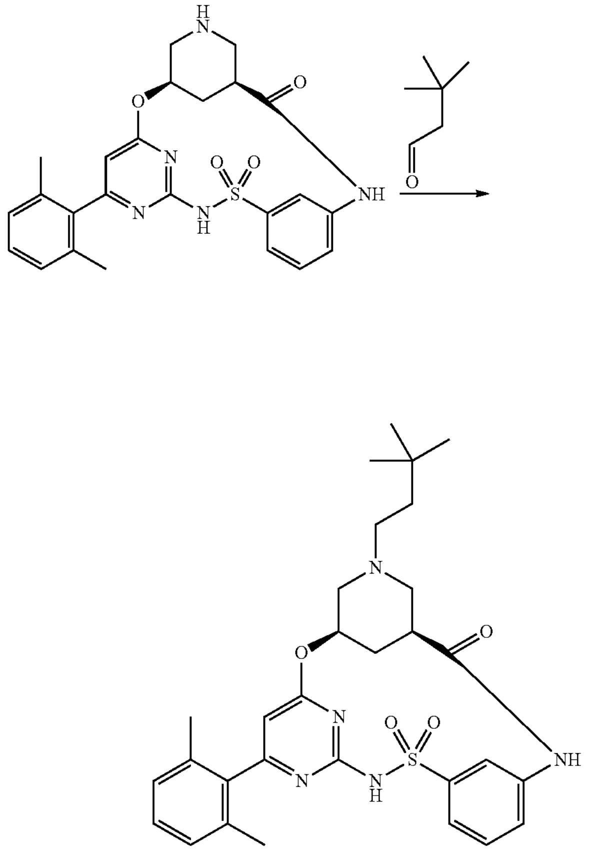

To a 3-mL vial, (3R,7S)-19-(2,6-dimethylphenyl)-2-oxa-$15\lambda^{6}$-thia-5,9,16,18,21-pentaazatetracyclo[15.3.1.13,7.110,14]tricosa-1(20),10,12,14(22),17(21),18-hexaene-8,15,15-trione (8.8 mg, 0.01835 mmol), acetic acid (500 μL), 3,3-dimethylbutanal (5.0 mg, 0.04992 mmol) and sodium triacetoxyborohydride (10 mg, 0.04718 mmol) were added, in this order. After standing at room temperature for 5 minutes, this mixture was diluted with MeOH (400 μL), filtered and purified by reverse phase HPLC (1-70% acetonitrile in water using HCl as a modifier) to give (3R,7S)-5-(3,3-dimethylbutyl)-19-(2,6-dimethylphenyl)-2-oxa-$15\lambda^{6}$-thia-5,9,16,18,21-pentaazatetracyclo[15.3.1.13,7.110,14]tricosa-1(21),10(22),11,13,17,19-hexaene-8,15,15-trione (hydrochloride salt) (6.3 mg, 57%) ESI-MS m/z calc. 563.25665, found 564.4 $(M+1)^+$; Retention time: 1.28 minutes; LC method A.

Example 10: Preparation of Compound 12

Step 1: (3S,7S)-5-(3,3-Dimethylbutyl)-19-(2,6-dimethylphenyl)-2-oxa-$15\lambda^{6}$-thia-5,9,16,18,21-pentaazatetracyclo[15.3.1.13,7.110,14]tricosa-1(21),10(22),11,13,17,19-hexaene-8,15,15-trione (Compound 12)

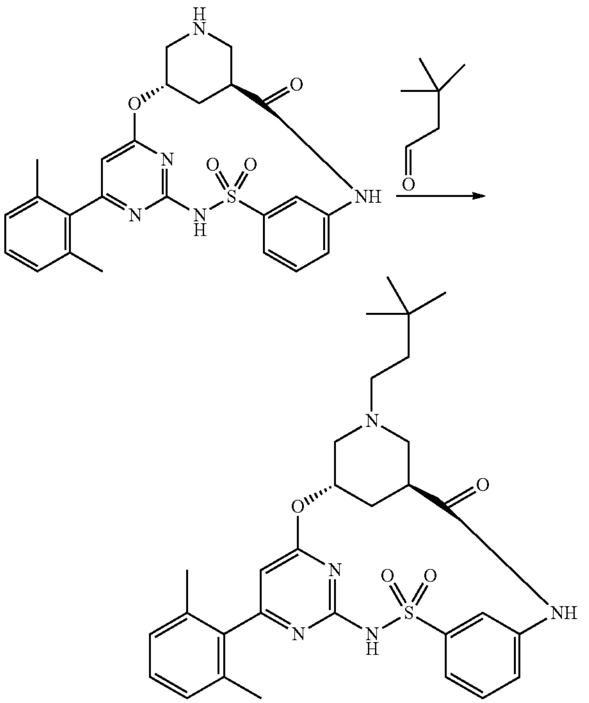

To a 3-mL vial, (3S,7S)-19-(2,6-dimethylphenyl)-2-oxa-$15\lambda^{6}$-thia-5,9,16,18,21-pentaazatetracyclo[15.3.1.13,7.110,14]tricosa-1(21),10(22),11,13,17,19-hexaene-8,15,15-trione (trifluoroacetate salt) (11 mg, 0.01853 mmol), acetic acid (500 μL), 3,3-dimethylbutanal (5.0 mg, 0.04992 mmol) and sodium triacetoxyborohydride (10 mg, 0.04718 mmol) were added, in this order. After standing at room temperature for 10 minutes, this mixture was diluted with MeOH (400 μL), filtered and purified by reverse phase HPLC (1-70% acetonitrile in water using HCl as a modifier) to give (3S,7S)-5-(3,3-dimethylbutyl)-19-(2,6-dimethylphenyl)-2-oxa-$15\lambda^{6}$-thia-5,9,16,18,21-pentaazatetracyclo[15.3.1.13,7.110,14]tricosa-1(21),10(22),11,13,17,19-hexaene-8,15,15-trione (hydrochloride salt) (1.2 mg, 10%) ESI-MS m/z calc. 563.25665, found 564.3 $(M+1)^+$; Retention time: 1.25 minutes; LC method A.

Example 11: Preparation of Compound 13

Step 1: 2,4-Dichloro-6-(2,6-dimethylphenyl)pyrimidine

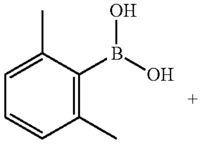

-continued

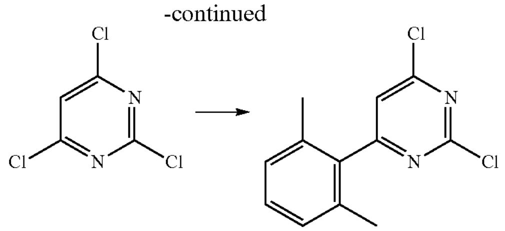

(2,6-Dimethylphenyl)boronic acid (102.06 g, 666.87 mmol) and 2,4,6-trichloropyrimidine (150.68 g, 94.470 mL, 805.06 mmol) was dissolved in a mixture of EtOH (870 mL) and Toluene (870 mL). To the previous solution was added an aqueous sodium bicarbonate (870 mL of 2 M, 1.7400 mol). The reaction mixture was purged with nitrogen, and then Pd(dppf)$Cl_2$ (22.10 g, 28.693 mmol) was added. The reaction was stirred at 80° C. for 16 h. The mixture was cooled to room temperature and the layers were separated. The aqueous layer was extracted with EtOAc (3×500 mL) and the combined organic layers were washed with saturated aqueous sodium chloride (500 mL), dried over anhydrous sodium sulfate, filtered, and concentrated under vacuum. The crude product was purified by silica gel chromatography (5% EtOAc in hexanes) to give a dark peach oil, 2,4-dichloro-6-(2,6-dimethylphenyl)pyrimidine (161.18 g, 49%) ESI-MS m/z calc. 252.0221, found 253.0 $(M+1)^+$; Retention time: 6.16 minutes; LC method S.

Step 2: O1-tert-Butyl O3-methyl 5-[2-chloro-6-(2,6-dimethylphenyl)pyrimidin-4-yl]oxypiperidine-1,3-dicarboxylate

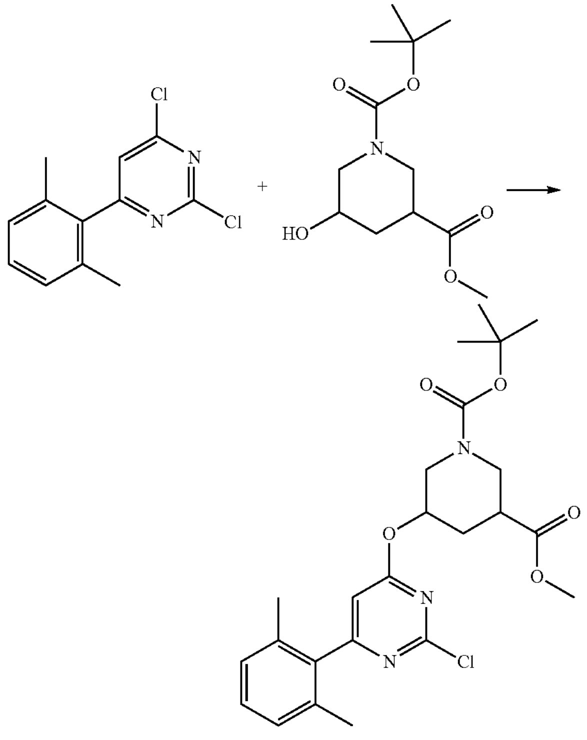

In a 50-mL round-bottomed flask, O1-tert-butyl O3-methyl 5-hydroxypiperidine-1,3-dicarboxylate (2.0191 g, 7.787 mmol) was dissolved in NMP (20 mL) and cooled in an dry ice-brine (−15° C.) bath. To this cooled solution, 60% NaH (0.3156 g, 7.891 mmol) was added in one portion, and the resulting mixture was stirred at −15° C. for 30 minutes. Then, 2,4-dichloro-6-(2,6-dimethylphenyl)pyrimidine (1.6438 g, 6.494 mmol) was added in one portion, and the reaction mixture was stirred at −15° C. for 2 h, and then allowed to warm to room temperature; this mixture was stirred for 18 h. The reaction was quenched with saturated aqueous ammonium chloride solution (20 mL), diluted with water (20 mL), and extracted with ethyl acetate (3×40 mL). The combined organic extracts were washed with water (60 mL) and saturated aqueous sodium chloride solution (60 mL), then dried over sodium sulfate, filtered, and evaporated in vacuo. This crude product was purified by silica gel chromatography (80 g of silica, 0 to 30% gradient of ethyl acetate/hexanes) to give the desired product, O1-tert-butyl O3-methyl 5-[2-chloro-6-(2,6-dimethylphenyl)pyrimidin-4-yl]oxypiperidine-1,3-dicarboxylate (1.9752 g, 64%) ESI-MS m/z calc. 475.1874, found 476.3 $(M+1)^+$; Retention time: 2.14 minutes; LC method A.

Step 3: tert-Butyl 19-(2,6-dimethylphenyl)-8,15,15-trioxo-2-oxa-15$\lambda^6$-thia-5,9,16,18,21,22-hexaazatetracyclo[15.3.1.13,7.110,14]tricosa-1(21),10,12,14(22),17,19-hexaene-5-carboxylate (Compound 13)

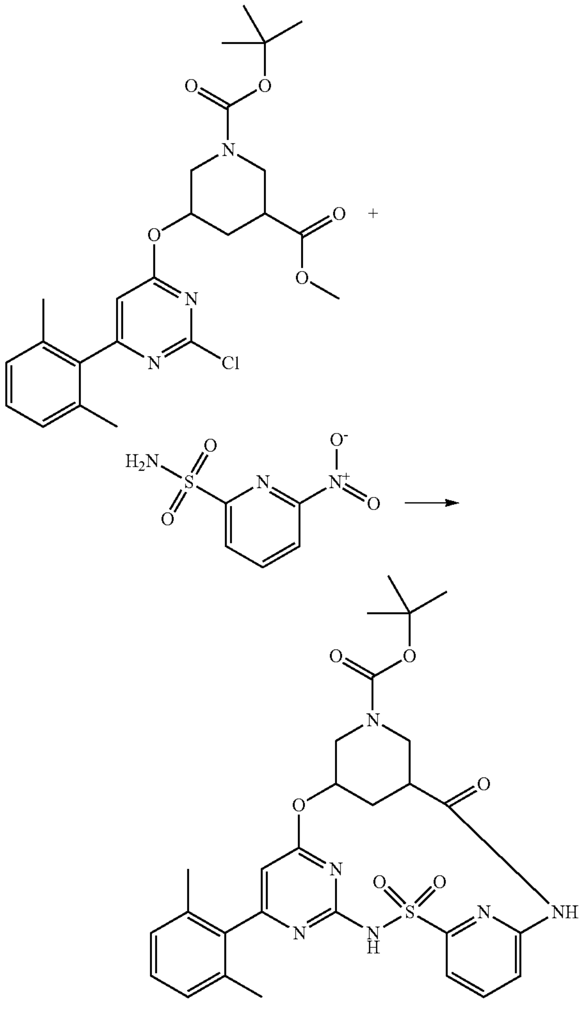

Stage 1: A dioxane (8 mL) mixture of O1-tert-butyl O3-methyl 5-[2-chloro-6-(2,6-dimethylphenyl)pyrimidin-4-yl]oxypiperidine-1,3-dicarboxylate (450 mg, 0.9454 mmol), 6-nitropyridine-2-sulfonamide (251.2 mg, 1.236 mmol), sodium tert-butoxide (280.3 mg, 2.917 mmol), and tBuX-Phos-Pd-G1 (230.1 mg, 0.3533 mmol) was sparged with nitrogen for 5 minutes and then stirred at room temperature for 16 hours. The reaction mixture was diluted with HCl (3.5 mL of 1 M, 3.500 mmol) and ethyl acetate (20 mL) and the organic layer was separated and washed with water (5 mL) followed by brine (5 mL). The organic layer was dried over anhydrous sodium sulfate, filtered, and concentrated in vacuo to give O1-tert-butyl O3-methyl 5-[6-(2,6-dimethylphenyl)-2-[(6-nitro-2-pyridyl)sulfonylamino]pyrimidin-4-yl]oxypiperidine-1,3-dicarboxylate (323 mg, 53%); ESI-MS m/z calc. 642.2108, found 643.4 $(M+1)^+$; Retention time: 1.47 minutes; LC method A. This material was used in the next stage without further purification.

Stage 2: O1-tert-butyl O3-methyl 5-[6-(2,6-dimethylphenyl)-2-[(6-nitro-2-pyridyl)sulfonylamino]pyrimidin-4-yl]oxypiperidine-1,3-dicarboxylate (323 mg, 53%) from Stage 1 was dissolved in THF (4 mL) and water (6.5 mL) and lithium hydroxide monohydrate (74.6 mg, 1.778 mmol) was added to the mixture. The reaction mixture was stirred at room temperature for 1 hour and then diluted with diethyl ether (15 mL). The aqueous layer was separated and diluted with ethyl acetate (20 mL) and then HCl (2.0 mL of 1 M, 2.000 mmol) was added to it. The two layers were mixed and then separated. The organic layer was washed with water (5 mL) and then brine (5 mL). The organic layer was dried over anhydrous sodium sulfate, filtered, and concentrated in vacuo to give 1-tert-butoxycarbonyl-5-[6-(2,6-dimethylphenyl)-2-[(6-nitro-2-pyridyl)sulfonylamino]pyrimidin-4-yl]oxy-piperidine-3-carboxylic acid (115 mg, 19%) ESI-MS m/z calc. 628.1951, found 629.2 $(M+1)^+$; Retention time: 0.61 minutes; LC method D.

Stage 3: In a 50 mL round-bottomed flask, 1-tert-butoxycarbonyl-5-[6-(2,6-dimethylphenyl)-2-[(6-nitro-2-pyridyl)sulfonylamino]pyrimidin-4-yl]oxy-piperidine-3-carboxylic acid (115 mg, 19%) from Stage 2 was dissolved in EtOH (10 mL). This solution was sparged with a balloon of hydrogen gas for 5 minutes. The cap was briefly removed, and dihydroxypalladium (43.2 mg, 0.03076 mmol) was added. This reaction mixture was stirred under hydrogen (161.3 mg, ∞ L, 80 mmol) at room temperature for 14 h then at 60° C. for 4 h, after which it was cooled to room temperature, filtered through Celite, and rinsed with methanol (20 mL). This solution was evaporated in vacuo to give 5-[2-[(6-amino-2-pyridyl)sulfonylamino]-6-(2,6-dimethylphenyl)pyrimidin-4-yl]oxy-1-tert-butoxycarbonyl-piperidine-3-carboxylic acid (106.9 mg, 19%) ESI-MS m/z calc. 598.22095, found 599.3 $(M+1)^+$; Retention time: 1.30 minutes and 1.34 minutes as a mixture of two diastereomers; LC method A. This product was not purified further at this stage.

Stage 4: The product from Stage 3, 5-[2-[(6-amino-2-pyridyl)sulfonylamino]-6-(2,6-dimethylphenyl)pyrimidin-4-yl]oxy-1-tert-butoxycarbonyl-piperidine-3-carboxylic acid (106.9 mg, 19%) was dissolved in DMF (4 mL) and treated with DIPEA (400 µL, 2.296 mmol) and 1-diphenylphosphoryloxy-2,3,4,5,6-pentafluoro-benzene (150.1 mg, 0.3906 mmol). This mixture was stirred at room temperature for 10 minutes, after which it was quenched with 0.5 N HCl (5 mL). This mixture was extracted with ethyl acetate (3×5 mL). The combined organic extracts were washed with water (10 mL) and saturated aqueous sodium chloride solution (10 mL), then dried over anhydrous sodium sulfate, filtered, and concentrated in vacuo. This crude product was purified by silica gel chromatography (4 g of silica, 0 to 60% gradient of ethyl acetate/hexanes) to give a white foam, the pentafluorophenyl ester intermediate O1-tert-butyl O3-(2,3,4,5,6-pentafluorophenyl) 5-[2-[(6-amino-2-pyridyl)sulfonylamino]-6-(2,6-dimethylphenyl)pyrimidin-4-yl]oxypiperidine-1,3-dicarboxylate (77.5 mg, 11%) as a mixture of two diastereomers; ESI-MS m/z calc. 764.20514, found 765.3 $(M+1)^+$; Retention time: 1.89 minutes; LC method A.

Stage 5: The product from Stage 4, O1-tert-butyl O3-(2,3,4,5,6-pentafluorophenyl) 5-[2-[(6-amino-2-pyridyl)sulfonylamino]-6-(2,6-dimethylphenyl)pyrimidin-4-yl]oxypiperidine-1,3-dicarboxylate (77.5 mg, 11%) was dissolved in NMP (10 mL) and heated at 140° C. for 5 h. The solution was then cooled to room temperature and mixed with water (10 mL). The mixture was extracted with ethyl acetate (3×10 mL). The combined organic extracts were washed with water (2nd brine (20 mL), then dried over sodium sulfate, filtered, and evaporated in vacuo. This crude product was purified by silica gel chromatography (4 g of silica, 0-70% gradient of ethyl acetate/hexanes) to give 13.8 mg of the less polar diastereomer of the macrocyclic products, 12.0 mg of the more polar diastereomer of the macrocyclic products. The desired products were yellow oils, so they were filtered, and purified by reverse phase HPLC (1-70% acetonitrile in water using HCl as modifier) to give a pure, white solid, less polar diastereomer tert-butyl 19-(2,6-dimethylphenyl)-8,15,15-trioxo-2-oxa-15$\lambda^6$-thia-5,9,16,18,21,22-hexaazatetracyclo[15.3.1.13,7.110,14]tricosa-1(21),10,12,14(22),17,19-hexaene-5-carboxylate (4.4 mg, 1%) ESI-MS m/z calc. 580.2104, found 581.3 $(M+1)^+$; Retention time: 1.6 minutes; LC method A.

Example 12: Preparation of Compound 14

Step 1: tert-Butyl 19-(2,6-dimethylphenyl)-8,15,15-trioxo-2-oxa-15$\lambda^6$-thia-5,9,12,16,18,21-hexaazatetracyclo[15.3.1.13,7.110,14]tricosa-1(21),10,12,14(22),17,19-hexaene-5-carboxylate (Compound 14)

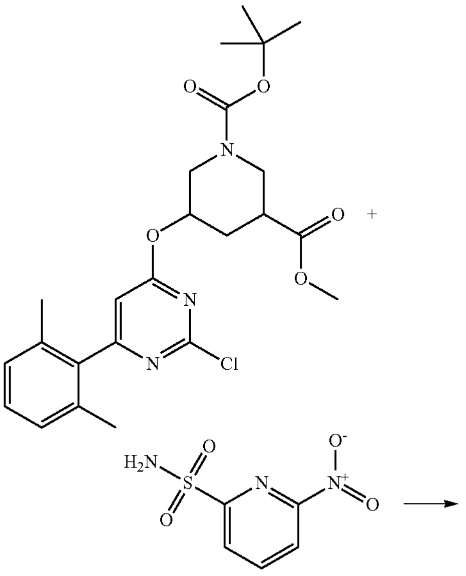

-continued

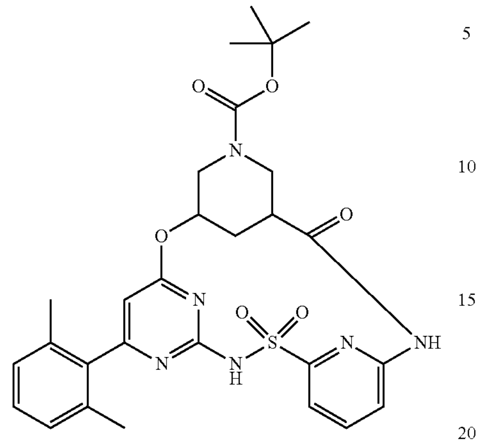

Stage 1: A dioxane (17 mL) mixture of O1-tert-butyl O3-methyl 5-[2-chloro-6-(2,6-dimethylphenyl)pyrimidin-4-yl]oxypiperidine-1,3-dicarboxylate (401.5 mg, 0.8435 mmol), 5-nitropyridine-3-sulfonamide (191.2 mg, 0.9411 mmol), cesium carbonate (823.7 mg, 2.528 mmol), and tBuXPhos-Pd-G1 (237.1 mg, 0.3641 mmol) was sparged with nitrogen for 15 minutes and then stirred at 50° C. for 16 hours under nitrogen purge. The reaction mixture was diluted with HCl (3 mL of 1 M, 3.000 mmol) and the organic layer was separated and washed with water (5 mL) followed by brine (5 mL). The organic layer was dried over anhydrous sodium sulfate, filtered, and concentrated in vacuo to give O1-tert-butyl O3-methyl 5-[6-(2,6-dimethylphenyl)-2-[(5-nitro-3-pyridyl)sulfonylamino]pyrimidin-4-yl]oxypiperidine-1,3-dicarboxylate (320 mg, 59%) ESI-MS m/z calc. 642.2108, found 643.3 $(M+1)^+$; Retention time: 1.85 minutes; LC method A. This material was used in the next step without further purification.

Stage 2: O1-tert-Butyl O3-methyl 5-[6-(2,6-dimethylphenyl)-2-[(5-nitro-3-pyridyl)sulfonylamino]pyrimidin-4-yl]oxypiperidine-1,3-dicarboxylate (320 mg, 59%) from Stage 1 was dissolved in THF (4 mL) and water (6.5 mL) and treated with lithium hydroxide monohydrate (75.2 mg, 1.792 mmol). The reaction mixture was stirred at room temperature for 1 hour and then HCl (6 mL of 0.5 M, 3.000 mmol) was added, and the reaction mixture was diluted with ethyl acetate (15 mL). The two layers were mixed and then separated. The organic layer was washed with water (5 mL) and then brine (5 mL). The organic layer was dried over anhydrous sodium sulfate, filtered, and concentrated in vacuo to give 1-tert-butoxycarbonyl-5-[6-(2,6-dimethylphenyl)-2-[(5-nitro-3-pyridyl)sulfonylamino]pyrimidin-4-yl]oxy-piperidine-3-carboxylic acid (192 mg, 36%) ESI-MS m/z calc. 628.1951, found 629.2 $(M+1)^+$; Retention time: 1.67 minutes; LC method A. This material was used without further purification.

Stage 3: In a 50 mL round-bottomed flask, 1-tert-butoxycarbonyl-5-[6-(2,6-dimethylphenyl)-2-[(5-nitro-3-pyridyl)sulfonylamino]pyrimidin-4-yl]oxy-piperidine-3-carboxylic acid (192 mg, 36%) from Stage 2 above was dissolved in EtOH (10 mL). This solution was sparged with a balloon of hydrogen gas for 5 minutes. The cap was briefly removed, and dihydroxypalladium (56.2 mg, 0.08004 mmol) was added. This reaction mixture was stirred under hydrogen balloon at room temperature for 5 hours at 60° C., after which it was cooled to room temperature, filtered through Celite and rinsed with methanol (20 mL). This solution was evaporated in vacuo to give 5-[2-[(5-amino-3-pyridyl)sulfonylamino]-6-(2,6-dimethylphenyl)pyrimidin-4-yl]oxy-1-tert-butoxycarbonyl-piperidine-3-carboxylic acid (121.7 mg, 24%) ESI-MS m/z calc. 598.22095, found 599.2 $(M+1)^+$; Retention time: 1.35 minutes; LC method A. This product was not purified at this stage.

Stage 4: The product from Stage 3, 5-[2-[(5-amino-3-pyridyl)sulfonylamino]-6-(2,6-dimethylphenyl)pyrimidin-4-yl]oxy-1-tert-butoxycarbonyl-piperidine-3-carboxylic acid (121.7 mg, 24%) was dissolved in DMF (4 mL) and treated with DIPEA (450 μL, 2.584 mmol) and 1-diphenylphosphoryloxy-2,3,4,5,6-pentafluoro-benzene (180.7 mg, 0.4703 mmol). This mixture was stirred at room temperature for 10 minutes, after which it was quenched with 0.5 N HCl (5 mL). This mixture was extracted with ethyl acetate (3×5 mL). The combined organic extracts were washed with water (10 mL) and then brine (5 mL), then dried over anhydrous sodium sulfate, filtered, and concentrated in vacuo. This crude product was purified by silica gel chromatography (4 g of silica, 0-60% gradient of ethyl acetate/hexanes) to give the pentafluorophenyl ester intermediate, O1-tert-butyl O3-(2,3,4,5,6-pentafluorophenyl) 5-[2-[(5-amino-3-pyridyl)sulfonylamino]-6-(2,6-dimethylphenyl)pyrimidin-4-yl]oxypiperidine-1,3-dicarboxylate (92.7 mg, 14%); ESI-MS m/z calc. 764.20514, found 765.3 $(M+1)^+$; Retention time: 1.84 minutes; LC method A.

Stage 5: The product from Stage 4, O1-tert-butyl O3-(2,3,4,5,6-pentafluorophenyl) 5-[2-[(5-amino-3-pyridyl)sulfonylamino]-6-(2,6-dimethylphenyl)pyrimidin-4-yl]oxypiperidine-1,3-dicarboxylate (92.7 mg, 14%) was dissolved in NMP (10 mL) and heated at 140° C. for 5 h. The solution was then cooled to room temperature. The mixture was filtered and purified by reverse-phase HPLC for chromatography using a 15 minute gradient of 1% MeCN in water to 70% MeCN with HCl modifier to afford the desired product as a solution in MeCN and water. This solution was extracted with ethyl acetate (3×10 mL) and the organic extracts were washed with water (3 mL) and then brine (3 mL). The organic layer was dried over anhydrous sodium sulfate, filtered, and concentrated in vacuo to give tert-butyl 19-(2,6-dimethylphenyl)-8,15,15-trioxo-2-oxa-15$\lambda^6$-thia-5,9,12,16,18,21-hexaazatetracyclo[15.3.1.13,7.110,14]tricosa-1(21),10,12,14(22),17,19-hexaene-5-carboxylate (3.1 mg, 1%) ESI-MS m/z calc. 580.2104, found 581.31 $(M+1)^+$; Retention time: 1.68 minutes; LC method A. The product was one diastereomer but was a racemic mixture.

Example 13: Preparation of Compound 15

Step 1: 19-(2,6-Dimethylphenyl)-2-oxa-15λ$^6$-thia-5,9,16,18,21,22-hexaazatetracyclo[15.3.1.13,7.110,14]tricosa-1(21),10,12,14(22),17,19-hexaene-8,15,15-trione

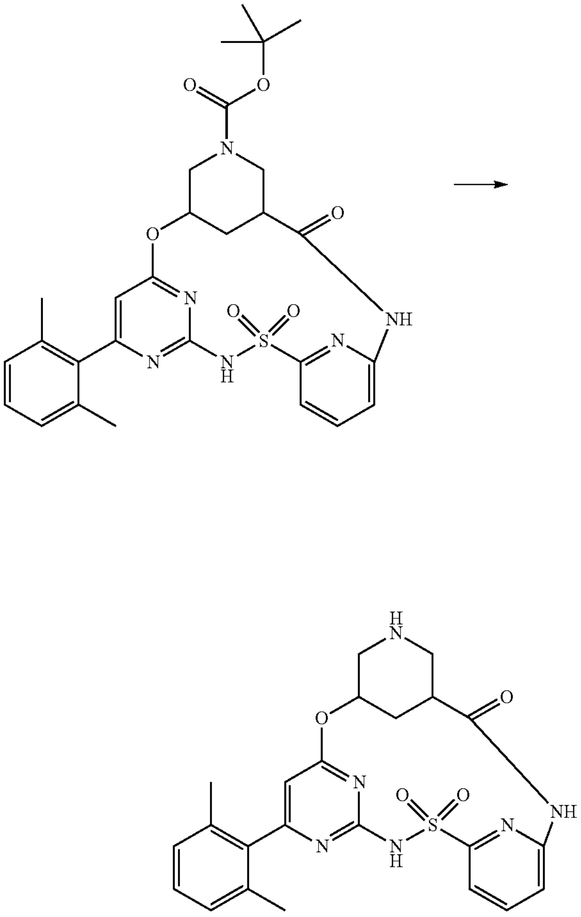

tert-Butyl 19-(2,6-dimethylphenyl)-8,15,15-trioxo-2-oxa-15λ$^6$-thia-5,9,16,18,21,22-hexaazatetracyclo[15.3.1.13,7.110,14]tricosa-1(21),10,12,14(22),17,19-hexaene-5-carboxylate (12.1 mg, 13%) was taken up in DCM (1.5 mL) and treated with TFA (100 μL, 1.298 mmol). The reaction mixture was stirred at room temperature for 1 hour and then concentrated in vacuo to give 19-(2,6-dimethylphenyl)-2-oxa-15λ$^6$-thia-5,9,16,18,21,22-hexaazatetracyclo[15.3.1.13,7.110,14]tricosa-1(21),10,12,14(22),17,19-hexaene-8,15,15-trione (6.2 mg, 8%) ESI-MS m/z calc. 480.15796, found 481.3 $(M+1)^+$; Retention time: 0.38 minutes; LC method D.

Step 2: 5-(3-Cyclopropyl-3-methylbutyl)-19-(2,6-dimethylphenyl)-2-oxa-15λ$^6$-thia-5,9,16,18,21,22-hexaazatetracyclo[15.3.1.13,7.110,14]tricosa-1(21),10,12,14(22),17,19-hexaene-8,15,15-trione (Compound 15)

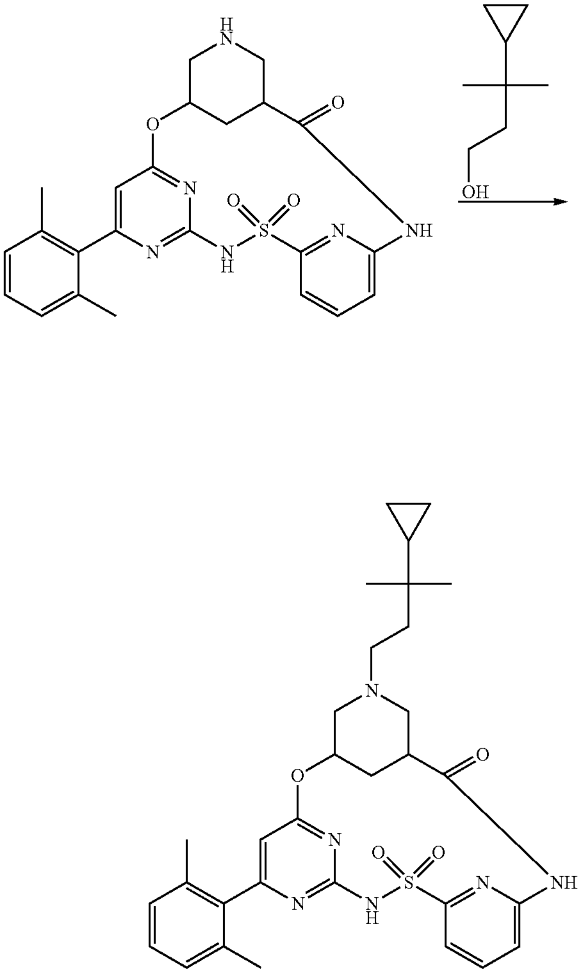

In a 2 mL vial (vial #1), 3-cyclopropyl-3-methyl-butan-1-ol (6.3 mg, 0.04914 mmol) was treated with DCM (0.2 mL) and Dess-Martin periodinane (22.5 mg, 0.05305 mmol), and this mixture was allowed to stand at room temperature for 30 minutes. Over this time, a white precipitate formed at the bottom of the vial. In a new 2-mL vial (vial #2), 19-(2,6-dimethylphenyl)-2-oxa-15λ$^6$-thia-5,9,16,18,21,22-hexaazatetracyclo[15.3.1.13,7.110,14]tricosa-1(21),10,12,14(22),17,19-hexaene-8,15,15-trione (4.4 mg, 0.009156 mmol) was dissolved in acetic acid (300 μL, 5.275 mmol), to which the soluble component of vial #1 was added, followed by sodium triacetoxyborohydride (10.6 mg, 0.05001 mmol). This reaction mixture was allowed to stand at room temperature for 5 minutes. The solutions were filtered and the filtrate dissolved in 0.7 mL DMSO, and purified by reverse-phase HPLC using a 15 minute gradient of 1% MeCN in water to 99% MeCN with ammonium formate modifier to give 5-(3-cyclopropyl-3-methylbutyl)-19-(2,6-dimethylphenyl)-2-oxa-$15\lambda^6$-thia-5,9,16,18,21,22-hexaazatetracyclo[15.3.1.13,7.110,14]tricosa-1(21),10,12,14(22),17,19-hexaene-8,15,15-trione (Formic Acid (1) (2.8 mg, 48%) ESI-MS m/z calc. 590.2675, found 591.36 $(M+1)^+$; Retention time: 1.41 minutes; LC method A.

Example 14: Preparation of Compound 16 and Compound 17

Step 1: tert-Butyl 19-(2,6-dimethylphenyl)-8,15,15-trioxo-2-oxa-$15\lambda^6$-thia-5,9,16,18,21,22-hexaazatetracyclo[15.3.1.13,7.110,14]tricosa-1(21),10,12,14(22),17,19-hexaene-5-carboxylate (Compound 16), and tert-butyl 19-(2,6-dimethylphenyl)-8,15,15-trioxo-2-oxa-$15\lambda^6$-thia-5,9,16,18,21,22-hexaazatetracyclo[15.3.1.13,7.110,14]tricosa-1(21),10,12,14(22),17,19-hexaene-5-carboxylate (Compound 17)

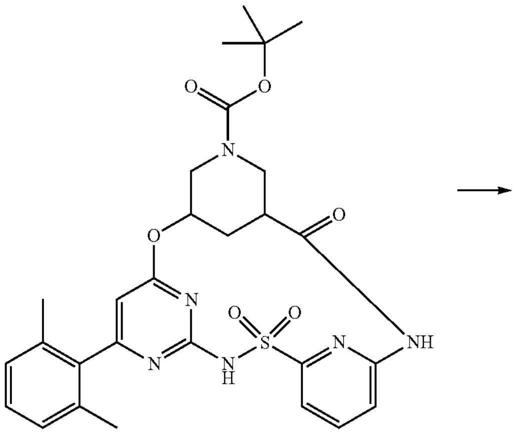

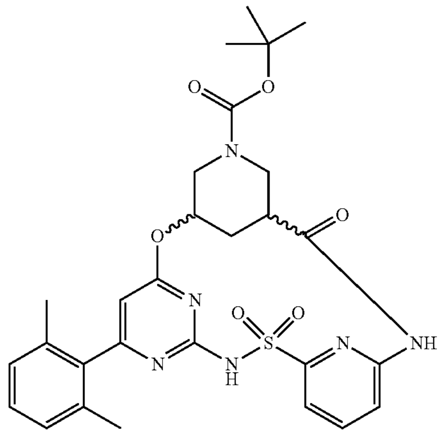

Peak 1

+

-continued

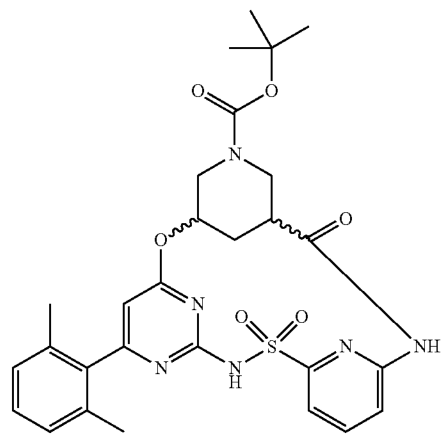

Peak 2 tert-Butyl 19-(2,6-dimethylphenyl)-8,15,15-trioxo-2-oxa-$15\lambda^6$-thia-5,9,16,18,21,22-hexaazatetracyclo[15.3.1.13,7.110,14]tricosa-1(21),10,12,14(22),17,19-hexaene-5-carboxylate (200 mg, 0.3444 mmol) was prepared purified by chiral SFC [ChiralCel OD-H column (250×21.2 mm, 5 μm particle size), with a mobile phase of 30% MeOH (+20 mM $NH_3$)+70% $CO_2$, a flow rate of 70 mL/min, an injection volume of 500 μL, and a pressure of 100 bar]. This gave: Peak 1, tert-butyl 19-(2,6-dimethylphenyl)-8,15,15-trioxo-2-oxa-$15\lambda^6$-thia-5,9,16,18,21,22-hexaazatetracyclo[15.3.1.13,7.110,14]tricosa-1(21),10,12,14(22),17,19-hexaene-5-carboxylate (5.3 mg, 2%) ESI-MS m/z calc. 580.2104, found 581.28 $(M+1)^+$; Retention time: 1.73 minutes; LC method A; and peak 2, tert-butyl 19-(2,6-dimethylphenyl)-8,15,15-trioxo-2-oxa-$15\lambda^6$-thia-5,9,16,18,21,22-hexaazatetracyclo[15.3.1.13,7.110,14]tricosa-1(21),10,12,14(22),17,19-hexaene-5-carboxylate (4.8 mg, 2%) ESI-MS m/z calc. 580.2104, found 581.24 $(M+1)^+$; Retention time: 1.75 minutes; LC method A.

Example 15: Characterization of Compounds 18-52

The compounds in the following tables were prepared in a manner analogous to that described above using commercially available reagents and intermediates described herein.

TABLE 3
| Compound Number | Structure | LCMS Rt (min) | Calc. Mass | M + 1 | LCMS Method |
|---|---|---|---|---|---|
| 18 | 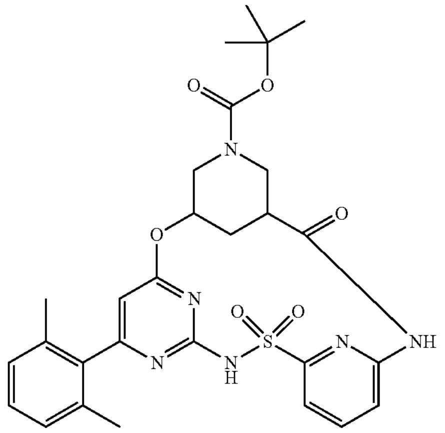 [SMILES: Cc1cccc(C)c1-c1cc2nc(n1)NS(=O)(=O)c1cccc(n1)NC(=O)C1CC(CN(C(=O)OC(C)(C)C)C1)O2] | 1.62 | 580.21 | 581.28 | A |
| 19 | 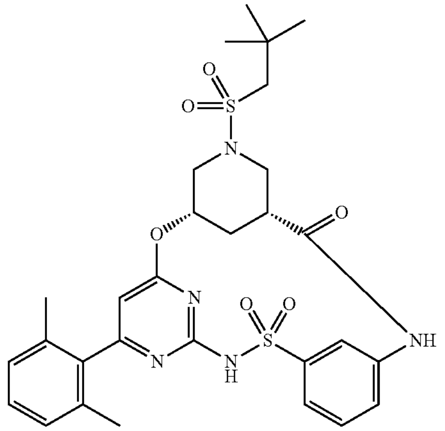 [SMILES: Cc1cccc(C)c1-c1cc2nc(n1)NS(=O)(=O)c1cccc(c1)NC(=O)[C@@H]1C[C@@H](CN(S(=O)(=O)CC(C)(C)C)C1)O2] | 1.69 | 613.203 | 614.4 | A |
| 20 | 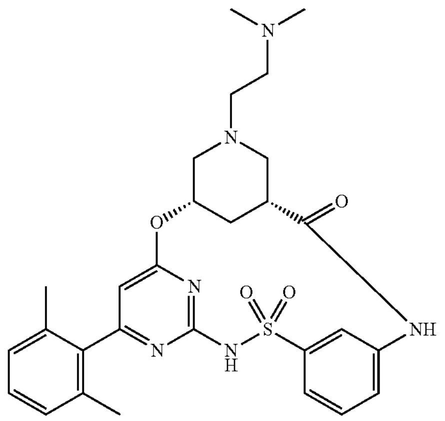 [SMILES: Cc1cccc(C)c1-c1cc2nc(n1)NS(=O)(=O)c1cccc(c1)NC(=O)[C@@H]1C[C@@H](CN(CCN(C)C)C1)O2] | 0.97 | 550.236 | 551.4 | A |

TABLE 3-continued
| Compound Number | Structure | LCMS Rt (min) | Calc. Mass | M + 1 | LCMS Method |
|---|---|---|---|---|---|
| 21 | 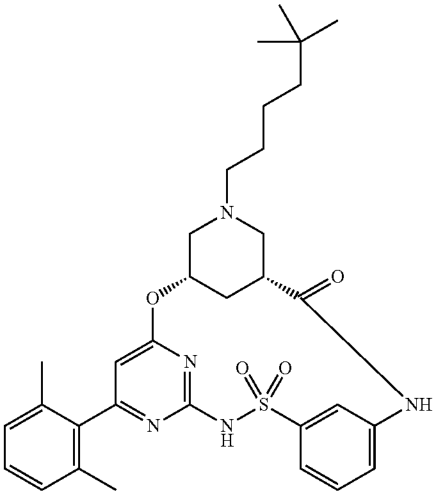 [SMILES: Cc1cccc(C)c1-c1cc2nc(n1)NS(=O)(=O)c1cccc(c1)NC(=O)[C@@H]1C[C@@H](CN(CCCCC(C)(C)C)C1)O2] | 1.48 | 591.288 | 592.4 | A |
| 22 | 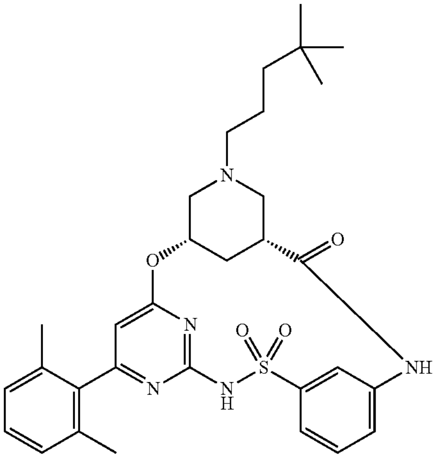 [SMILES: Cc1cccc(C)c1-c1cc2nc(n1)NS(=O)(=O)c1cccc(c1)NC(=O)[C@@H]1C[C@@H](CN(CCCC(C)(C)C)C1)O2] | 1.38 | 577.272 | 578.3 | A |
| 23 | 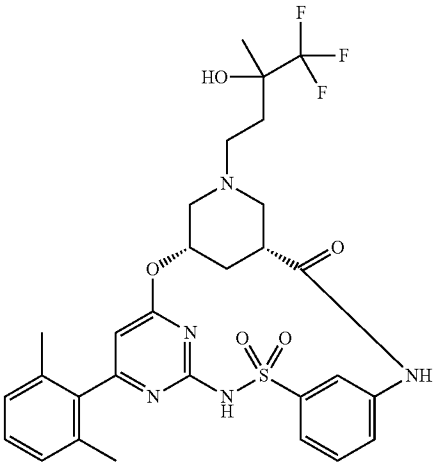 [SMILES: Cc1cccc(C)c1-c1cc2nc(n1)NS(=O)(=O)c1cccc(c1)NC(=O)[C@@H]1C[C@@H](CN(CCC(C)(O)C(F)(F)F)C1)O2] | 1.12 | 619.208 | 620.3 | A |

TABLE 3-continued
| Compound Number | Structure | LCMS Rt (min) | Calc. Mass | M + 1 | LCMS Method |
|---|---|---|---|---|---|
| 24 | 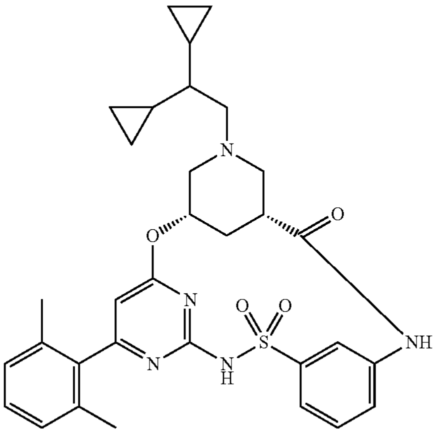 [SMILES: Cc1cccc(C)c1-c1cc2nc(n1)NS(=O)(=O)c1cccc(c1)NC(=O)[C@@H]1C[C@@H](CN(CC(C3CC3)C3CC3)C1)O2] | 1.29 | 587.257 | 588.4 | A |
| 25 | 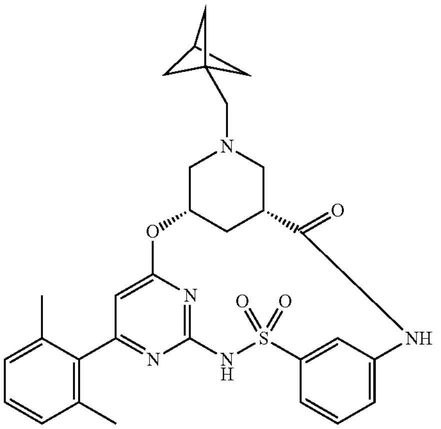 [SMILES: Cc1cccc(C)c1-c1cc2nc(n1)NS(=O)(=O)c1cccc(c1)NC(=O)[C@@H]1C[C@@H](CN(CC34CC(C3)C4)C1)O2] | 1.16 | 559.225 | 560.4 | A |
| 26 | 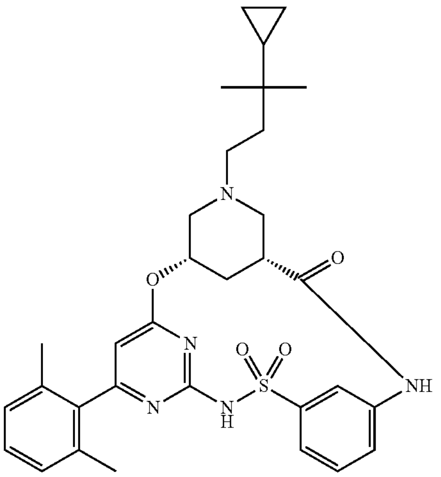 [SMILES: Cc1cccc(C)c1-c1cc2nc(n1)NS(=O)(=O)c1cccc(c1)NC(=O)[C@@H]1C[C@@H](CN(CCC(C)(C)C3CC3)C1)O2] | 1.37 | 589.272 | 590.4 | A |

TABLE 3-continued
| Compound Number | Structure | LCMS Rt (min) | Calc. Mass | M + 1 | LCMS Method |
|---|---|---|---|---|---|
| 27 | 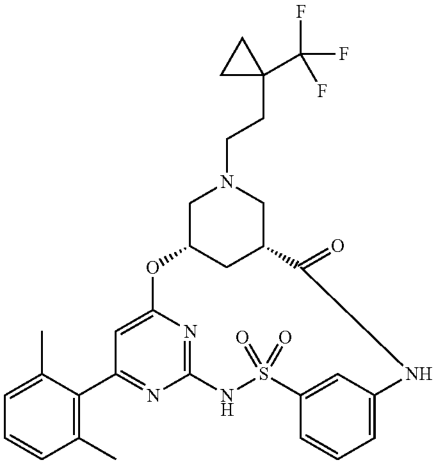 [SMILES: Cc1cccc(C)c1-c1cc2nc(n1)NS(=O)(=O)c1cccc(c1)NC(=O)[C@@H]1C[C@@H](CN(CCC3(C(F)(F)F)CC3)C1)O2] | 1.27 | 615.213 | 616.3 | A |
| 28 | 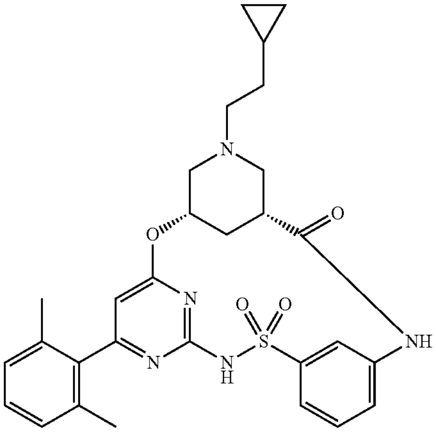 [SMILES: Cc1cccc(C)c1-c1cc2nc(n1)NS(=O)(=O)c1cccc(c1)NC(=O)[C@@H]1C[C@@H](CN(CCC3CC3)C1)O2] | 1.13 | 547.225 | 548.4 | A |
| 29 | 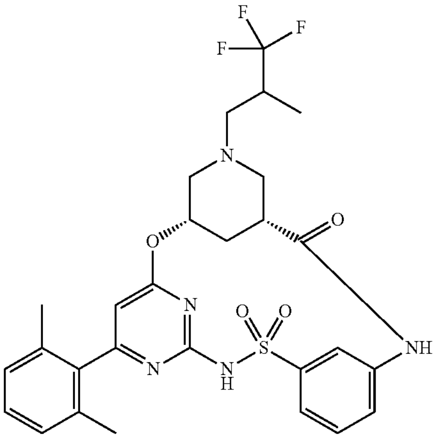 [SMILES: Cc1cccc(C)c1-c1cc2nc(n1)NS(=O)(=O)c1cccc(c1)NC(=O)[C@@H]1C[C@@H](CN(CC(C)C(F)(F)F)C1)O2] | 1.36 | 589.197 | 590.3 | A |

TABLE 3-continued
| Compound Number | Structure | LCMS Rt (min) | Calc. Mass | M + 1 | LCMS Method |
|---|---|---|---|---|---|
| 30 | 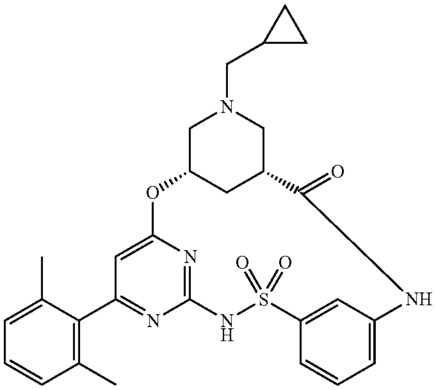 [SMILES: Cc1cccc(C)c1-c1cc2nc(n1)NS(=O)(=O)c1cccc(c1)NC(=O)[C@@H]1C[C@@H](CN(CC3CC3)C1)O2] | 1.07 | 533.21 | 534.3 | A |
| 31 | 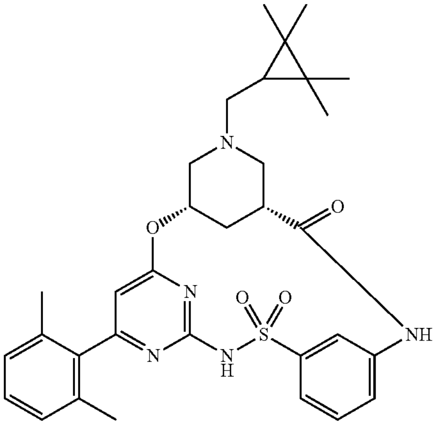 [SMILES: Cc1cccc(C)c1-c1cc2nc(n1)NS(=O)(=O)c1cccc(c1)NC(=O)[C@@H]1C[C@@H](CN(CC3C(C)(C)C3(C)C)C1)O2] | 1.41 | 589.272 | 590.4 | A |
| 32 | 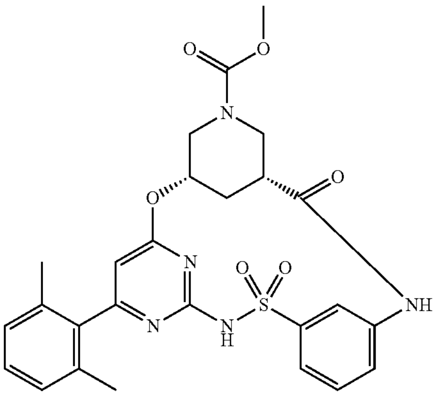 [SMILES: COC(=O)N1C[C@@H]2C[C@H](C1)C(=O)Nc1cccc(c1)S(=O)(=O)Nc1nc(cc(-c3c(C)cccc3C)n1)O2] | 1.36 | 537.168 | 538.2 | A |

TABLE 3-continued
| Compound Number | Structure | LCMS Rt (min) | Calc. Mass | M + 1 | LCMS Method |
|---|---|---|---|---|---|
| 33 | 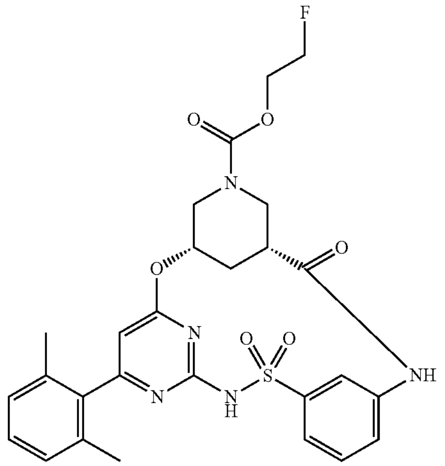 [SMILES: Cc1cccc(C)c1-c1cc2nc(n1)NS(=O)(=O)c1cccc(c1)NC(=O)[C@@H]1C[C@@H](CN(C(=O)OCCF)C1)O2] | 1.41 | 569.174 | 570.2 | A |
| 34 | 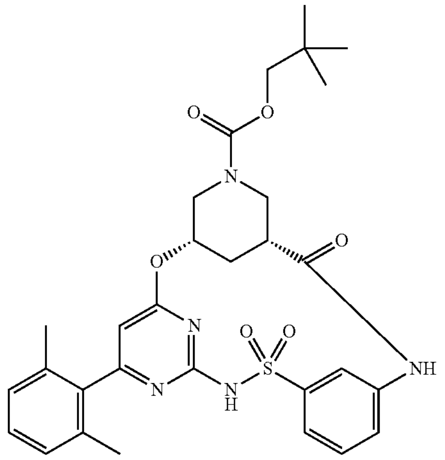 [SMILES: Cc1cccc(C)c1-c1cc2nc(n1)NS(=O)(=O)c1cccc(c1)NC(=O)[C@@H]1C[C@@H](CN(C(=O)OCC(C)(C)C)C1)O2] | 1.78 | 593.231 | 594.3 | A |
| 35 | 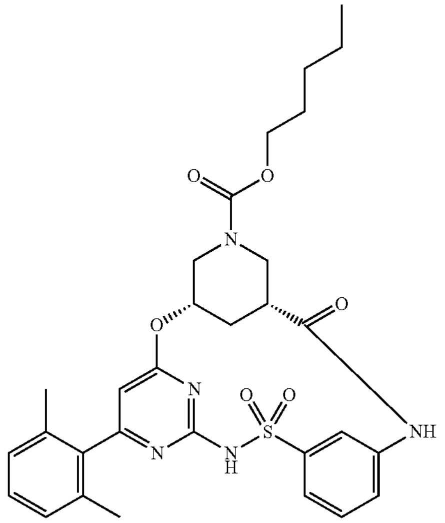 [SMILES: CCCCCOC(=O)N1C[C@@H]2C[C@H](C1)C(=O)Nc1cccc(c1)S(=O)(=O)Nc1nc(cc(-c3c(C)cccc3C)n1)O2] | 1.82 | 593.231 | 594.3 | A |

TABLE 3-continued
| Compound Number | Structure | LCMS Rt (min) | Calc. Mass | M + 1 | LCMS Method |
| --- | --- | --- | --- | --- | --- |
| 36 | 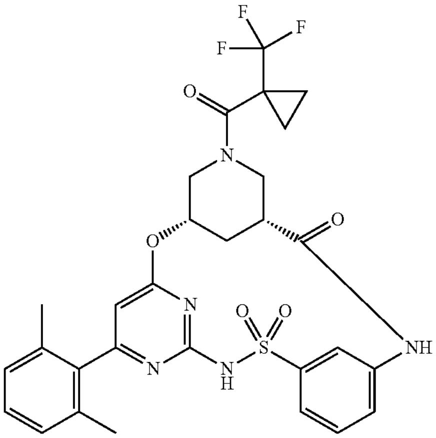 [SMILES: Cc1cccc(C)c1-c1cc2nc(n1)NS(=O)(=O)c1cccc(c1)NC(=O)[C@@H]1C[C@@H](CN(C(=O)C3(C(F)(F)F)CC3)C1)O2] | 1.52 | 615.176 | 616.2 | A |
| 37 | 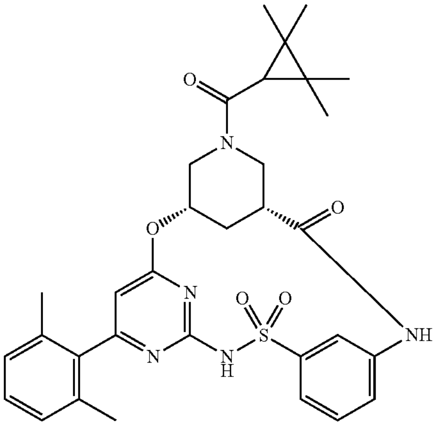 [SMILES: Cc1cccc(C)c1-c1cc2nc(n1)NS(=O)(=O)c1cccc(c1)NC(=O)[C@@H]1C[C@@H](CN(C(=O)C3C(C)(C)C3(C)C)C1)O2] | 1.73 | 603.252 | 604.3 | A |
| 38 | 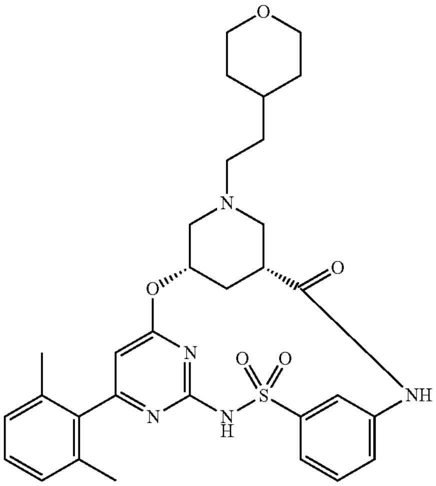 [SMILES: Cc1cccc(C)c1-c1cc2nc(n1)NS(=O)(=O)c1cccc(c1)NC(=O)[C@@H]1C[C@@H](CN(CCC3CCOCC3)C1)O2] | 1.06 | 591.252 | 592.5 | A |

TABLE 3-continued
| Compound Number | Structure | LCMS Rt (min) | Calc. Mass | M + 1 | LCMS Method |
|---|---|---|---|---|---|
| 39 | 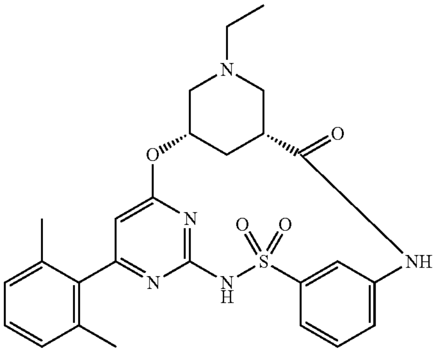 [SMILES: CCN1C[C@@H]2C[C@H](C1)C(=O)Nc1cccc(c1)S(=O)(=O)Nc1nc(cc(-c3c(C)cccc3C)n1)O2] | 0.94 | 507.194 | 508.3 | A |
| 40 | 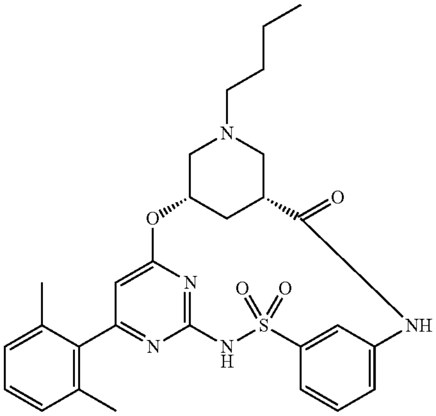 | 1.11 | 535.225 | 536.3 | A |
| 41 | 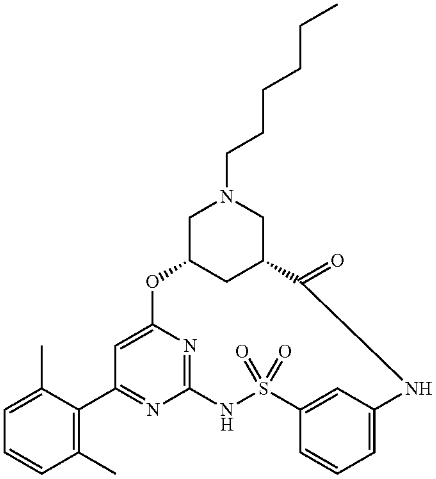 [SMILES: CCCCCCN1C[C@@H]2C[C@H](C1)C(=O)Nc1cccc(c1)S(=O)(=O)Nc1nc(cc(-c3c(C)cccc3C)n1)O2] | 1.33 | 563.257 | 564.3 | A |

TABLE 3-continued
| Compound Number | Structure | LCMS Rt (min) | Calc. Mass | M + 1 | LCMS Method |
|---|---|---|---|---|---|
| 42 | 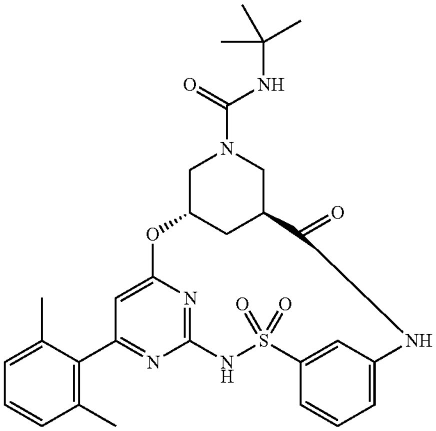 [SMILES: Cc1cccc(C)c1-c1cc2nc(n1)NS(=O)(=O)c1cccc(c1)NC(=O)[C@H]1C[C@@H](CN(C(=O)NC(C)(C)C)C1)O2] | 1.44 | 578.231 | 579.2 | A |
| 43 | 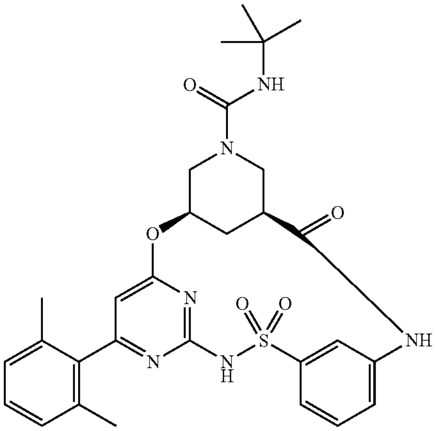 [SMILES: Cc1cccc(C)c1-c1cc2nc(n1)NS(=O)(=O)c1cccc(c1)NC(=O)[C@H]1C[C@H](CN(C(=O)NC(C)(C)C)C1)O2] | 1.5 | 578.231 | 579.2 | A |
| 44 | 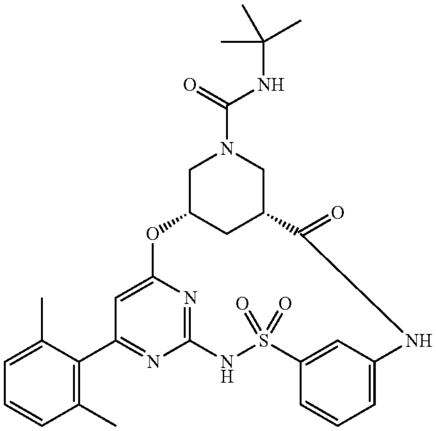 [SMILES: Cc1cccc(C)c1-c1cc2nc(n1)NS(=O)(=O)c1cccc(c1)NC(=O)[C@@H]1C[C@@H](CN(C(=O)NC(C)(C)C)C1)O2] | 1.49 | 578.231 | 579.3 | A |

TABLE 3-continued
| Compound Number | Structure | LCMS Rt (min) | Calc. Mass | M + 1 | LCMS Method |
|---|---|---|---|---|---|
| 45 | 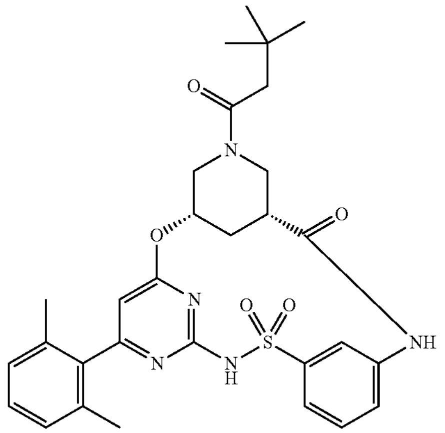 [SMILES: Cc1cccc(C)c1-c1cc2nc(n1)NS(=O)(=O)c1cccc(c1)NC(=O)[C@@H]1C[C@@H](CN(C(=O)CC(C)(C)C)C1)O2] | 1.6 | 577.236 | 578.3 | A |
| 46 | 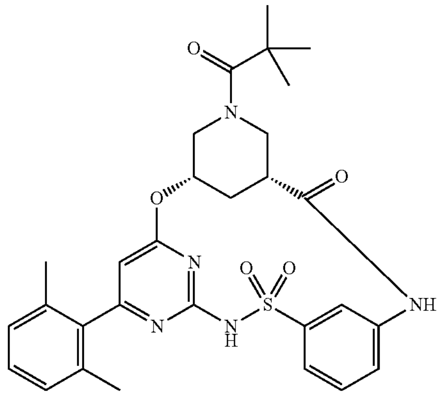 [SMILES: Cc1cccc(C)c1-c1cc2nc(n1)NS(=O)(=O)c1cccc(c1)NC(=O)[C@@H]1C[C@@H](CN(C(=O)C(C)(C)C)C1)O2] | 1.5 | 563.22 | 564.2 | A |
| 47 | 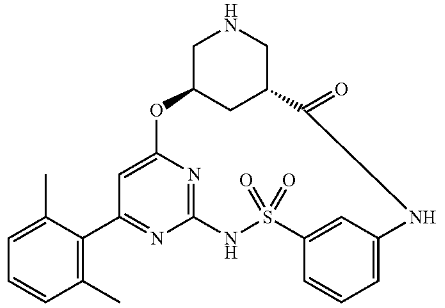 [SMILES: Cc1cccc(C)c1-c1cc2nc(n1)NS(=O)(=O)c1cccc(c1)NC(=O)[C@H]1CNC[C@@H](C1)O2] | 0.82 | 479.163 | 480.1 | A |
| 48 | 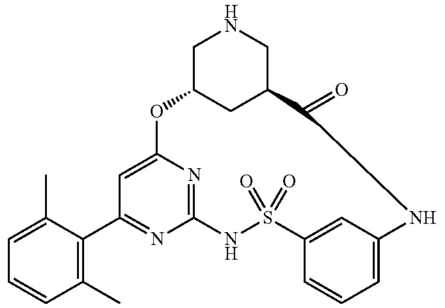 [SMILES: Cc1cccc(C)c1-c1cc2nc(n1)NS(=O)(=O)c1cccc(c1)NC(=O)[C@@H]1CNC[C@H](C1)O2] | 0.82 | 479.163 | 480.1 | A |

TABLE 3-continued
| Compound Number | Structure | LCMS Rt (min) | Calc. Mass | M + 1 | LCMS Method |
|---|---|---|---|---|---|
| 49 | 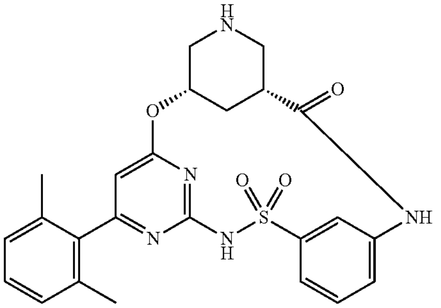 [SMILES: Cc1cccc(C)c1-c1cc2nc(n1)NS(=O)(=O)c1cccc(c1)NC(=O)[C@H]1CNC[C@H](C1)O2] | 0.89 | 479.163 | 480.2 | A |
| 50 | 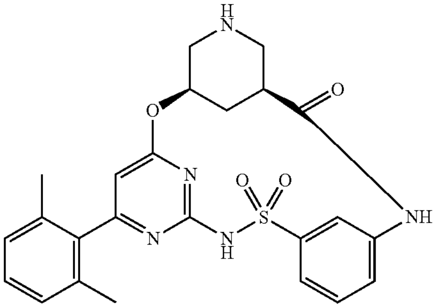 [SMILES: Cc1cccc(C)c1-c1cc2nc(n1)NS(=O)(=O)c1cccc(c1)NC(=O)[C@@H]1CNC[C@@H](C1)O2] | 0.88 | 479.163 | 480.2 | A |
| 51 | 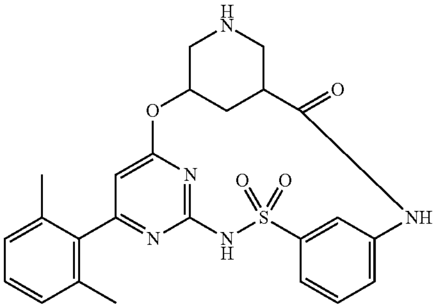 | 0.82 | 479.163 | 480.3 | A |
| 52 | 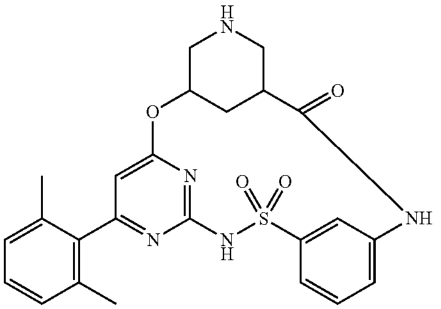 | 0.77 | 479.163 | 480.3 | A |
TABLE 4
| Compound Number | NMR |
|---|---|
| 25 | $^1$H NMR (400 MHz, dimethylsulfoxide-$d_6$) δ 10.56-10.38 (bs, 1H, $D_2O$ exchangeable), 10.36 (s, 1H, $D_2O$ exchangeable), 7.95 (s, 1H), 7.55 (s, 2H), 7.35 (s, 1H), 7.25 (t, J = 7.6 Hz, 1H), 7.12 (d, J = 7.6 Hz, 2H), 6.46 (s, 1H), 5.48-5.35 (m, 1H), 3.87-3.70 (m, 3H), 3.45-3.18 (m, 4H), 2.66-2.56 (m, 1H), 2.56 (s, 1H), 2.03 (s, 6H), 1.98 (s, 6H), 1.48 (q, J = 12.0 Hz, 1H) |
| 26 | $^1$H NMR (400 MHz, dimethylsulfoxide-$d_6$) δ 13.62-11.21 (bs, 1H, $D_2O$ exchangeable), 9.99 (s, 1H, $D_2O$ exchangeable), 8.05 (s, 1H), 7.47 (s, 2H), 7.25 (s, 1H), 7.23 (t, J = 7.6 Hz, 1H), 7.11 (d, J = 7.6 Hz, 2H), 6.32 (s, 1H), 5.15-4.97 |

TABLE 4-continued

| Compound Number | NMR |
|---|---|
| | (m, 1H), 3.33-3.09 (m, 3H), 2.65-2.53 (m, 3H), 2.19 (q, J = 10.4, 9.7 Hz, 2H), 2.03 (s, 6H), 1.56-1.43 (m, 2H), 1.09 (q, J = 11.7 Hz, 1H), 0.75 (s, 6H), 0.69 (tt, J = 8.4, 5.7 Hz, 1H), 0.30-0.14 (m, 4H) |
| 27 | $^1$H NMR (400 MHz, dimethylsulfoxide-$d_6$) δ 10.80-10.54 (bs, 1H, $D_2O$ exchangeable), 10.37 (s, 1H, $D_2O$ exchangeable), 7.94 (s, 1H), 7.63-7.49 (bs, 2H), 7.39-7.28 (bs, 1H), 7.25 (t, J = 7.6 Hz, 1H), 7.12 (d, J = 7.6 Hz, 2H), 6.45 (s, 1H), 5.42-5.27 (m, 1H), 3.94-3.77 (m, 2H), 3.71-3.59 (m, 1H), 3.41-3.17 (m, 4H), 2.66-2.53 (m, 1H), 2.17-2.04 (m, 2H), 2.03 (s, 6H), 1.47 (q, J = 11.9 Hz, 1H), 1.05-0.97 (m, 2H), 0.93-0.86 (m, 2H) |
| 28 | $^1$H NMR (400 MHz, dimethylsulfoxide-$d_6$) δ 10.68-10.43 (bs, 1H, $D_2O$ exchangeable), 10.37 (s, 1H, $D_2O$ exchangeable), 7.94 (s, 1H), 7.63-7.48 (m, 2H), 7.40-7.29 (bs, 1H), 7.25 (t, J = 7.6 Hz, 1H), 7.12 (d, J = 7.6 Hz, 2H), 6.45 (s, 1H), 5.46-5.30 (m, 1H), 3.90-3.62 (m, 3H), 3.40-3.12 (m, 4H), 2.66-2.53 (m, 1H), 2.03 (s, 6H), 1.67 (q, J = 7.8 Hz, 2H), 1.49 (q, J = 11.9 Hz, 1H), 0.82-0.66 (m, 1H), 0.56-0.41 (m, 2H), 0.23-0.09 (m, 2H) |
| 30 | $^1$H NMR (400 MHz, dimethylsulfoxide-$d_6$) δ 10.64-10.42 (bs, 1H, $D_2O$ exchangeable), 10.37 (s, 1H, $D_2O$ exchangeable), 7.97 (s, 1H), 7.63-7.48 (m, 2H), 7.40-7.29 (bs, 1H), 7.25 (t, J = 7.6 Hz, 1H), 7.12 (d, J = 7.6 Hz, 2H), 6.46 (s, 1H), 5.48-5.34 (m, 1H), 3.94-3.68 (m, 3H), 3.34-3.15 (m, 4H), 2.66-2.56 (m, 1H), 2.03 (s, 6H), 1.50 (q, J = 11.9 Hz, 1H), 1.28-1.12 (m, 1H), 0.76-0.64 (m, 2H), 0.50-0.39 (m, 2H) |
| 37 | $^1$H NMR (400 MHz, dimethylsulfoxide-$d_6$) δ 13.68-11.42 (broad d, 1H, $D_2O$ exchangeable), 10.28-9.93 (broad d, 1H, $D_2O$ exchangeable), 8.11-7.96 (broad d, 1H), 7.62-7.42 (bs, 2H), 7.37-7.25 (bs, 1H), 7.24 (t, J = 7.6 Hz, 1H), 7.11 (d, J = 7.6 Hz, 2H), 6.64-6.17 (bs, 1H), 5.04-4.63 (m, 2H), 4.41-4.24 (m, 1H), 3.35-3.00 (m, 2H), 2.83-2.55 (m, 2H), 2.03 (s, 6H), 1.59-1.53 (m, 1H), 1.48-1.36 (m, 1H), 1.23-1.03 (a collection of singlets due to rotamers, 12H) |
| 38 | $^1$H NMR (400 MHz, dimethylsulfoxide-$d_6$) δ 10.90-10.67 (bs, 1H, $D_2O$ exchangeable), 10.37 (s, 1H, $D_2O$ exchangeable), 7.95 (s, 1H), 7.60-7.51 (m, 2H), 7.37-7.30 (m, 1H), 7.25 (t, J = 7.6 Hz, 1H), 7.12 (d, J = 7.6 Hz, 2H), 6.45 (s, 1H), 5.44-5.33 (m, 1H), 3.88-3.81 (m, 3H), 3.80-3.72 (m, 2H), 3.36-3.19 (m, 6H), 2.67-2.55 (m, 1H), 2.03 (s, 6H), 1.77-1.67 (m, 2H), 1.67-1.55 (m, 3H), 1.50 (q, J = 11.8 Hz, 1H), 1.28-1.15 (m, 2H) |
| 39 | $^1$H NMR (400 MHz, dimethylsulfoxide-$d_6$) δ 11.16-10.75 (bs, 1H, $D_2O$ exchangeable), 10.38 (s, 1H, $D_2O$ exchangeable), 7.95 (s, 1H), 7.63-7.48 (m, 2H), 7.40-7.29 (bs, 1H), 7.25 (t, J = 7.6 Hz, 1H), 7.12 (d, J = 7.6 Hz, 2H), 6.44 (s, 1H), 5.45-5.33 (m, 1H), 3.91-3.63 (m, 3H), 3.41-3.13 (m, 4H), 2.66-2.56 (m, 1H), 2.03 (s, 6H), 1.52 (q, J = 11.9 Hz, 1H), 1.33 (t, J = 7.2 Hz, 3H) |
| 40 | $^1$H NMR (400 MHz, dimethylsulfoxide-$d_6$) δ 10.70-10.49 (bs, 1H, $D_2O$ exchangeable), 10.36 (s, 1H, $D_2O$ exchangeable), 7.95 (s, 1H), 7.61-7.51 (m, 2H), 7.38-7.29 (bs, 1H), 7.25 (t, J = 7.6 Hz, 1H), 7.12 (d, J = 7.6 Hz, 2H), 6.45 (s, 1H), 5.44-5.33 (m, 1H), 3.89-3.59 (m, 3H, overlaps with H2O peak), 3.30-3.18 (m, 4H), 2.65-2.55 (m, 1H), 2.03 (s, 6H), 1.74 (pentet, J = 7.7 Hz, 2H), 1.50 (q, J = 12.0 Hz, 1H), 1.36 (hextet, J = 7.4 Hz, 2H), 0.94 (t, J = 7.3 Hz, 3H) |
| 41 | $^1$H NMR (400 MHz, dimethylsulfoxide-$d_6$) δ 10.75-10.51 (bs, 1H, $D_2O$ exchangeable), 10.37 (s, 1H, $D_2O$ exchangeable), 7.95 (s, 1H), 7.55 (s, 2H), 7.38-7.29 (bs, 1H), 7.25 (t, J = 7.6 Hz, 1H), 7.12 (d, J = 7.6 Hz, 2H), 6.45 (s, 1H), 5.44-5.33 (m, 1H), 3.89-3.61 (m, 3H), 3.30-3.15 (m, 4H), 2.65-2.55 (m, 1H), 2.03 (s, 6H), 1.81-1.69 (m, 2H), 1.50 (q, J = 11.9 Hz, 1H), 1.37-1.28 (m, 6H), 0.89 (t, J = 6.5 Hz, 3H) |
| 44 | $^1$H NMR (400 MHz, dimethylsulfoxide-$d_6$) δ 13.53-11.57 (broad d, 1H), 10.07 (s, 1H), 8.03 (s, 1H), 7.64-7.39 (bs, 2H), 7.38-7.19 (m, 2H), 7.12 (d, J = 7.6 Hz, 2H), 6.59-6.21 (bs, 1H), 6.12 (s, 1H), 4.98-4.72 (m, 1H), 4.39-4.18 (m, 2H), 3.20-3.09 (m, 1H), 2.87-2.72 (m, 2H), 2.65-2.53 (m, 1H), 2.02 (s, 6H), 1.38-1.20 (m, 1H), 1.28 (s, 9H) |
| 45 | $^1$H NMR (400 MHz, dimethylsulfoxide-$d_6$) δ 13.68-11.41 (broad d, 1H, $D_2O$ exchangeable), 10.25-9.95 (broad d, 1H, $D_2O$ exchangeable), 8.12-7.95 (bs, 1H), 7.64-7.40 (bs, 2H), 7.35-7.19 (m, 2H), 7.11 (d, J = 7.6 Hz, 2H), 6.57-6.20 (bs, 1H), 4.99-4.69 (m, 2H), 4.38-4.18 (m, 1H), 3.25-3.05 (m, 1H), 2.83-2.55 (m, 2H), 2.48-2.40 (m, 1H), 2.38-2.25 (m, 1H), 2.02 (s, 6H), 1.47-1.32 (m, 1H), 1.04 and 1.01 (9H) |
| 52 | $^1$H NMR (400 MHz, dimethylsulfoxide-$d_6$) δ 10.24 (s, 1H, $D_2O$ exchangeable), 10.05-9.52 (bs, 1H, $D_2O$ exchangeable), 8.99-8.48 (bs, 1H, $D_2O$ exchangeable), 8.53 (s, 1H), 7.61-7.49 (m, 2H), 7.32-7.19 (m, 2H), 7.17-7.07 (m, 2H), 6.52 (s, 1H), 5.58 (s, 1H), 3.56-3.31 (m, 3H), 3.27-3.07 (m, 2H), 2.23-2.05 (m, 2H), 2.02 (s, 6H) |

Example 16: Preparation of Compound 53

Step 1: 5-(2,6-Dimethylphenyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (Compound 53)

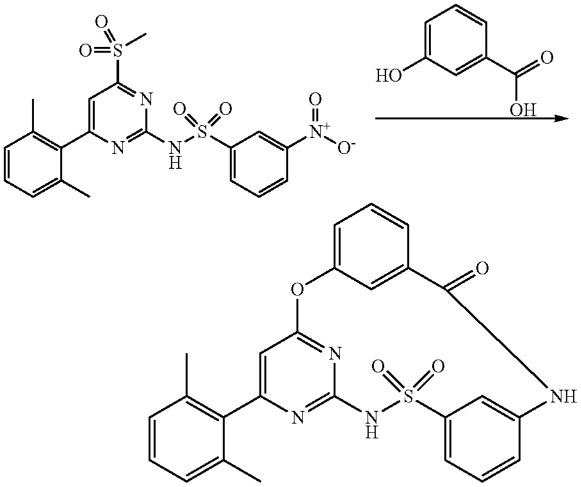

Stage 1: To a 20 mL vial equipped with a magnetic stir bar, N-[4-(2,6-dimethylphenyl)-6-methylsulfonyl-pyrimidin-2-yl]-3-nitro-benzenesulfonamide (99.0 mg, 0.2141 mmol), NMP (3.0 mL) and 3-hydroxybenzoic acid (95.2 mg, 0.6893 mmol) were added, followed by potassium carbonate (99.5 mg, 0.7199 mmol). This solution was stirred at 140° C. for 2 h. The reaction mixture was then cooled to room temperature, quenched with 1 N HCl (5 mL), and extracted with ethyl acetate (3x5 mL). The combined organic extracts were washed with water (2x5 mL) and saturated aqueous sodium chloride solution (5 mL), then dried over sodium sulfate, filtered, and evaporated in vacuo. Purification was not conducted at this stage.

Stage 2: In a 10 mL microwave vial equipped with a magnetic stir bar, the crude product from Stage 1 was dissolved in EtOH (3.0 mL). This solution was sparged with a balloon of hydrogen gas for 5 minutes. The cap was briefly removed, and 10% $Pd(OH)_2/C$ (20.3 mg, 0.01446 mmol) was added. This reaction mixture was stirred under a hydrogen balloon at 70° C. for 20 h, after which it was filtered through Celite and rinsed with methanol (8 mL). This solution was evaporated in vacuo to give a brown oil, which was purified by reverse phase HPLC (1-70% acetonitrile in water using HCl as a modifier) to give 36.8 mg of an ~80% pure intermediate.

Stage 3: The product from Stage 2 was dissolved in DMF (700 μL) and treated with DIPEA (100 μL, 0.5741 mmol) and $Ph_2P(O)$—$OC_6F_5$ (35.2 mg, 0.09161 mmol). This mixture was stirred at room temperature for 20 minutes, after which a second portion of $Ph_2P(O)$—$OC_6F_5$ (38.2 mg, 0.09942 mmol) was added. This mixture was stirred at room temperature for 20 minutes, after which a third portion of $Ph_2P(O)$—$OC_6F_5$ (40.2 mg, 0.1046 mmol) was added. This mixture was then filtered and purified by reverse phase HPLC (1-99% acetonitrile in water using HCl as a modifier) to give (2,3,4,5,6-pentafluorophenyl) 3-[2-[(3-aminophenyl)sulfonylamino]-6-(2,6-dimethylphenyl)pyrimidin-4-yl]oxybenzoate (6.0 mg, 4%) ESI-MS m/z calc. 656.1153, found 657.2 $(M+1)^+$; Retention time: 0.78 minutes; LC method D.

Stage 4: The product from Stage 3 was dissolved in NMP (400 μL) and stirred at 100° C. for 30 minutes. This solution was cooled to room temperature and purified by reverse phase HPLC (1-50% acetonitrile in water using HCl as a modifier) to give 5-(2,6-dimethylphenyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (1.9 mg, 2%) ESI-MS m/z calc. 472.1205, found 473.2 $(M+1)^+$; Retention time: 1.36 minutes; LC method A.

Example 17: Preparation of Compound 54

Step 1: 3-[2-[(3-Aminophenyl)sulfonylamino]-6-(o-tolyl)pyrimidin-4-yl]oxybenzoic Acid

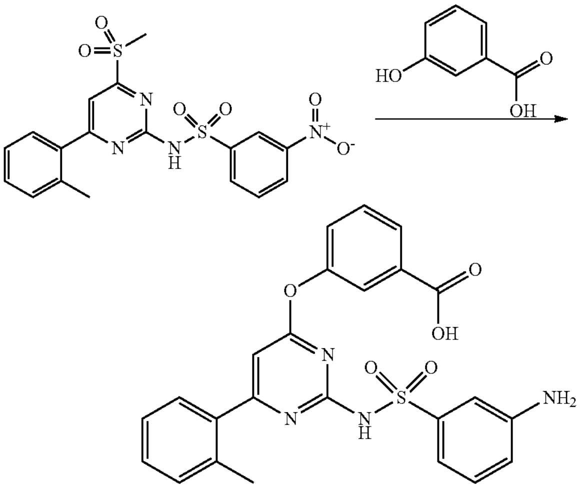

To a 100 mL round-bottomed flask equipped with a magnetic stir bar, N-[4-methylsulfonyl-6-(o-tolyl)pyrimidin-2-yl]-3-nitro-benzenesulfonamide (0.5819 g, 1.298 mmol), N-methylpyrrolidinone (16 mL) and 3-hydroxybenzoic acid (0.6000 g, 4.344 mmol) were added, followed by potassium carbonate (0.9200 g, 6.657 mmol). This solution was stirred at 100° C. for 16 h. The reaction mixture was then cooled to room temperature, quenched with 1 N HCl (4 mL), and extracted with ethyl acetate (3x4 mL). The combined organic extracts were washed with water (2x4 mL) and saturated aqueous sodium chloride solution (3 mL), then dried over sodium sulfate, filtered, and evaporated in vacuo. The crude product obtained above was dissolved in ethanol (10 mL) and transferred to a 20 mL microwave vial equipped with a magnetic stir bar. This solution was purged with a balloon of hydrogen gas for 5 minutes. The cap was briefly removed, and $Pd(OH)_2/C$ (20.0 mg, 0.02848 mmol) was added. This reaction mixture was stirred under a balloon of hydrogen gas at 60° C. for 21 h. It was cooled to room temperature, filtered through Celite and rinsed with ethanol (5 mL), then evaporated in vacuo. Purification by silica gel chromatography (12 g of silica, 0 to 70% gradient of ethyl acetate/hexanes) gave two batches of product, which contain 3-[2-[(3-aminophenyl)sulfonylamino]-6-(o-tolyl)pyrimidin-4-yl]oxybenzoic acid (hydrochloride salt) (475 mg, 71%). $^1H$ NMR (400 MHz, Chloroform-d) δ 8.02 (dt, J=7.8, 1.3 Hz, 1H), 7.88 (dd, J=2.5, 1.5 Hz, 1H), 7.59 (t, J=7.9 Hz, 1H), 7.48 (ddd, J=8.2, 2.5, 1.1 Hz, 1H), 7.40-7.25 (m, 4H), 6.96

(t, J=7.9 Hz, 1H), 6.91 (t, J=2.1 Hz, 1H), 6.84 (ddd, J=7.8, 1.8, 1.0 Hz, 1H), 6.69 (ddd, J=8.0, 2.4, 1.0 Hz, 1H), 6.62 (s, 1H), 6.50-5.50 (bs, 4H), 2.39 (s, 3H). ESI-MS m/z calc. 476.11545, found 477.2 $(M+1)^+$; Retention time: 0.54 minutes; LC method D.

Step 2: 5-(o-Tolyl)-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (Compound 54)

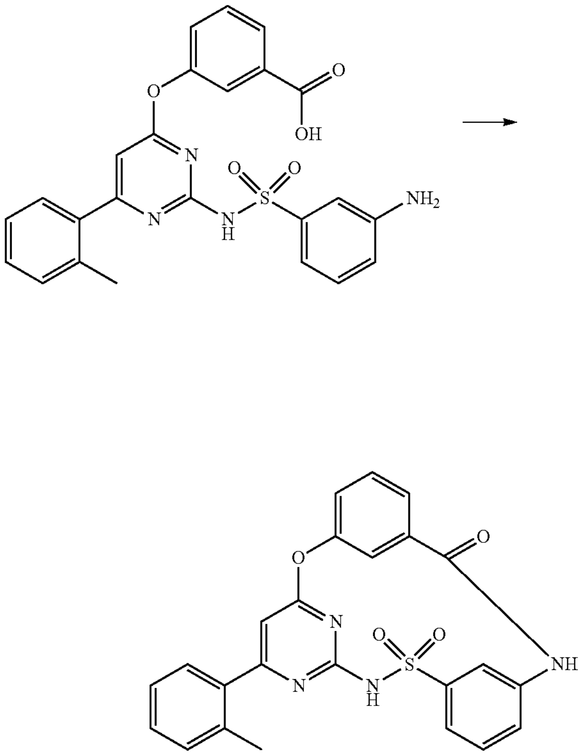

In a 20 mL vial, 3-[2-[(3-aminophenyl)sulfonylamino]-6-(o-tolyl)pyrimidin-4-yl]oxybenzoic acid (hydrochloride salt) (375 mg, 0.7310 mmol) was dissolved in DMF (9 mL) and treated with diisopropylethylamine (600 μL, 3.445 mmol) and HATU (470 mg, 1.236 mmol). This mixture was stirred at room temperature for 20 minutes, after which it was filtered, separated into 10 portions and purified by reverse phase HPLC (1-99% acetonitrile in water using HCl as a modifier) to give the desired 5-(o-tolyl)-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (151.0 mg, 45%) $^1$H NMR (400 MHz, Chloroform-d) δ 8.97 (s, 1H), 7.83 (d, J=7.6 Hz, 1H), 7.68 (t, J=7.9 Hz, 1H), 7.50-7.25 (m, 7H), 7.22 (s, 2H), 6.95 (s, 1H), 6.65 (s, 1H), 2.41 (s, 3H). ESI-MS m/z calc. 458.1049, found 459.1 $(M+1)^+$; Retention time: 1.36 minutes; LC method A.

Example 18: Preparation of Compound 55

Step 1: 5-[2-[(3-Aminophenyl)sulfonylamino]-6-(2,6-dimethylphenyl)pyrimidin-4-yl]oxy-2-chloro-benzoic Acid

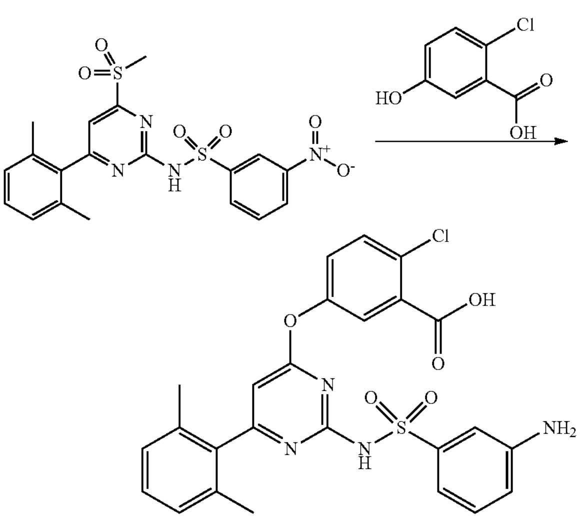

A mixture of N-[4-(2,6-dimethylphenyl)-6-methylsulfonyl-pyrimidin-2-yl]-3-nitro-benzenesulfonamide (155 mg, 0.3351 mmol), 2-chloro-5-hydroxy-benzoic acid (172 mg, 0.9967 mmol) and potassium carbonate (210 mg, 1.519 mmol) in NMP (5 mL) was heated at 110° C. for 16 hours. The reaction mixture was poured into water, the pH adjusted to ~3 with 1N HCl. The solid was filtered off, washed with water (2×) and dried on the frit. The precipitate was taken up in EtOH (2 mL) and to this was added Fe (200 mg, 3.581 mmol) followed by HCl (0.5 mL of 1 M, 0.5000 mmol) and the reaction mixture stirred at 60° C. for 2 hours. The reaction mixture was diluted with EtOH, filtered through Celite, the Celite was washed with water (2×) and EtOH (3×) and then evaporated to dryness to give 5-[2-[(3-aminophenyl)sulfonylamino]-6-(2,6-dimethylphenyl)pyrimidin-4-yl]oxy-2-chloro-benzoic acid (135 mg, 77%) as a tan solid. ESI-MS m/z calc. 524.0921, found 525.1 $(M+1)^+$; Retention time: 0.58 minutes; LC method D.

Step 2: 18-chloro-5-(2,6-dimethylphenyl)-9,9-dioxo-2-oxa-9$\lambda^6$-thia-6,8,15,23-tetraazatetracyclo[15.3.1.13,7.110,14]tricosa-1(21),3,5,7(23),10(22),11,13,17,19-nonaen-16-one (Compound 55)

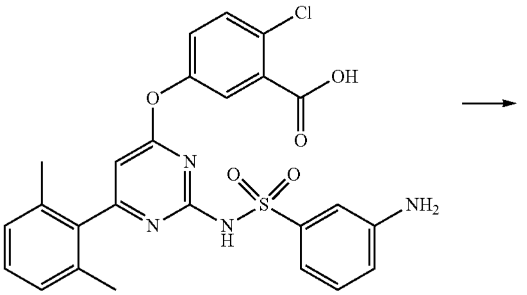

-continued

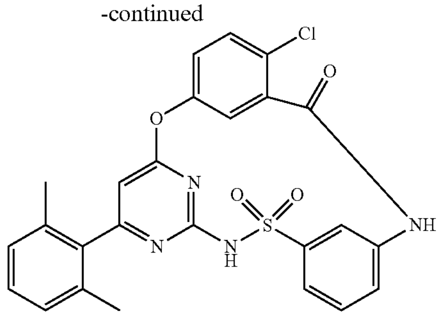

To a solution of 5-[2-[(3-aminophenyl)sulfonylamino]-6-(2,6-dimethylphenyl)pyrimidin-4-yl]oxy-2-chloro-benzoic acid (28 mg, 0.05334 mmol) and HATU (26 mg, 0.06838 mmol) was added DiPEA (approximately 27.58 mg, 37.17 µL, 0.2134 mmol) and the reaction mixture stirred at room temperature for 1 hour. The RM was diluted with MeOH, filtered and purification by HPLC (1-99% ACN in water (HCl modifier)) gave 18-chloro-5-(2,6-dimethylphenyl)-9,9-dioxo-2-oxa-9$\lambda^6$-thia-6,8,15,23-tetraazatetracyclo[15.3.1.13,7.110,14]tricosa-1(21),3,5,7(23),10(22),11,13,17,19-nonaen-16-one (10.4 mg, 38%) as a solid. ESI-MS m/z calc. 506.08154, found 507.2 $(M+1)^+$; Retention time: 1.43 minutes; LC method A.

Example 19: Preparation of Compound 56

Step 1: 18-Bromo-5-(2,6-dimethylphenyl)-2-oxa-9$\lambda^6$-thia-6,8,15,23-tetraazatetracyclo[15.3.1.13,7.110,14]tricosa-1(20),3(23),4,6,10,12,14(22),17(21),18-nonaene-9,9,16-trione

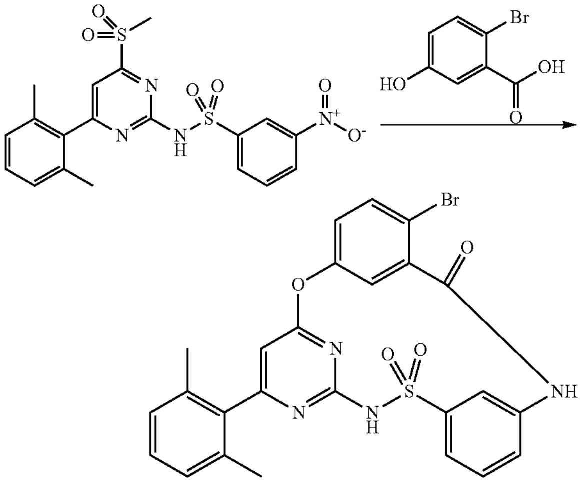

Stage 1: To a 250 mL round-bottomed flask equipped with a magnetic stir bar, N-[4-(2,6-dimethylphenyl)-6-methylsulfonyl-pyrimidin-2-yl]-3-nitro-benzenesulfonamide (1.015 g, 2.195 mmol), N-methylpyrrolidinone (80 mL) and 2-bromo-5-hydroxy-benzoic acid (1.302 g, 6.000 mmol) were added, followed by potassium carbonate (1.107 g, 8.010 mmol). This solution was stirred at 110° C. for 17 h. The reaction mixture was then cooled to room temperature, quenched with 1 N HCl (80 mL), and extracted with ethyl acetate (3×80 mL). The combined organic extracts were washed with water (2×100 mL) and saturated aqueous sodium chloride solution (100 mL), then dried over sodium sulfate, filtered, and evaporated in vacuo to give a brown oil. Purification by silica gel chromatography (40 g of silica, 0 to 50% gradient of ethyl acetate/hexanes) gave 1.884 g of a yellow oil.

Stage 2: The product from Stage 1 was dissolved in ethanol (20 mL) and transferred to a 100 mL round-bottomed flask equipped with a magnetic stir bar. Aqueous HCl (5.0 mL of 0.5 M, 2.500 mmol) was added, followed by a fine dust of iron (0.907 g, 16.24 mmol). This reaction mixture was stirred at 60° C. for 15 minutes. It was cooled to room temperature, filtered through Celite, rinsed with methanol (40 mL), and evaporated in vacuo to give a dark brown oil.

Stage 3: The product from Stage 2 was dissolved in dimethylformamide (50 mL) and transferred to a 100 mL round-bottomed flask equipped with a magnetic stir bar. DIPEA (5.0 mL, 28.71 mmol) and HATU (1.204 g, 3.167 mmol) were added, and this solution was stirred at room temperature for 5 minutes. The reaction mixture was quenched with water (150 mL) then extracted with ethyl acetate (3×150 mL). The combined organic extracts was washed with water (150 mL) and saturated aqueous sodium chloride solution (150 mL), then dried over sodium sulfate, filtered, and evaporated in vacuo to give 240 mg of dark brown product. Purification by silica gel chromatography (24 g of silica, 0 to 50% gradient of ethyl acetate/hexanes) gave an off-white solid, 18-bromo-5-(2,6-dimethylphenyl)-2-oxa-9$\lambda^6$-thia-6,8,15,23-tetraazatetracyclo[15.3.1.13,7.110,14]tricosa-1(20),3(23),4,6,10,12,14(22),17(21),18-nonaene-9,9,16-trione (0.2397 g, 20%); ESI-MS m/z calc. 550.03107, found 551.1 $(M+1)^+$; Retention time: 1.44 minutes; LC method A.

Step 2: 5-(2,6-Dimethylphenyl)-9,9-dioxo-18-(1-piperidyl)-2-oxa-9$\lambda^6$-thia-6,8,15,23-tetraazatetracyclo[15.3.1.13,7.110,14]tricosa-1(21),3,5,7(23),10(22),11,13,17,19-nonaen-16-one (Compound 56)

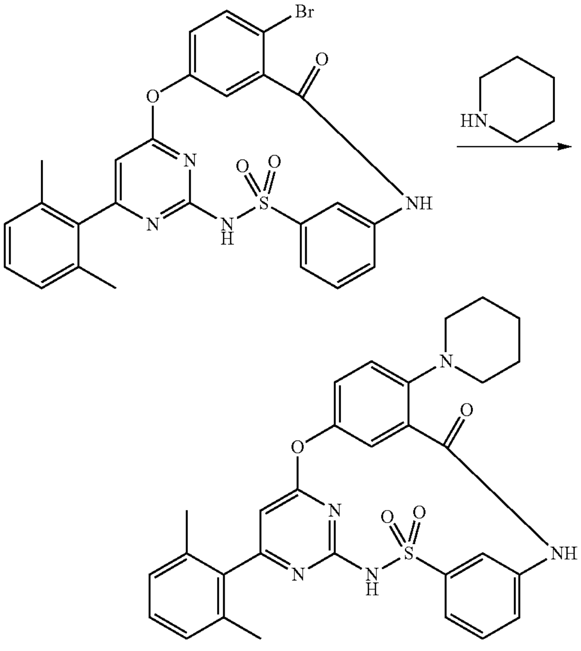

To a 10 mL microwave vial equipped with a magnetic stir bar, 18-bromo-5-(2,6-dimethylphenyl)-2-oxa-9$\lambda^6$-thia-6,8,15,23-tetraazatetracyclo[15.3.1.13,7.110,14]tricosa-1(20),3(23),4,6,10,12,14(22),17(21),18-nonaene-9,9,16-trione (20.0 mg, 0.0362 mmol), copper (I) iodide (0.9 mg, 0.0047 mmol), pyrrole-2-carboxylic acid (1.0 mg, 0.0090 mmol), potassium carbonate (15.3 mg, 0.111 mmol), and piperidine (5.1 mg, 0.060 mmol) were added, followed by dimethylsulfoxide (1.0 mL). This mixture was sparged with a balloon of nitrogen gas for 5 minutes. This mixture was then capped and stirred at 110° C. for 30 minutes. The reaction mixture was then cooled to room temperature, filtered and purified by reverse phase HPLC (1-70% acetonitrile in water using HCl as a modifier) to give the desired product, 5-(2,6-dimethylphenyl)-9,9-dioxo-18-(1-piperidyl)-2-oxa-9$\lambda^6$-thia-6,8,15,23-tetraazatetracyclo[15.3.1.13,7.110,14]tricosa-1(21),3,5,7(23),10(22),11,13,17,19-nonaen-16-one (5.5 mg, 27%). $^1H$ NMR (400 MHz, dimethylsulfoxide-$d_6$) δ 10.74 (s, 1H, $D_2O$ exchangeable), 7.68 (s, 1H), 7.53-7.42 (m, 2H), 7.36 (dd, J=7.9, 2.0 Hz, 2H), 7.25 (t, J=7.5 Hz, 1H), 7.14 (d, J=7.6 Hz, 2H), 7.03 (d, J=2.7 Hz, 1H), 6.87 (s, 1H), 6.73 (s, 1H), 3.50-3.15 (bs, 4H), 2.06 (s, 6H), 1.76 (s, 4H), 1.60 (s, 2H). ESI-MS m/z calc. 555.19403, found 556.3 $(M+1)^+$; Retention time: 1.19 minutes; LC method A.

Example 20: Preparation of Compound 57 and 4-Chloro-5-(2,6-dimethylphenyl)-20-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one Step 1: 5-(2,6-Dimethylphenyl)-20-methyl-2-oxa-9$\lambda^6$-thia-6,8,15,23-tetraazatetracyclo[15.3.1.13,7.110,14]tricosa-1(21),3(23),4,6,10,12,14(22),17,19-nonaene-9,9,16-trione (Compound 57)

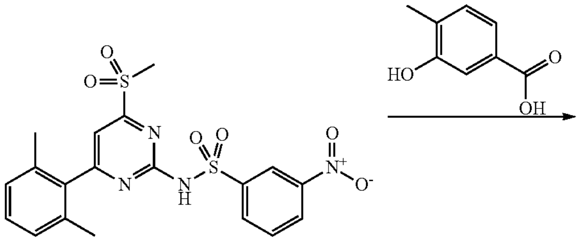

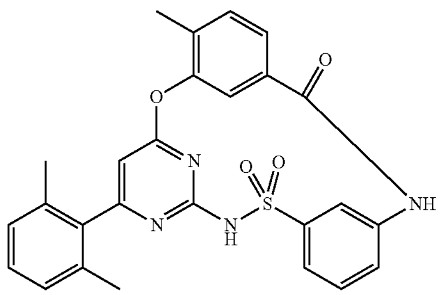

Stage 1: To a 20 mL vial equipped with a magnetic stir bar, N-[4-(2,6-dimethylphenyl)-6-methylsulfonyl-pyrimidin-2-yl]-3-nitro-benzenesulfonamide (149.2 mg, 0.3226 mmol), 3-hydroxy-4-methyl-benzoic acid (151.5 mg, 0.9957 mmol) and N-methylpyrrolidinone (4.0 mL) were added, followed by potassium carbonate (179.2 mg, 1.297 mmol). This solution was stirred at 110° C. for 17 h. The reaction mixture was then cooled to room temperature, quenched with 1 N HCl (4 mL), and extracted with ethyl acetate (3×4 mL). The combined organic extracts were washed with water (2×4 mL) and saturated aqueous sodium chloride solution (3 mL), then dried over sodium sulfate, filtered, and evaporated in vacuo to give 390 mg of a brown oil. This was purified by silica gel chromatography (12 g of silica, 0 to 40% gradient of ethyl acetate/hexanes) to give 344.2 mg of a white foam, which was not very pure (~40% pure) but was carried onward.

Stage 2: The product from Stage 1 was dissolved in a mixture of ethanol (2.0 mL) and ethyl acetate (2.0 mL) and transferred to a 10 mL vial equipped with a magnetic stir bar. This solution was purged with a balloon of hydrogen gas for 5 minutes. The cap was briefly removed, and 10% $Pd(OH)_2/C$ (20.4 mg, 0.01453 mmol) was added. This reaction mixture was stirred under a balloon of hydrogen gas at 70° C. for 50 h. It was cooled to room temperature, filtered through Celite and rinsed with methanol (10 mL), then evaporated in vacuo. Purification by reverse phase HPLC (1-99% acetonitrile in water using HCl as a modifier) provided a white solid, 3-[2-[(3-aminophenyl)sulfonylamino]-6-(2,6-dimethylphenyl)pyrimidin-4-yl]oxy-4-methyl-benzoic acid (hydrochloride salt) (84.0 mg, 48%) ESI-MS m/z calc. 504.14673, found 505.3 $(M+1)^+$; Retention time: 1.47 minutes; LC method A.

Stage 3: The product from Step 2 was dissolved in dimethylformamide (2.0 mL) and transferred to a 10 mL vial equipped with a magnetic stir bar. To this solution were added DIPEA (70 μL, 0.4019 mmol) and HATU (80.4 mg, 0.2115 mmol). This mixture was stirred at room temperature for 5 minutes, after which it was filtered and purified by reverse phase HPLC (1-99% acetonitrile in water using HCl as a modifier) to give 5-(2,6-dimethylphenyl)-20-methyl-2-oxa-9$\lambda^6$-thia-6,8,15,23-tetraazatetracyclo[15.3.1.13,7.110,14]tricosa-1(21),3(23),4,6,10,12,14(22),17,19-nonaene-9,9,16-trione (40.8 mg, 26%) ESI-MS m/z calc. 486.13617, found 487.2 $(M+1)^+$; Retention time: 1.46 minutes; LC method A.

Step 2: 4-Chloro-5-(2,6-dimethylphenyl)-20-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one

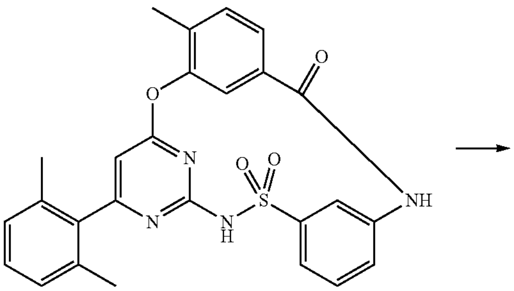

-continued

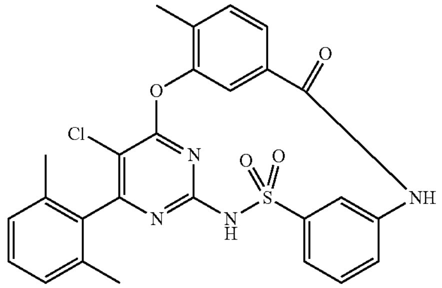

In a 3 mL vial equipped with a magnetic stir bar, 5-(2,6-dimethylphenyl)-20-methyl-2-oxa-9λ$^6$-thia-6,8,15,23-tetraazatetracyclo[15.3.1.13,7.110,14]tricosa-1(21),3(23),4,6,10,12,14(22),17,19-nonaene-9,9,16-trione (12.6 mg, 0.02590 mmol) and N-chlorosuccinimide (10.2 mg, 0.07639 mmol) were dissolved in dichloroethane (300 μL) and stirred at 90° C. for 6 h. After this time, a second batch of N-chlorosuccinimide (10.2 mg, 0.07639 mmol) was added and the reaction mixture was stirred at 90° C. for 6 h. This solution was cooled to room temperature, diluted with 1:1 methanol: dimethylsulfoxide (500 μL), filtered, and purified by reverse phase HPLC (1-70% acetonitrile in water using HCl as a modifier) to give 4-chloro-5-(2,6-dimethylphenyl)-20-methyl-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (8.3 mg, 62%). $^1$H NMR (400 MHz, dimethylsulfoxide-d$_6$) δ 12.18 (bs, 1H, $D_2O$ exchangeable), 10.55 (s, 1H, $D_2O$ exchangeable), 7.61 (s, 2H), 7.54 (t, J=7.9 Hz, 1H), 7.41-7.33 (m, 2H), 7.27 (dd, J=8.1, 7.0 Hz, 1H), 7.16 (d, J=7.6 Hz, 2H), 7.00 (s, 1H), 6.84 (t, J=2.0 Hz, 1H), 2.17 (s, 3H), 1.99 (s, 6H). ESI-MS m/z calc. 520.0972, found 521.2 (M+1)$^+$; Retention time: 1.7 minutes; LC method A.

Example 21: Preparation of Compound 58

Step 1: 5-(1-Naphthyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (Compound 58)

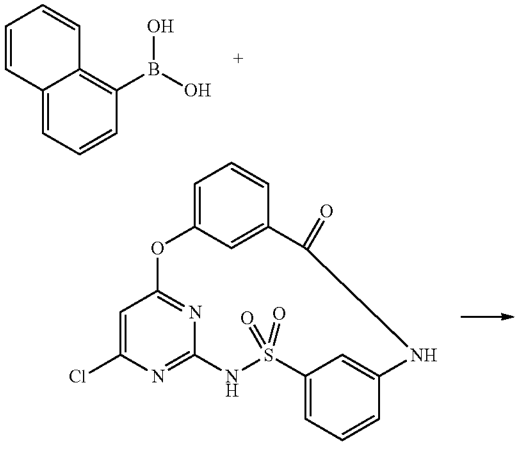

-continued

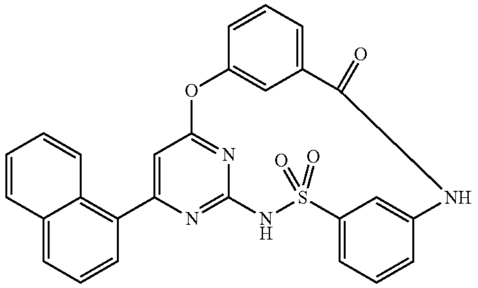

A heterogeneous solution 1-naphthylboronic acid (approximately 18.9 mg, 0.110 mmol), 5-chloro-2-oxa-9λ$^6$-thia-6,8,15,23-tetraazatetracyclo[15.3.1.13,7.110,14]tricosa-1(20),3,5,7(23),10,12,14(22),17(21),18-nonaene-9,9,16-trione (20.1 mg, 0.0500 mmol), tetrakis (triphenylphosphine)palladium(0) (approximately 11.6 mg, 0.0100 mmol), and potassium carbonate (28 mg, 0.20 mmol) in Dioxane (208 μL) and water (41.8 μL) was microwaved in a sealed vial to 120° C. for 30 minutes. The reaction mixture was acidified using acetic acid (45 μL, 0.79 mmol), diluted with DMSO (0.5 mL) and filtered. The crude solution was separated by HPLC (acetonitrile in water with 0.1% hydrochloric acid) to give 5-(1-naphthyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (6 mg, 22%). ESI-MS m/z calc. 494.1049, found 495.4 (M+1)$^+$; Retention time: 1.67 minutes; LC method A.

Example 22: Preparation of Compound 59

Step 1: 5-(2,6-Dimethylphenyl)-21-methyl-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (Compound 59)

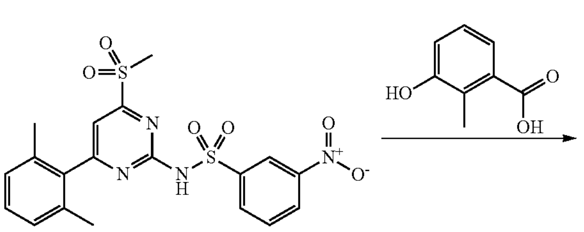

-continued

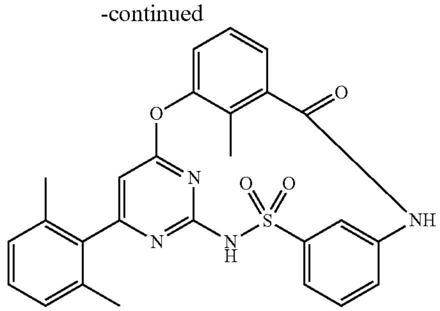

atropisomers (racemic)

Stage 1: To a 100 mL round-bottomed flask equipped with a magnetic stir bar, N-[4-(2,6-dimethylphenyl)-6-methylsulfonyl-pyrimidin-2-yl]-3-nitro-benzenesulfonamide (1.947 g, 4.210 mmol), 3-hydroxy-2-methyl-benzoic acid (1.958 g, 12.87 mmol) and N-methylpyrrolidinone (50 mL) were added, followed by potassium carbonate (2.407 g, 17.42 mmol). This slurry was stirred at 110° C. for 17 h. The reaction mixture was then cooled to room temperature, quenched with 1 N HCl (75 mL), and extracted with ethyl acetate (3×75 mL). The combined organic extracts were washed with water (2×150 mL) and saturated aqueous sodium chloride solution (150 mL), then dried over sodium sulfate, filtered, and evaporated in vacuo to give ~3 g of a brown oil. This was purified by silica gel chromatography (120 g of silica, 0 to 40% gradient of ethyl acetate/hexanes) to give 1.385 g of white solid flakes, which was not very pure (only ~55% pure) but was carried onward.

Stage 2: The product from Stage 1 was dissolved in ethanol (20 mL) and transferred to a 100 mL round-bottomed flask equipped with a magnetic stir bar. This solution was purged with a balloon of hydrogen gas for 5 minutes. The cap was briefly removed, and 10% $Pd(OH)_2/C$ (0.219 g, 0.1559 mmol) was added. This reaction mixture was stirred under hydrogen gas (2 L, 79.37 mmol) at 70° C. for 17 h. It was cooled to room temperature, filtered through Celite and rinsed with methanol (60 mL), then evaporated in vacuo to give 1.385 g of a ~60% pure material that was taken onward to the next step without purification.

Stage 3: The product from Stage 2 was dissolved in dimethylformamide (50 mL) and transferred to a 100 mL round-bottomed flask equipped with a magnetic stir bar. To this solution were added DIPEA (2.0 mL, 11.48 mmol) and HATU (3.022 g, 7.948 mmol). This mixture was stirred at room temperature for 5 minutes, after which it was quenched with water (150 mL). This mixture was extracted with ethyl acetate (3×150 mL). The combined organic extracts was washed with water (150 mL) and saturated aqueous sodium chloride solution (150 mL), then dried over sodium sulfate, filtered, and evaporated in vacuo. The obtained solid was triturated with cold methanol (10 mL) and filtered on a Büchner funnel. The filtered solid was dried in vacuo to give 5-(2,6-dimethylphenyl)-21-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (0.6859 g, 33%); $^1$H NMR (400 MHz, dimethylsulfoxide-$d_6$) δ 12.10-11.60 (bs, 1H, $D_2O$ exchangeable), 10.90-10.50 (bs, 1H, $D_2O$ exchangeable), 7.60-7.47 (m, 3H), 7.45-7.31 (m, 3H), 7.30-7.21 (m, 1H), 7.14 (d, J=7.6 Hz, 2H), 6.90-6.68 (bs, 1H), 6.54 (s, 1H), 2.05 (s, 6H), 1.45 (s, 3H). ESI-MS m/z calc. 486.13617, found 487.2 $(M+1)^+$; Retention time: 1.4 minutes; LC method A.

Example 23: Preparation of Compound 60 and Compound 61

Step 1: (+)-5-(2,6-Dimethylphenyl)-21-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (Compound 60) and (−)-5-(2,6-dimethylphenyl)-21-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (Compound 61)

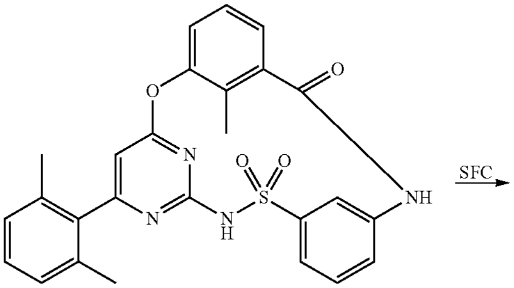

atropisomers (racemic)

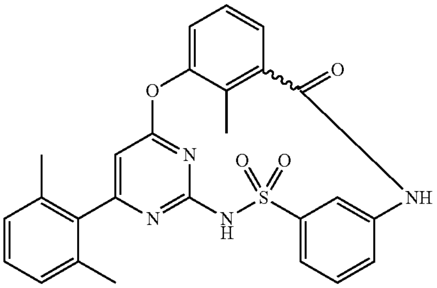

\+

Peak 1

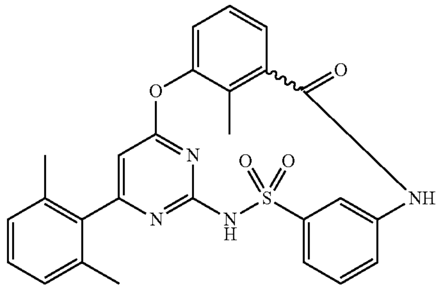

Peak 2

Racemic 5-(2,6-dimethylphenyl)-21-methyl-9,9-dioxo-2-oxa-9$\lambda^6$-thia-6,8,15,23-tetraazatetracyclo[15.3.1.13,7.110,14]tricosa-1(20),3,5,7(23),10(22),11,13,17(21),18-nonaen-16-one (200.7 mg, 0.4125 mmol) was dissolved in DMSO (6.0 mL) to achieve a concentration of ca. 33 mg/mL. Separation of the enantiomers was achieved with an SFC purification method using a ChiralCel OJ-H column (150×21.2 mm, 5 μm particle size), with a mobile phase of 30% MeOH (no modifier)+70% $CO_2$, a flow rate of 70 mL/min, an injection volume of 500 μL, and a pressure of 100 bar. The collected batches were labeled “Peak 1” and “Peak 2”.

The solution of “Peak 1” was evaporated in vacuo, maintaining the bath temperature at 25° C. This resulted in a white solid, (+)-5-(2,6-dimethylphenyl)-21-methyl-9,9-dioxo-2-oxa-9$\lambda^6$-thia-6,8,15,23-tetraazatetracyclo[15.3.1.13, 7.110,14]tricosa-1(20),3,5,7(23),10(22),11,13,17(21),18-nonaen-16-one (82.5 mg, 41%). $^1$H NMR (400 MHz, dimethylsulfoxide-$d_6$) δ 12.40-11.50 (bs, 1H, $D_2O$ exchangeable), 10.67 (s, 1H, $D_2O$ exchangeable), 7.60-7.47 (m, 3H), 7.45-7.32 (m, 3H), 7.25 (t, J=7.6 Hz, 1H), 7.14 (d, J=7.6 Hz, 2H), 6.76 (s, 1H), 6.54 (s, 1H), 2.05 (s, 6H), 1.46 (s, 3H) ESI-MS m/z calc. 486.13617, found 487.2 $(M+1)^+$; Retention time: 1.39 minutes; LC method A. Analytical SFC retention time: 3.42 minutes. The amount of enantioenrichment was recorded by chiral analytical SFC, using a 4 minute gradient 5-50% MeOH (no modifier), 2 μL injection, 150×2.1 mm AS-3 chiral column, 3.0 μm particle size, and variable flow (1.2-2.4 ml/min). Optical rotation α=+1.589° in a l=1 dm cell at a concentration of 9.6 mg in 2.0 mL of methanol (c=0.48 g/100 mL); specific rotation $[\alpha]^D$=±331°.

The solution of "Peak 2" was also evaporated in vacuo, maintaining the bath temperature at 25° C. This resulted in a white solid, (−)-5-(2,6-dimethylphenyl)-21-methyl-9,9-dioxo-2-oxa-9λ$^6$-thia-6,8,15,23-tetraazatetracyclo[15.3.1.13, 7.110,14]tricosa-1(20),3,5,7(23),10(22),11,13,17(21),18-nonaen-16-one (83.9 mg, 42%) ESI-MS m/z calc. 486.13617, found 487.2 $(M+1)^+$; Retention time: 1.39 minutes. Analytical SFC retention time: 3.02 minutes. The amount of enantioenrichment was recorded by chiral analytical SFC, using a 4 minute gradient 5-50% MeOH (no modifier), 2 μL injection, 150×2.1 mm AS-3 chiral column, 3.0 μm particle size, and variable flow (1.2-2.4 ml/min). Optical rotation α=−1.677° in a l=1 dm cell at a concentration of 10.2 mg in 2.0 mL of methanol (c=0.51 g/100 mL); specific rotation $[\alpha]^D$=329°.

Example 24: Preparation of Compound 62

Step 1: 5-(o-Tolyl)-2-oxa-9λ$^6$-thia-6,8,15,23-tetraazatetracyclo[15.3.1.13,7.110,14]tricosa-1(20),3,5,7(23),10(22),11,13,17(21),18-nonaene 9,9-dioxide (Compound 62)

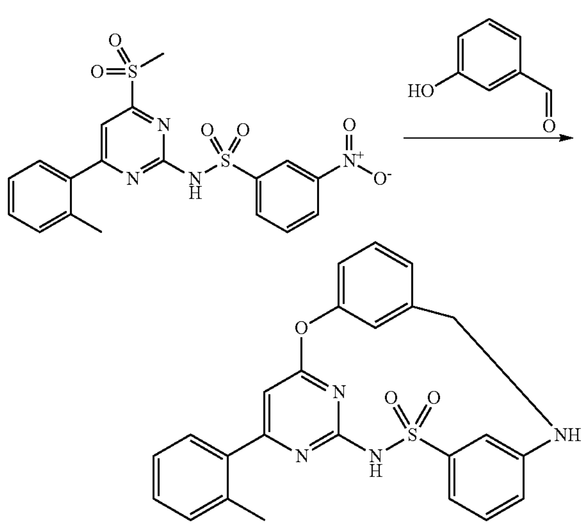

Stage 1: To a 20 mL vial equipped with a magnetic stir bar, N-[4-methylsulfonyl-6-(o-tolyl)pyrimidin-2-yl]-3-nitro-benzenesulfonamide (170.0 mg, 0.3791 mmol), N-methylpyrrolidinone (5.0 mL) and 3-hydroxybenzaldehyde (150.0 mg, 1.228 mmol) were added, followed by potassium carbonate (270.0 mg, 1.954 mmol). This solution was stirred at 100° C. for 16 h. The reaction mixture was then cooled to room temperature, quenched with 1 N HCl (4 mL), and extracted with ethyl acetate (3×4 mL). The combined organic extracts were washed with water (2×4 mL) and saturated aqueous sodium chloride solution (3 mL), then dried over sodium sulfate, filtered, and evaporated in vacuo. Purification by silica gel chromatography (4 g of silica, 0 to 40% gradient of ethyl acetate/hexanes) gave 180 mg of a yellow oil.

Stage 2: The material from Stage 1 was dissolved in ethanol (1.5 mL) and transferred to a 10 mL microwave vial equipped with a magnetic stir bar. Aqueous HCl (0.75 mL of 0.5 M, 0.3750 mmol) was added, followed by a fine dust of iron (240.0 mg, 4.298 mmol). This reaction mixture was stirred at 50° C. for 30 minutes. It was cooled to room temperature, filtered, and purified by reverse phase HPLC (1-99% acetonitrile in water using HCl as a modifier) to give 20 mg of the macrocyclization precursor.

Stage 3: To a vial containing 20 mg from the Stage 2 were added acetic acid (0.75 mL), trifluoroacetic acid (15 μL, 0.1947 mmol) and sodium triacetoxyborohydride (40.0 mg, 0.1887 mmol). This white slurry was stirred at room temperature for 5 minutes, after which it was filtered and purified by reverse phase HPLC (1-99% acetonitrile in water using HCl as a modifier) to give 5-(o-tolyl)-2-oxa-9λ$^6$-thia-6,8,15,23-tetraazatetracyclo[15.3.1.13,7.110,14]tricosa-1(20),3,5,7(23),10(22),11,13,17(21),18-nonaene 9,9-dioxide (hydrochloride salt) (2.3 mg, 1%) $^1$H NMR (400 MHz, dimethylsulfoxide-$d_6$) δ 7.48 (t, J=7.8 Hz, 1H), 7.41 (d, J=7.6 Hz, 1H), 7.37 (dd, J=7.5, 1.5 Hz, 1H), 7.36-7.24 (m, 4H), 7.19-6.96 (m, 3H), 6.82 (s, 1H), 6.74 (t, J=2.1 Hz, 1H), 6.72 (s, 1H), 4.54 (s, 2H), 4.36-3.94 (bs, 7H, NH+water), 2.35 (s, 3H). ESI-MS m/z calc. 444.1256, found 445.2 $(M+1)^+$; Retention time: 0.58 minutes; LC method D.

Example 25: Preparation of Compound 63

Step 1: 5-(o-Tolyl)-9,9-dioxo-2-oxa-9λ$^6$-thia-6,8,15,23-tetraazatetracyclo[15.2.2.13,7.110,14]tricosa-1(19),3,5,7(23),10(22),11,13,17,20-nonaen-16-one (Compound 63)

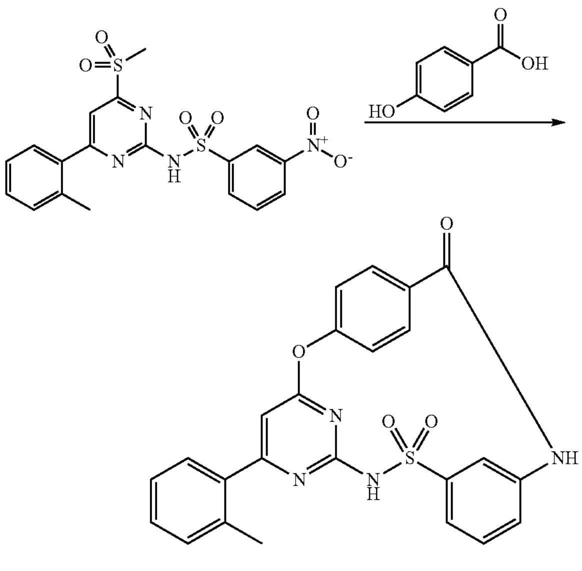

Stage 1: To a 20 mL vial equipped with a magnetic stir bar, N-[4-methylsulfonyl-6-(o-tolyl)pyrimidin-2-yl]-3-nitro-benzenesulfonamide (170.0 mg, 0.3791 mmol), N-methylpyrrolidinone (5.0 mL) and 4-hydroxybenzoic acid (170.0 mg, 1.231 mmol) were added, followed by potassium carbonate (270.0 mg, 1.954 mmol). This solution was stirred at 100° C. for 16 hours then at 120° C. for 3 hours. The reaction mixture was then cooled to room temperature, quenched with 1 N HCl (4 mL), and extracted with ethyl acetate (3×4 mL). The combined organic extracts was washed with water (2×4 mL) and saturated aqueous sodium chloride solution (3 mL), then dried over sodium sulfate, filtered, and evaporated in vacuo.

Stage 2: The crude product obtained above was dissolved in ethanol (3.0 mL) and transferred to a 10 mL microwave vial equipped with a magnetic stir bar. This solution was purged with a balloon of hydrogen gas for 5 minutes. The cap was briefly removed, and $Pd(OH)_2/C$ (8.0 mg, 0.05697 mmol) was added. This reaction mixture was stirred under a balloon of hydrogen gas at 60° C. for 19 h. It was cooled to room temperature, filtered through Celite and rinsed with ethanol (5 mL), then evaporated in vacuo. Purification by silica gel chromatography (4 g of silica, 0 to 80% gradient of ethyl acetate/hexanes) gave 210 mg of ~80% pure product. 180 mg was used for Stage 3.

Stage 3: 180 mg from Stage 2 was dissolved in DMF (2.4 mL), to which DIPEA (150 μL, 0.8612 mmol) and HATU (207.0 mg, 0.5444 mmol) were added. This mixture was stirred at room temperature for 10 minutes, after which it was filtered and purified by reverse phase HPLC (1-99% acetonitrile in water using HCl as a modifier) to give 24 mg of ~80% pure product. 8 mg from this batch was taken and purified by reverse phase HPLC (1-99% acetonitrile in water using HCl as a modifier) to give the desired macrocyclized product, 5-(o-tolyl)-9,9-dioxo-2-oxa-$9\lambda^6$-thia-6,8,15,23-tetraazatetracyclo[15.2.2.13,7.110,14]tricosa-1(19),3,5,7(23),10(22),11,13,17,20-nonaen-16-one (2.3 mg, 1%) ESI-MS m/z calc. 458.1049, found 459.1 $(M+1)^+$; Retention time: 1.38 minutes; LC method A.

Example 26: Preparation of 11-(o-Tolyl)-8-oxa-$15\lambda^6$-thia-2,12,14,21-tetraazatetracyclo[14.3.1.13,7.19,13]docosa-1(19),3(22),4,6,9,11,13(21),16(20),17-nonaene 15,15-dioxide

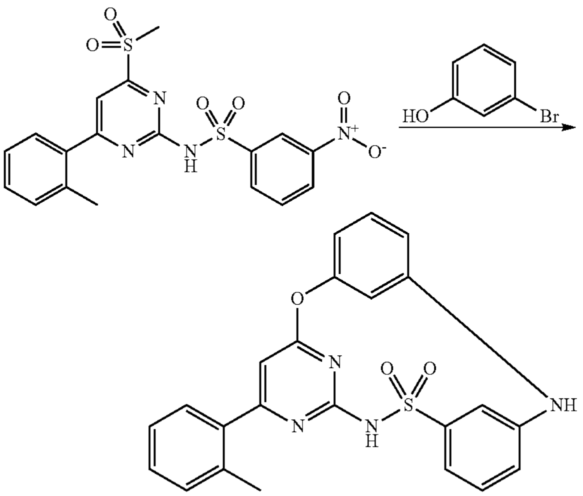

Stage 1: To a 20 mL vial equipped with a magnetic stir bar, N-[4-methylsulfonyl-6-(o-tolyl)pyrimidin-2-yl]-3-nitro-benzenesulfonamide (200.8 mg, 0.4477 mmol), N-methylpyrrolidinone (5.0 mL) and 3-bromophenol (254.3 mg, 1.470 mmol) were added, followed by potassium carbonate (259.9 mg, 1.881 mmol). This solution was stirred at 110° C. for 19 h. The reaction mixture was then cooled to room temperature, quenched with 1 N HCl (4 mL), and extracted with ethyl acetate (3×4 mL). The combined organic extracts was washed with water (2×4 mL) and saturated aqueous sodium chloride solution (3 mL), then dried over sodium sulfate, filtered, and evaporated in vacuo. This crude product was purified by silica gel chromatography (4 g of silica, 0 to 50% gradient of ethyl acetate/hexanes) to give 185.4 mg of white solid.

Stage 2: The product obtained in Stage 1 was dissolved in ethanol (1.5 mL) and transferred to a 10 mL vial equipped with a magnetic stir bar. Aqueous HCl (1.2 mL of 0.5 M, 0.6000 mmol) was added, followed by a fine dust of iron (171.2 mg, 3.066 mmol). This reaction mixture was stirred at 70° C. for 20 minutes. It was cooled to room temperature, diluted with water (3.0 mL), extracted with dichloromethane (3×5.0 mL), and dried over sodium sulfate, filtered, and evaporated in vacuo. This crude product was purified by a silica gel plug (1 g of silica, ethyl acetate) to give 108.1 mg of white solid.

Stage 3: A portion of the product from Stage 2 (30.0 mg, 0.0587 mmol) was dissolved in dimethylsulfoxide (0.9 mL) in a 10 mL vial, to which was added CuI (2.3 mg, 0.01208 mmol), pyrrole-2-carboxylic acid (2.3 mg, 0.02070 mmol), and potassium phosphate (20.3 mg, 0.09563 mmol). This mixture was purged with a balloon of nitrogen gas under sonication for 5 minutes. This mixture was then stirred at 100° C. for 21 h, then at 120° C. for 6 h. A second addition of CuI (2.3 mg, 0.01208 mmol) and pyrrole-2-carboxylic acid (2.3 mg, 0.02070 mmol) was made, and the reaction mixture was stirred for an additional 6 hours at 140° C. It was cooled to room temperature, then filtered and purified by reverse phase HPLC (1-99% acetonitrile in water using HCl as a modifier) to give 11-(o-tolyl)-8-oxa-$15\lambda^6$-thia-2,12,14,21-tetraazatetracyclo[14.3.1.13,7.19,13]docosa-1(19),3(22),4,6,9,11,13(21),16(20),17-nonaene 15,15-dioxide (4.2 mg, 2%) ESI-MS m/z calc. 430.10995, found 431.1 $(M+1)^+$; Retention time: 1.73 minutes; LC method A.

Example 27: Preparation of Compound 65

Step 1: N-[4-(3-allylphenoxy)-6-(2,6-dimethylphenyl)pyrimidin-2-yl]-3-nitro-benzenesulfonamide

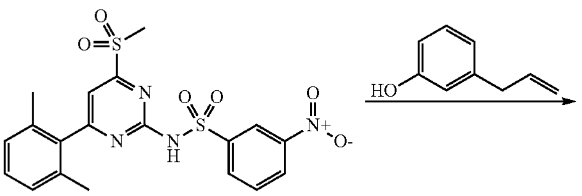

-continued

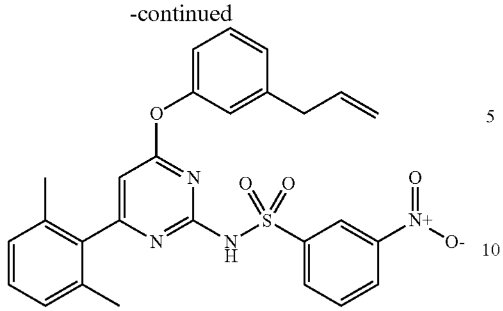

To a 20 mL vial equipped with a magnetic stir bar, N-[4-(2,6-dimethylphenyl)-6-methylsulfonyl-pyrimidin-2-yl]-3-nitro-benzenesulfonamide (0.5031 g, 1.088 mmol), N-methylpyrrolidinone (10.0 mL) and 3-allylphenol (0.5001 g, 3.727 mmol) were added, followed by potassium carbonate (0.5213 g, 3.772 mmol). This solution was stirred at 110° C. for 17 h. The reaction mixture was then cooled to room temperature, quenched with 1 N HCl (10 mL), and extracted with ethyl acetate (3×15 mL). The combined organic extracts were washed with water (2×25 mL) and saturated aqueous sodium chloride solution (25 mL), then dried over sodium sulfate, filtered, and evaporated in vacuo to give a brown oil. Purification by silica gel chromatography (24 g of silica, 0 to 40% gradient of ethyl acetate/hexanes) gave a white foam, N-[4-(3-allylphenoxy)-6-(2,6-dimethylphenyl)pyrimidin-2-yl]-3-nitro-benzenesulfonamide (342.5 mg, 61%) ESI-MS m/z calc. 516.1467, found 517.3 $(M+1)^+$; Retention time: 2.04 minutes; LC method A.

Step 2: (E)-4-[3-[6-(2,6-Dimethylphenyl)-2-[(3-nitrophenyl)sulfonylamino]pyrimidin-4-yl]oxyphenyl]but-2-enoic Acid

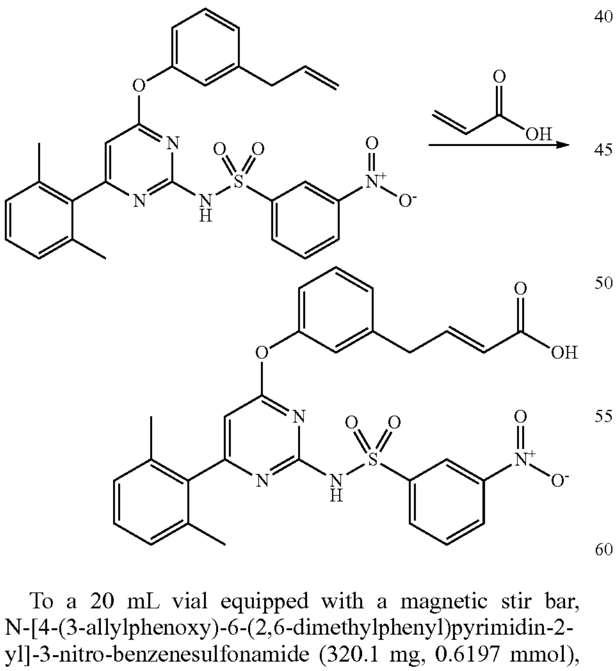

To a 20 mL vial equipped with a magnetic stir bar, N-[4-(3-allylphenoxy)-6-(2,6-dimethylphenyl)pyrimidin-2-yl]-3-nitro-benzenesulfonamide (320.1 mg, 0.6197 mmol), dichloroethane (8.0 mL), and acrylic acid (0.4 mL, 5.834 mmol) were added, followed by Hoveyda-Grubbs 2nd generation catalyst (35.2 mg, 0.05617 mmol). This solution was stirred at 70° C. for 90 minutes. The reaction mixture was then cooled to room temperature, filtered through Celite (rinsed with 10 mL dichloromethane), and evaporated in vacuo. Purification by silica gel chromatography (24 g of silica, 0 to 50% gradient of ethyl acetate/hexanes) gave a yellow foam, (E)-4-[3-[6-(2,6-dimethylphenyl)-2-[(3-nitrophenyl)sulfonylamino]pyrimidin-4-yl]oxyphenyl]but-2-enoic acid (223.4 mg, 51%) ESI-MS m/z calc. 560.1366, found 561.2 $(M+1)^+$; Retention time: 1.65 minutes; LC method A.

Step 3: 4-[3-[2-[(3-Aminophenyl)sulfonylamino]-6-(2,6-dimethylphenyl)pyrimidin-4-yl]oxyphenyl]butanoic Acid

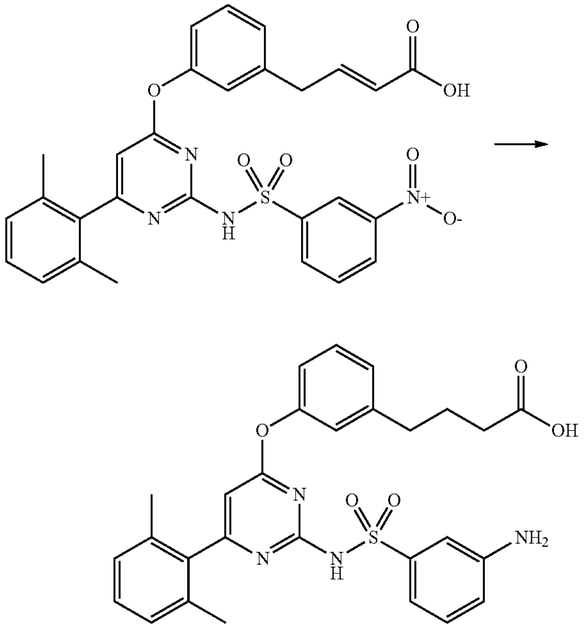

In a 10 mL vial equipped with a magnetic stir bar, (E)-4-[3-[6-(2,6-dimethylphenyl)-2-[(3-nitrophenyl)sulfonylamino]pyrimidin-4-yl]oxyphenyl]but-2-enoic acid (101.2 mg, 0.1444 mmol) was dissolved in ethanol (4.0 mL). This solution was sparged with a balloon of hydrogen gas for 5 minutes. The cap was briefly removed, and 10% $Pd(OH)_2/C$ (20.3 mg, 0.01446 mmol) was added. This reaction mixture was stirred under hydrogen gas (2 L, 79.37 mmol) at 60° C. for 17 h. It was cooled to room temperature, filtered through Celite and rinsed with methanol (6 mL), then evaporated in vacuo. Purification by reverse phase HPLC (1-99% acetonitrile in water using HCl as a modifier) gave the desired 4-[3-[2-[(3-aminophenyl)sulfonylamino]-6-(2,6-dimethylphenyl)pyrimidin-4-yl]oxyphenyl]butanoic acid (hydrochloride salt) (57.6 mg, 70%); $^1H$ NMR (400 MHz, dimethylsulfoxide-$d_6$) δ 12.20-11.40 (bs, 1H), 7.42 (t, J=7.8 Hz, 1H), 7.22 (dd, J=8.2, 7.0 Hz, 1H), 7.17 (d, J=7.8 Hz, 1H), 7.14-7.05 (m, 4H), 6.99 (s, 1H), 6.94 (t, J=7.9 Hz, 1H), 6.75 (d, J=8.1 Hz, 1H), 6.62 (d, J=7.7 Hz, 1H), 6.50 (s, 1H), 3.95-3.30 (bs, 2H), 2.65 (d, J=7.7 Hz, 2H), 2.24 (t, J=7.4 Hz, 2H), 1.97 (s, 6H), 1.84 (p, J=7.4 Hz, 2H). ESI-MS m/z calc. 532.17804, found 533.3 $(M+1)^+$; Retention time: 1.52 minutes; LC method A.

Step 4: 5-(2,6-Dimethylphenyl)-9,9-dioxo-2-oxa-9λ$^{6}$-thia-6,8,15,26-tetraazatetracyclo[18.3.1.13,7.110,14]hexacosa-1(23),3,5,7(26),10(25),11,13,20(24),21-nonaen-16-one (Compound 65)

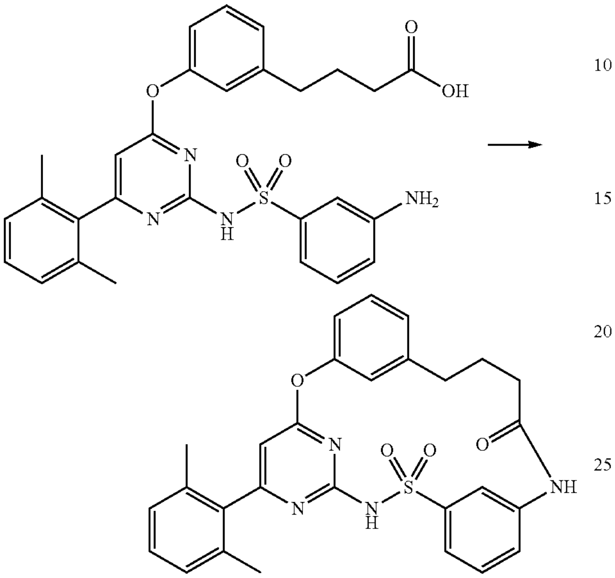

In a 3 mL vial, 4-[3-[2-[(3-aminophenyl)sulfonylamino]-6-(2,6-dimethylphenyl)pyrimidin-4-yl]oxyphenyl]butanoic acid (hydrochloride salt) (29.1 mg, 0.05114 mmol) was dissolved in DMF (0.9 mL) and treated with DIPEA (30 μL, 0.1722 mmol) and HATU (25.3 mg, 0.06654 mmol). This mixture was stirred at room temperature for 2 minutes, after which it was filtered and purified by reverse phase HPLC (1-70% acetonitrile in water using HCl as a modifier) to give the desired 5-(2,6-dimethylphenyl)-9,9-dioxo-2-oxa-9λ$^{6}$-thia-6,8,15,26-tetraazatetracyclo[18.3.1.13,7.110,14]hexacosa-1(23),3,5,7(26),10(25),11,13,20(24),21-nonaen-16-one (7.3 mg, 28%) ESI-MS m/z calc. 514.1675, found 515.3 $(M+1)^+$; Retention time: 1.56 minutes; LC method A.

Example 28: Preparation of Compound 66

Step 1: 5-(2,6-Dimethylphenyl)-22-methyl-9,9-dioxo-2-oxa-9λ$^{6}$-thia-6,8,15,25-tetraazatetracyclo[17.3.1.13,7.110,14]pentacosa-1(22),3,5,7(25),10(24),11,13,19(23),20-nonaen-16-one (Compound 66)

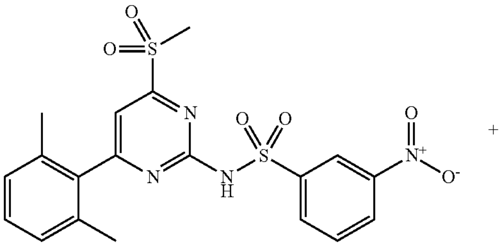

-continued

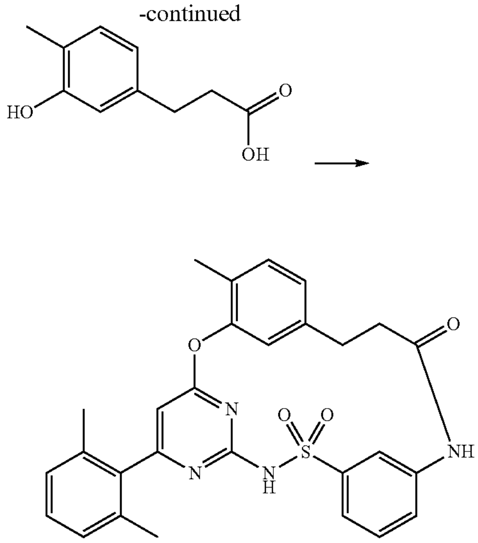

Stage 1: To a 20 mL vial equipped with a magnetic stir bar, N-[4-(2,6-dimethylphenyl)-6-methylsulfonyl-pyrimidin-2-yl]-3-nitro-benzenesulfonamide (165.5 mg, 0.3578 mmol), NMP (4.0 mL) and 3-(3-hydroxy-4-methyl-phenyl)propanoic acid (195.6 mg, 1.085 mmol) were added, followed by potassium carbonate (182.2 mg, 1.318 mmol). This solution was stirred at 140° C. for 2 h. The reaction mixture was then cooled to room temperature, quenched with 1 N HCl (5 mL), and extracted with ethyl acetate (3×5 mL). The combined organic extracts was washed with water (2×5 mL) and saturated aqueous sodium chloride solution (5 mL), then dried over sodium sulfate, filtered, and evaporated in vacuo. Purification by silica gel chromatography (12 g of silica, 0 to 45% gradient of ethyl acetate/hexanes) gave 158.2 mg of a yellow foam.

Stage 2: In a 10 mL microwave vial equipped with a magnetic stir bar, the product from Stage 1 was dissolved in EtOH (3.0 mL). This solution was sparged with a balloon of hydrogen gas for 5 minutes. The cap was briefly removed, and 10% $Pd(OH)_2/C$ (25.3 mg, 0.01802 mmol) was added. This reaction mixture was stirred under a balloon of hydrogen at 70° C. for 17 h, after which it was filtered through Celite and rinsed with EtOH (5.0 mL). This solution was evaporated in vacuo to give 142.2 mg of a yellow foam, which was used directly in the next step without further purification.

Stage 3: 71.1 mg from Stage 2 was dissolved in DMF (1.0 mL) and treated with DIPEA (40 μL, 0.2296 mmol) and $Ph_2P(O)—OC_6F_5$ (69.2 mg, 0.1801 mmol). This mixture was stirred at room temperature for 10 minutes, after which it was filtered and purified by reverse phase HPLC (1-99% acetonitrile in water using HCl as a modifier) to give 47.2 mg of the pentafluorophenyl ester product.

Stage 4: The product from Stage 3 was dissolved in NMP (1.0 mL) and stirred at 100° C. for 1 h. This solution was cooled to room temperature and purified by reverse phase HPLC (1-99% acetonitrile in water using HCl as a modifier) to give 5-(2,6-dimethylphenyl)-22-methyl-9,9-dioxo-2-oxa-9λ$^{6}$-thia-6,8,15,25-tetraazatetracyclo[17.3.1.13,7.110,14]pentacosa-1(22),3,5,7(25),10(24),11,13,19(23),20-nonaen-16-one (11.6 mg, 6%). ESI-MS m/z calc. 514.1675, found 515.2 $(M+1)^+$; Retention time: 1.6 minutes; LC method A.

Example 29: Preparation of Compound 67

Step 1: 5-(2,6-Dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one (Compound 67)

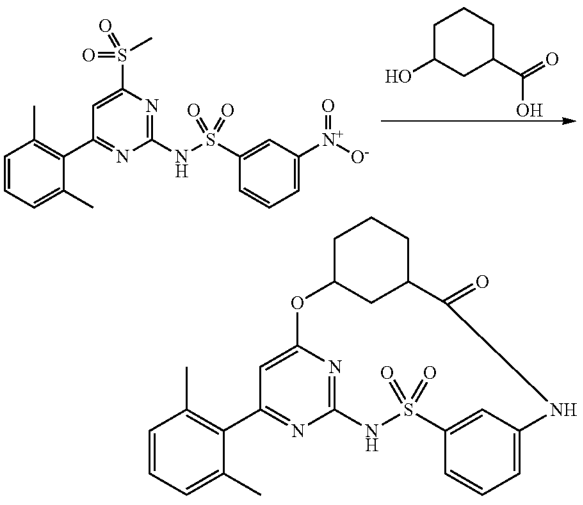

mixture of 4 stereoisomers

Stage 1: To a 20 mL vial equipped with a magnetic stir bar, 3-hydroxycyclohexanecarboxylic acid (180.0 mg, 1.249 mmol) was dissolved in N-methylpyrrolidinone (5.0 mL), and this solution was cooled to 0° C. 60% NaH (110.2 mg, 2.755 mmol) was added in one portion, and this slurry was stirred at room temperature for 15 minutes. The reaction mixture was cooled to 0° C., upon which N-[4-(2,6-dimethylphenyl)-6-methylsulfonyl-pyrimidin-2-yl]-3-nitro-benzenesulfonamide (200.0 mg, 0.4324 mmol) was added. This solution was stirred at room temperature for 30 minutes, then at 70° C. for 30 minutes. The reaction mixture was then cooled to 0° C., quenched slowly with 1 N HCl (5 mL), and extracted with ethyl acetate (3×6 mL). The combined organic extracts was washed with water (2×10 mL) and saturated aqueous sodium chloride solution (10 mL), then dried over sodium sulfate, filtered, and evaporated in vacuo. This crude product was purified by silica gel chromatography (12 g of silica, 0 to 40% gradient of ethyl acetate/hexanes) to give 129.5 mg (0.246 mmol, 57%) of product as a white foam.

Stage 2: The product from Stage 1 was dissolved in ethanol (3.0 mL) and transferred to a 10 mL vial equipped with a magnetic stir bar. This solution was sparged with a balloon of hydrogen gas for 5 minutes. The cap was briefly removed, and 10% $Pd(OH)_2/C$ (30.0 mg, 0.02136 mmol) was added. This reaction mixture was stirred under a balloon of hydrogen gas at 50° C. for 62 h. It was cooled to room temperature, filtered through Celite and rinsed with methanol (7 mL), then evaporated in vacuo to give 123.5 mg of >90% pure product. 94.5 mg of this product was used in Stage 3; 29.0 mg was kept aside.

Stage 3: In a 20 mL vial, the product from Stage 2 (94.5 mg, 0.190 mmol) was dissolved in DMF (1.9 mL) and treated with DIPEA (0.1 mL, 0.5741 mmol) and HATU (98.7 mg, 0.2596 mmol). This mixture was stirred at room temperature for 5 minutes, after which it was filtered and purified by reverse phase HPLC (1-70% acetonitrile in water using HCl as a modifier) to give the desired 5-(2,6-dimethylphenyl)-9,9-dioxo-2-oxa-9λ$^6$-thia-6,8,15,23-tetraazatetracyclo[15.3.1.13,7.110,14]tricosa-3,5,7(23),10(22),11,13-hexaen-16-one (41.1 mg, 20%) $^1$H NMR (400 MHz, dimethylsulfoxide-$d_6$) δ 9.93 (s, 1H, $D_2O$ exchangeable), 8.11 (s, 1H), 7.47 (s, 2H), 7.30 (s, 1H), 7.24 (t, J=7.6 Hz, 1H), 7.11 (d, J=7.6 Hz, 2H), 6.32 (s, 1H), 5.17-5.00 (m, 1H), 3.09 (t, J=11.1 Hz, 1H), 2.47 (d, J=10.5 Hz, 1H), 2.03 (s, 6H), 2.05-1.83 (m, 3H), 1.70-1.40 (m, 3H), 1.15 (q, J=11.7 Hz, 1H). ESI-MS m/z calc. 478.16748, found 479.3 $(M+1)^+$; Retention time: 1.45 minutes; LC method A.

Example 30: Preparation of Compound 68, Compound 69, Compound 70, and Compound 71

Step 1: 5-(2,6-Dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one, Enantiomer 1 (Compound 70), 5-(2,6-dimethylphenyl)-9,9-dioxo-2-oxa-9λ$^6$-thia-6,8,15, 23-tetraazatetracyclo[15.3.1.13,7.110,14]tricosa-3,5, 7(23),10(22),11,13-hexaen-16-one, Enantiomer 2 (Compound 71), 5-(2,6-dimethylphenyl)-9,9-dioxo-2-oxa-9λ$^6$-thia-6,8,15,23-tetraazatetracyclo [15.3.1.13,7.110,14]tricosa-3,5,7(23),10(22),11,13-hexaen-16-one, Enantiomer 3, (Compound 68) and 5-(2,6-dimethylphenyl)-9,9-dioxo-2-oxa-9λ$^6$-thia-6, 8,15,23-tetraazatetracyclo[15.3.1.13,7.110,14]tricosa-3,5,7(23),10(22),11,13-hexaen-16-one, Enantiomer 4, (Compound 69)

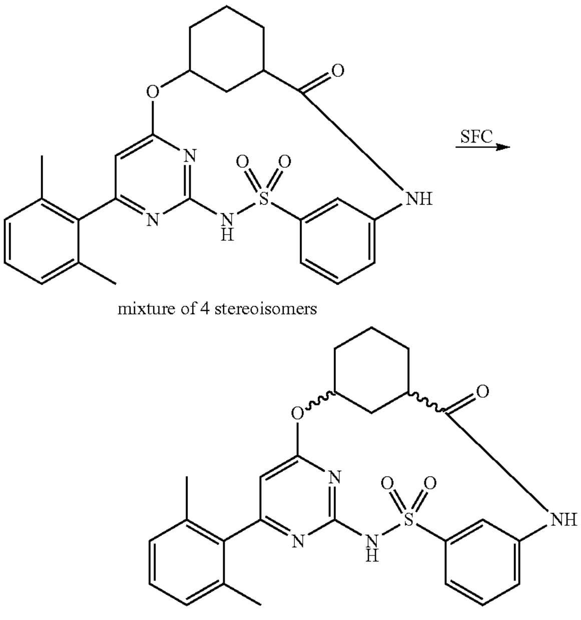

mixture of 4 stereoisomers seperated into individual stereoisomers, Peak 1~4

A mixture of all 4 stereoisomers of 5-(2,6-dimethylphenyl)-9,9-dioxo-2-oxa-9λ$^6$-thia-6,8,15,23-tetraazatetracyclo [15.3.1.13,7.110,14]tricosa-3,5,7(23),10(22),11,13-hexaen-16-one (29.0 mg, 0.06060 mmol) was dissolved in 5:1 MeOH:DMSO (1.8 mL) to achieve a concentration of ca. 16 mg/mL. Separation of the all 4 stereoisomers was achieved with an SFC purification method using a Regis R,R-WhelkO column (250×10 mm, 3 m particle size), with a mobile phase of 35% MeOH (no modifier)+65% $CO_2$, a flow rate of 10 mL/min, an injection volume of 70 μL, and a pressure of 100 bar. The collected batches were labeled "Peak 1", "Peak 2", "Peak 3" and "Peak 4". "Peak 1" and "Peak 2" were enantiomers of each other and were present in minor amounts; "Peak 3" and "Peak 4" were enantiomers of each other and were present in major amounts.

Enantiomer 1, "Peak 1": 5-(2,6-dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one (1.5 mg, 5%) ESI-MS m/z calc. 478.16748, found 479.2 $(M+1)^+$; Retention time: 1.47 minutes; LC method A. Analytical SFC retention time: 2.46 minutes. The amount of enantioenrichment was recorded by chiral analytical SFC, using a 4 minute gradient 5-50% MeOH (no modifier), 2 μL injection, 50×2.1 mm LUX Cellulose3 column, 3.0 μm particle size, and variable flow (1.8-3.2 ml/min).

Enantiomer 2, "Peak 2": 5-(2,6-dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one (1.4 mg, 5%) ESI-MS m/z calc. 478.16748, found 479.2 $(M+1)^+$; Retention time: 1.47 minutes; LC method A. Analytical SFC retention time: 2.42 minutes. The amount of enantioenrichment was recorded by chiral analytical SFC, using a 4 minute gradient 5-50% MeOH (no modifier), 2 μL injection, 50×2.1 mm LUX Cellulose3 column, 3.0 m particle size, and variable flow (1.8-3.2 ml/min).

Enantiomer 3, "Peak 3": 5-(2,6-dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one (11 mg, 38%) ESI-MS m/z calc. 478.16748, found 479.3 $(M+1)^+$; Retention time: 1.43 minutes; LC method A. Analytical SFC retention time: 2.16 minutes. The amount of enantioenrichment was recorded by chiral analytical SFC, using a 4 minute gradient 5-50% MeOH (no modifier), 2 μL injection, 50×2.1 mm LUX Cellulose3 column, 3.0 μm particle size, and variable flow (1.8-3.2 ml/min).

Enantiomer 4: "Peak 4" 5-(2,6-dimethylphenyl)-9,9-dioxo-2-oxa-9λ$^6$-thia-6,8,15,23-tetraazatetracyclo[15.3.1.13, 7.110,14]tricosa-3,5,7(23),10(22),11,13-hexaen-16-one (10.7 mg, 37%) ESI-MS m/z calc. 478.16748, found 479.3 $(M+1)^+$; Retention time: 1.44 minutes; LC method A. Analytical SFC retention time: 2.79 minutes. The amount of enantioenrichment was recorded by chiral analytical SFC, using a 4 minute gradient 5-50% MeOH (no modifier), 2 μL injection, 50×2.1 mm LUX Cellulose3 column, 3.0 m particle size, and variable flow (1.8-3.2 ml/min).

Example 31: Preparation of Compound 72

Step 1: 6-(2,6-Dimethylphenyl)-2,2-dioxo-9-oxa-2λ$^6$-thia-3,5,15,21-tetrazatricyclo[14.3.1.14,8]henicosa-1(20),4(21),5,7,16,18-hexaen-14-one (Compound 72)

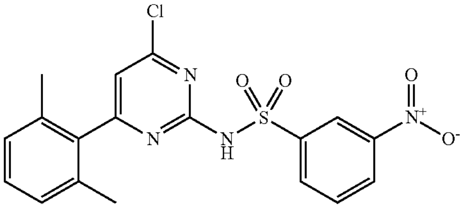

+

-continued

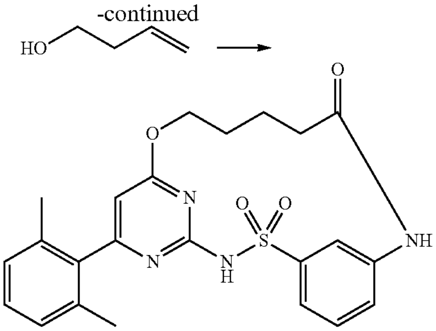

Stage 1: In a 20 ml vial, a solution of but-3-en-1-ol (60 μL, 0.7015 mmol) in NMP (4.0 mL) was treated with 60% NaH (66.7 mg, 1.668 mmol) and was stirred at room temperature for 10 minutes. Then, N-[4-chloro-6-(2,6-dimethylphenyl) pyrimidin-2-yl]-3-nitro-benzenesulfonamide (150.0 mg, 0.3581 mmol) was added, and the reaction mixture was stirred at room temperature for 20 minutes, then at 70° C. for 40 minutes. This mixture was cooled to room temperature and quenched with 1 N HCl (5 mL); this was extracted with ethyl acetate (3×5 mL). The combined organic extracts was washed with water (10 mL) and saturated aqueous sodium chloride solution (10 mL), then dried over sodium sulfate, filtered, and evaporated in vacuo to give a dark brown oil. This crude product was purified by silica gel chromatography (12 g of silica, 0 to 40% gradient of ethyl acetate/hexanes) to give N-[4-but-3-enoxy-6-(2,6-dimethylphenyl) pyrimidin-2-yl]-3-nitro-benzenesulfonamide (23.5 mg, 14%) ESI-MS m/z calc. 454.1311, found 455.3 $(M+1)^+$; Retention time: 1.68 minutes; LC method A.

Stage 2: In a 3 mL vial, the product from Stage 1 (23.5 mg, 0.0517 mmol) was dissolved in DCE (1.0 mL), to which methyl acrylate (50 μL, 0.5552 mmol) and Hoveyda-Grubbs 2nd generation catalyst (4.0 mg, 0.006383 mmol) were added. This solution was stirred at 60° C. for 5 minutes. The reaction mixture was then cooled to room temperature, filtered through a silica pipette plug (rinsed with 2 mL ethyl acetate), and evaporated in vacuo. No further purification was performed at this stage.

Stage 3: In a 3 mL vial, the crude product from Stage 2 was dissolved in THF (0.5 mL) and water (0.5 mL), to which LiOH (10.5 mg, 0.4384 mmol) was added. This solution was stirred at room temperature for 13 h, after which it was quenched with 1 N HCl (2 mL) and extracted with ethyl acetate (3×2 mL). The combined organic extracts was washed with water (4 mL) and saturated aqueous sodium chloride solution (4 mL), then dried over sodium sulfate, filtered, and evaporated in vacuo. This crude product was partially purified by a silica gel plug (100 mg of silica, 10 mL 1:1 ethyl acetate:hexanes) to give 19.8 mg of a yellow oil.

Stage 4: In a 3 mL vial equipped with a magnetic stir bar, the product from Stage 3 was dissolved in EtOH (2.0 mL). This solution was sparged with a balloon of hydrogen gas for 5 minutes. The cap was briefly removed, and 10% Pd(OH)$_2$/C (4.9 mg, 0.003489 mmol) was added. This reaction mixture was stirred under a balloon of hydrogen at 60° C. for 1 h. It was cooled to room temperature, filtered through Celite and rinsed with methanol (5 mL), then evaporated in vacuo. No further purification was performed at this stage.

Stage 5: The crude product from Stage 4 was dissolved in DMF (1.0 mL), then treated with DIPEA (20 μL, 0.1148 mmol) and HATU (22.1 mg, 0.05812 mmol). This mixture was stirred at room temperature for 5 minutes, after which it was filtered and purified by reverse phase HPLC (1-40% acetonitrile in water using HCl as a modifier) to give 6-(2,6-dimethylphenyl)-2,2-dioxo-9-oxa-$2\lambda^6$-thia-3,5,15,21-tetrazatricyclo[14.3.1.14,8]henicosa-1(20),4(21),5,7,16,18-hexaen-14-one (4.8 mg, 3%) ESI-MS m/z calc. 452.15182, found 453.3 $(M+1)^+$; Retention time: 1.2 minutes; LC method A.

Example 32: Preparation of Compound 73 and Compound 74

Step 1: 1-Benzyl-5-[[tert-butyl(diphenyl)silyl]oxymethyl]piperidin-2-one

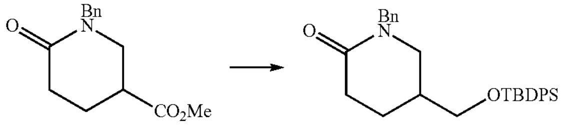

Stage 1: In a 100-mL round-bottomed flask, methyl 1-benzyl-6-oxo-piperidine-3-carboxylate (4.9286 g, 18.93 mmol) was dissolved in THF (25.0 mL) and this solution was cooled to 0° C. A THF solution of LiBH4 (20.8 mL of 2.0 M, 41.60 mmol) was added dropwise over 5 minutes, and this mixture was stirred at 0° C. for 2 h, then at room temperature for 3 h. This mixture was slowly poured into a cooled 250-mL round-bottomed flask containing EtOAc (70 mL). This mixture was then evaporated in vacuo until there was ca. 30 mL left in the flask. The flask was then cooled in an ice-water bath, to which 20 g of silica gel was added (CAUTION: EVOLUTION OF HEAT AND GAS). This slurry was then evaporated in vacuo to dryness. The product-silica mixture was then loaded onto a fritted funnel, eluted with 1:9 MeOH:EtOAc (500 mL) and evaporated in vacuo to give a white foam, 1-benzyl-5-(hydroxymethyl)piperidin-2-one (5.26 g, 127%).

Stage 2: The material obtained in Stage 1 was dissolved in DMF (60 mL) and treated with imidazole (5.8 g, 85.20 mmol) and TBDPS-Cl (7.5 g, 27.29 mmol). This solution was then stirred at 60° C. under nitrogen atmosphere for 6 h, after which it was evaporated in vacuo and purified by silica gel chromatography (220 g of silica, 0 to 100% gradient of ethyl acetate/hexanes followed by a 10% methanol/ethyl acetate flush) to give a viscous oil, 1-benzyl-5-[[tert-butyl(diphenyl)silyl]oxymethyl]piperidin-2-one (3.0836 g, 36%). $^1H$ NMR (400 MHz, dimethylsulfoxide-$d_6$) δ 7.59-7.51 (m, 4H), 7.48-7.38 (m, 6H), 7.36-7.30 (m, 2H), 7.29-7.20 (m, 3H), 4.50 (AB quartet, ΔδAB=0.12, JAB=14.7 Hz, 2H), 3.59 (dd, J=10.1, 5.4 Hz, 1H), 3.52 (dd, J=10.1, 7.0 Hz, 1H), 3.28 (dd, J=12.0, 4.9 Hz, 1H), 3.00 (dd, J=12.0, 10.1 Hz, 1H), 2.41-2.28 (m, 2H), 2.10-1.96 (m, 1H), 1.81-1.69 (m, 1H), 1.56-1.41 (m, 1H), 0.93 (s, 9H) ESI-MS m/z calc. 457.2437, found 458.4 $(M+1)^+$; Retention time: 2.42 minutes; LC method A.

Step 2: [1-Benzyl-5-[[tert-butyl(diphenyl)silyl]oxymethyl]-2-oxo-3-piperidyl] acetate and [1-benzyl-5-[[tert-butyl(diphenyl)silyl]oxymethyl]-2-thioxo-3-piperidyl] acetate

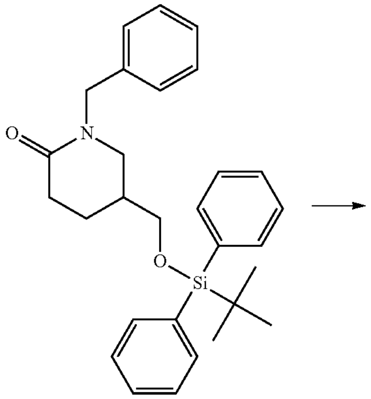

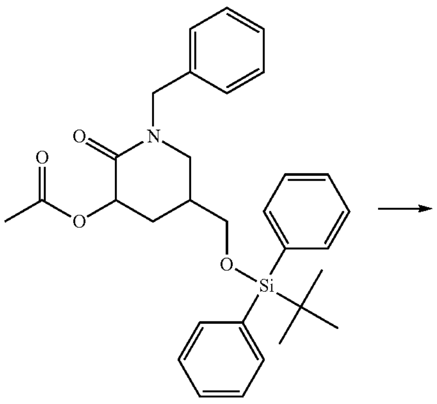

mixture of stereoisomers

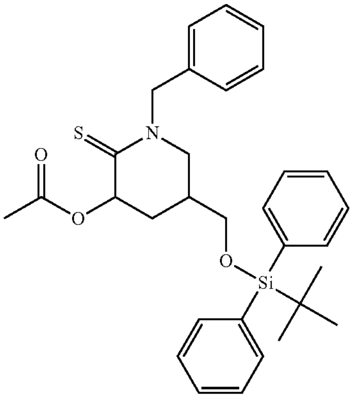

mixture of stereoisomers

A solution of 1.0 M LiHMDS in THF was first prepared by mixing hexamethyl disilazane (1.1 mL, 5.214 mmol)

with THF (2.0 mL), and adding a hexanes solution of n-BuLi (2.0 mL of 2.5 M, 5.000 mmol) at −78° C.

Stage 1: In a 20-mL microwave vial, 1-benzyl-5-[[tert-butyl(diphenyl)silyl]oxymethyl]piperidin-2-one (0.9901 g, 2.163 mmol) was mixed with THF (8.0 mL), cooled to −78° C., treated with 1.0 M LiHMDS in THF (2.5 mL, 2.5 mmol), and then warmed to 0° C. After stirring at 0° C. for 15 minutes, bis(trimethylsilyl)peroxide (1.1802 g, 6.616 mmol) was added in one portion (without using a metal needle to prevent peroxide decomposition). This mixture was stirred at 0° C. for 30 minutes. The reaction was not complete, and therefore an additional amount of 1.0 M LiHMDS in THF (2.5 mL, 2.5 mmol) was introduced. This mixture was stirred at 0° C. for 30 minutes. The reaction mixture was quenched onto cooled MeOH (25 mL) in a 250-mL round-bottomed flask, and treated with sodium borohydride (0.4025 g, 10.64 mmol). This mixture was stirred at 0° C. for 10 minutes. The reaction mixture was quenched dropwise with acetic acid (10 mL), and this mixture was warmed to room temperature over 10 minutes. This was then evaporated to dryness in vacuo. This crude material [1-benzyl-5-[[tert-butyl(diphenyl)silyl]oxymethyl]-3-hydroxy-piperidin-2-one] was then mixed with DCM (20 mL), and treated with TEA (2.0 mL, 14.35 mmol), Ac2O (2.0 mL, 21.20 mmol), and DMAP (3.5 mg, 0.02865 mmol). This mixture was stirred at room temperature for 10 minutes, after which it was quenched with water (50 mL) and extracted with DCM (3×50 mL). The combined organic extracts was washed with water (50 mL) and saturated aqueous sodium chloride solution (50 mL), then dried over sodium sulfate, filtered, and evaporated in vacuo to give a yellow liquid, [1-benzyl-5-[[tert-butyl(diphenyl)silyl]oxymethyl]-2-oxo-3-piperidyl] acetate (1.11 g, 100%) ESI-MS m/z calc. 515.2492, found 516.4 $(M+1)^+$; Retention time: 2.35 minutes; LC method A.

Stage 2: In a 250-mL round-bottomed flask, [1-benzyl-5-[[tert-butyl(diphenyl)silyl]oxymethyl]-2-oxo-3-piperidyl] acetate (1.11 g, 2.152 mmol) was dissolved in PhMe (20 mL), to which Lawesson's reagent (1.41 g, 3.486 mmol) was added. This mixture was stirred at 80° C. for 30 minutes, after which it was cooled to room temperature, and directly purified by a silica gel plug (10 g of silica, 100 mL of 25% ethyl acetate/hexanes) to give a brown oil. This was further purified by silica gel chromatography (40 g of silica, 0 to 30% gradient of ethyl acetate/hexanes) to give a very viscous yellow oil, [1-benzyl-5-[[tert-butyl(diphenyl)silyl]oxymethyl]-2-thioxo-3-piperidyl] acetate (0.7385 g, 64%). Major diastereomer (each proton has an integration of 1.2) $^1$H NMR (400 MHz, dimethylsulfoxide-$d_6$) δ 7.55-7.50 (m, 4H), 7.49-7.29 (m, 11H), 5.60 (t, J=5.7 Hz, 1H), 5.41 (d, J=14.4 Hz, 1H), 5.13 (d, J=14.4 Hz, 1H), 3.68-3.37 (m, 4H), 2.23-2.12 (m, 1H), 2.08 (s, 3H), 1.82 (dd, J=7.9, 5.7 Hz, 2H), 0.93 (s, 9H). Minor diastereomer (each proton has an integration of 1.0) $^1$H NMR (400 MHz, dimethylsulfoxide-$d_6$) δ 7.55-7.50 (m, 4H), 7.49-7.29 (m, 11H), 5.53 (dd, J=10.8, 5.9 Hz, 1H), 5.25 (AB quartet, ΔδAB=0.034, JAB=14.4 Hz, 2H), 3.68-3.37 (m, 4H), 2.45-2.33 (m, 1H), 2.12-2.05 (m, 1H), 2.08 (s, 3H), 1.55 (dt, J=12.7, 10.6 Hz, 1H), 0.93 (s, 9H). ESI-MS m/z calc. 531.2263, found 532.4 $(M+1)^+$; Retention time: 2.48 minutes; LC method A.

Step 3: 1-Benzyl-5-[[tert-butyl(diphenyl)silyl]oxymethyl]-2,2-dimethyl-piperidin-3-ol

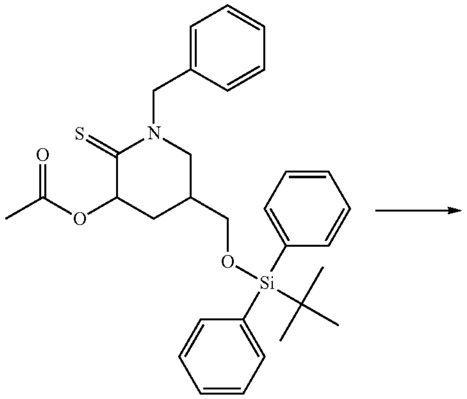

mixture of stereoisomers

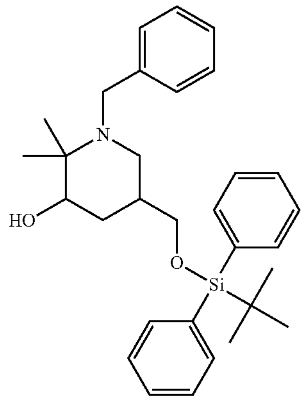

mixture of stereoisomers

Stage 1: In a 20-mL microwave vial, [1-benzyl-5-[[tert-butyl(diphenyl)silyl]oxymethyl]-2-thioxo-3-piperidyl] acetate (600 mg, 1.128 mmol) was dissolved in diethylether (7.0 mL) and this solution was cooled to 0° C. MeOTf (220 μL, 2.006 mmol) was added in one portion, and this mixture was stirred at 0° C. for 2 minutes. Then, MeMgBr (1.0 mL of 3.0 M, 3.000 mmol) was added dropwise, and this mixture was stirred at 0° C. for 5 minutes. This reaction was quenched with 1 N HCl solution (5 mL), and then water (30 mL) was added. The mixture was extracted with ethyl acetate (3×50 mL). The combined organic extracts was washed with water (100 mL) and saturated aqueous sodium chloride solution (100 mL), then dried over sodium sulfate, filtered, and evaporated in vacuo. This gave 630 mg (>100%) of an off-white foam. Since a mixture of acetylated and non-acetylated products had formed, the next step (saponification) was conducted without further purification.

Stage 2: The product obtained in Stage 1 was mixed with THF (5.0 mL) and water (5.0 mL), to which LiOH (146.5 mg, 6.117 mmol) was added. This mixture was refluxed under nitrogen gas for 4 days. This mixture was cooled to room temperature and quenched with 1 N HCl solution (10 mL), upon which water (30 mL) was added. The mixture was extracted with ethyl acetate (3×50 mL). The combined organic extracts was washed with water (100 mL) and saturated aqueous sodium chloride solution (100 mL), then dried over sodium sulfate, filtered, and evaporated in vacuo.

This gave an orange foam, 1-benzyl-5-[[tert-butyl(diphenyl) silyl]oxymethyl]-2,2-dimethyl-piperidin-3-ol (602.8 mg, >100%) ESI-MS m/z calc. 487.29065, found 488.5 $(M+1)^+$; Retention time: 1.72 minutes; LC method A. This impure product was taken onto the next step without further purification.

Step 4: [1-Benzyl-5-[2-chloro-6-(2,6-dimethylphenyl)pyrimidin-4-yl]oxy-6,6-dimethyl-3-piperidyl]methoxy-tert-butyl-diphenyl-silane

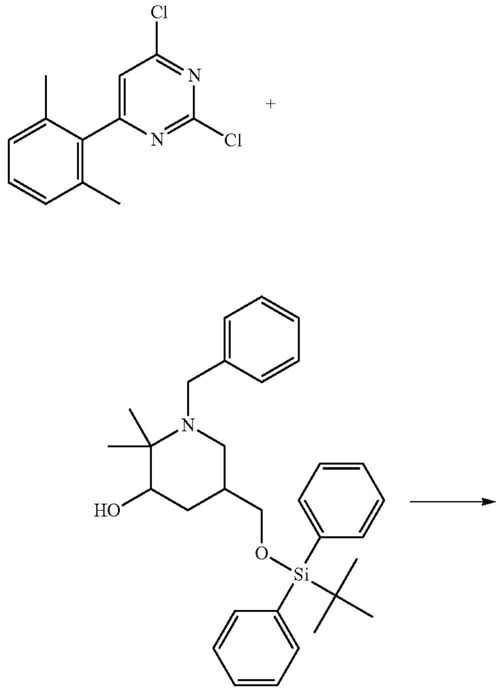

mixture of stereoisomers

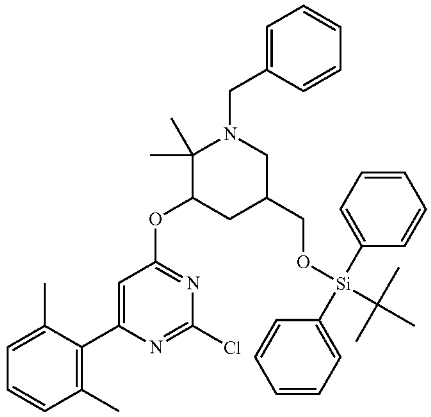

mixture of stereoisomers

In a 20-mL vial, 1-benzyl-5-[[tert-butyl(diphenyl)silyl] oxymethyl]-2,2-dimethyl-piperidin-3-ol (580.2 mg, 1.190 mmol) and 2,4-dichloro-6-(2,6-dimethylphenyl)pyrimidine (580.2 mg, 2.292 mmol) were mixed in THF (5.0 mL), to which NaH (62.5 mg of 60% w/w, 1.563 mmol) was added. This mixture was stirred at room temperature for 6 h. A second portion of NaH (62.5 mg of 60% w/w, 1.563 mmol) was added, and this mixture was stirred for 1 h. A third portion of NaH (62.5 mg of 60% w/w, 1.563 mmol) was added, and this mixture was stirred for 1 h. This mixture was then quenched dropwise with 1 N HCl solution (5 mL) and diluted with water (10 mL). The mixture was extracted with ethyl acetate (3×15 mL). The combined organic extracts were washed with water (30 mL) and saturated aqueous sodium chloride solution (30 mL), then dried over sodium sulfate, filtered, and evaporated in vacuo to give 1.0212 g of an orange foam. This crude product was purified by silica gel chromatography (80 g of silica, 0 to 100% gradient of ethyl acetate/hexanes), followed by purification with reverse phase HPLC (1-99% acetonitrile in water using HCl as a modifier) to give 3 batches of product: 1) More polar "Peak 1": [1-benzyl-5-[2-chloro-6-(2,6-dimethylphenyl)pyrimidin-4-yl]oxy-6,6-dimethyl-3-piperidyl]methoxy-tert-butyl-diphenyl-silane (hydrochloride salt) (38.3 mg, 4%). ESI-MS m/z calc. 703.33606, found 704.5 $(M+1)^+$; Retention time: 2.22 minutes; LC method A. 2) Mix of "Peak 1" and "Peak 2": 142.6 mg, 16%. 3) Less polar "Peak 2": 48.8 mg, [1-benzyl-5-[2-chloro-6-(2,6-dimethylphenyl)pyrimidin-4-yl]oxy-6,6-dimethyl-3-piperidyl]methoxy-tert-butyl-diphenyl-silane (hydrochloride salt) (48.8 mg, 6%). $^1H$ NMR (400 MHz, dimethylsulfoxide-$d_6$) δ 10.54-10.12 (bs, 1H, $D_2O$ exchangeable), 7.70-7.62 (m, 2H), 7.57-7.36 (m, 13H), 7.29-7.24 (m, 1H), 7.18-7.13 (m, 2H), 7.08 (s, 1H), 5.67 (dd, J=11.9, 4.3 Hz, 1H), 4.79 (d, J=12.3 Hz, 1H), 4.14 (dd, J=13.0, 8.7 Hz, 1H), 3.65-3.52 (m, 2H), 3.26-3.14 (m, 1H), 3.10-2.97 (m, 1H), 2.41-2.27 (m, 1H), 2.07-2.04 (m, 1H), 2.06 (s, 6H), 1.70 (s, 3H), 1.66-1.57 (m, 1H), 1.53 (s, 3H), 0.89 (s, 9H). ESI-MS m/z calc. 703.33606, found 704.5 $(M+1)^+$; Retention time: 2.25 minutes; LC method A.

Step 5: 1-Benzyl-5-[6-(2,6-dimethylphenyl)-2-[(3-nitrophenyl)sulfonylamino]pyrimidin-4-yl]oxy-6,6-dimethyl-piperidine-3-carboxylic Acid

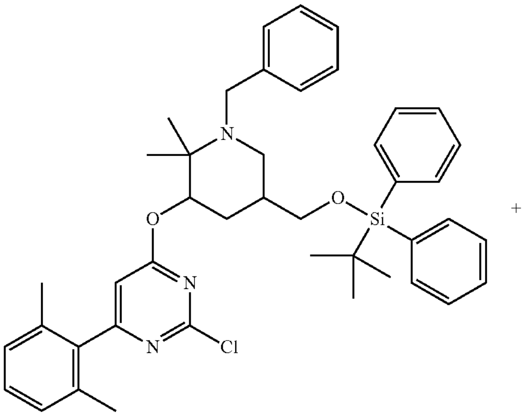

mixture of stereoisomers

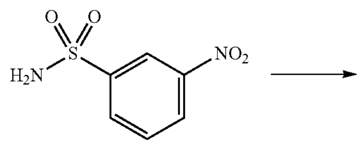

-continued

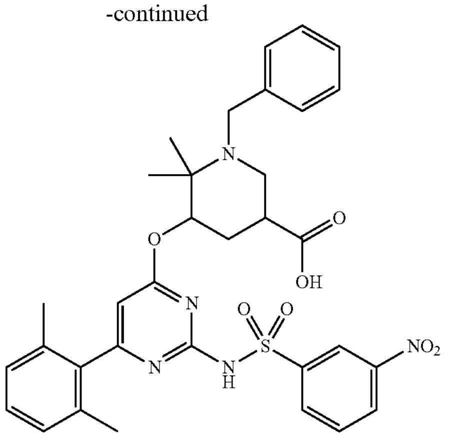

mixture of stereoisomers

Stage 1: Only the mix of "Peak 1" and "Peak 2" from the previous experiment was used. In a 20-mL microwave vial equipped with a magnetic stir bar, [1-benzyl-5-[2-chloro-6-(2,6-dimethylphenyl)pyrimidin-4-yl]oxy-6,6-dimethyl-3-piperidyl]methoxy-tert-butyl-diphenyl-silane (hydrochloride salt) (142.6 mg, 0.1925 mmol), 3-nitrobenzenesulfonamide (101.2 mg, 0.5005 mmol), cesium carbonate (250.5 mg, 0.7688 mmol), XantPhos (20.2 mg, 0.03491 mmol) and $Pd(OAc)_2$ (8.1 mg, 0.03608 mmol) were mixed with dioxane (3.0 mL). This mixture was degassed by three vacuum/nitrogen sequences. This mixture was then stirred at 120° C. for 19 h. This mixture was cooled to room temperature, filtered through Celite, and eluted with ethyl acetate (40 mL). The filtered solution was washed with water (20 mL) and saturated aqueous sodium chloride solution (20 mL), then dried over sodium sulfate, filtered, and evaporated in vacuo to give a brown oil, N-[4-[[1-benzyl-5-[[tert-butyl(diphenyl)silyl]oxymethyl]-2,2-dimethyl-3-piperidyl]oxy]-6-(2,6-dimethylphenyl)pyrimidin-2-yl]-3-nitro-benzenesulfonamide (232.1 mg, >100%).

Stage 2: In a 25-mL round-bottomed flask equipped with a magnetic stir bar, the crude product from Stage 1 was dissolved in THF (1.4 mL), to which was added a THF solution of TBAF (600 μL of 1.0 M, 0.6000 mmol). This mixture was stirred at room temperature for 1 h. A second portion of TBAF (600 μL of 1.0 M, 0.6000 mmol) was added, and this mixture was stirred at room temperature for 1 hour then at 60° C. for 1 h. The reaction mixture was cooled to room temperature then evaporated in vacuo to give N-[4-[[1-benzyl-5-(hydroxymethyl)-2,2-dimethyl-3-piperidyl]oxy]-6-(2,6-dimethylphenyl)pyrimidin-2-yl]-3-nitrobenzenesulfonamide. This crude product was taken onto the next step without further purification, but it contained tetrabutylammonium salts (from the TBAF reagent).

Stage 3: In a 25-mL round-bottomed flask, the crude product from Stage 2 was dissolved in acetone (2.0 mL), to which a solution of Jones reagent (approximately 1.2 mL of a 2 M solution, made by mixing $CrO_3$ (238 mg, 2.380 mmol) with water (1.0 mL) and conc. sulfuric acid (0.20 mL, 3.752 mmol)) was added in two portions. This mixture was stirred at room temperature for 30 minutes, after which it was quenched with isopropyl alcohol (5 mL). After 5 minutes, water (8 mL) was added, then the mixture was extracted with ethyl acetate (3×8 mL). The combined organic extracts was washed with water (10 mL) then saturated aqueous sodium chloride solution (10 mL), then dried over sodium sulfate, filtered, and evaporated in vacuo. Purification by reverse phase HPLC (1-99% acetonitrile in water using HCl as a modifier) gave 1-benzyl-5-[6-(2,6-dimethylphenyl)-2-[(3-nitrophenyl)sulfonylamino]pyrimidin-4-yl]oxy-6,6-dimethyl-piperidine-3-carboxylic acid (36.0 mg, 29%) ESI-MS m/z calc. 645.2257, found 646.4 $(M+1)^+$; Retention time: 1.24 minutes; LC method A. This product was taken onto the next step without further purification, but this product still contained tetrabutylammonium salts (from the TBAF reagent).

Step 6: 5-Benzyl-19-(2,6-dimethylphenyl)-4,4-dimethyl-2-oxa-15λ$^6$-thia-5,9,16,18,21-pentaazatetracyclo[15.3.1.13,7.110,14]tricosa-1(21),10,12,14(22),17,19-hexaene-8,15,15-trione, diastereomer 1 (Compound 73), and 5-benzyl-19-(2,6-dimethylphenyl)-4,4-dimethyl-2-oxa-15λ$^6$-thia-5,9,16,18,21-pentaazatetracyclo[15.3.1.13,7.110,14]tricosa-1(21),10,12,14(22),17,19-hexaene-8,15,15-trione, Diastereomer 4 (Compound 74)

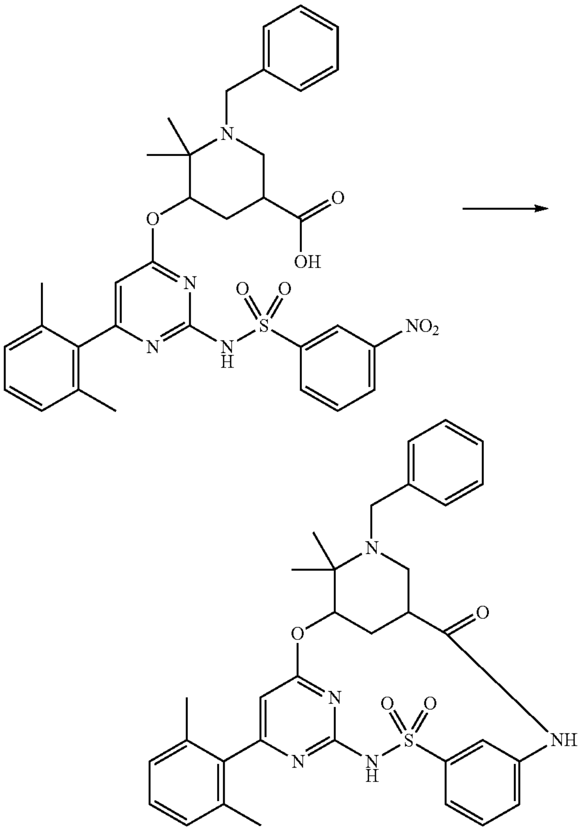

separated into 2 out of 4 diastereomers

Stage 1: In a 3-mL vial, 1-benzyl-5-[6-(2,6-dimethylphenyl)-2-[(3-nitrophenyl)sulfonylamino]pyrimidin-4-yl]oxy-6,6-dimethyl-piperidine-3-carboxylic acid (36.0 mg, 0.05575 mmol) was dissolved in EtOH (500 μL), to which aqueous HCl (200 μL of 1.0 M, 0.2000 mmol) was added, followed by a fine dust of Fe (25.2 mg, 0.4512 mmol). This reaction mixture was stirred at room temperature for 40 minutes. It was cooled to room temperature, filtered, and purified by reverse phase HPLC (1-50% acetonitrile in water using HCl as a modifier) to give 4 separable diastereomers, in decreasing order of polarity: "Diastereomer 1": 3.5 mg, "Diastereomer 2": 2.5 mg but contains significant amounts of tetrabutylammonium salts from the previous step, "Diastereomer 3": 3.5 mg but contains significant amounts of tetrabutylammonium salts from the previous step, "Diastereomer 4": 2.5 mg. Total: 5-[2-[(3-aminophenyl) sulfonylamino]-6-(2,6-dimethylphenyl)pyrimidin-4-yl]oxy-1-benzyl-6,6-dimethyl-piperidine-3-carboxylic acid (hydrochloride salt) (12.0 mg, 33%).

Stage 2: In a 3-mL vial, the 4 batches of products in Stage 1 were separately dissolved in DMF (500 μL), and treated with DIPEA (10 μL, 0.05741 mmol) and HATU (5.0 mg, 0.01315 mmol). After 5 minutes at room temperature, the reaction mixture was quenched with MeOH (300 μL), filtered and purified by reverse phase HPLC (1-50% acetonitrile in water using HCl as a modifier) to give the desired macrocyclized products: "Diastereomer 1": 5-benzyl-19-(2,6-dimethylphenyl)-4,4-dimethyl-2-oxa-$15\lambda^6$-thia-5,9,16,18,21-pentaazatetracyclo[15.3.1.13,7.110,14]tricosa-1(21),10,12,14(22),17,19-hexaene-8,15,15-trione (hydrochloride salt) (2.9 mg, 8%). ESI-MS m/z calc. 597.24097, found 598.4 $(M+1)^+$; Retention time: 1.22 minutes; LC method A. "Diastereomer 2": Very little product contaminated with tetrabutylammonium salts. "Diastereomer 3": very little product contaminated by tetrabutylammonium salts. "Diastereomer 4": 5-benzyl-19-(2,6-dimethylphenyl)-4,4-dimethyl-2-oxa-$15\lambda^6$-thia-5,9,16,18,21-pentaazatetracyclo [15.3.1.13,7.110,14]tricosa-1(21),10,12,14(22),17,19-hexaene-8,15,15-trione (hydrochloride salt) (1.6 mg, 5%). ESI-MS m/z calc. 597.24097, found 598.4 $(M+1)^+$; Retention time: 1.3 minutes; ESI-MS m/z calc. 597.24097, found 598.4 $(M+1)^+$; Retention time: 1.3 minutes; LC method A.

Example 33: Preparation of Compound 75

Step 1: Ethyl 3-(2,2-dimethylcyclohexyl)-3-oxo-propanoate

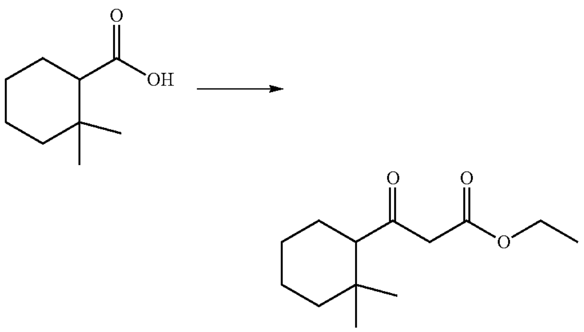

Stage 1: To a solution of 2,2-dimethylcyclohexanecarboxylic acid (5 g, 32.01 mmol) and DMF (approximately 117.0 mg, 123.9 μL, 1.600 mmol) in dichloromethane/hexanes (1:1, 128.0 mL) at 0° C. was slowly added oxalyl chloride (approximately 24.38 g, 16.76 mL, 192.1 mmol). The reaction was stirred for 1 hour or until bubbling ceased. The reaction mixture was concentrated and placed under vacuum for a brief period of time.

Stage 2: To a solution of LDA (approximately 32.33 mL of 2 M, 64.66 mmol) at −78° C. was added dropwise ethyl acetate (approximately 5.725 g, 6.347 mL, 64.98 mmol). After 10 minutes, a solution of the acid chloride from Stage 1 dissolved in THF (32 mL) was added dropwise. The reaction was allowed to warm to 23° C. and was quenched with acetic acid (approximately 2.883 g, 2.730 mL, 48.01 mmol). Water was added and the aqueous layer was extracted with ethyl acetate (3×). The combined organics were dried with brine, magnesium sulfate, filtered and concentrated under reduced pressure. The crude residue was purified by flash column chromatography on silica gel (0 to 100% Ethyl acetate in hexanes). ethyl 3-(2,2-dimethylcyclohexyl)-3-oxo-propanoate (6.29 g, 87%) was isolated as a light yellow oil. ESI-MS m/z calc. 226.15689, found 227.22 $(M+1)^+$; Retention time: 0.85 minutes; LC method D.

Step 2: 2-Amino-4-(2,2-dimethylcyclohexyl)-1H-pyrimidin-6-one

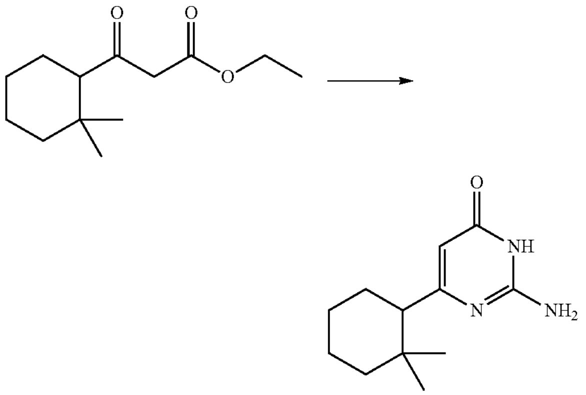

To a solution of ethyl 3-(2,2-dimethylcyclohexyl)-3-oxo-propanoate (6.29 g, 27.79 mmol) and guanidine (hydrochloride salt) (approximately 3.186 g, 33.35 mmol) in methanol (55.45 mL) at 23° C. was added 2-methylpropan-2-olate (Potassium Ion (1)) (approximately 16.84 g, 150.1 mmol) portionwise. The reaction was heated to 85° C. for 12 hours in a pressure vessel. The reaction was cooled to 23° C. and 12 mL of acetic acid was added and then further diluted with 50 mL of methanol. The crude mixture was concentrated on to silica gel. The separation was performed by flash column chromatography on silica gel (10% methanol in dichloromethane). 2-amino-4-(2,2-dimethylcyclohexyl)-1H-pyrimidin-6-one (3.52 g, 57%) was isolated as a yellow solid. ESI-MS m/z calc. 221.15282, found 222.25 $(M+1)^+$; Retention time: 0.36 minutes; LC method D.

Step 3: 4-Chloro-6-(2,2-dimethylcyclohexyl)pyrimidin-2-amine

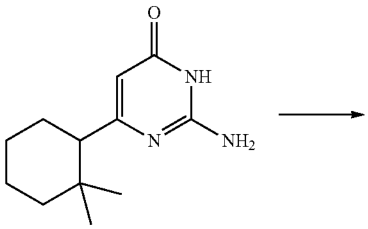

-continued

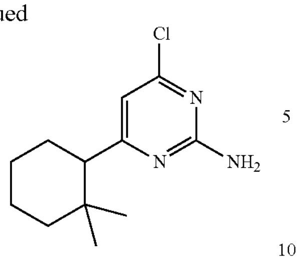

2-Amino-4-(2,2-dimethylcyclohexyl)-1H-pyrimidin-6-one (3.52 g, 15.91 mmol) was dissolved in $POCl_3$ (approximately 29.27 g, 17.79 mL, 190.9 mmol) and the resulting solution was heated to 95° C. for 4 h. The excess $POCl_3$ was removed in vacuo. The crude residue was dissolved in dichloromethane and a saturated aqueous solution of sodium bicarbonate was added. The biphasic mixture was stirred rapidly for 20 minutes. The organic layer was removed, and the aqueous layer was further extracted with dichloromethane (4×). The combined organic layers were dried over sodium sulfate, filtered, and concentrated in vacuo. The crude residue was submitted to flash column chromatography on silica gel (20% ethyl acetate in hexanes). 4-chloro-6-(2,2-dimethylcyclohexyl)pyrimidin-2-amine (1.91 g, 40%) was isolated as a white solid. ESI-MS m/z calc. 239.11893, found 240.22 $(M+1)^+$; Retention time: 0.62 minutes; LC method D.

Step 4: 5-(2,2-Dimethylcyclohexyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one (Compound 75)

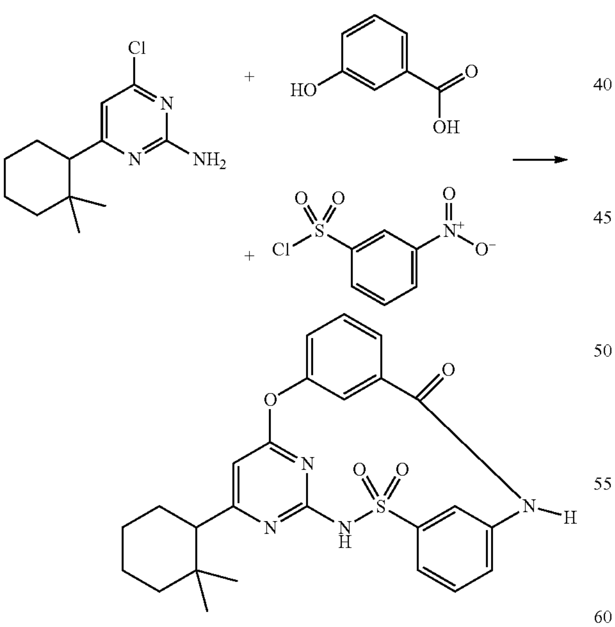

Stage 1: To a solution of 4-chloro-6-(2,2-dimethylcyclohexyl)pyrimidin-2-amine (118 mg, 0.3938 mmol) in DMF (1.575 mL) at 0° C. was added sodium hydride (approximately 37.80 mg, 1.575 mmol) and the reaction mixture was stirred at this temperature for 5 minutes, then removed from the cooling bath and stirred at room temperature for 10 minutes. The reaction mixture was cooled to 0° C. and 3-nitrobenzenesulfonyl chloride (approximately 174.5 mg, 0.7876 mmol) dissolved in DMF (1.0 mL) was added dropwise over 1 minute. The reaction mixture was stirred at this temperature for 5 minutes, then removed from the cooling bath and stirred at room temperature for 12 minutes. The reaction mixture was cooled back to 0° C. and quenched with hydrochloric acid (approximately 174.6 μL of 37% w/v, 1.772 mmol) then diluted with a solution of ethyl acetate/hexanes (1:1) and water. A saturated aqueous solution of sodium bicarbonate was added until the heterogeneous mixture was completely dissolved and the acidic solution was neutralized. The organic layer was removed and the aqueous layer was further extracted with ethyl acetate/hexanes (1:1, 5×). The combined organic extracts were dried with brine and magnesium sulfate. The solution was filtered and the filtrate was concentrated in vacuo.

Stage 2: The crude residue from Stage 1, 3-hydroxybenzoic acid (approximately 163.1 mg, 1.181 mmol), and cesium carbonate (approximately 769.9 mg, 2.363 mmol) in NMP (1.575 mL) were sealed in a small vial and heated to 115° C. for 14 h. The reaction was cooled to 23° C. and acidified with hydrochloric acid (approximately 5.513 mL of 1 M, 5.513 mmol). The aqueous solution was extracted with ethyl acetate/hexanes (1:1, 5×). The combined organic extracts were dried over magnesium sulfate, filtered and concentrated in vacuo.

Stage 3: The crude residue from Stage 2 was dissolved in ethyl acetate/acetic acid (3:1, 4.0 mL) and 10% palladium on carbon (approximately 20.95 mg, 0.1969 mmol) was added. Hydrogen gas was introduced and the reaction was stirred for 16 h. The solution was filtered and concentrated in vacuo. The crude residue containing acetic acid was dried by azeotropic distillation with benzene (3×).

Stage 4: The crude residue from Stage 3 was dissolved in DMF (3.2 mL). diisopropylethyl amine (approximately 509.0 mg, 686.0 μL, 3.938 mmol) was added followed by HATU (approximately 748.7 mg, 1.969 mmol). After 1 h, the reaction was diluted with methanol and separated directly by reverse-phase column chromatography (acetonitrile in water with 0.1% hydrochloric acid). The compound was further separated by flash column chromatography on silica gel (gradient: 0 to 100% ethyl acetate in hexanes). 5-(2,2-dimethylcyclohexyl)-9,9-dioxo-2-oxa-9λ$^6$-thia-6,8,15,23-tetraazatetracyclo[15.3.1.13,7.110,14]tricosa-1(20),3,5,7(23),10(22),11,13,17(21),18-nonaen-16-one 7,7-dioxide (20.3 mg, 11%) was isolated as a white solid. $^1H$ NMR (400 MHz, Chloroform-d) δ 9.44 (s, 1H), 7.84 (dt, J=7.7, 1.3 Hz, 1H), 7.65 (t, J=7.9 Hz, 1H), 7.61-7.35 (m, 3H), 7.32-7.27 (m, 1H), 7.23 (t, J=2.0 Hz, 1H), 6.91 (t, J=1.9 Hz, 1H), 6.20 (s, 1H), 2.56 (dd, J=12.6, 3.2 Hz, 1H), 1.89 (s, 2H), 1.71-1.43 (m, 4H), 1.42-1.17 (m, 4H), 0.90 (d, J=2.1 Hz, 6H). ESI-MS m/z calc. 478.16748, found 479.39 $(M+1)^+$; Retention time: 1.52 minutes; LC method A.

Example 34: Preparation of Compound 76

Step 1: N-[6-Chloro-4-(2,6-dimethylphenyl)pyridine-2-yl]-3-nitrobenzene-1-sulfonamide

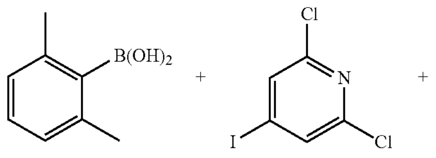

-continued

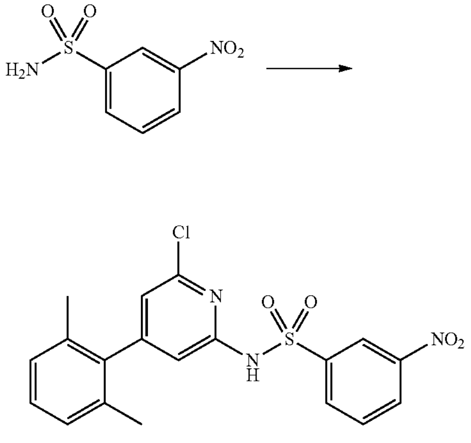

Stage 1: In five 20 mL microwave vials, each was added 2,6-dichloro-4-iodopyridine (1.0 g, 3.65 mmol), 2,6-dimethylphenylboronic acid (0.71 g, 4.74 mmol) and potassium carbonate (1.51 g, 10.95 mmol) in a solvent mixture of ethanol (4 mL) and water (4 mL). The reaction mixture was degassed for 3 minutes. Tetrakis(triphenylphosphine)palladium(0) (211 mg, 0.183 mmol) was added to reaction vessel. The reaction was flashed with nitrogen gas and then sealed. The reaction vials were then irradiated at 100° C. for 3 hours in a microwave. After all five reactions were completed, the reaction mixtures were combined and worked up together. Water (30 mL) and dichloromethane (50 mL) were added to the reaction mixture. Two layers were separated. The aqueous layer was extracted with dichloromethane (3×50 mL). The combined organic layers were washed with brine, dried over anhydrous sodium sulfate, and concentrated under vacuum. The residue was purified by silica gel chromatography using ethyl acetate-hexane gradient method (0% to 60%) to furnish 2,6-dichloro-4-(2,6-dimethylphenyl)pyridine (2.20 g, 48%) as a white solid. ESI-MS m/z calc. 251.0, 253.0, found 251.9, 254.2 $(M+1)^+$. Retention time: 3.82 minutes (LC method B).

Stage 2: Into a 20 mL microwave vial was added 2,6-dichloro-4-(2,6-dimethylphenyl)pyridine (2.20 g, 8.73 mmol), 3-nitrobenzenesulfonamide (1.76 g, 8.73 mmol) and potassium carbonate (2.41 g, 17.5 mmol) in dimethyl sulfoxide (20 mL). The reaction mixture was irradiated in a microwave reactor for 8 hours at 160° C. After completion, the reaction was diluted with water (30 mL) and ethyl acetate (50 mL). Two layers were separated, and the aqueous layer was extracted with ethyl acetate (3×50 mL). The combined organic layers were washed with water (2×20 mL), dried over anhydrous sodium sulfate, and then concentrated under vacuum. The residue was purified by silica gel chromatography using ethyl acetate-hexane gradient method (0% to 40%). The crude product was triturated with 20% ethyl acetate in hexane. The solid was filtered and dried under vacuum to furnish N-[6-chloro-4-(2,6-dimethylphenyl)pyridine-2-yl]-3-nitrobenzene-1-sulfonamide (1.05 g, 29%) as a light yellow solid. $^{1}$H NMR (250 MHz, DMSO-$d_6$) δ 11.84 (bs, 1H); 8.77 (s, 1H), 8.55 (d, J=8.3 Hz, 1H), 8.41 (d, J=7.7 Hz, 1H), 7.94 (t, J=8 Hz, 1H), 7.18 (m, 1H), 7.13 (d, J=7 Hz, 2H), 7.03 (s, 1H), 6.75 (s, 1H), 1.91 (s, 6H). ESI-MS m/z calc. 417.1, 419.1, found 418.2, 420.0 $(M+1)^+$. Retention time: 3.56 minutes (LC method B).

Step 2: 5-(2,6-Dimethylphenyl)-9,9-dioxo-2-oxa-$9\lambda^6$-thia-8,15,23-triazatetracyclo[15.3.1.13,7.110,14]tricosa-1(21),3(23),4,6,10,12,14(22),17,19-nonaen-16-one (Compound 76)

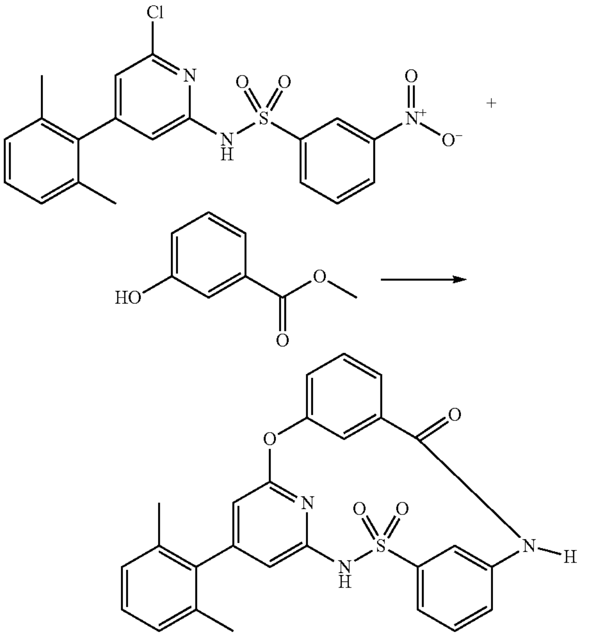

Stage 1: In a 3 mL vial, a mixture of N-[6-chloro-4-(2,6-dimethylphenyl)-2-pyridyl]-3-nitro-benzenesulfonamide (100.5 mg, 0.2405 mmol), methyl 3-hydroxybenzoate (45.2 mg, 0.2971 mmol), potassium carbonate (90.4 mg, 0.6541 mmol), Cu (20.1 mg, 0.3163 mmol), and CuI (20.2 mg, 0.1061 mmol) in nitrobenzene (1.0 mL) was stirred at 160° C. for 3 days. After cooling to room temperature, this mixture was filtered through Celite and rinsed with dioxane (5.0 mL).

Stage 2: The dioxane solution from Stage 1 was mixed with water (2.5 mL), to which LiOH (15.9 mg, 0.6639 mmol) was added. This solution was stirred at 70° C. for 30 minutes, after which it was cooled to room temperature. First, adding hexanes (10 mL) and water (10 mL), shaking thoroughly, partitioning the layers and retaining the aqueous layer, and washing the aqueous layer with ethyl acetate (5 mL) removed most of the nitrobenzene. Second, adding 1 N HCl (5 mL) and ethyl acetate (10 mL), shaking thoroughly, partitioning the layers and retaining the organic layer, and then washing the organic layer with saturated aqueous sodium chloride solution (10 mL) partially purified the product. This solution was dried over sodium sulfate, filtered, and evaporated in vacuo. This dark brown crude product was purified by a silica gel plug (1 g of silica, 30 mL 1:3 ethyl acetate:hexanes) to give 130.5 mg of a yellow oil.

Stage 3: The product from Stage 2 was dissolved in EtOH (3.0 mL), and this solution was sparged with a balloon of hydrogen gas for 5 minutes. The cap was briefly removed, and 10% $Pd(OH)_2/C$ (29.8 mg, 0.02122 mmol) was added. This reaction mixture was stirred under a balloon of hydrogen at 50° C. for 17 h, after which it was filtered through Celite and rinsed with methanol (7 mL). This solution was evaporated in vacuo to give 115.0 mg of a light yellow foam, which was used directly in the next step without further purification.

Stage 4: From the product vial of Stage 3, 50 mg was placed aside. 65.0 mg of the product from Stage 3 was dissolved in DMF (1.8 mL), to which TEA (0.2 mL, 1.435 mmol) and pentafluorophenyl diphenylphosphinate (101.2 mg, 0.2634 mmol) were added. After stirring for 15 minutes at room temperature, a second batch of pentafluorophenyl diphenylphosphinate (102.2 mg, 0.2660 mmol) was added and the reaction was stirred for another 15 minutes at room temperature. This solution was then filtered and purified by reverse phase HPLC (1-99% acetonitrile in water using HCl as a modifier) to give a white foam, (2,3,4,5,6-pentafluorophenyl) 3-[[6-[(3-aminophenyl)sulfonylamino]-4-(2,6-dimethylphenyl)-2-pyridyl]oxy]benzoate (36.0 mg, 23%) ESI-MS m/z calc. 655.12006, found 656.3 $(M+1)^+$; Retention time: 2.33 minutes; LC method A.

Stage 5: The product from Stage 4 was dissolved in NMP (1.0 mL) and stirred at 100° C. for 3 h. This solution was then cooled to room temperature, filtered and purified by reverse phase HPLC (1-70% acetonitrile in water using HCl as a modifier) to give a white solid, 5-(2,6-dimethylphenyl)-9,9-dioxo-2-oxa-$9\lambda^6$-thia-8,15,23-triazatetracyclo [15.3.1.13,7.110,14]tricosa-1(21),3(23),4,6,10,12,14(22), 17,19-nonaen-16-one (20.7 mg, 18%) ESI-MS m/z calc. 471.12527, found 472.2 $(M+1)^+$; Retention time: 1.66 minutes; LC method A.

Example 35: Preparation of Compound 77

Step 1: N-[4-Chloro-6-(2,6-dimethylphenyl)pyridin-2-yl]-3-nitrobenzene-1-sulfonamide

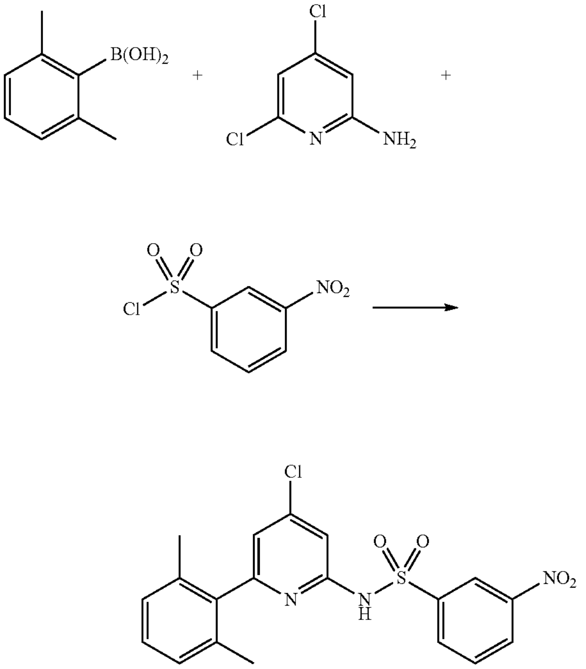

Stage 1: Into a 20 mL microwave vial was charged with 4,6-dichloropyridin-2-amine (1.00 g, 6.135 mmol), 2,6-dimethylboronic acid (1.20 g, 7.98 mmol) and cesium carbonate (6.00 g, 18.41 mmol) in a solvent mixture of dimethoxyethane (8 mL) and water (8 mL). The solution was degassed, and then [1,1'-bis(diphenylphosphino)ferrocene]palladium (II) dichloride (224 mg, 0.307 mmol) was added to the reaction vial. The reaction mixture was irradiated in a microwave reactor for 2 hours at 100° C. The reaction mixture was diluted with ethyl acetate (30 mL) and water (30 mL). Two layers were separated. The aqueous layer was extracted with ethyl acetate (3×30 mL). The combined organic layers were washed with brine (30 mL), dried over anhydrous sodium sulfate, concentrated in vacuo. The residue was purified by silica gel chromatography using ethyl acetate-hexane gradient method (0% to 30%) to give 4-chloro-6-(2,6-dimethylphenyl)pyridine-2-amine (0.72 g, 50%) as a white solid. ESI-MS m/z calc. 232.1, 234.1, found 233.0, 234.9 $(M+1)^+$. Retention time: 2.07 minutes (LC method B).

Stage 2: Into a 250 mL round bottom flask was charged with 4-chloro-6-(2,6-dimethylphenyl)pyridin-2-amine (2.05 g, 8.80 mmol) in anhydrous pyridine (20 mL). 3-Nitrobenzenesulfonyl chloride (2.93 g, 13.2 mmol) was added to the reaction mixture at 0° C. a several portions. The reaction was then stirred at room temperature for 1 hour. The reaction was quenched with aqueous hydrogen chloride (1 N, 100 mL). The product was extracted from the aqueous layer with ethyl acetate (3×50 mL). The combined organic layers were washed with aqueous hydrogen chloride (1 N, 50 mL), saturated sodium bicarbonate (aqueous), and brine. It was then dried over anhydrous sodium sulfate and concentrated in vacuo. The residue was purified by silica gel flash chromatography eluent with ethyl acetate in hexane (0% to 30%). The crude product was further purified by another silica gel chromatography eluent with ethyl acetate in dichloromethane (0% to 20%). The combined fractions were concentrated under vacuum, and then it was triturated with hexane, dried in a vacuum oven at 40° C. overnight to furnish N-[4-chloro-6-(2,6-dimethylphenyl)pyridine-2-yl]-3-nitrobenzene-1-sulfonamide (1.473 g, 40%) as a white solid. $^1H$ NMR (250 MHz, $CDCl_3$) δ 10.1 (s, br, 1H), 8.73 (t, J=1.8 Hz, 1H), 8.37 (d, J=8.0 Hz, 1H), 8.24 (d, J=7.8 Hz, 1H), 7.68 (d, J=8.0 Hz, 1H), 7.26 (m, 1H), 7.12 (m, 3H), 6.71 (d, J=1.8 Hz, 1H), 2.10 (s, 6H). ESI-MS m/z calc. 417.1, 419.1, found 418.1, 420.1 $(M+1)^+$. Retention time: 3.40 minutes (LC method B).

Step 2: 5-(2,6-Dimethylphenyl)-9,9-dioxo-2-oxa-$9\lambda^6$-thia-6,8,15-triazatetracyclo[15.3.1.13,7.110,14] tricosa-1(20),3,5,7(23),10(22),11,13,17(21),18-nonaen-16-one (Compound 77)

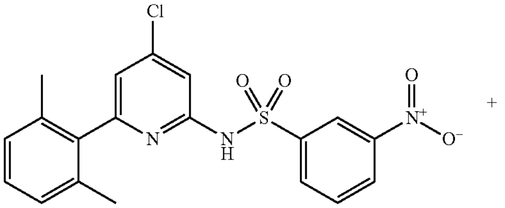

-continued

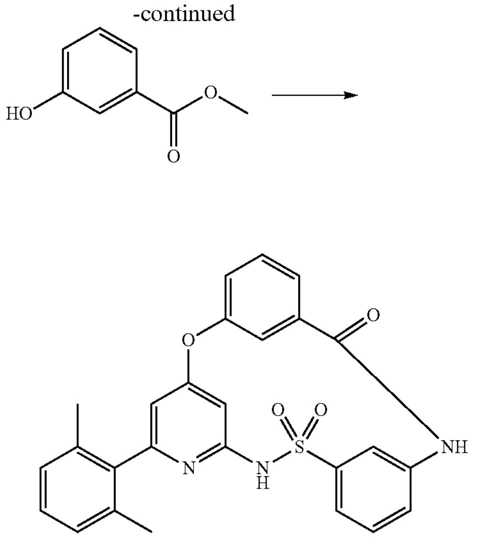

Stage 1: In a 20 mL vial, a mixture of N-[4-chloro-6-(2,6-dimethylphenyl)-2-pyridyl]-3-nitro-benzenesulfonamide (450.5 mg, 1.078 mmol), methyl 3-hydroxybenzoate (225.2 mg, 1.480 mmol), potassium carbonate (451.8 mg, 3.269 mmol), Cu (90.8 mg, 1.429 mmol), and CuI (91.4 mg, 0.4799 mmol) in nitrobenzene (5.0 mL) was stirred at 180° C. for 17 h. After cooling to room temperature, this mixture was filtered through Celite and rinsed with dioxane (20 mL).

Stage 2: The dioxane solution from Stage 1 was mixed with water (10 mL), to which LiOH (89.6 mg, 3.741 mmol) was added. This solution was stirred at 50° C. for 2 h, after which it was cooled to room temperature. First, adding 1:1 hexanes:ethyl acetate (40 mL) and water (40 mL), shaking thoroughly, partitioning the layers and retaining the aqueous layer, and washing the aqueous layer with ethyl acetate (20 mL) removed most of the nitrobenzene. Second, adding 1 N HCl (20 mL) and 1:1 hexanes:ethyl acetate (40 mL), shaking thoroughly, partitioning the layers and retaining the organic layer, and then washing the organic layer with saturated aqueous sodium chloride solution (40 mL) partially purified the product. This solution was dried over sodium sulfate, filtered, and evaporated in vacuo. This black crude product was purified by silica gel chromatography (24 g of silica, 0 to 60% gradient of ethyl acetate/hexanes) to give 440 mg of a yellow foam.

Stage 3: The product from Stage 2 was dissolved in EtOH (10 mL), and this solution was sparged with a balloon of hydrogen gas for 5 minutes. The cap was briefly removed, and 10% $Pd(OH)_2/C$ (140.5 mg, 0.1000 mmol) was added. This reaction mixture was stirred under a balloon of hydrogen at 70° C. for 14 h, after which it was filtered through Celite and rinsed with methanol (20 mL). This solution was evaporated in vacuo to give 243.7 mg of a light yellow foam, which was used directly in the next step without further purification.

Stage 4: From the product vial of Stage 3, 180 mg was placed aside. 63.7 mg of the product from Stage 3 (ca. 0.13 mmol) was dissolved in DMF (1.0 mL), to which DIPEA (0.1 mL, 0.5741 mmol) and HATU (90.2 mg, 0.2372 mmol) were added. After stirring for 5 minutes at room temperature, this solution was filtered and purified by reverse phase HPLC (1-50% acetonitrile in water using HCl as a modifier) to give a white solid, 5-(2,6-dimethylphenyl)-9,9-dioxo-2-oxa-9$\lambda^6$-thia-6,8,15-triazatetracyclo[15.3.1.13,7.110,14]tricosa-1(20),3,5,7(23),10(22),11,13,17(21),18-nonaen-16-one (31.9 mg, 60%). $^1H$ NMR (400 MHz, dimethylsulfoxide-$d_6$) δ 13.30-11.24 (broad m, 1H, $D_2O$ exchangeable), 10.59 (s, 1H, $D_2O$ exchangeable), 7.88-7.75 (m, 2H), 7.57-7.45 (m, 2H), 7.43-7.21 (m, 3H), 7.18-7.09 (m, 2H), 7.03-6.77 (m, 2H), 6.61 (s, 1H), 5.81 (s, 1H), 2.04 (s, 6H) ESI-MS m/z calc. 471.12527, found 472.2 $(M+1)^+$; Retention time: 1.38 minutes; LC method A.

Example 36: Characterization of Compounds 78-118

The compounds in the following tables were prepared in a manner analogous to that described above using commercially available reagents and intermediates described herein.

TABLE 5

| Compound Number | Structure | LCMS Rt (min) | Calc. Mass | M + 1 | LCMS Method |
|---|---|---|---|---|---|
| 78 | 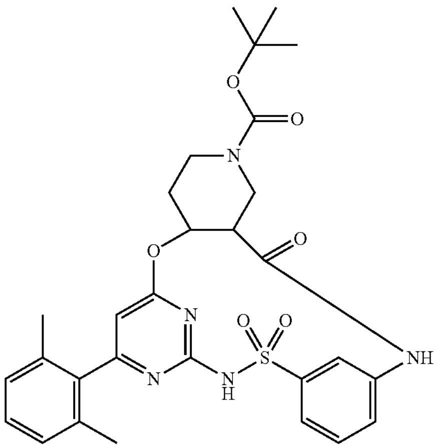 [SMILES: Cc1cccc(C)c1-c1cc2nc(n1)NS(=O)(=O)c1cccc(c1)NC(=O)C1CN(C(=O)OC(C)(C)C)CCC1O2] | 1.63 | 579.215 | 580.32 | A |

TABLE 5-continued
| Compound Number | Structure | LCMS Rt (min) | Calc. Mass | M + 1 | LCMS Method |
|---|---|---|---|---|---|
| 79 | 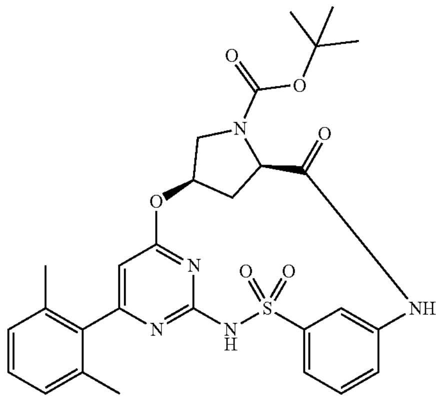 [SMILES: Cc1cccc(C)c1-c1cc2nc(n1)NS(=O)(=O)c1cccc(c1)NC(=O)[C@H]1C[C@H](CN1C(=O)OC(C)(C)C)O2] | 1.58 | 565.2 | 566.28 | A |
| 80 | 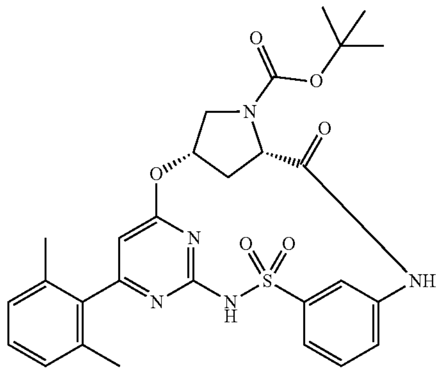 [SMILES: Cc1cccc(C)c1-c1cc2nc(n1)NS(=O)(=O)c1cccc(c1)NC(=O)[C@@H]1C[C@@H](CN1C(=O)OC(C)(C)C)O2] | 1.47 | 565.2 | 566.07 | A |
| 81 | 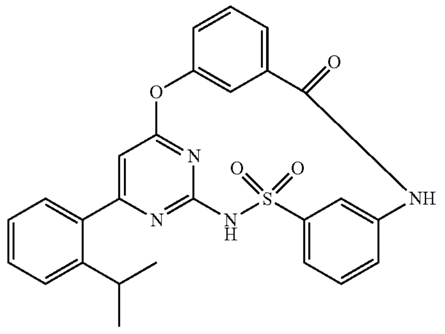 [SMILES: CC(C)c1ccccc1-c1cc2nc(n1)NS(=O)(=O)c1cccc(c1)NC(=O)c1cccc(c1)O2] | 1.6 | 486.136 | 487.1 | A |
| 82 | 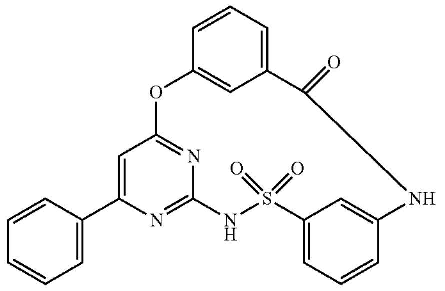 [SMILES: O=C1Nc2cccc(c2)S(=O)(=O)Nc2nc(cc(-c3ccccc3)n2)Oc2cccc1c2] | 1.4 | 444.089 | 445 | A |

TABLE 5-continued
| Compound Number | Structure | LCMS Rt (min) | Calc. Mass | M + 1 | LCMS Method |
|---|---|---|---|---|---|
| 83 | 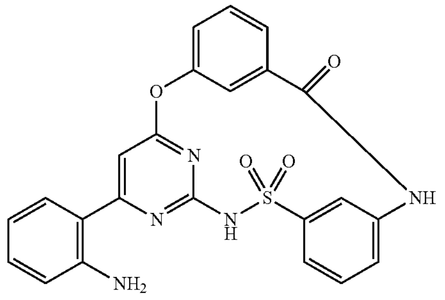 [SMILES: Nc1ccccc1-c1cc2nc(n1)NS(=O)(=O)c1cccc(c1)NC(=O)c1cccc(c1)O2] | 1.24 | 459.1 | 460.1 | A |
| 84 | 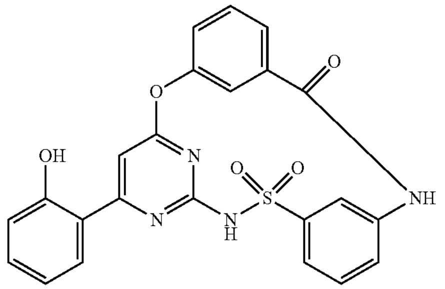 [SMILES: O=C1Nc2cccc(c2)S(=O)(=O)Nc2nc(cc(-c3ccccc3O)n2)Oc2cccc1c2] | 1.54 | 460.084 | 461.39 | A |
| 85 | 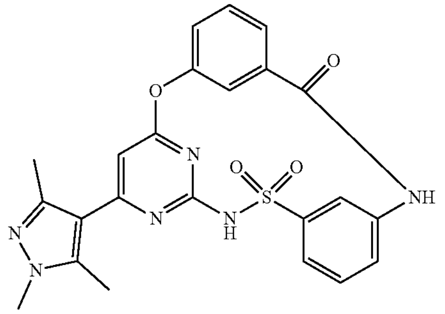 [SMILES: Cc1nn(C)c(C)c1-c1cc2nc(n1)NS(=O)(=O)c1cccc(c1)NC(=O)c1cccc(c1)O2] | 1.05 | 476.127 | 477 | A |
| 86 | 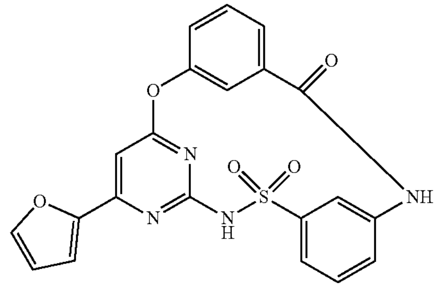 [SMILES: O=C1Nc2cccc(c2)S(=O)(=O)Nc2nc(cc(-c3ccco3)n2)Oc2cccc1c2] | 1.25 | 434.068 | 435 | A |
| 87 | 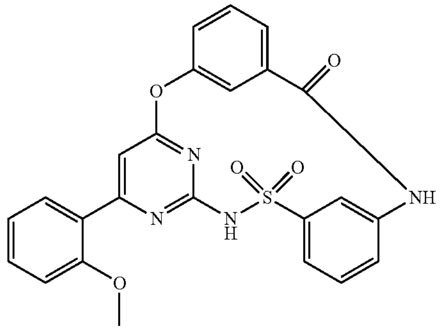 [SMILES: COc1ccccc1-c1cc2nc(n1)NS(=O)(=O)c1cccc(c1)NC(=O)c1cccc(c1)O2] | 1.29 | 474.1 | 475 | A |

TABLE 5-continued
| Compound Number | Structure | LCMS Rt (min) | Calc. Mass | M + 1 | LCMS Method |
| --- | --- | --- | --- | --- | --- |
| 88 | 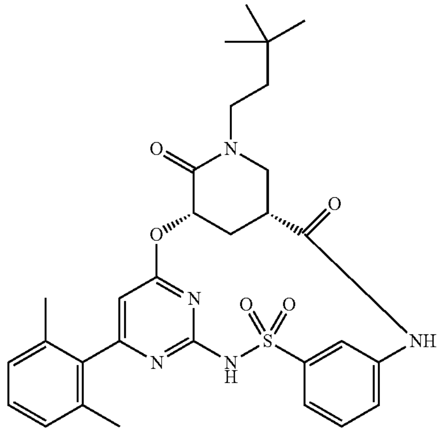 | 1.6 | 577.236 | 578.4 | A |
| 89 | 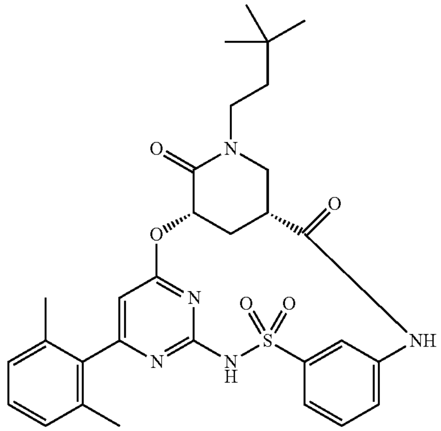 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | 1.6 | 577.236 | 578.4 | A |
| 90 | 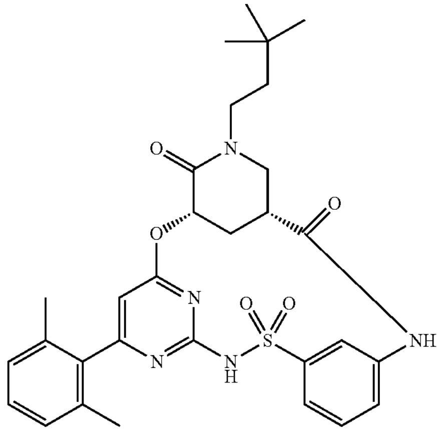 | 1.6 | 577.236 | 578.4 | A |

TABLE 5-continued
| Compound Number | Structure | LCMS Rt (min) | Calc. Mass | M + 1 | LCMS Method |
|---|---|---|---|---|---|
| 91 | 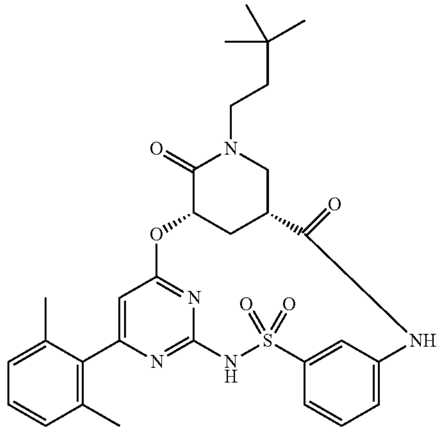 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | 1.6 | 577.236 | 578.4 | A |
| 92 | 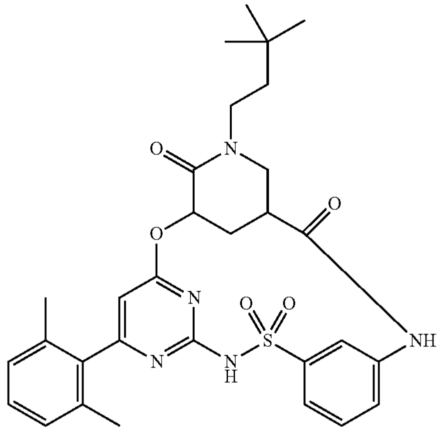 [SMILES: Cc1cccc(C)c1-c1cc2nc(n1)NS(=O)(=O)c1cccc(c1)NC(=O)C1CC(O2)C(=O)N(CCC(C)(C)C)C1] | 1.56 | 577.236 | 578.4 | A |
| 93 | 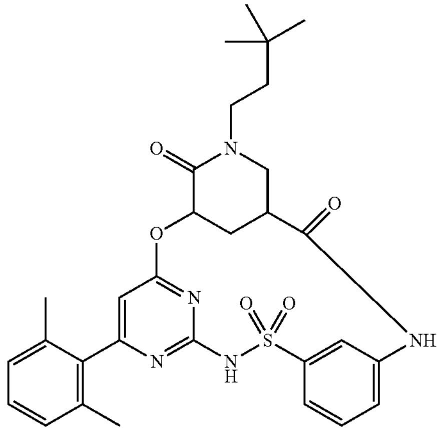 [SMILES: Cc1cccc(C)c1-c1cc2nc(n1)NS(=O)(=O)c1cccc(c1)NC(=O)C1CC(O2)C(=O)N(CCC(C)(C)C)C1] | 1.55 | 577.236 | 578.4 | A |
| 94 | 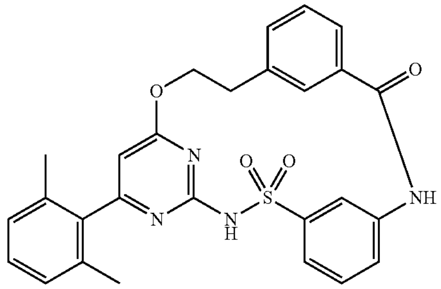 [SMILES: Cc1cccc(C)c1-c1cc2nc(n1)NS(=O)(=O)c1cccc(c1)NC(=O)c1cccc(c1)CCO2] | 1.41 | 500.152 | 501.3 | A |

TABLE 5-continued
| Compound Number | Structure | LCMS Rt (min) | Calc. Mass | M + 1 | LCMS Method |
|---|---|---|---|---|---|
| 95 | 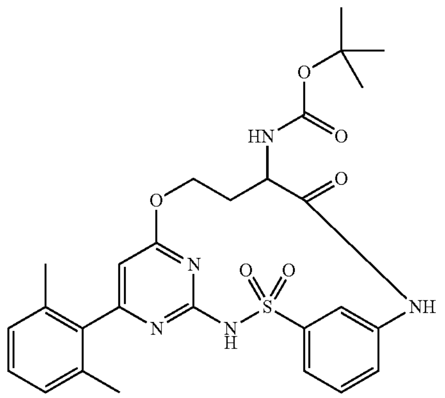 [SMILES: Cc1cccc(C)c1-c1cc2nc(n1)NS(=O)(=O)c1cccc(c1)NC(=O)C(NC(=O)OC(C)(C)C)CCO2] | 1.49 | 553.2 | 554.3 | A |
| 96 | 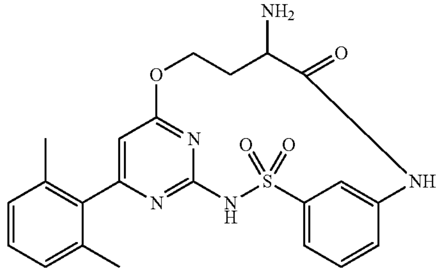 [SMILES: Cc1cccc(C)c1-c1cc2nc(n1)NS(=O)(=O)c1cccc(c1)NC(=O)C(N)CCO2] | 0.76 | 453.147 | 454.2 | A |
| 97 | 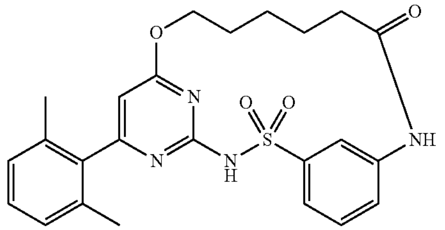 [SMILES: Cc1cccc(C)c1-c1cc2nc(n1)NS(=O)(=O)c1cccc(c1)NC(=O)CCCCCO2] | 1.36 | 466.167 | 467.3 | A |
| 98 | 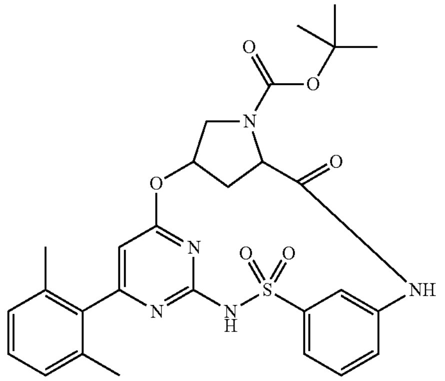 [SMILES: Cc1cccc(C)c1-c1cc2nc(n1)NS(=O)(=O)c1cccc(c1)NC(=O)C1CC(CN1C(=O)OC(C)(C)C)O2] | 1.47 | 565.2 | 566.3 | A |

TABLE 5-continued
| Compound Number | Structure | LCMS Rt (min) | Calc. Mass | M + 1 | LCMS Method |
|---|---|---|---|---|---|
| 99 | 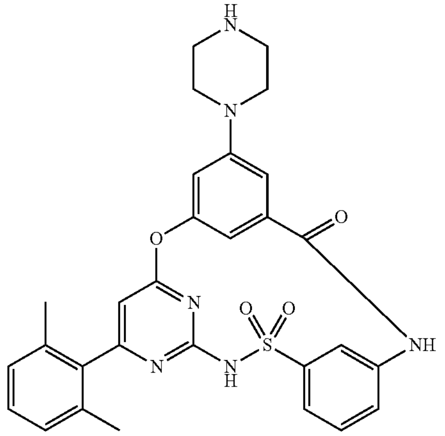 [SMILES: Cc1cccc(C)c1-c1cc2nc(n1)NS(=O)(=O)c1cccc(c1)NC(=O)c1cc(cc(N3CCNCC3)c1)O2] | 1.16 | 556.189 | 557.3 | A |
| 100 | 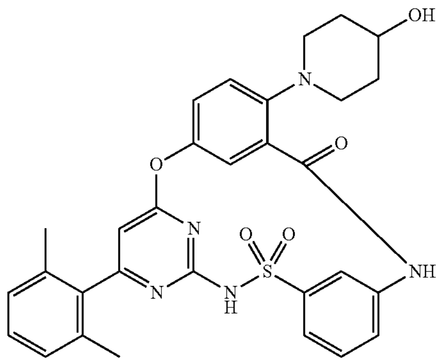 [SMILES: Cc1cccc(C)c1-c1cc2nc(n1)NS(=O)(=O)c1cccc(c1)NC(=O)c1cc(ccc1N1CCC(O)CC1)O2] | 1.16 | 571.189 | 572.2 | A |
| 101 | 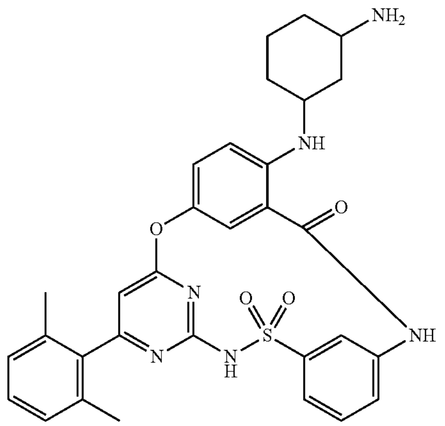 [SMILES: Cc1cccc(C)c1-c1cc2nc(n1)NS(=O)(=O)c1cccc(c1)NC(=O)c1cc(ccc1NC1CCCC(N)C1)O2] | 1.18 | 584.221 | 585.3 | A |

TABLE 5-continued
| Compound Number | Structure | LCMS Rt (min) | Calc. Mass | M + 1 | LCMS Method |
|---|---|---|---|---|---|
| 102 | 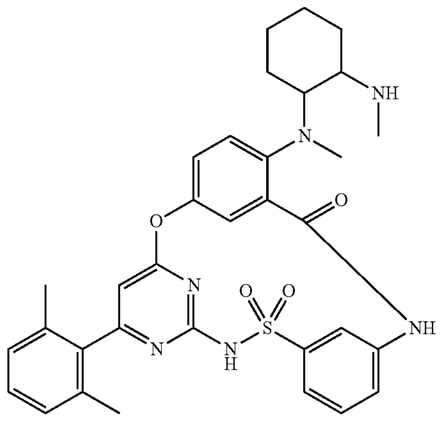 [SMILES: CNC1CCCCC1N(C)c1ccc2cc1C(=O)Nc1cccc(c1)S(=O)(=O)Nc1nc(cc(-c3c(C)cccc3C)n1)O2] | 1.22 | 612.252 | 613.3 | A |
| 103 | 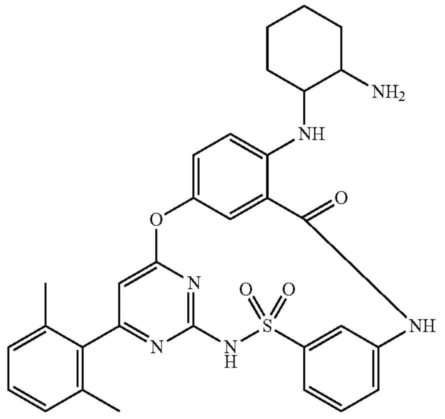 [SMILES: Cc1cccc(C)c1-c1cc2nc(n1)NS(=O)(=O)c1cccc(c1)NC(=O)c1cc(ccc1NC1CCCCC1N)O2] | 1.24 | 584.221 | 585.3 | A |
| 104 | 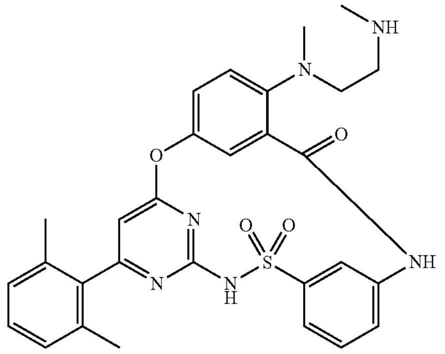 [SMILES: CNCCN(C)c1ccc2cc1C(=O)Nc1cccc(c1)S(=O)(=O)Nc1nc(cc(-c3c(C)cccc3C)n1)O2] | 1.07 | 558.205 | 559.3 | A |
| 105 | 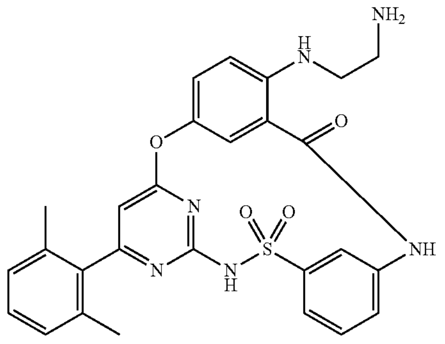 [SMILES: Cc1cccc(C)c1-c1cc2nc(n1)NS(=O)(=O)c1cccc(c1)NC(=O)c1cc(ccc1NCCN)O2] | 1.06 | 530.174 | 531.2 | A |

TABLE 5-continued
| Compound Number | Structure | LCMS Rt (min) | Calc. Mass | M + 1 | LCMS Method |
|---|---|---|---|---|---|
| 106 | 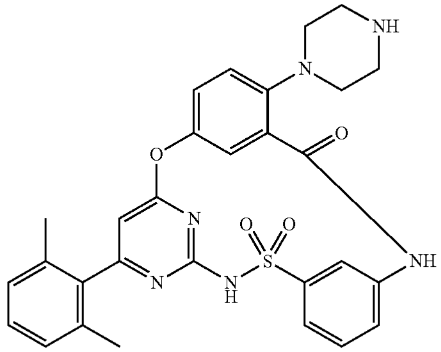 [SMILES: Cc1cccc(C)c1-c1cc2nc(n1)NS(=O)(=O)c1cccc(c1)NC(=O)c1cc(ccc1N1CCNCC1)O2] | 1.05 | 556.189 | 557.2 | A |
| 57 | 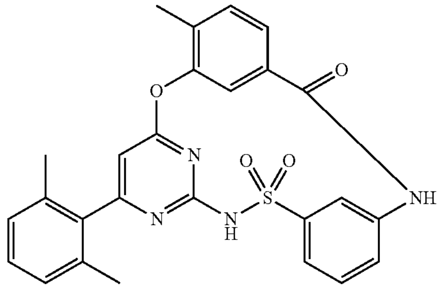 [SMILES: Cc1ccc2cc1Oc1cc(-c3c(C)cccc3C)nc(n1)NS(=O)(=O)c1cccc(c1)NC2=O] | 1.46 | 486.136 | 487.2 | A |
| 107 | 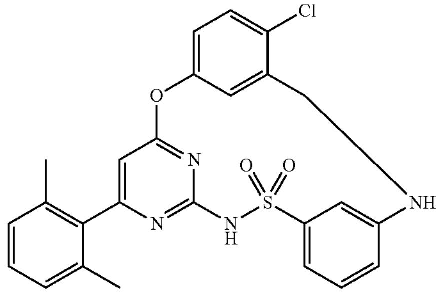 [SMILES: Cc1cccc(C)c1-c1cc2nc(n1)NS(=O)(=O)c1cccc(c1)NCc1cc(ccc1Cl)O2] | 1.825 | 492.102 | 493.15 | A |
| 108 | 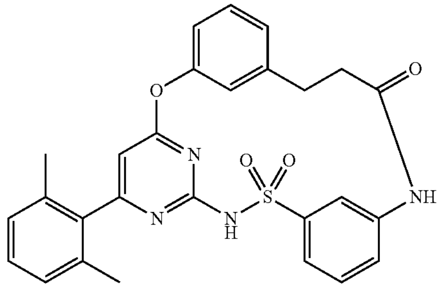 [SMILES: Cc1cccc(C)c1-c1cc2nc(n1)NS(=O)(=O)c1cccc(c1)NC(=O)CCc1cccc(c1)O2] | 1.45 | 500.152 | 501.2 | A |
| 109 | 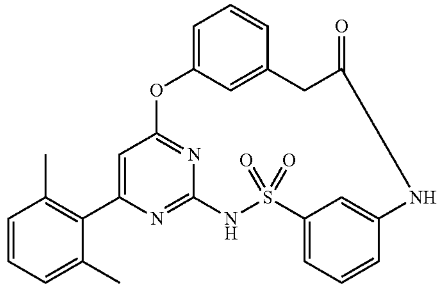 [SMILES: Cc1cccc(C)c1-c1cc2nc(n1)NS(=O)(=O)c1cccc(c1)NC(=O)Cc1cccc(c1)O2] | 1.39 | 486.136 | 487.2 | A |

TABLE 5-continued
| Compound Number | Structure | LCMS Rt (min) | Calc. Mass | M + 1 | LCMS Method |
|---|---|---|---|---|---|
| 110 | 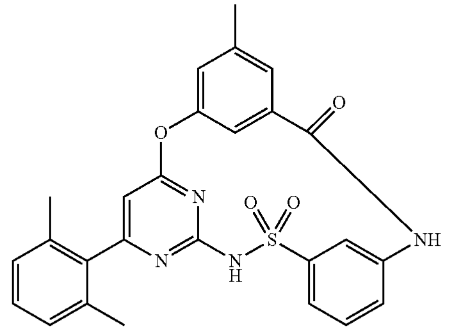 [SMILES: Cc1cc2cc(c1)C(=O)Nc1cccc(c1)S(=O)(=O)Nc1nc(cc(-c3c(C)cccc3C)n1)O2] | 1.48 | 486.136 | 487.2 | A |
| 111 | 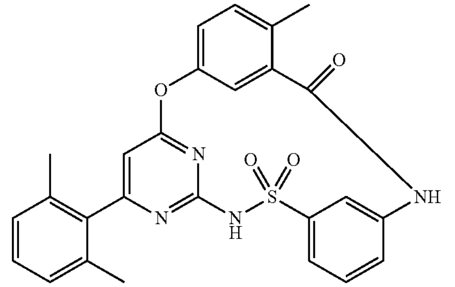 [SMILES: Cc1ccc2cc1C(=O)Nc1cccc(c1)S(=O)(=O)Nc1nc(cc(-c3c(C)cccc3C)n1)O2] | 1.43 | 486.136 | 487.1 | A |
| 113 | 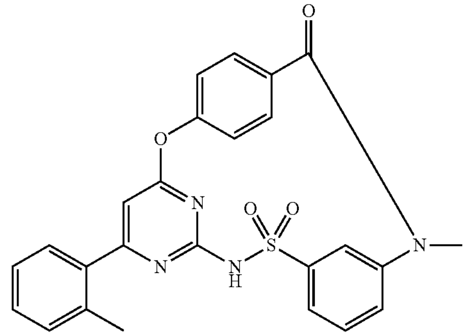 [SMILES: Cc1ccccc1-c1cc2nc(n1)NS(=O)(=O)c1cccc(c1)N(C)C(=O)c1ccc(cc1)O2] | 1.26 | 472.121 | 473.1 | A |
| 115 | 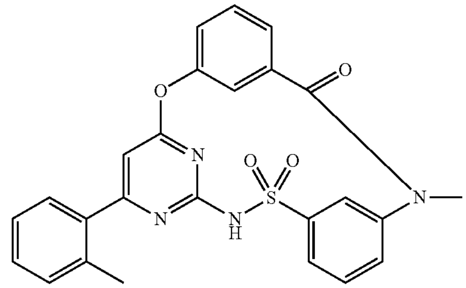 [SMILES: Cc1ccccc1-c1cc2nc(n1)NS(=O)(=O)c1cccc(c1)N(C)C(=O)c1cccc(c1)O2] | 1.28 | 472.121 | 473.1 | A |
| 116 | 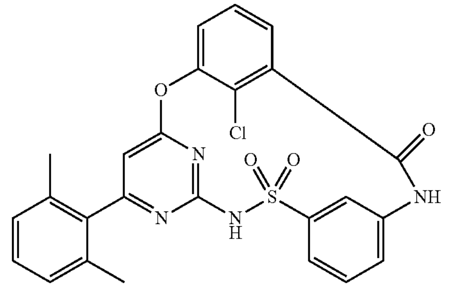 [SMILES: Cc1cccc(C)c1-c1cc2nc(n1)NS(=O)(=O)c1cccc(c1)NC(=O)c1cccc(c1Cl)O2] | 1.62 | 506.082 | 507.2 | A |

TABLE 5-continued

| Compound Number | Structure | LCMS Rt (min) | Calc. Mass | M + 1 | LCMS Method |
|---|---|---|---|---|---|
| 117 | 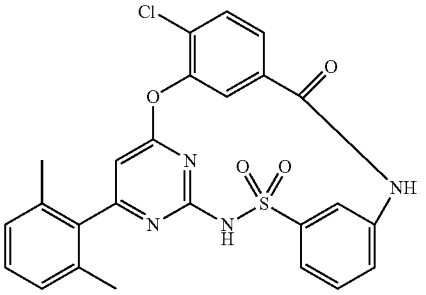 [SMILES: Cc1cccc(C)c1-c1cc2nc(n1)NS(=O)(=O)c1cccc(c1)NC(=O)c1ccc(Cl)c(c1)O2] | 1.55 | 506.082 | 507.2 | A |
| 118 | 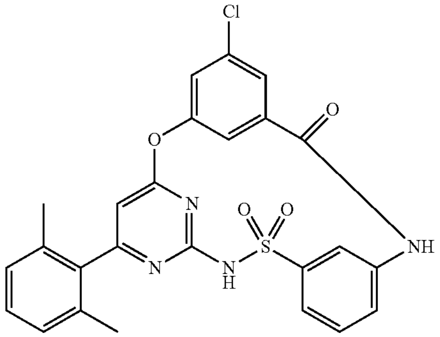 [SMILES: Cc1cccc(C)c1-c1cc2nc(n1)NS(=O)(=O)c1cccc(c1)NC(=O)c1cc(Cl)cc(c1)O2] | 1.57 | 506.082 | 507.2 | A |

TABLE 6

| Compound Number | NMR |
|---|---|
| 92 | $^1$H NMR (400 MHz, dimethylsulfoxide-$d_6$) δ 13.78-11.42 (broad doublet, 1H, $D_2O$ exchangeable), 10.17 (s, 1H, $D_2O$ exchangeable), 8.10 (s, 1H), 7.53 (s, 2H), 7.36-7.18 (m, 2H), 7.12 (d, J = 7.6 Hz, 2H), 6.43 (s, 1H), 5.61 (d, J = 7.9 Hz, 1H), 4.06-3.86 (m, 1H), 3.68 (t, J = 11.4 Hz, 1H), 3.53-3.29 (m, 3H), 2.36-2.23 (m, 1H), 2.03 (s, 6H), 1.79 (q, J = 12.1 Hz, 1H), 1.47 (m, 2H), 0.94 (s, 9H) |
| 93 | $^1$H NMR (400 MHz, dimethylsulfoxide-$d_6$) δ 13.62-11.01 (broad doublet, 1H, $D_2O$ exchangeable), 9.91 (s, 1H, $D_2O$ exchangeable), 8.51 (s, 1H), 7.49 (s, 2H), 7.35-7.18 (m, 2H), 7.12 (d, J = 7.6 Hz, 2H), 6.40 (s, 1H), 5.73 (d, J = 9.8 Hz, 1H), 3.62 (d, J = 12.3 Hz, 1H), 3.54 (dd, J = 12.3, 5.2 Hz, 1H), 3.45-3.28 (m, 3H), 2.33-2.13 (m, 2H), 2.03 (s, 6H), 1.48 (t, J = 8.3 Hz, 2H), 0.93 (s, 9H) |
| 99 | $^1$H NMR (400 MHz, dimethylsulfoxide-$d_6$) δ 10.55 (s, 1H, $D_2O$ exchangeable), 9.37 (s, 2H, $D_2O$ exchangeable), 7.49 (t, J = 7.9 Hz, 1H), 7.37 (d, J = 7.9 Hz, 1H), 7.32 (dd, J = 8.0, 2.3 Hz, 1H), 7.26 (t, J = 7.6 Hz, 1H), 7.24 (dd, J = 3.0, 1.5 Hz, 1H), 7.14 (d, J = 7.7 Hz, 2H), 7.07 (t, J = 2.2 Hz, 1H), 6.95 (t, J = 2.0 Hz, 1H), 6.68 (s, 1H), 6.39 (s, 1H), 3.62-3.52 (bs, 4H), 3.28-3.18 (bs, 4H), 2.07 (s, 6H). |
| 107 | $^1$H NMR (400 MHz, DMSO-$d_6$) δ 11.57 (s, 1H), 7.59 (d, J = 8.6 Hz, 1H), 7.35-7.26 (m br, 1H), 7.26-7.18 (m, 2H), 7.12 (d, J = 7.6 Hz, 2H), 7.09-6.96 (m br, 3H), 6.89-6.78 (m br, 1H), 6.70 (s br, 2H), 4.46 (s, 2H), 2.02 (s, 6H). |

Example 37: Preparation of Compound 119

Step 1: N-[4-Chloro-6-(2,6-dimethylphenyl)pyrimidin-2-yl]-3-(hydroxymethyl)benzenesulfonamide

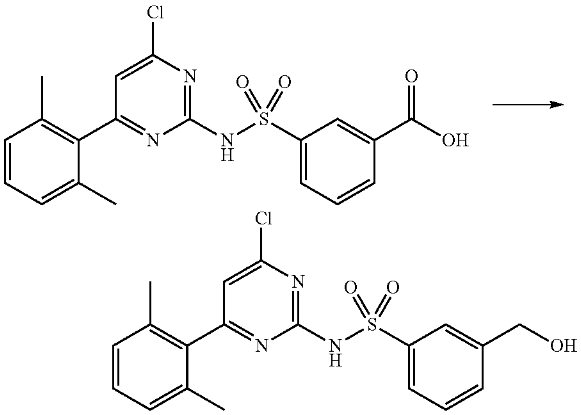

3-[[4-chloro-6-(2,6-dimethylphenyl)pyrimidin-2-yl]sulfamoyl]benzoic acid (3.235 g, 7.742 mmol) was dissolved in THF (35 mL) and cooled to 0° C. in an ice bath. Borane methylsulfide (20 mL of 2 M, 40.00 mmol) was added slowly, and the reaction mixture was removed from the ice bath and allowed to warm to room temperature. After 5 hours, the reaction mixture was cooled to 0° C. and was quenched by slow addition to a 1 M HCl aqueous solution (bubbled vigorously) also at 0° C. The aqueous layer was diluted with water and was extracted 3× with ethyl acetate and the combined organics were washed with brine, dried over sodium sulfate, and concentrated to give a foaming white solid, which was used in the next step without further purification. N-[4-chloro-6-(2,6-dimethylphenyl)pyrimidin-2-yl]-3-(hydroxymethyl)benzenesulfonamide (3.08 g, 99%) ESI-MS m/z calc. 403.07574, found 404.2 (M+1)$^+$; Retention time: 1.46 minutes (LC method J).

Step 2: 3-(Bromomethyl)-N-[4-chloro-6-(2,6-dimethylphenyl)pyrimidin-2-yl]benzenesulfonamide

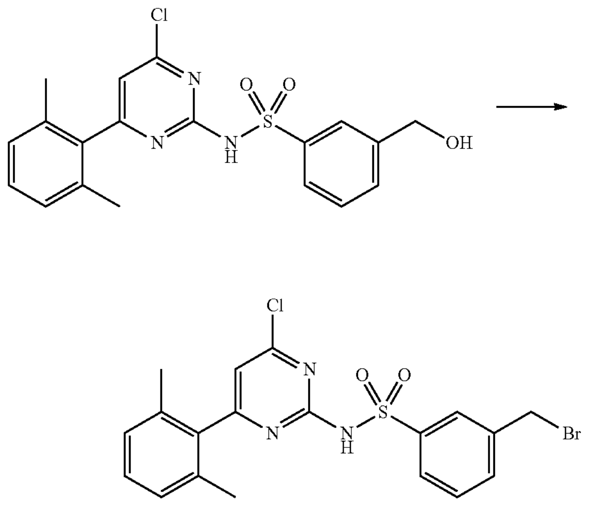

To a solution of N-[4-chloro-6-(2,6-dimethylphenyl)pyrimidin-2-yl]-3-(hydroxymethyl)benzenesulfonamide (116.0 mg, 0.2872 mmol) and carbon tetrabromide (approximately 104.8 mg, 0.3159 mmol) in DCM (1.044 mL) at 0° C. was added a solution of triphenylphosphane (approximately 82.86 mg, 0.3159 mmol) in DCM (104.4 μL). The reaction was allowed to stir for 4 hours before concentrating in vacuo onto silica gel. The silica gel was subjected to flash column chromatography (gradient: 10 to 100% ethyl acetate in hexanes) which afforded 3-(bromomethyl)-N-[4-chloro-6-(2,6-dimethylphenyl)pyrimidin-2-yl]benzenesulfonamide (96.0 mg, 72%) as a white solid. ESI-MS m/z calc. 464.99133, found 468.04 (M+1)$^+$; Retention time: 0.74 minutes, LC method D.

Step 3: tert-Butyl 19-(2,6-dimethylphenyl)-15,15-dioxo-2,8-dioxa-15λ$^6$-thia-5,16,18,21-tetraazatetracyclo[15.3.1.13,7.110,14]tricosa-1(21),10,12,14(22),17,19-hexaene-5-carboxylate (Compound 119)

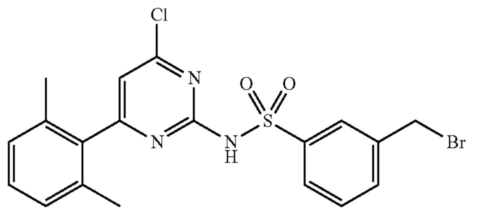

+

-continued

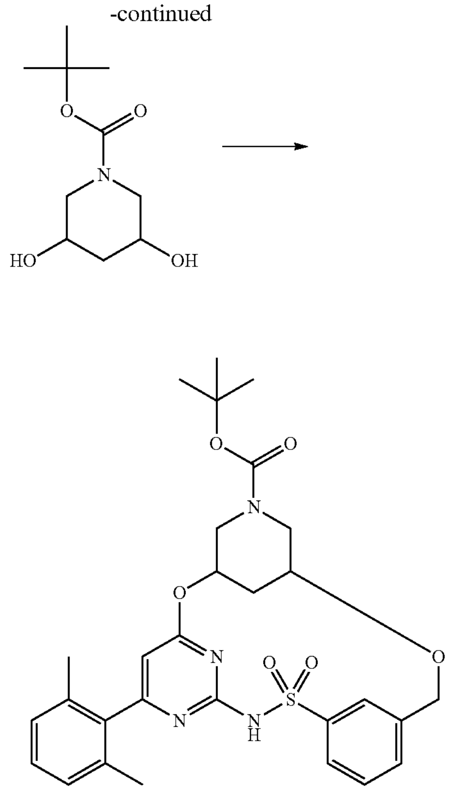

To a solution of tert-butyl 3,5-dihydroxypiperidine-1-carboxylate (approximately 4.654 mg, 0.02142 mmol) in DMF (214.2 μL) was added sodium hydride (approximately 6.855 mg of 60% w/w, 0.1714 mmol). The solution was stirred for 30 minutes before adding 3-(bromomethyl)-N-[4-chloro-6-(2,6-dimethylphenyl)pyrimidin-2-yl]benzenesulfonamide (10 mg, 0.02142 mmol) as a solution in DMF (214.2 μL) at 0° C. The reaction was allowed to warm up to 23° C. over 1 h. The reaction was quenched with acetic acid (approximately 25.73 mg, 24.37 μL, 0.4284 mmol) and filtered. The sample was purified by reverse phase HPLC (Phenomenex Luna $C_{18}$ column (75×30 mm, 5 μm particle size), gradient: 1-99% acetonitrile in water (5 mM ammonium formate) over 15.0 minutes) which afforded tert-butyl 19-(2,6-dimethylphenyl)-15,15-dioxo-2,8-dioxa-15λ$^6$-thia-5,16,18,21-tetraazatetracyclo[15.3.1.13,7.110,14]tricosa-1(21),10,12,14(22),17,19-hexaene-5-carboxylate (1.8 mg, 15%) as a white solid. $^1$H NMR (400 MHz, Chloroform-d) δ 8.35 (d, J=1.9 Hz, 1H), 7.85 (s, 1H), 7.65-7.45 (m, 2H), 7.25-7.19 (m, 1H), 7.09 (d, J=7.6 Hz, 2H), 6.13 (s, 1H), 4.83 (d, J=12.0 Hz, 1H), 4.75-4.57 (m, 2H), 4.35 (d, J=70.5 Hz, 2H), 3.62 (s, 1H), 2.60 (d, J=65.1 Hz, 2H), 2.08 (s, 6H), 1.50 (s, 9H), 0.89 (q, J=11.4 Hz, 2H). ESI-MS m/z calc. 566.2199, found 567.3 (M+1)$^+$; Retention time: 1.85 minutes, LC method A.

Example 38: Characterization of Compounds 120-122

The compounds in the following tables were prepared in a manner analogous to that described above using commercially available reagents and intermediates described herein.

TABLE 7

| Cmpd Number | Structure | LC Rt (min) | Calc. Mass | M + 1 | LC Met. | NMR |
|---|---|---|---|---|---|---|
| 120 | 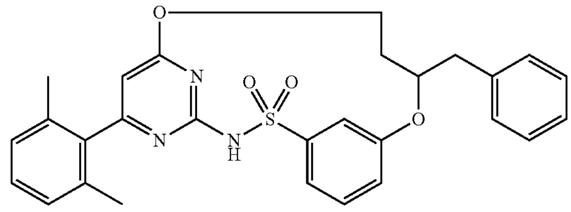 [SMILES: Cc1cccc(C)c1-c1cc2nc(n1)NS(=O)(=O)c1cccc(c1)OC(Cc1ccccc1)CCO2] | 3.44 | 501.172 | 502.3 | W | $^1$H NMR (500 MHz, DMSO-$d_6$) δ 8.03 (t, J = 2.1, 2.1 Hz, 1H), 7.49-7.42 (m, 3H), 7.41 (d, J = 7.6 Hz, 1H), 7.36 (t, J = 7.6, 7.6 Hz, 2H), 7.31-7.20 (m, 2H), 7.11 (d, J = 7.7 Hz, 3H), 6.32 (s, 1H), 5.03-4.94 (m, 1H), 4.65 (q, J = 7.0, 7.0, 7.0 Hz, 1H), 3.68-3.58 (m, 1H), 3.20 (dd, J = 13.4, 7.2 Hz, 1H), 3.07 (dd, J = 13.4, 6.3 Hz, 1H), 2.03 (s, 6H), 2.00-1.92 (m, 2H). |
| 121 | 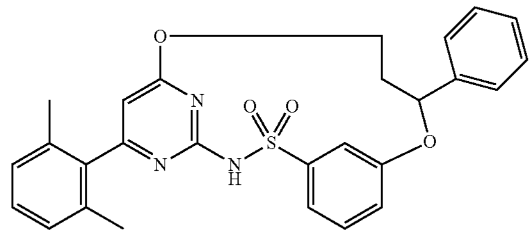 [SMILES: Cc1cccc(C)c1-c1cc2nc(n1)NS(=O)(=O)c1cccc(c1)OC(c1ccccc1)CCO2] | 3.11 | 487.157 | 488.2 | W | $^1$H NMR (500 MHz, DMSO-$d_6$) δ 8.25 (s, 1H), 7.67-7.58 (m, 2H), 7.54-7.43 (m, 4H), 7.43-7.37 (m, 1H), 7.30-7.19 (m, 2H), 7.12 (d, J = 7.7 Hz, 2H), 6.35 (s, 1H), 5.59 (d, J = 7.8 Hz, 1H), 5.25 (t, J = 11.4, 11.4 Hz, 1H), 4.37-4.24 (m, 1H), 2.44-2.35 (m, 1H), 2.19-2.12 (m, 1H), 2.05 (s, 6H) |
| 122 | 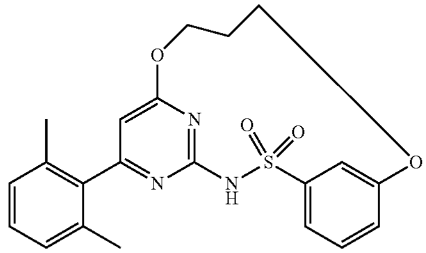 [SMILES: Cc1cccc(C)c1-c1cc2nc(n1)NS(=O)(=O)c1cccc(c1)OCCCO2] | 2.18 | 411.125 | 412.3 | W | $^1$H NMR (500 MHz, DMSO-$d_6$) δ 8.03 (s, 1H), 7.44 (d, J = 19.0 Hz, 2H), 7.23 (d, J = 7.8 Hz, 1H), 7.12 (d, J = 7.6 Hz, 3H), 6.34 (s, 1H), 4.70 (s, 2H), 4.33 (t, J = 6.1 Hz, 2H), 2.05 (s, 6H), 2.01-1.94 (m, 2H). |

V. Biological Activity of Compounds

A. Bioactivity Assays 1. 3T3 Assay a. Membrane Potential Optical Methods for Assaying F508del Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response is the creation of a chloride ion gradient in conjunction with channel activation by a single liquid addition step after the cells have previously been treated with compounds and subsequently loaded with a voltage sensing dye.

b. Identification of Corrector Compounds

To identify correctors of F508del, a single-addition HTS assay format was developed. This HTS assay utilizes fluorescent voltage sensing dyes to measure changes in membrane potential on the FLIPR III as a measurement for increase in gating (conductance) of F508del in F508del NIH 3T3 cells. The F508del NIH 3T3 cell cultures were incubated with the corrector compounds at a range of concentrations for 18-24 hours at 37° C., and subsequently loaded with a redistribution dye. The driving force for the response is a $Cl^-$ ion gradient in conjunction with channel activation with forskolin in a single liquid addition step using a fluorescent plate reader such as FLIPR III. The efficacy and potency of the putative F508del correctors was compared to that of the known corrector, lumacaftor, in combination with acutely added 300 nM Ivacaftor.

c. Solutions

Bath Solution #1: (in mM) NaCl 160, KCl 4.5, $CaCl_2$ 2, $MgCl_2$ 1, HEPES 10, pH 7.4 with NaOH.

Chloride-free bath solution: Chloride salts in Bath Solution #1 (above) are substituted with gluconate salts.

d. Cell Culture

NIH3T3 mouse fibroblasts stably expressing F508del are used for optical measurements of membrane potential. The cells are maintained at 37° C. in 5% $CO_2$ and 90% humidity in Dulbecco's modified Eagle's medium supplemented with 2 mM glutamine, 10% fetal bovine serum, 1×NEAA, b-ME, 1× pen/strep, and 25 mM HEPES in 175 $cm^2$ culture flasks. For all optical assays, the cells were seeded at ~20,000/well in 384-well Matrigel-coated plates. For the correction assays, the cells are cultured at 37° C. with and without compounds for 16-24 hours.

2. Enteroid Assay a. Solutions

Base medium (ADF+++) consisted of Advanced DMEM/Ham's F12, 2 mM Glutamax, 10 mM HEPES, 1 µg/mL penicillin/streptomycin.

Intestinal enteroid maintenance medium (IEMM) consisted of ADF+++, 1×B27 supplement, 1×N2 supplement, 1.25 mM N-acetyl cysteine, 10 mM Nicotinamide, 50 ng/mL hEGF, 10 nM Gastrin, 1 µg/mL hR-spondin-1, 100 ng/mL hNoggin, TGF-b type 1 inhibitor A-83-01, 100 µg/mL Primocin, 10 µM P38 MAPK inhibitor SB202190.

Bath 1 Buffer consisted of 1 mM $MgCl_2$, 160 mM NaCl, 4.5 mM KCl, 10 mM HEPES, 10 mM Glucose, 2 mM $CaCl_2$.

Chloride Free Buffer consisted of 1 mM Magnesium Gluconate, 2 mM Calcium Gluconate, 4.5 mM Potassium Gluconate, 160 mM Sodium Gluconate, 10 mM HEPES, 10 mM Glucose.

Bath1 Dye Solution consisted of Bath 1 Buffer, 0.04% Pluronic F127, 20 µM Methyl Oxonol, 30 µM CaCCinh-A01, 30 µM Chicago Sky Blue.

Chloride Free Dye Solution consisted of Chloride Free Buffer, 0.04% Pluronic F127, 20 µM Methyl Oxonol, 30 µM CaCCinh-A01, 30 µM Chicago Sky Blue.

Chloride Free Dye Stimulation Solution consisted of Chloride Free Dye Solution, 10 µM forskolin, 100 µM IBMX, and 300 nM Compound III.

b. Cell Culture

Human intestinal epithelial enteroid cells were obtained from the Hubrecht Institute for Developmental Biology and Stem Cell Research, Utrecht, The Netherlands and expanded in T-Flasks as previously described (Dekkers J F, Wiegerinck C L, de Jonge H R, Bronsveld I, Janssens H M, de Winter-de Groot K M, Brandsma A M, de Jong N W M, Bijvelds M J C, Scholte B J, Nieuwenhuis E E S, van den Brink S, Clevers H, van der Ent C K, Middendorp S and M Beekman J M. A functional CFTR assay using primary cystic fibrosis intestinal organoids. Nat Med. 2013 July; 19(7):939-45).

c. Enteroid Cell Harvesting and Seeding

Cells were recovered in cell recovery solution, collected by centrifugation at 650 rpm for 5 minutes at 4° C., resuspended in TrypLE and incubated for 5 minutes at 37° C. Cells were then collected by centrifugation at 650 rpm for 5 minutes at 4° C. and resuspended in IEMM containing 10 µM ROCK inhibitor (RI). The cell suspension was passed through a 40 µm cell strainer and resuspended at 1×106 cells/mL in IEMM containing 10 µM RI. Cells were seeded at 5000 cells/well into multi-well plates and incubated for overnight at 37° C., 95% humidity and 5% $CO_2$ prior to assay.

d. Membrane Potential Dye, Enteroid Assay A

Enteroid cells were incubated with test compound in IEMM for 18-24 hours at 37° C., 95% humidity and 5% $CO_2$. Following compound incubations, a membrane potential dye assay was employed using a FLIPR Tetra to directly measure the potency and efficacy of the test compound on CFTR-mediated chloride transport following acute addition of 10 µM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added, and the cells were incubated for 25 minutes at room temperature. Following dye incubation, cells were washed 3 times in Chloride Free Dye Solution. Chloride transport was initiated by addition of Chloride Free Dye Stimulation Solution and the fluorescence signal was read for 15 minutes. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 3 µM N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide, 3 µM (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide and 300 nM acute N-[2,4-bis(1,1-dimethylethyl)-5-hydroxyphenyl]-1,4-dihydro-4-oxoquinoline-3-carboxamide triple combination control (% Activity).

e. Membrane Potential Dye, Enteroid Assay B

Enteroid cells were incubated with test compound in IEMM for 18-24 hours at 37° C., 95% humidity and 5% $CO_2$. Following compound incubations, a membrane potential dye assay was employed using a FLIPR Tetra to directly measure the potency and efficacy of the test compound on CFTR-mediated chloride transport following acute addition of 10 µM forskolin and 300 nM N-[2,4-bis(1,1-dimethylethyl)-5-hydroxyphenyl]-1,4-dihydro-4-oxoquinoline-3-carboxamide. Briefly, cells were washed 5 times in Bath 1 Buffer. Bath 1 Dye Solution was added and the cells were incubated for 25 minutes at room temperature. Following dye incubation, cells were washed 3 times in Chloride Free Dye Solution. Chloride transport was initiated by addition of Chloride Free Dye Stimulation Solution and the fluorescence signal was read for 15 minutes. The CFTR-mediated chloride transport for each condition was determined from the AUC of the fluorescence response to acute forskolin and 300 nM N-[2,4-bis(1,1-dimethylethyl)-5-hydroxyphenyl]-1,4-dihydro-4-oxoquinoline-3-carboxamide stimulation. Chloride transport was then expressed as a percentage of the chloride transport following treatment with 1 µM (14S)-8-[3-(2-{Dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.111,14.05,10]tetracosa-1(22),5,7,9,19(23),20-hexaene-2,2,4-trione, 3 µM (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide and 300 nM acute N-[2,4-bis(1,1-dimethylethyl)-5-hydroxyphenyl]-1,4-dihydro-4-oxoquinoline-3-carboxamide triple combination control (% Activity).

B. Biological Activity Data

The following table represents CFTR modulating activity for representative compounds of the disclosure generated using one or more of the assays disclosed herein ($EC_{50}$: +++ is <1 μM; ++ is 1-<3 μM; + is 3-<30 μM; and ND is "not detected in this assay." % Activity: +++ is >60%; ++ is 30-60%; + is <30%).
TABLE 8
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 1 | 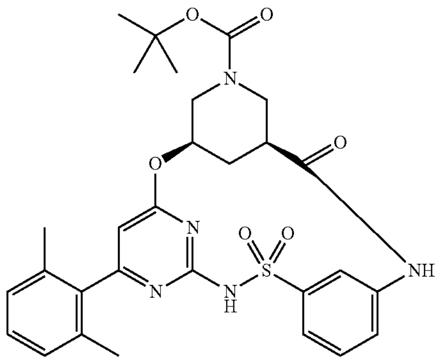 [SMILES: Cc1cccc(C)c1-c1cc2nc(n1)NS(=O)(=O)c1cccc(c1)NC(=O)[C@H]1C[C@H](CN(C(=O)OC(C)(C)C)C1)O2] | +++ | ++ | ND | + | | |
| 2 | 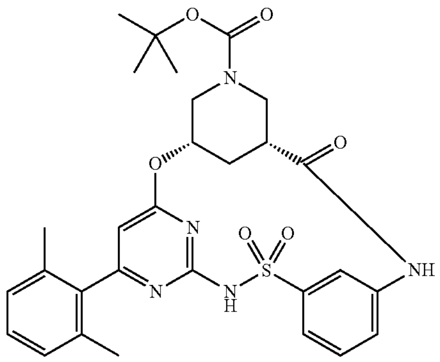 [SMILES: Cc1cccc(C)c1-c1cc2nc(n1)NS(=O)(=O)c1cccc(c1)NC(=O)[C@@H]1C[C@@H](CN(C(=O)OC(C)(C)C)C1)O2] | +++ | +++ | +++ | +++ | | |
| 3 | 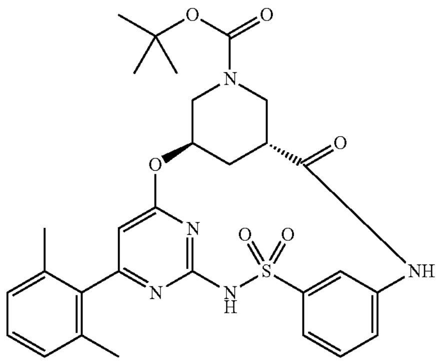 [SMILES: Cc1cccc(C)c1-c1cc2nc(n1)NS(=O)(=O)c1cccc(c1)NC(=O)[C@@H]1C[C@H](CN(C(=O)OC(C)(C)C)C1)O2] | ++ | +++ | ++ | + | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 4 | 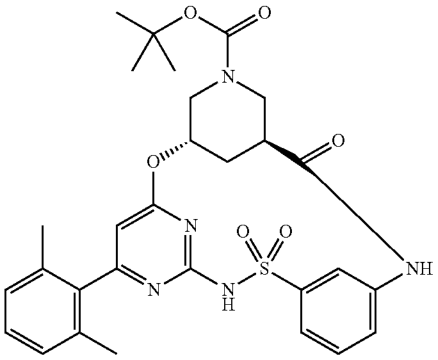 [SMILES: Cc1cccc(C)c1-c1cc2nc(n1)NS(=O)(=O)c1cccc(c1)NC(=O)[C@H]1C[C@@H](CN(C(=O)OC(C)(C)C)C1)O2] | +++ | +++ | | | | |
| 5 | 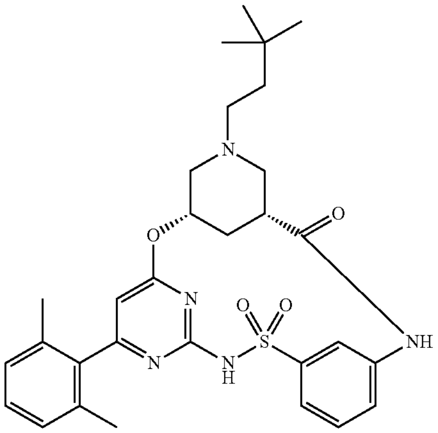 [SMILES: Cc1cccc(C)c1-c1cc2nc(n1)NS(=O)(=O)c1cccc(c1)NC(=O)[C@@H]1C[C@@H](CN(CCC(C)(C)C)C1)O2] | +++ | +++ | +++ | +++ | | |
| 6 | 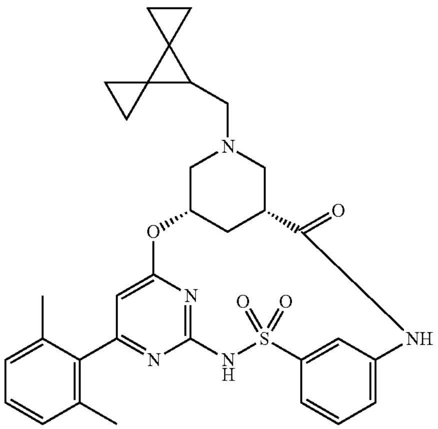 [SMILES: Cc1cccc(C)c1-c1cc2nc(n1)NS(=O)(=O)c1cccc(c1)NC(=O)[C@@H]1C[C@@H](CN(CC3C4(CC4)C34CC4)C1)O2] | | | +++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 7 | 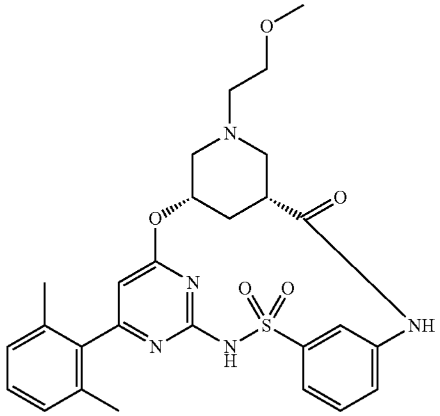 [SMILES: COCCN1C[C@@H]2C[C@H](C1)C(=O)Nc1cccc(c1)S(=O)(=O)Nc1nc(cc(-c3c(C)cccc3C)n1)O2] | +++ | +++ | ++ | +++ | | |
| 8 | 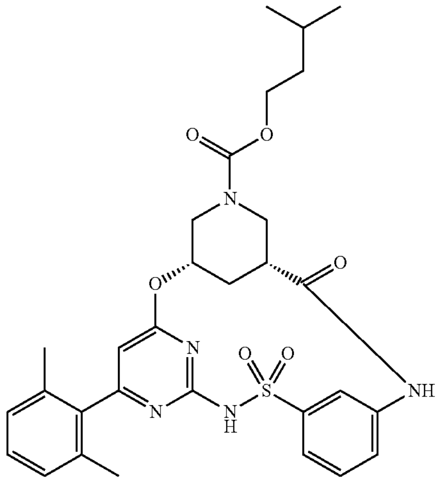 [SMILES: Cc1cccc(C)c1-c1cc2nc(n1)NS(=O)(=O)c1cccc(c1)NC(=O)[C@@H]1C[C@@H](CN(C(=O)OCCC(C)C)C1)O2] | +++ | +++ | +++ | +++ | | |
| 9 | 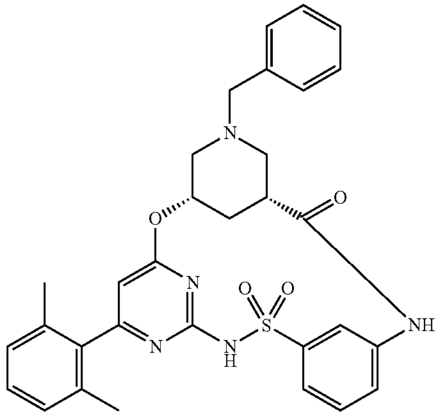 [SMILES: Cc1cccc(C)c1-c1cc2nc(n1)NS(=O)(=O)c1cccc(c1)NC(=O)[C@@H]1C[C@@H](CN(Cc3ccccc3)C1)O2] | | | +++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 10 | 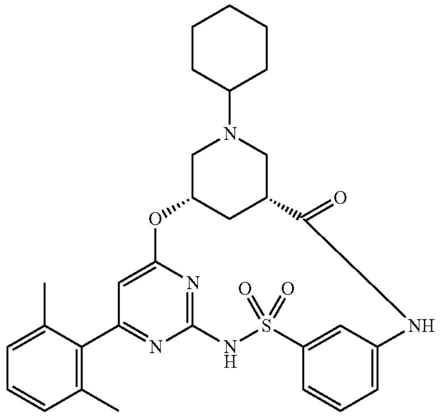 [SMILES: Cc1cccc(C)c1-c1cc2nc(n1)NS(=O)(=O)c1cccc(c1)NC(=O)[C@@H]1C[C@@H](CN(C3CCCCC3)C1)O2] | +++ | +++ | ++ | ++ | | |
| 11 | 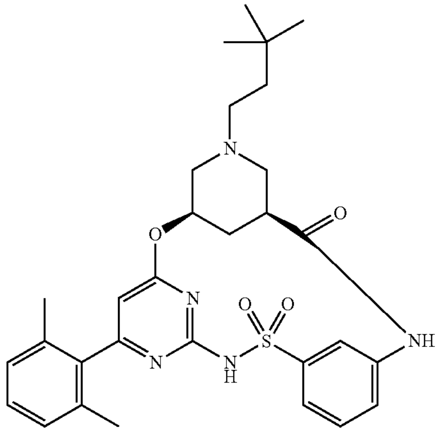 [SMILES: Cc1cccc(C)c1-c1cc2nc(n1)NS(=O)(=O)c1cccc(c1)NC(=O)[C@H]1C[C@H](CN(CCC(C)(C)C)C1)O2] | +++ | +++ | ND | + | | |
| 12 | 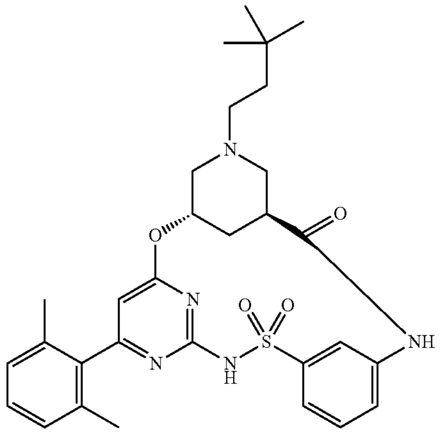 [SMILES: Cc1cccc(C)c1-c1cc2nc(n1)NS(=O)(=O)c1cccc(c1)NC(=O)[C@H]1C[C@@H](CN(CCC(C)(C)C)C1)O2] | +++ | +++ | ++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 13 | 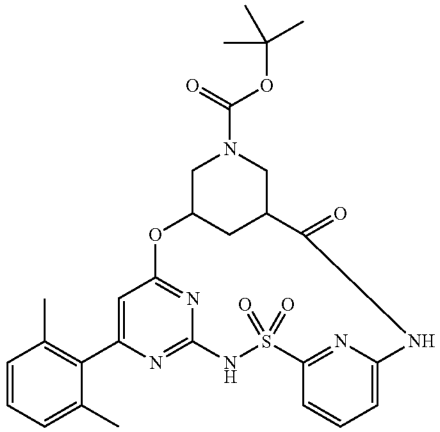 [SMILES: Cc1cccc(C)c1-c1cc2nc(n1)NS(=O)(=O)c1cccc(n1)NC(=O)C1CC(CN(C(=O)OC(C)(C)C)C1)O2] | | | +++ | +++ | | |
| 14 | 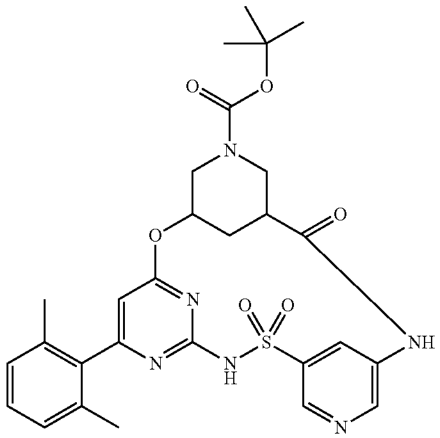 [SMILES: Cc1cccc(C)c1-c1cc2nc(n1)NS(=O)(=O)c1cncc(c1)NC(=O)C1CC(CN(C(=O)OC(C)(C)C)C1)O2] | | | +++ | + | | |
| 15 | 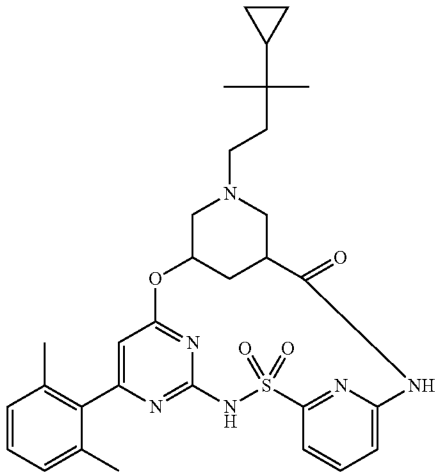 [SMILES: Cc1cccc(C)c1-c1cc2nc(n1)NS(=O)(=O)c1cccc(n1)NC(=O)C1CC(CN(CCC(C)(C)C3CC3)C1)O2] | +++ | +++ | +++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 16 | 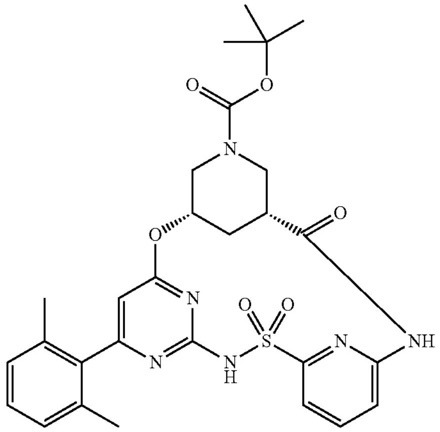 [SMILES: Cc1cccc(C)c1-c1cc2nc(n1)NS(=O)(=O)c1cccc(n1)NC(=O)[C@@H]1C[C@@H](CN(C(=O)OC(C)(C)C)C1)O2] | | | +++ | +++ | | |
| 17 | 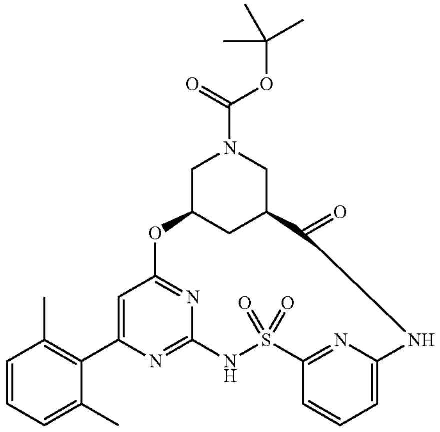 [SMILES: Cc1cccc(C)c1-c1cc2nc(n1)NS(=O)(=O)c1cccc(n1)NC(=O)[C@H]1C[C@H](CN(C(=O)OC(C)(C)C)C1)O2] | | | ND | + | | |
| 18 | 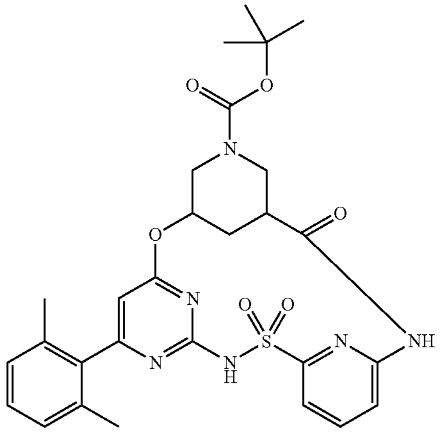 [SMILES: Cc1cccc(C)c1-c1cc2nc(n1)NS(=O)(=O)c1cccc(n1)NC(=O)C1CC(CN(C(=O)OC(C)(C)C)C1)O2] | | | + | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 19 | 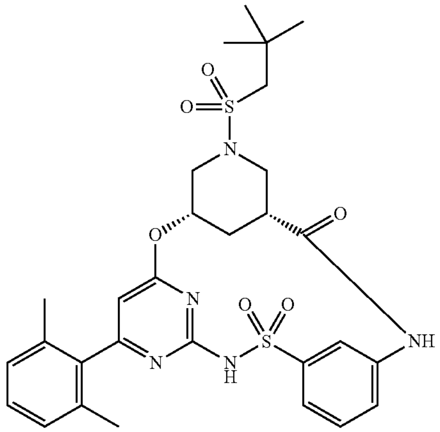 [SMILES: Cc1cccc(C)c1-c1cc2nc(n1)NS(=O)(=O)c1cccc(c1)NC(=O)[C@@H]1C[C@@H](CN(S(=O)(=O)CC(C)(C)C)C1)O2] | | | +++ | ++ | | |
| 20 | 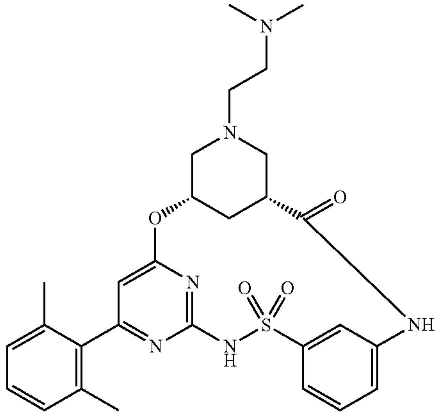 [SMILES: Cc1cccc(C)c1-c1cc2nc(n1)NS(=O)(=O)c1cccc(c1)NC(=O)[C@@H]1C[C@@H](CN(CCN(C)C)C1)O2] | | | + | + | | |
| 21 | 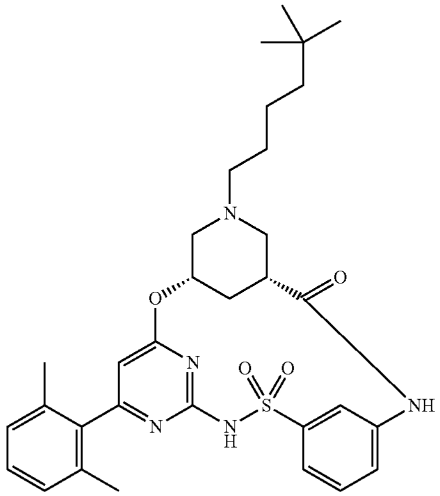 [SMILES: Cc1cccc(C)c1-c1cc2nc(n1)NS(=O)(=O)c1cccc(c1)NC(=O)[C@@H]1C[C@@H](CN(CCCCC(C)(C)C)C1)O2] | +++ | +++ | +++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 22 | 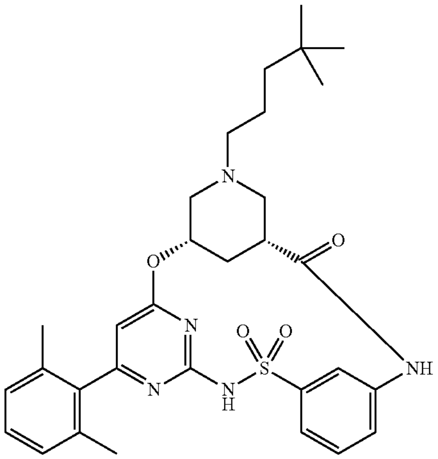 [SMILES: Cc1cccc(C)c1-c1cc2nc(n1)NS(=O)(=O)c1cccc(c1)NC(=O)[C@@H]1C[C@@H](CN(CCCC(C)(C)C)C1)O2] | | | +++ | ++ | | |
| 23 | 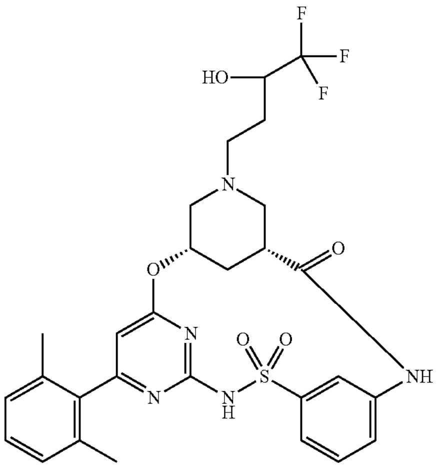 [SMILES: Cc1cccc(C)c1-c1cc2nc(n1)NS(=O)(=O)c1cccc(c1)NC(=O)[C@@H]1C[C@@H](CN(CCC(O)C(F)(F)F)C1)O2] | | | ++ | +++ | | |
| 24 | 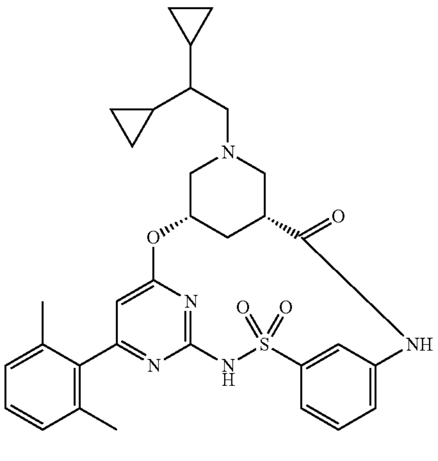 [SMILES: Cc1cccc(C)c1-c1cc2nc(n1)NS(=O)(=O)c1cccc(c1)NC(=O)[C@@H]1C[C@@H](CN(CC(C3CC3)C3CC3)C1)O2] | +++ | +++ | +++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 25 | 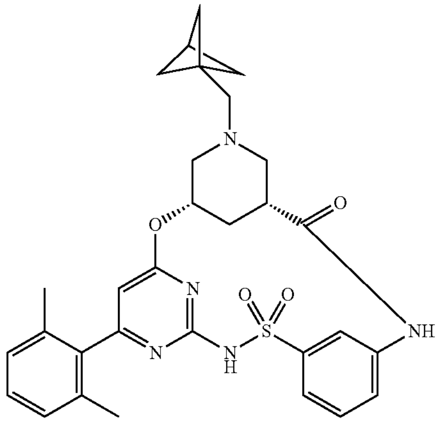 [SMILES: Cc1cccc(C)c1-c1cc2nc(n1)NS(=O)(=O)c1cccc(c1)NC(=O)[C@@H]1C[C@@H](CN(CC34CC(C3)C4)C1)O2] | +++ | +++ | +++ | ++ | | |
| 26 | 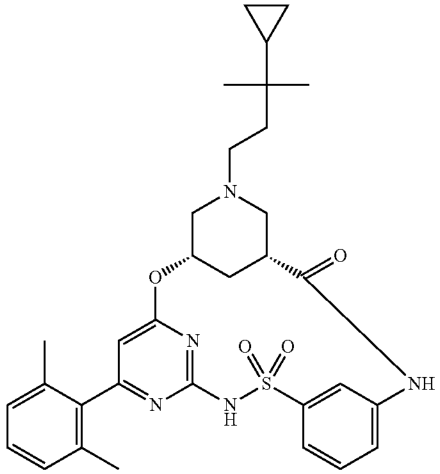 [SMILES: Cc1cccc(C)c1-c1cc2nc(n1)NS(=O)(=O)c1cccc(c1)NC(=O)[C@@H]1C[C@@H](CN(CCC(C)(C)C3CC3)C1)O2] | | | +++ | +++ | | |
| 27 | 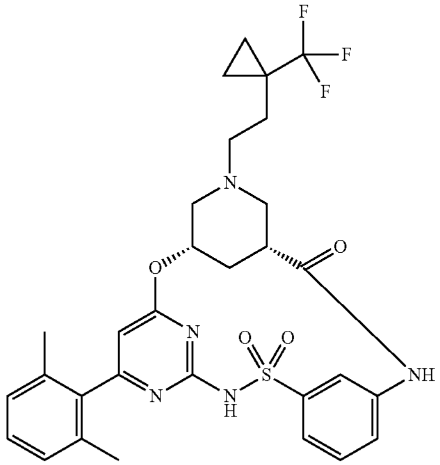 [SMILES: Cc1cccc(C)c1-c1cc2nc(n1)NS(=O)(=O)c1cccc(c1)NC(=O)[C@@H]1C[C@@H](CN(CCC3(C(F)(F)F)CC3)C1)O2] | +++ | +++ | +++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 28 | 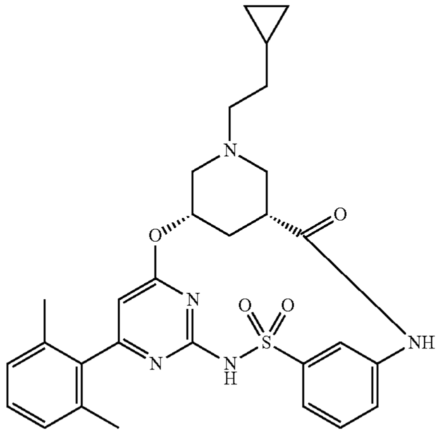 [SMILES: Cc1cccc(C)c1-c1cc2nc(n1)NS(=O)(=O)c1cccc(c1)NC(=O)[C@@H]1C[C@@H](CN(CCC3CC3)C1)O2] | +++ | +++ | +++ | ++ | | |
| 29 | 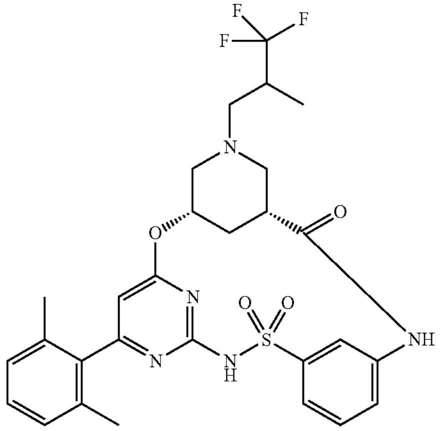 [SMILES: Cc1cccc(C)c1-c1cc2nc(n1)NS(=O)(=O)c1cccc(c1)NC(=O)[C@@H]1C[C@@H](CN(CC(C)C(F)(F)F)C1)O2] | | | +++ | +++ | | |
| 30 | 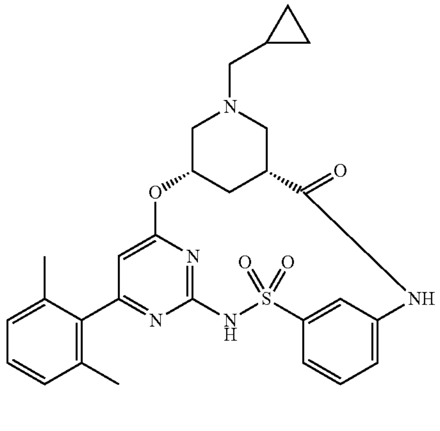 [SMILES: Cc1cccc(C)c1-c1cc2nc(n1)NS(=O)(=O)c1cccc(c1)NC(=O)[C@@H]1C[C@@H](CN(CC3CC3)C1)O2] | +++ | +++ | ++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 31 | 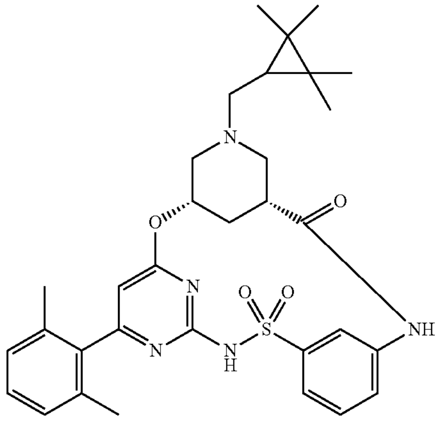 [SMILES: Cc1cccc(C)c1-c1cc2nc(n1)NS(=O)(=O)c1cccc(c1)NC(=O)[C@@H]1C[C@@H](CN(CC3C(C)(C)C3(C)C)C1)O2] | | | +++ | ++ | | |
| 32 | 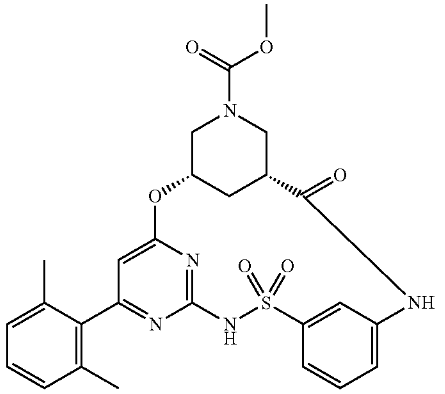 [SMILES: COC(=O)N1C[C@@H]2C[C@H](C1)C(=O)Nc1cccc(c1)S(=O)(=O)Nc1nc(cc(-c3c(C)cccc3C)n1)O2] | | | ++ | +++ | | |
| 33 | 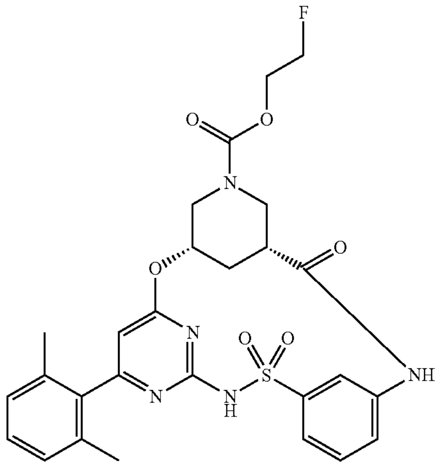 [SMILES: Cc1cccc(C)c1-c1cc2nc(n1)NS(=O)(=O)c1cccc(c1)NC(=O)[C@@H]1C[C@@H](CN(C(=O)OCCF)C1)O2] | +++ | +++ | ++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 34 | 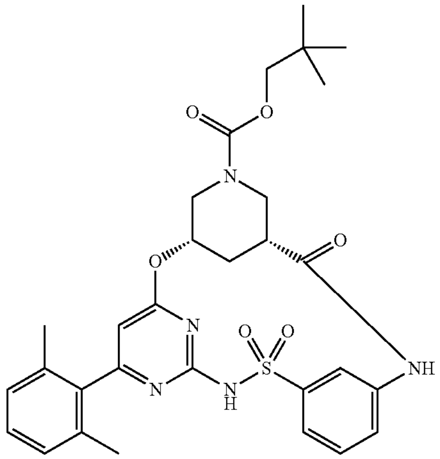 [SMILES: Cc1cccc(C)c1-c1cc2nc(n1)NS(=O)(=O)c1cccc(c1)NC(=O)[C@@H]1C[C@@H](CN(C(=O)OCC(C)(C)C)C1)O2] | | | +++ | +++ | | |
| 35 | 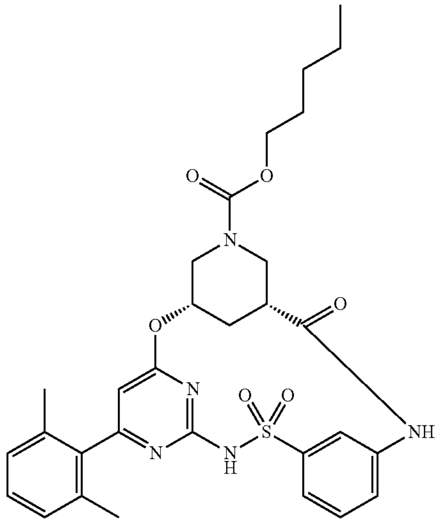 [SMILES: CCCCCOC(=O)N1C[C@@H]2C[C@H](C1)C(=O)Nc1cccc(c1)S(=O)(=O)Nc1nc(cc(-c3c(C)cccc3C)n1)O2] | | | +++ | +++ | | |
| 36 | 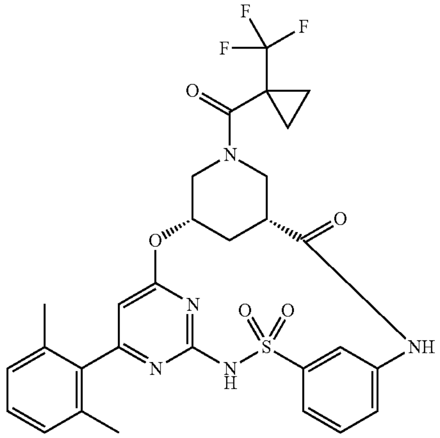 [SMILES: Cc1cccc(C)c1-c1cc2nc(n1)NS(=O)(=O)c1cccc(c1)NC(=O)[C@@H]1C[C@@H](CN(C(=O)C3(C(F)(F)F)CC3)C1)O2] | | | +++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 37 | 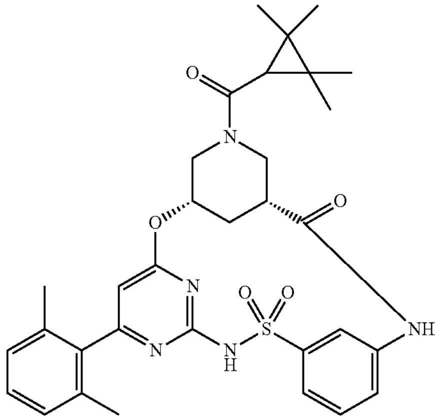 [SMILES: Cc1cccc(C)c1-c1cc2nc(n1)NS(=O)(=O)c1cccc(c1)NC(=O)[C@@H]1C[C@@H](CN(C(=O)C3C(C)(C)C3(C)C)C1)O2] | | | +++ | ++ | | |
| 38 | 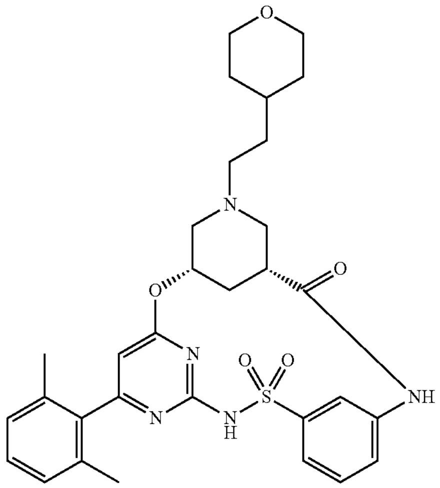 [SMILES: Cc1cccc(C)c1-c1cc2nc(n1)NS(=O)(=O)c1cccc(c1)NC(=O)[C@@H]1C[C@@H](CN(CCC3CCOCC3)C1)O2] | | | ++ | ++ | | |
| 39 | 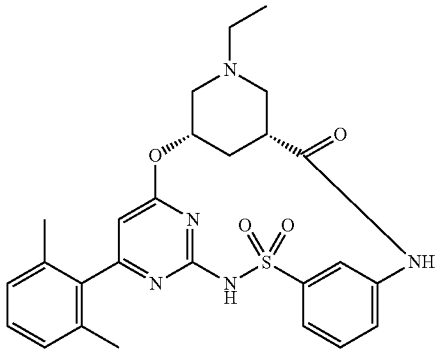 [SMILES: CCN1C[C@@H]2C[C@H](C1)C(=O)Nc1cccc(c1)S(=O)(=O)Nc1nc(cc(-c3c(C)cccc3C)n1)O2] | | | + | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 40 | 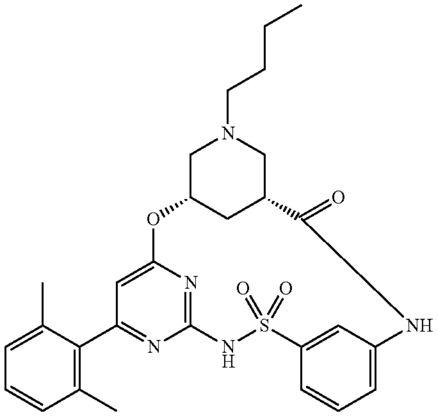 [SMILES: CCCCN1C[C@@H]2C[C@H](C1)C(=O)Nc1cccc(c1)S(=O)(=O)Nc1nc(cc(-c3c(C)cccc3C)n1)O2] | | | +++ | ++ | | |
| 41 | 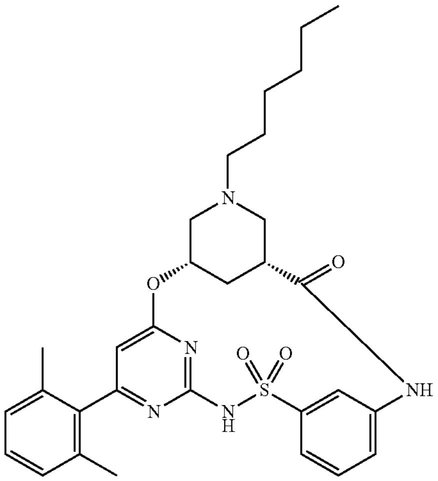 [SMILES: CCCCCCN1C[C@@H]2C[C@H](C1)C(=O)Nc1cccc(c1)S(=O)(=O)Nc1nc(cc(-c3c(C)cccc3C)n1)O2] | | | +++ | +++ | | |
| 42 | 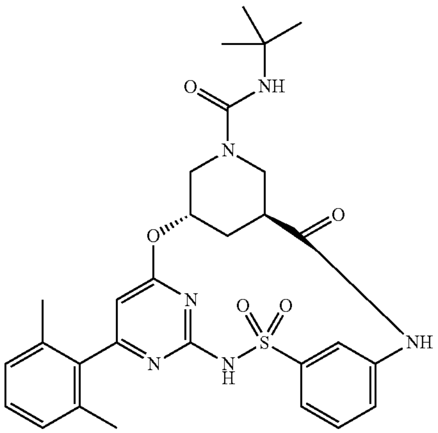 [SMILES: Cc1cccc(C)c1-c1cc2nc(n1)NS(=O)(=O)c1cccc(c1)NC(=O)[C@H]1C[C@@H](CN(C(=O)NC(C)(C)C)C1)O2] | + | +++ | ND | + | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 43 | 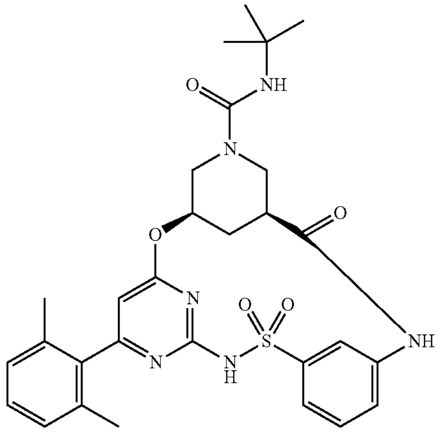 [SMILES: Cc1cccc(C)c1-c1cc2nc(n1)NS(=O)(=O)c1cccc(c1)NC(=O)[C@H]1C[C@H](CN(C(=O)NC(C)(C)C)C1)O2] | + | +++ | ND | + | | |
| 44 | 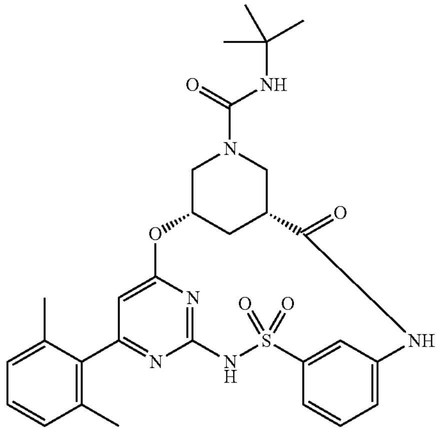 [SMILES: Cc1cccc(C)c1-c1cc2nc(n1)NS(=O)(=O)c1cccc(c1)NC(=O)[C@@H]1C[C@@H](CN(C(=O)NC(C)(C)C)C1)O2] | +++ | +++ | + | +++ | | |
| 45 | 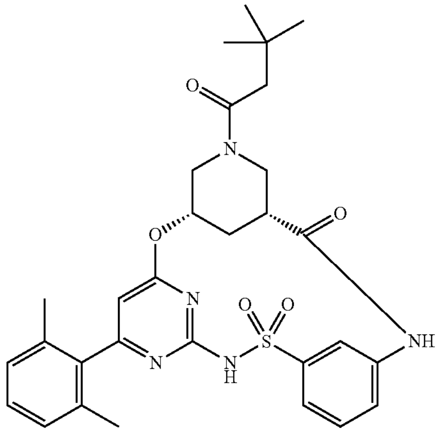 [SMILES: Cc1cccc(C)c1-c1cc2nc(n1)NS(=O)(=O)c1cccc(c1)NC(=O)[C@@H]1C[C@@H](CN(C(=O)CC(C)(C)C)C1)O2] | +++ | +++ | ++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 46 | 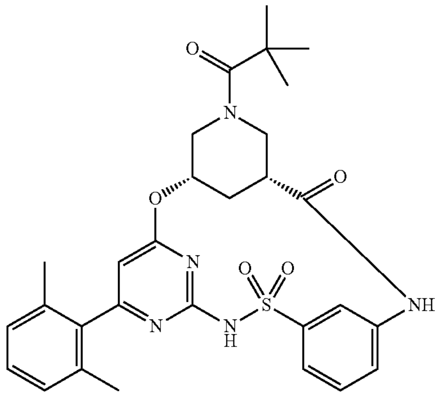 [SMILES: Cc1cccc(C)c1-c1cc2nc(n1)NS(=O)(=O)c1cccc(c1)NC(=O)[C@@H]1C[C@@H](CN(C(=O)C(C)(C)C)C1)O2] | +++ | +++ | ++ | +++ | | |
| 47 | 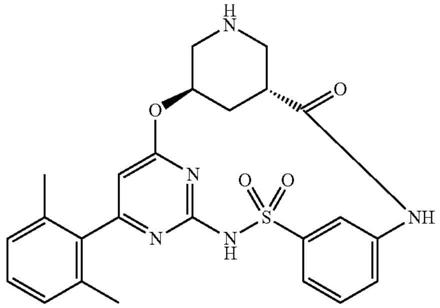 [SMILES: Cc1cccc(C)c1-c1cc2nc(n1)NS(=O)(=O)c1cccc(c1)NC(=O)[C@H]1CNC[C@@H](C1)O2] | ND | ++ | ND | + | | |
| 48 | 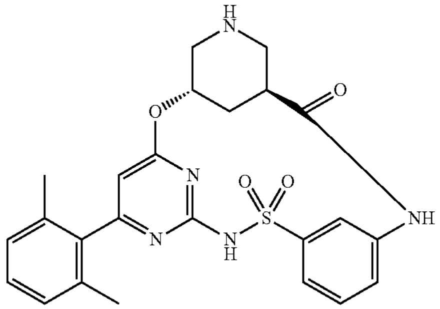 [SMILES: Cc1cccc(C)c1-c1cc2nc(n1)NS(=O)(=O)c1cccc(c1)NC(=O)[C@@H]1CNC[C@H](C1)O2] | ++ | +++ | ND | ++ | | |
| 49 | 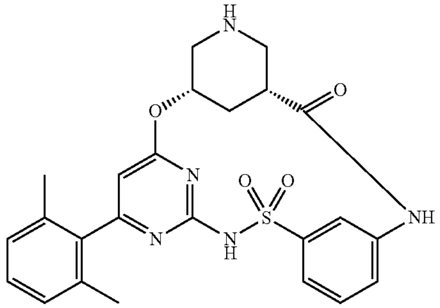 [SMILES: Cc1cccc(C)c1-c1cc2nc(n1)NS(=O)(=O)c1cccc(c1)NC(=O)[C@H]1CNC[C@H](C1)O2] | ++ | +++ | ND | + | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 50 | 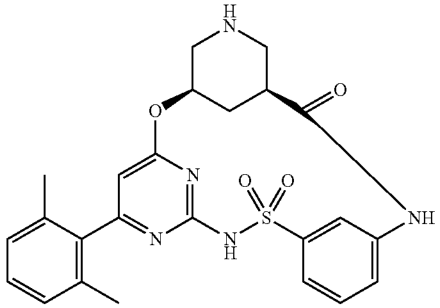 [SMILES: Cc1cccc(C)c1-c1cc2nc(n1)NS(=O)(=O)c1cccc(c1)NC(=O)[C@@H]1CNC[C@@H](C1)O2] | ND | + | ND | + | | |
| 51 | 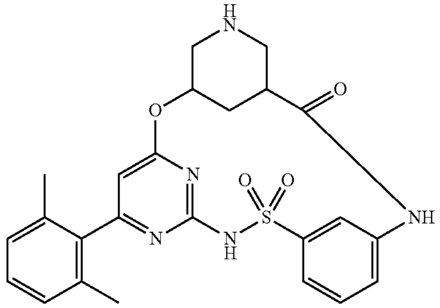 [SMILES: Cc1cccc(C)c1-c1cc2nc(n1)NS(=O)(=O)c1cccc(c1)NC(=O)C1CNCC(C1)O2] | + | +++ | + | ++ | | |
| 52 | 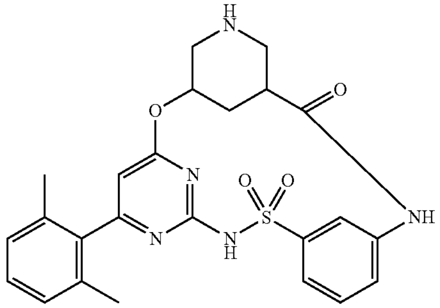 [SMILES: Cc1cccc(C)c1-c1cc2nc(n1)NS(=O)(=O)c1cccc(c1)NC(=O)C1CNCC(C1)O2] | ND | + | + | + | | |
| 53 | 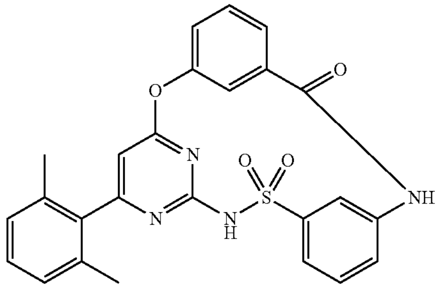 [SMILES: Cc1cccc(C)c1-c1cc2nc(n1)NS(=O)(=O)c1cccc(c1)NC(=O)c1cccc(c1)O2] | +++ | +++ | + | +++ | | |
| 54 | 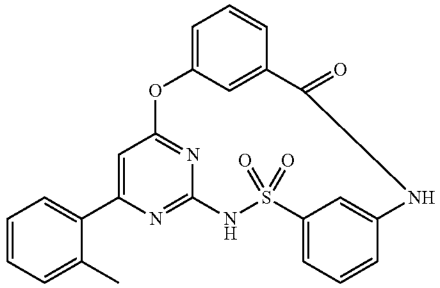 [SMILES: Cc1ccccc1-c1cc2nc(n1)NS(=O)(=O)c1cccc(c1)NC(=O)c1cccc(c1)O2] | +++ | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 55 | 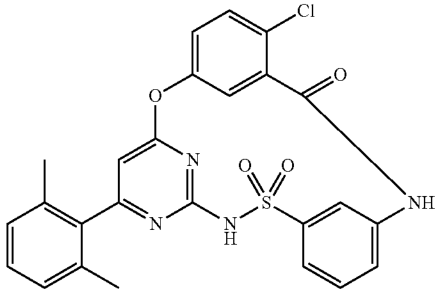 [SMILES: Cc1cccc(C)c1-c1cc2nc(n1)NS(=O)(=O)c1cccc(c1)NC(=O)c1cc(ccc1Cl)O2] | +++ | +++ | ++ | +++ | | |
| 56 | 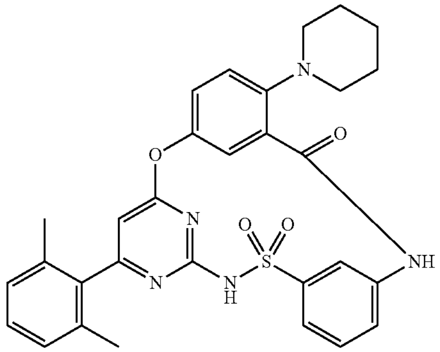 [SMILES: Cc1cccc(C)c1-c1cc2nc(n1)NS(=O)(=O)c1cccc(c1)NC(=O)c1cc(ccc1N1CCCCC1)O2] | +++ | +++ | | | | |
| 57 | 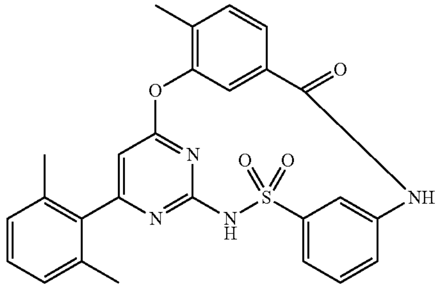 [SMILES: Cc1ccc2cc1Oc1cc(-c3c(C)cccc3C)nc(n1)NS(=O)(=O)c1cccc(c1)NC2=O] | +++ | +++ | +++ | ++ | | |
| 58 | 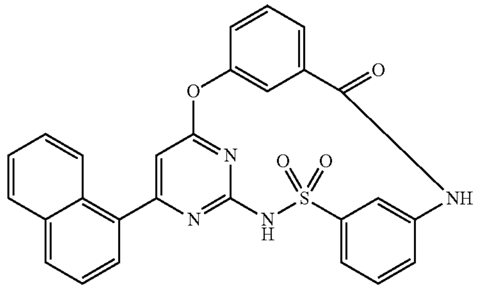 [SMILES: O=C1Nc2cccc(c2)S(=O)(=O)Nc2nc(cc(-c3cccc4ccccc34)n2)Oc2cccc1c2] | +++ | +++ | ++ | ++ | | |
| 59 | 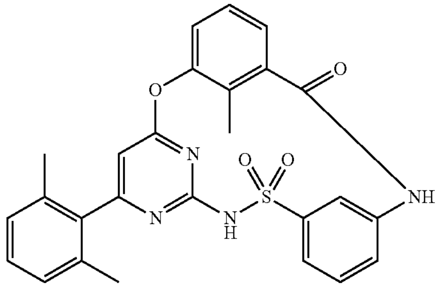 [SMILES: Cc1cccc(C)c1-c1cc2nc(n1)NS(=O)(=O)c1cccc(c1)NC(=O)c1cccc(c1C)O2] | +++ | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 60 | 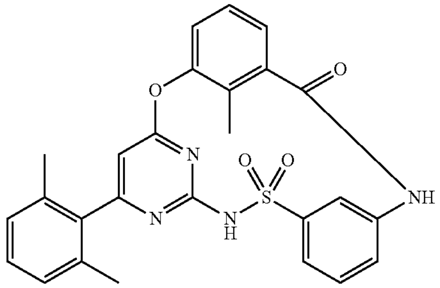 [SMILES: Cc1cccc(C)c1-c1cc2nc(n1)NS(=O)(=O)c1cccc(c1)NC(=O)c1cccc(c1C)O2] | +++ | +++ | | | | |
| 61 | 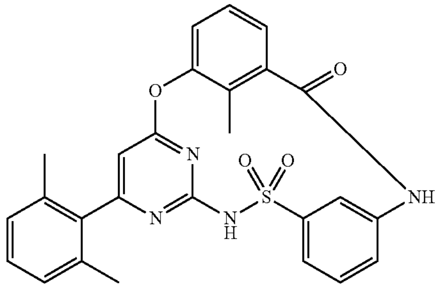 [SMILES: Cc1cccc(C)c1-c1cc2nc(n1)NS(=O)(=O)c1cccc(c1)NC(=O)c1cccc(c1C)O2] | +++ | +++ | | | | |
| 62 | 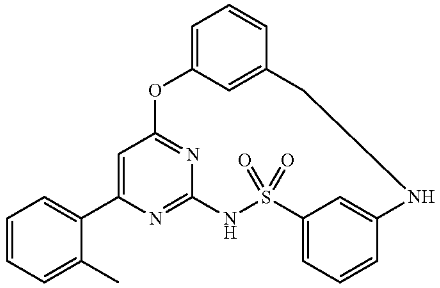 [SMILES: Cc1ccccc1-c1cc2nc(n1)NS(=O)(=O)c1cccc(c1)NCc1cccc(c1)O2] | +++ | +++ | | | | |
| 63 | 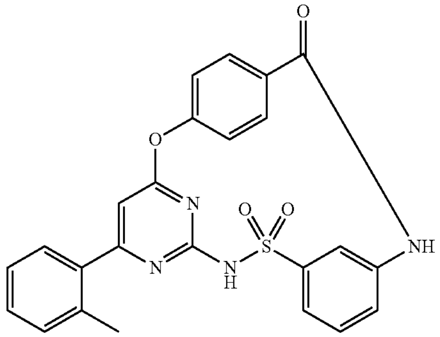 [SMILES: Cc1ccccc1-c1cc2nc(n1)NS(=O)(=O)c1cccc(c1)NC(=O)c1ccc(cc1)O2] | ++ | +++ | | | | |
| 65 | 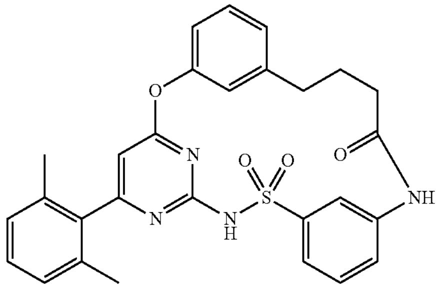 [SMILES: Cc1cccc(C)c1-c1cc2nc(n1)NS(=O)(=O)c1cccc(c1)NC(=O)CCCc1cccc(c1)O2] | +++ | +++ | ++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 66 | 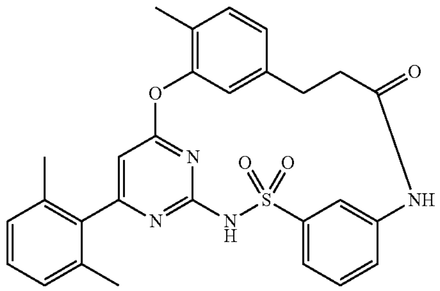 [SMILES: Cc1ccc2cc1Oc1cc(-c3c(C)cccc3C)nc(n1)NS(=O)(=O)c1cccc(c1)NC(=O)CC2] | +++ | +++ | ++ | +++ | | |
| 67 | 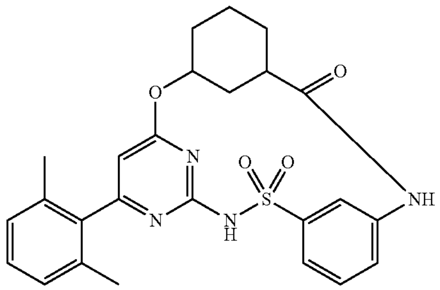 [SMILES: Cc1cccc(C)c1-c1cc2nc(n1)NS(=O)(=O)c1cccc(c1)NC(=O)C1CCCC(C1)O2] | +++ | +++ | | | | |
| 68 | 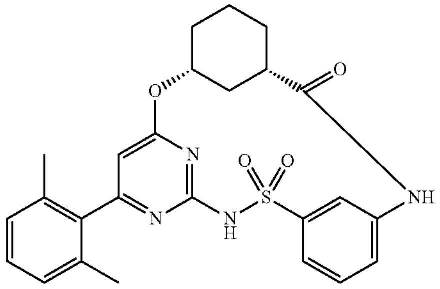 [SMILES: Cc1cccc(C)c1-c1cc2nc(n1)NS(=O)(=O)c1cccc(c1)NC(=O)[C@H]1CCC[C@H](C1)O2] | +++ | +++ | + | ++ | | |
| 69 | 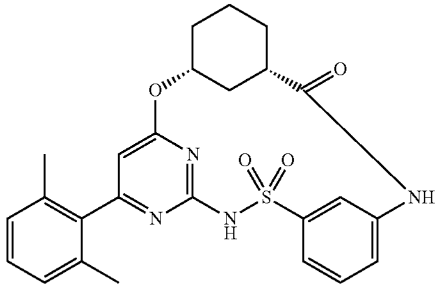 [SMILES: Cc1cccc(C)c1-c1cc2nc(n1)NS(=O)(=O)c1cccc(c1)NC(=O)[C@H]1CCC[C@H](C1)O2] | +++ | +++ | ++ | ++ | | |
| 70 | 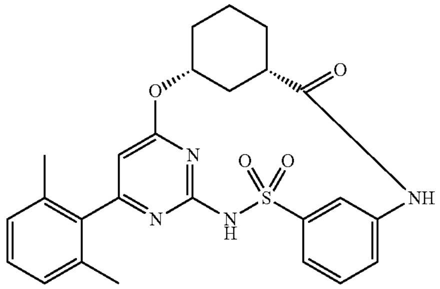 [SMILES: Cc1cccc(C)c1-c1cc2nc(n1)NS(=O)(=O)c1cccc(c1)NC(=O)[C@H]1CCC[C@H](C1)O2] | ++ | +++ | ++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 71 | 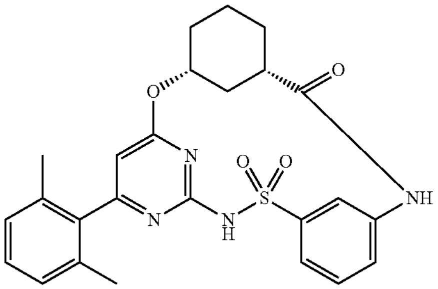 [SMILES: Cc1cccc(C)c1-c1cc2nc(n1)NS(=O)(=O)c1cccc(c1)NC(=O)[C@H]1CCC[C@H](C1)O2] | ++ | +++ | ++ | +++ | | |
| 72 | 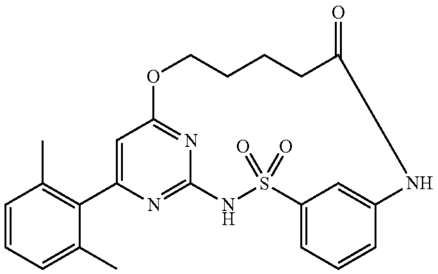 [SMILES: Cc1cccc(C)c1-c1cc2nc(n1)NS(=O)(=O)c1cccc(c1)NC(=O)CCCCO2] | +++ | +++ | | | | |
| 73 | 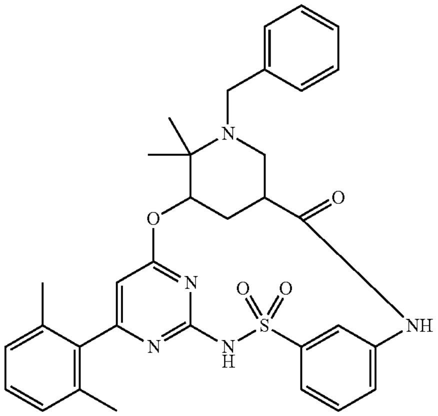 [SMILES: Cc1cccc(C)c1-c1cc2nc(n1)NS(=O)(=O)c1cccc(c1)NC(=O)C1CC(O2)C(C)(C)N(Cc2ccccc2)C1] | | | +++ | + | | |
| 74 | 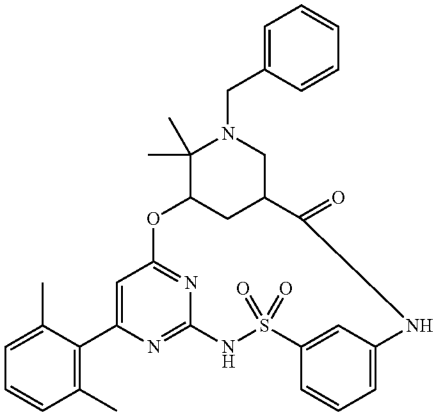 [SMILES: Cc1cccc(C)c1-c1cc2nc(n1)NS(=O)(=O)c1cccc(c1)NC(=O)C1CC(O2)C(C)(C)N(Cc2ccccc2)C1] | | | ND | + | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 75 | 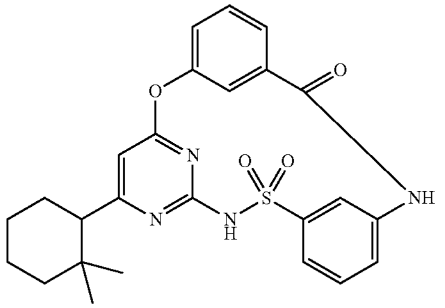 [SMILES: CC1(C)CCCCC1c1cc2nc(n1)NS(=O)(=O)c1cccc(c1)NC(=O)c1cccc(c1)O2] | +++ | +++ | | | | |
| 76 | 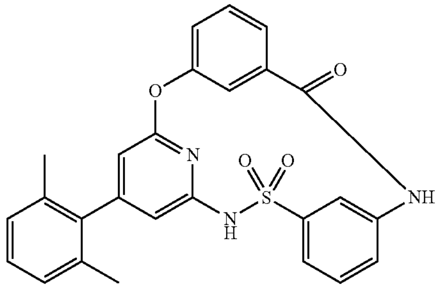 [SMILES: Cc1cccc(C)c1-c1cc2nc(c1)Oc1cccc(c1)C(=O)Nc1cccc(c1)S(=O)(=O)N2] | ND | + | ND | + | | |
| 77 | 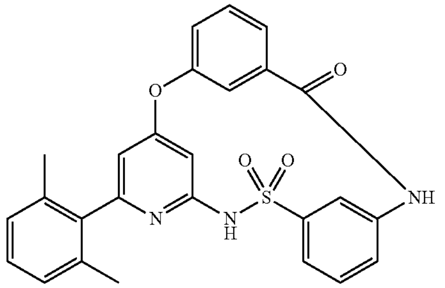 [SMILES: Cc1cccc(C)c1-c1cc2cc(n1)NS(=O)(=O)c1cccc(c1)NC(=O)c1cccc(c1)O2] | +++ | +++ | + | ++ | | |
| 78 | 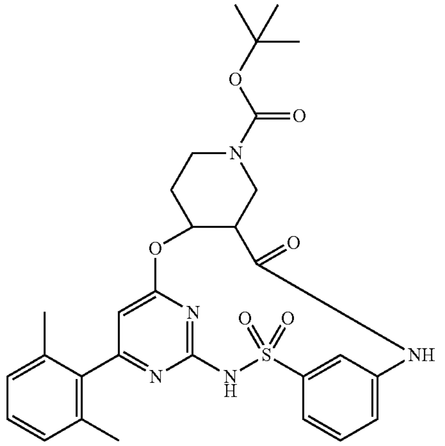 [SMILES: Cc1cccc(C)c1-c1cc2nc(n1)NS(=O)(=O)c1cccc(c1)NC(=O)C1CN(C(=O)OC(C)(C)C)CCC1O2] | | | ++ | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 79 | 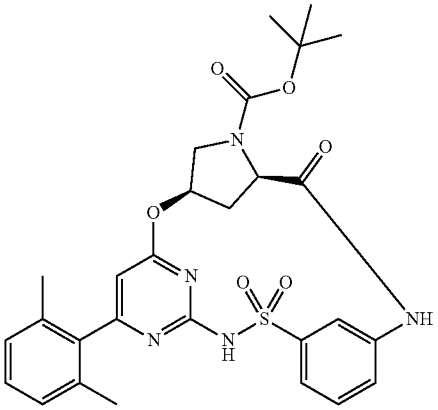 [SMILES: Cc1cccc(C)c1-c1cc2nc(n1)NS(=O)(=O)c1cccc(c1)NC(=O)[C@H]1C[C@H](CN1C(=O)OC(C)(C)C)O2] | | | ND | + | | |
| 80 | 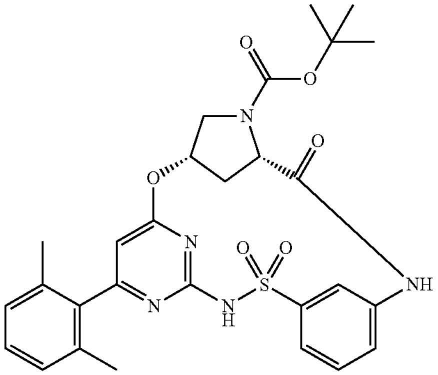 [SMILES: Cc1cccc(C)c1-c1cc2nc(n1)NS(=O)(=O)c1cccc(c1)NC(=O)[C@@H]1C[C@@H](CN1C(=O)OC(C)(C)C)O2] | | | ND | + | | |
| 81 | 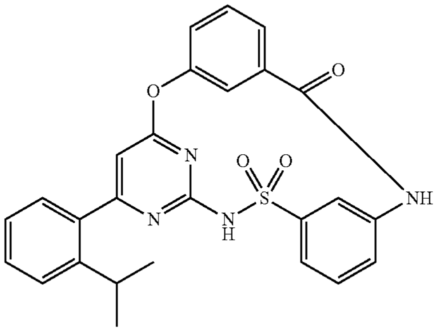 [SMILES: CC(C)c1ccccc1-c1cc2nc(n1)NS(=O)(=O)c1cccc(c1)NC(=O)c1cccc(c1)O2] | +++ | +++ | + | ++ | | |
| 82 | 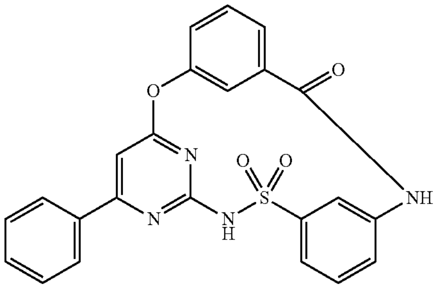 [SMILES: O=C1Nc2cccc(c2)S(=O)(=O)Nc2nc(cc(-c3ccccc3)n2)Oc2cccc1c2] | ++ | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 83 | 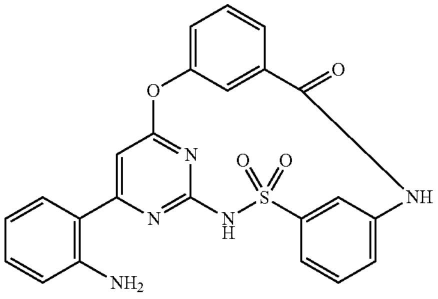 [SMILES: Nc1ccccc1-c1cc2nc(n1)NS(=O)(=O)c1cccc(c1)NC(=O)c1cccc(c1)O2] | + | +++ | | | | |
| 84 | 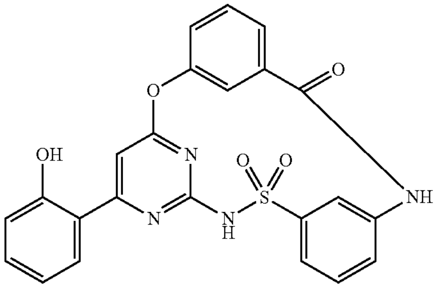 [SMILES: O=C1Nc2cccc(c2)S(=O)(=O)Nc2nc(cc(-c3ccccc3O)n2)Oc2cccc1c2] | + | +++ | | | | |
| 85 | 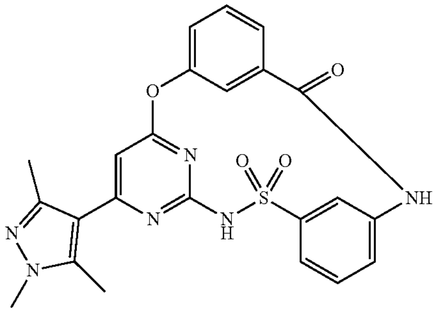 [SMILES: Cc1nn(C)c(C)c1-c1cc2nc(n1)NS(=O)(=O)c1cccc(c1)NC(=O)c1cccc(c1)O2] | ND | + | | | | |
| 86 | 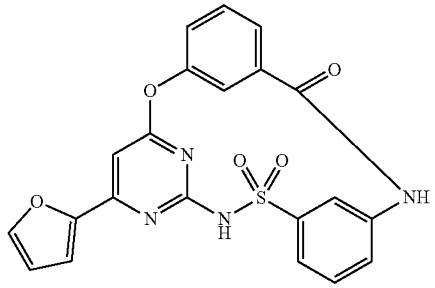 [SMILES: O=C1Nc2cccc(c2)S(=O)(=O)Nc2nc(cc(-c3ccco3)n2)Oc2cccc1c2] | + | +++ | | | | |
| 87 | 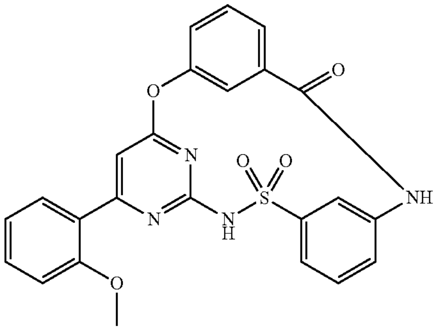 [SMILES: COc1ccccc1-c1cc2nc(n1)NS(=O)(=O)c1cccc(c1)NC(=O)c1cccc(c1)O2] | ++ | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 88 | 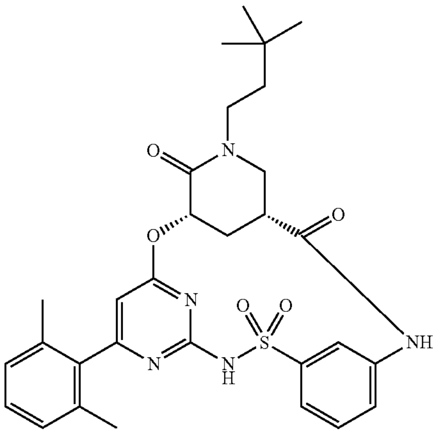 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | | | + | ++ | | |
| 89 | 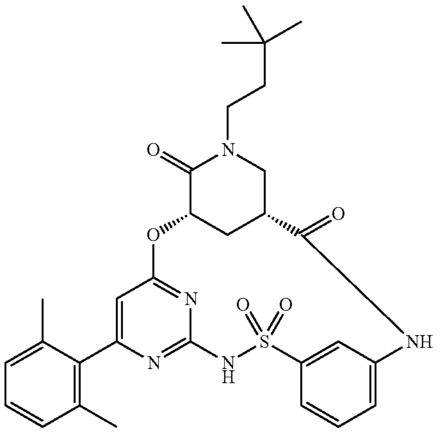 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | | | ND | + | | |
| 90 | 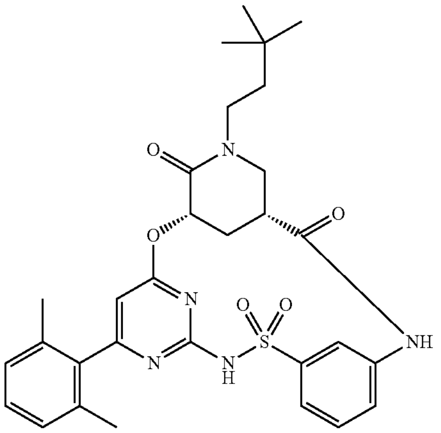 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | | | + | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 91 | 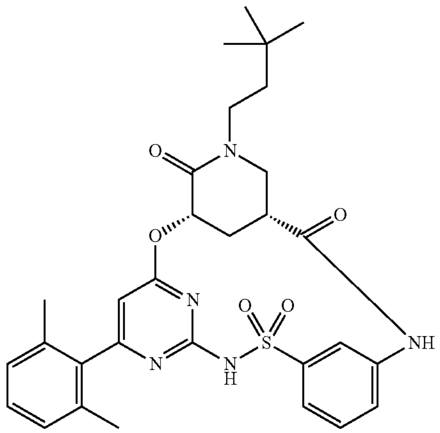 [SMILES: Cc1cccc(C)c1-c1cc2nc(n1)NS(=O)(=O)c1cccc(c1)NC(=O)[C@@H]1C[C@H](O2)C(=O)N(CCC(C)(C)C)C1] | | | + | + | | |
| 92 | 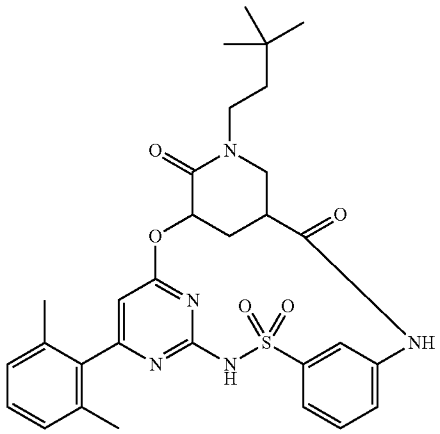 [SMILES: Cc1cccc(C)c1-c1cc2nc(n1)NS(=O)(=O)c1cccc(c1)NC(=O)C1CC(O2)C(=O)N(CCC(C)(C)C)C1] | | | ND | + | | |
| 93 | 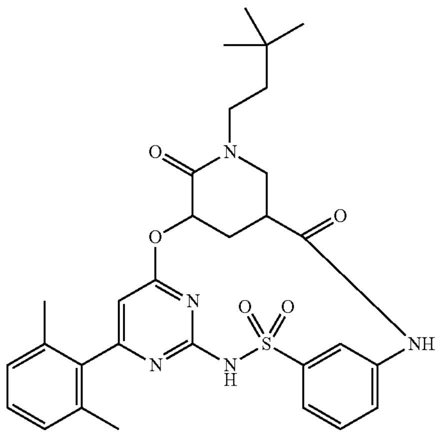 [SMILES: Cc1cccc(C)c1-c1cc2nc(n1)NS(=O)(=O)c1cccc(c1)NC(=O)C1CC(O2)C(=O)N(CCC(C)(C)C)C1] | | | ND | ++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 94 | 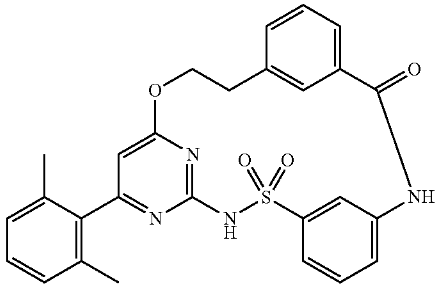 [SMILES: Cc1cccc(C)c1-c1cc2nc(n1)NS(=O)(=O)c1cccc(c1)NC(=O)c1cccc(c1)CCO2] | ++ | ++ | | | | |
| 95 | 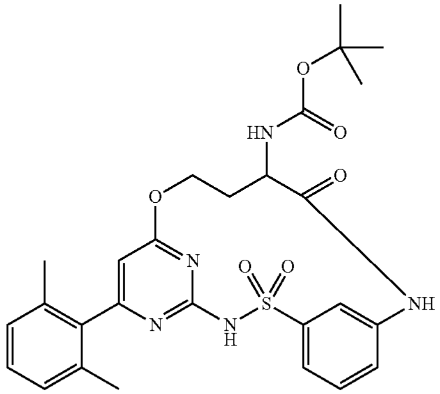 [SMILES: Cc1cccc(C)c1-c1cc2nc(n1)NS(=O)(=O)c1cccc(c1)NC(=O)C(NC(=O)OC(C)(C)C)CCO2] | +++ | +++ | | | | |
| 96 | 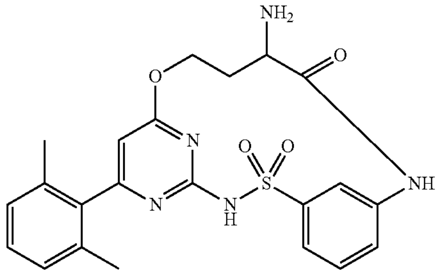 [SMILES: Cc1cccc(C)c1-c1cc2nc(n1)NS(=O)(=O)c1cccc(c1)NC(=O)C(N)CCO2] | ++ | +++ | | | | |
| 97 | 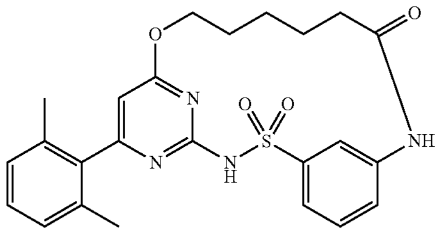 [SMILES: Cc1cccc(C)c1-c1cc2nc(n1)NS(=O)(=O)c1cccc(c1)NC(=O)CCCCCO2] | +++ | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 98 | 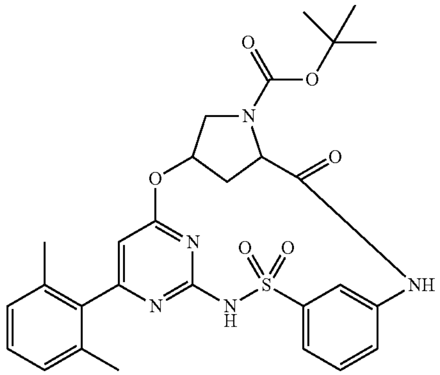 [SMILES: Cc1cccc(C)c1-c1cc2nc(n1)NS(=O)(=O)c1cccc(c1)NC(=O)C1CC(CN1C(=O)OC(C)(C)C)O2] | ++ | +++ | | | | |
| 99 | 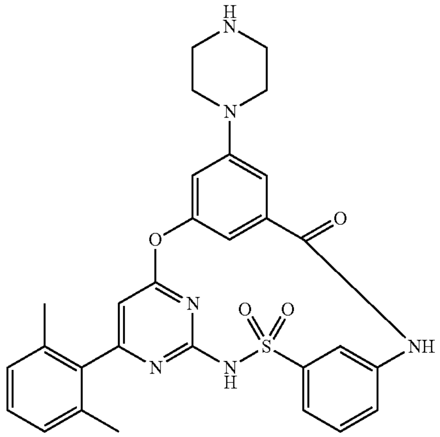 [SMILES: Cc1cccc(C)c1-c1cc2nc(n1)NS(=O)(=O)c1cccc(c1)NC(=O)c1cc(cc(N3CCNCC3)c1)O2] | + | ++ | | | | |
| 100 | 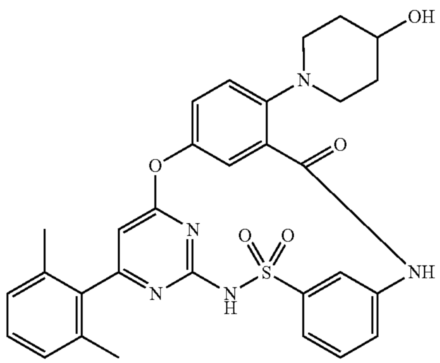 [SMILES: Cc1cccc(C)c1-c1cc2nc(n1)NS(=O)(=O)c1cccc(c1)NC(=O)c1cc(ccc1N1CCC(O)CC1)O2] | + | +++ | | | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 101 | 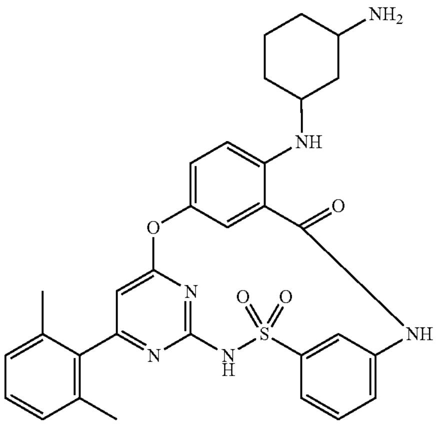 [SMILES: Cc1cccc(C)c1-c1cc2nc(n1)NS(=O)(=O)c1cccc(c1)NC(=O)c1cc(ccc1NC1CCCC(N)C1)O2] | + | +++ | | | | |
| 102 | 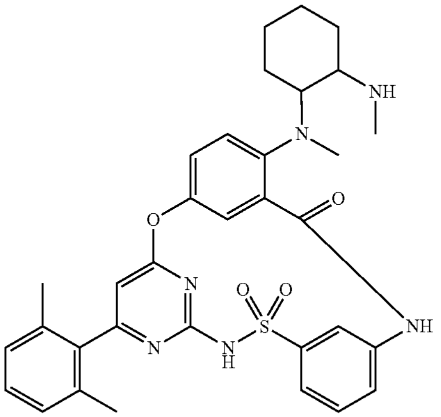 [SMILES: CNC1CCCCC1N(C)c1ccc2cc1C(=O)Nc1cccc(c1)S(=O)(=O)Nc1nc(cc(-c3c(C)cccc3C)n1)O2] | ND | ++ | | | | |
| 103 | 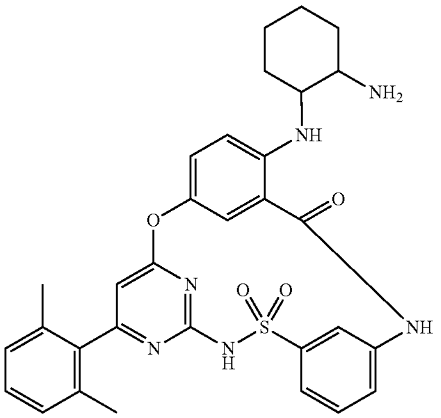 [SMILES: Cc1cccc(C)c1-c1cc2nc(n1)NS(=O)(=O)c1cccc(c1)NC(=O)c1cc(ccc1NC1CCCCC1N)O2] | ++ | +++ | | | | |

TABLE 8-continued
| Cmpd No. | Structure | 3T3 EC$_{50}$ (μM) | 3T3 Max Activity (%) | Ent. A EC$_{50}$ (μM) | Ent. A Max Activity (%) | Ent. B EC$_{50}$ (μM) | Ent. B Max Activity (%) |
|---|---|---|---|---|---|---|---|
| 104 | 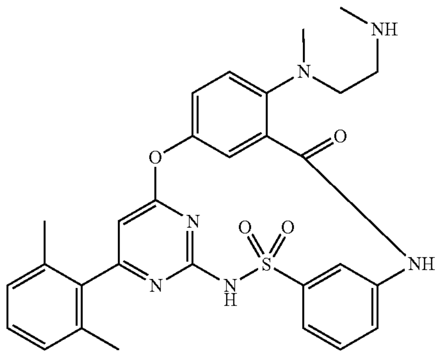 [SMILES: CNCCN(C)c1ccc2cc1C(=O)Nc1cccc(c1)S(=O)(=O)Nc1nc(cc(-c3c(C)cccc3C)n1)O2] | + | ++ | | | | |
| 105 | 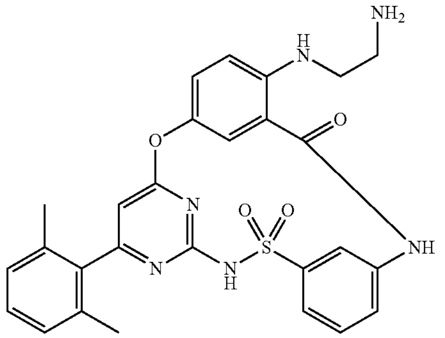 [SMILES: Cc1cccc(C)c1-c1cc2nc(n1)NS(=O)(=O)c1cccc(c1)NC(=O)c1cc(ccc1NCCN)O2] | ++ | +++ | | | | |
| 106 | 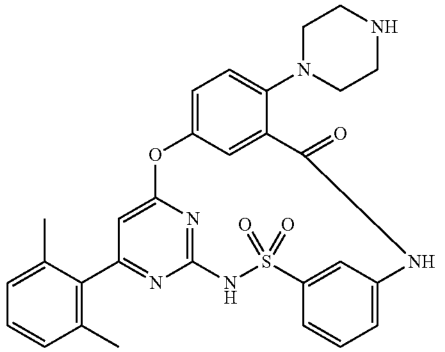 [SMILES: Cc1cccc(C)c1-c1cc2nc(n1)NS(=O)(=O)c1cccc(c1)NC(=O)c1cc(ccc1N1CCNCC1)O2] | + | +++ | | | | |
| 107 | 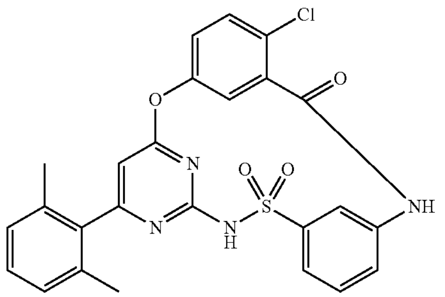 [SMILES: Cc1cccc(C)c1-c1cc2nc(n1)NS(=O)(=O)c1cccc(c1)NC(=O)c1cc(ccc1Cl)O2] | +++ | +++ | ++ | ++ | | |

TABLE 8-continued
| Cmpd No. | Structure | 3T3 EC$_{50}$ (µM) | 3T3 Max Activity (%) | Ent. A EC$_{50}$ (µM) | Ent. A Max Activity (%) | Ent. B EC$_{50}$ (µM) | Ent. B Max Activity (%) |
|---|---|---|---|---|---|---|---|
| 108 | 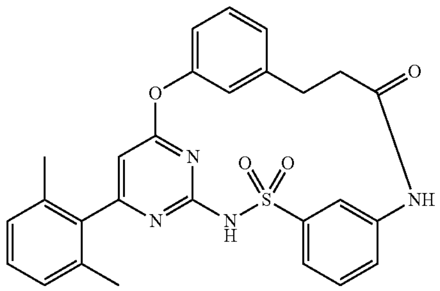 [SMILES: Cc1cccc(C)c1-c1cc2nc(n1)NS(=O)(=O)c1cccc(c1)NC(=O)CCc1cccc(c1)O2] | +++ | +++ | + | +++ | | |
| 109 | 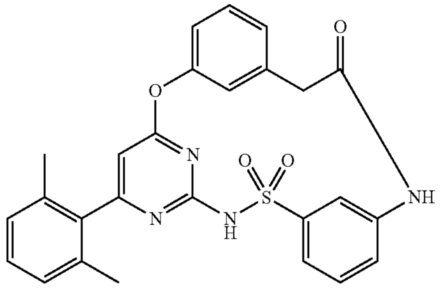 [SMILES: Cc1cccc(C)c1-c1cc2nc(n1)NS(=O)(=O)c1cccc(c1)NC(=O)Cc1cccc(c1)O2] | ++ | +++ | + | ++ | | |
| 110 | 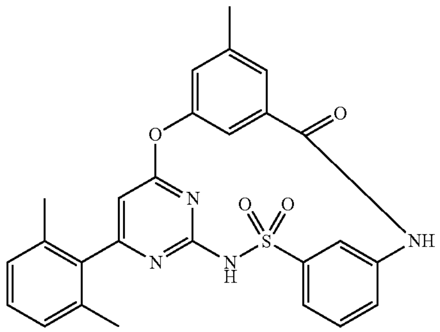 [SMILES: Cc1cc2cc(c1)C(=O)Nc1cccc(c1)S(=O)(=O)Nc1nc(cc(-c3c(C)cccc3C)n1)O2] | +++ | +++ | ++ | ++ | | |
| 111 | 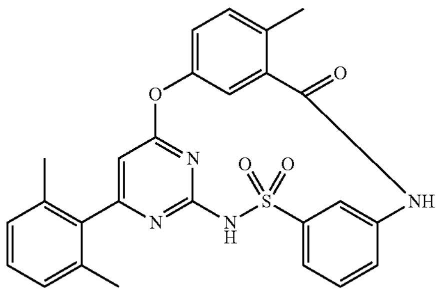 [SMILES: Cc1ccc2cc1C(=O)Nc1cccc(c1)S(=O)(=O)Nc1nc(cc(-c3c(C)cccc3C)n1)O2] | +++ | +++ | + | ++ | | |

TABLE 8-continued
| Cmpd No. | Structure | 3T3 EC$_{50}$ (μM) | 3T3 Max Activity (%) | Ent. A EC$_{50}$ (μM) | Ent. A Max Activity (%) | Ent. B EC$_{50}$ (μM) | Ent. B Max Activity (%) |
|---|---|---|---|---|---|---|---|
| 113 | 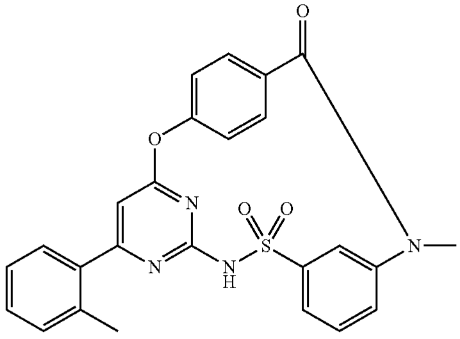 [SMILES: Cc1ccccc1-c1cc2nc(n1)NS(=O)(=O)c1cccc(c1)N(C)C(=O)c1ccc(cc1)O2] | ND | + | | | | |
| 115 | 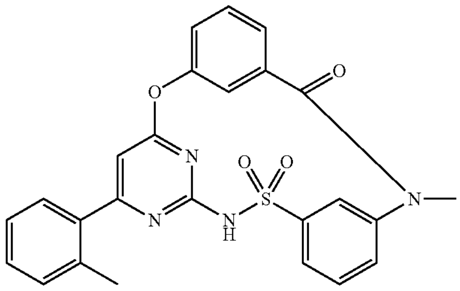 [SMILES: Cc1ccccc1-c1cc2nc(n1)NS(=O)(=O)c1cccc(c1)N(C)C(=O)c1cccc(c1)O2] | + | +++ | | | | |
| 116 | 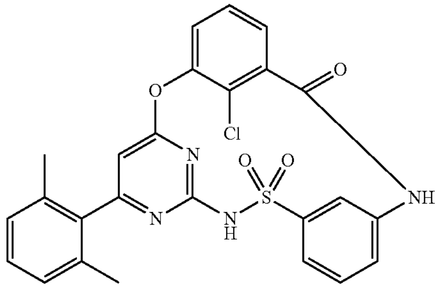 [SMILES: Cc1cccc(C)c1-c1cc2nc(n1)NS(=O)(=O)c1cccc(c1)NC(=O)c1cccc(c1Cl)O2] | +++ | +++ | | | | |
| 117 | 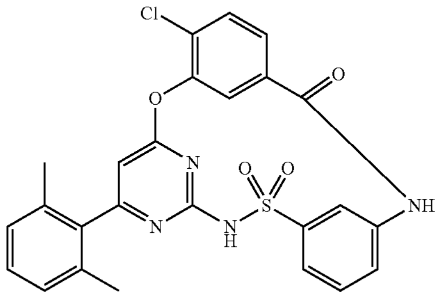 [SMILES: Cc1cccc(C)c1-c1cc2nc(n1)NS(=O)(=O)c1cccc(c1)NC(=O)c1ccc(Cl)c(c1)O2] | +++ | +++ | ++ | +++ | | |

TABLE 8-continued
| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 118 | 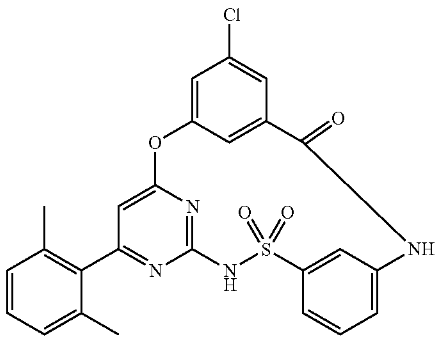 [SMILES: Cc1cccc(C)c1-c1cc2nc(n1)NS(=O)(=O)c1cccc(c1)NC(=O)c1cc(Cl)cc(c1)O2] | +++ | +++ | ++ | +++ | | |
| 119 | 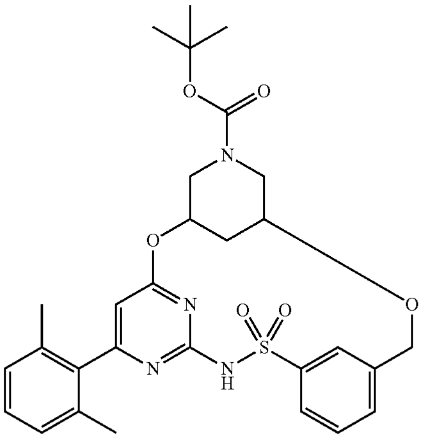 [SMILES: Cc1cccc(C)c1-c1cc2nc(n1)NS(=O)(=O)c1cccc(c1)COCC1CC(CN(C(=O)OC(C)(C)C)C1)O2] | | | ND | + | | |
| 120 | 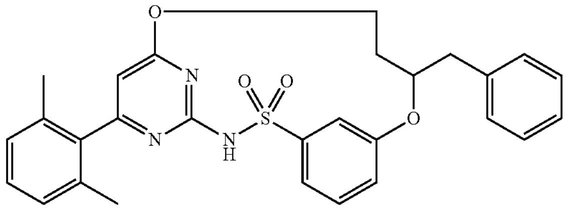 [SMILES: Cc1cccc(C)c1-c1cc2nc(n1)NS(=O)(=O)c1cccc(c1)OC(Cc1ccccc1)CCO2] | | | | | +++ | ++ |
| 121 | 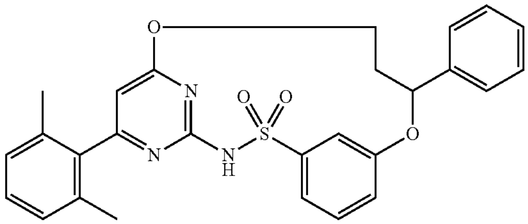 [SMILES: Cc1cccc(C)c1-c1cc2nc(n1)NS(=O)(=O)c1cccc(c1)OC(c1ccccc1)CCO2] | | | | | +++ | +++ |
| 122 | 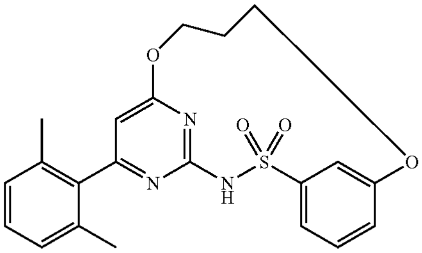 [SMILES: Cc1cccc(C)c1-c1cc2nc(n1)NS(=O)(=O)c1cccc(c1)OCCCO2] | | | | | + | + |

TABLE 8-continued

| Cmpd No. | Structure | 3T3 $EC_{50}$ (μM) | 3T3 Max Activity (%) | Ent. A $EC_{50}$ (μM) | Ent. A Max Activity (%) | Ent. B $EC_{50}$ (μM) | Ent. B Max Activity (%) |
|---|---|---|---|---|---|---|---|
| 123 | 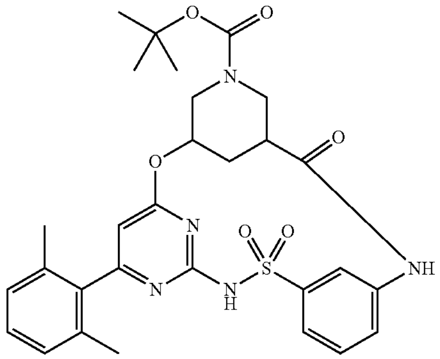 [SMILES: Cc1cccc(C)c1-c1cc2nc(n1)NS(=O)(=O)c1cccc(c1)NC(=O)C1CC(CN(C(=O)OC(C)(C)C)C1)O2] | +++ | +++ | +++ | ++ | | |
| 124 | 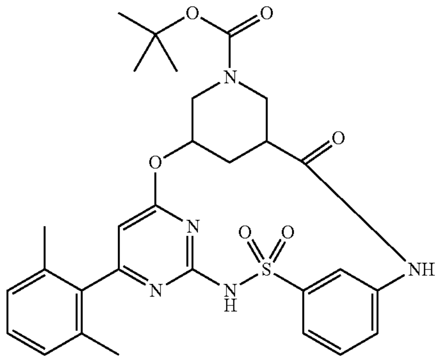 [SMILES: Cc1cccc(C)c1-c1cc2nc(n1)NS(=O)(=O)c1cccc(c1)NC(=O)C1CC(CN(C(=O)OC(C)(C)C)C1)O2] | ++ | +++ | + | ++ | | |

VI. Synthesis of (6R,12R)-17-amino-12-methyl-6,15-bis(trifluoromethyl)-13,19-dioxa-3,4,18-triazatricyclo [12.3.1.12,5] nonadeca-1(18),2,4,14,16-pentaen-6-ol

A. General Methods

Reagents and starting materials were obtained by commercial sources unless otherwise stated and were used without purification.

Proton and carbon NMR spectra were acquired on either a Bruker Biospin DRX 400 MHz FTNMR spectrometer operating at a $^{1}H$ and $^{13}C$ resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^{1}H$ using a 45 degree pulse angle, a spectral width of 4800 Hz and 28860 points of acquisition. FID were zero-filled to 32 k points and a line broadening of 0.3 Hz was applied before Fourier transform. $^{19}F$ NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^{1}H$ using a 30 degree pulse angle, a spectral width of 8000 Hz and 128 k points of acquisition. FID were zero-filled to 256 k points and a line broadening of 0.3 Hz was applied before Fourier transform. $^{19}F$ NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Unless stated to the contrary in the following examples, final purity of compounds was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C. Final purity was calculated by averaging the area under the curve (AUC) of two UV traces (220 nm, 254 nm). Low-resolution mass spectra were reported as $[M+1]^+$ species obtained using a single quadrupole mass spectrometer equipped with an electrospray ionization (ESI) source capable of achieving a mass accuracy of 0.1 Da and a minimum resolution of 1000 (no units on resolution) across the detection range.

Solid-state NMR (SSNMR) spectra were recorded on a Bruker-Biospin 400 MHz wide-bore spectrometer equipped with Bruker-Biospin 4 mm HFX probe. Samples were packed into 4 mm $ZrO_2$ rotors and spun under Magic Angle Spinning (MAS) condition with spinning speed typically set to 12.5 kHz. The proton relaxation time was measured using $^{1}$H MAS $T_1$ saturation recovery relaxation experiment in order to set up proper recycle delay of the $^{13}$C cross-polarization (CP) MAS experiment. The fluorine relaxation time was measured using $^{19}$F MAS $T_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

B. Procedures for the Synthesis of Intermediates

Intermediate 1: Preparation of methyl 3-[bis(tert-butoxycarbonyl)amino]-6-bromo-5-(trifluoromethyl) pyridine-2-carboxylate

Step 1: Methyl 3-(benzhydrylideneamino)-5-(trifluoromethyl)pyridine-2-carboxylate A mixture of methyl 3-chloro-5-(trifluoromethyl)pyridine-2-carboxylate (47.3 g, 197.43 mmol), diphenylmethanimine (47 g, 259.33 mmol), Xantphos (9.07 g, 15.675 mmol), and cesium carbonate (131 g, 402.06 mmol) in dioxane (800 mL) was degassed with bubbling nitrogen for 30 minutes. $Pd(OAc)_2$ (3.52 g, 15.679 mmol) was added and the system was purged with nitrogen three times. The reaction mixture was heated at 100° C. for 18 hours. The reaction was cooled to room temperature and filtered on a pad of Celite. The cake was washed with EtOAc and solvents were evaporated under reduced pressure to give methyl 3-(benzhydrylideneamino)-5-(trifluoromethyl)pyridine-2-carboxylate (90 g, 84%) as yellow solid. ESI-MS m/z calc. 384.10855, found 385.1 $(M+1)^+$; Retention time: 2.24 minutes. LCMS Method: Kinetex $C_{18}$ 4.6×50 mm 2.6 μM, 2.0 mL/min, 95% $H_2O$ (0.1% formic acid)+5% acetonitrile (0.1% formic acid) to 95% acetonitrile (0.1% formic acid) gradient (2.0 min) then held at 95% acetonitrile (0.1% formic acid) for 1.0 minute.

Step 2: Methyl 3-amino-5-(trifluoromethyl)pyridine-2-carboxylate

To a suspension of methyl 3-(benzhydrylideneamino)-5-(trifluoromethyl)pyridine-2-carboxylate (65 g, 124.30 mmol) in methanol (200 mL) was added HCl (3 M in methanol) (146 mL of 3 M, 438.00 mmol). The mixture was stirred at room temperature for 1.5 hours, then the solvent was removed under reduced pressure. The residue was taken up in ethyl acetate (2 L) and dichloromethane (500 mL). The organic phase was washed with 5% aqueous sodium bicarbonate solution (3×500 mL) and brine (2×500 mL), dried over anhydrous sodium sulfate, filtered and the solvent was removed under reduced pressure. The residue was triturated with heptanes (2×50 mL), and the mother liquors were discarded. The solid obtained was triturated with a mixture of dichloromethane and heptanes (1:1, 40 mL) and filtered to afford methyl 3-amino-5-(trifluoromethyl)pyridine-2-carboxylate (25.25 g, 91%) as yellow solid. $^{1}$H NMR (300 MHz, $CDCl_3$) δ 8.24 (s, 1H), 7.28 (s, 1H), 5.98 (br. s, 2H), 4.00 (s, 3H) ppm. $^{19}$F NMR (282 MHz, $CDCl_3$) δ −63.23 (s, 3F) ppm. ESI-MS m/z calc. 220.046, found 221.1 $(M+1)^+$; Retention time: 1.62 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Step 3: Methyl 3-amino-6-bromo-5-(trifluoromethyl)pyridine-2-carboxylate

To a solution of methyl 3-amino-5-(trifluoromethyl)pyridine-2-carboxylate (18.75 g, 80.91 mmol) in acetonitrile (300 mL) at 0° C. was added portion wise N-bromosuccinimide (18.7 g, 105.3 mmol). The mixture was stirred overnight at 25° C. Ethyl acetate (1000 mL) was added. The organic layer was washed with 10% sodium thiosulfate solution (3×200 mL) which was back extracted with ethyl acetate (2×200 mL). The combined organic extracts were washed with saturated sodium bicarbonate solution (3×200 mL), brine (200 mL), dried over sodium sulfate and concentrated in vacuo to provide methyl 3-amino-6-bromo-5-(trifluoromethyl)pyridine-2-carboxylate (25.46 g, 98%). $^{1}$H NMR (300 MHz, $CDCl_3$) δ 3.93-4.03 (m, 3H), 6.01 (br. s., 2H), 7.37 (s, 1H) ppm. $^{19}$F NMR (282 MHz, $CDCl_3$) ppm −64.2 (s, 3F). ESI-MS m/z calc. 297.9565, found 299.0 $(M+1)^+$; Retention time: 2.55 minutes. LCMS Method: Kinetex $C_{18}$ 4.6×50 mm 2.6 μM. Temp: 45° C., Flow: 2.0 mL/min, Run Time: 6 minutes. Mobile Phase: Initial 95% $H_2O$ (0.1% formic acid) and 5% acetonitrile (0.1% formic acid) linear gradient to 95% acetonitrile (0.1% formic acid) for 4.0 minutes, then held at 95% acetonitrile (0.1% formic acid) for 2.0 minutes.

Step 4: Methyl 3-[bis(tert-butoxycarbonyl)amino]-6-bromo-5-(trifluoro methyl)pyridine-2-carboxylate A mixture of methyl 3-amino-6-bromo-5-(trifluoromethyl)pyridine-2-carboxylate (5 g, 15.549 mmol), $(Boc)_2O$ (11 g, 11.579 mL, 50.402 mmol), DMAP (310 mg, 2.5375 mmol) and $CH_2Cl_2$ (150 mL) was stirred at room temperature overnight. The reaction mixture was concentrated under reduced pressure, and purification by silica gel chromatography (0-15% ethyl acetate in heptane) provided methyl 3-[bis(tert-butoxycarbonyl)amino]-6-bromo-5-(trifluoromethyl)pyridine-2-carboxylate (6.73 g, 87%) as light yellow solid. $^{1}$H NMR (300 MHz, $CDCl_3$) δ 1.42 (s, 18H), 3.96 (s, 3H), 7.85 (s, 1H) ppm. $^{19}$F NMR (282 MHz, $CDCl_3$) δ −63.9 (s, 3F) ppm. ESI-MS m/z calc. 498.06134, Retention time: 2.34 minutes. LCMS Method: Kinetex $C_{18}$ 4.6×50 mm 2.6 μM. Temp: 45° C., Flow: 2.0 mL/min, Run Time: 3 minutes. Mobile Phase: Initial 95% $H_2O$ (0.1% formic acid) and 5% acetonitrile (0.1% formic acid) linear gradient to 95% acetonitrile (0.1% formic acid) for 2.0 minutes, then held at 95% acetonitrile (0.1% formic acid) for 1.0 minute.

Intermediate 2: Preparation of 6-bromo-3-(tert-butoxycarbonylamino)-5-(trifluoromethyl)pyridine-2-carboxylic Acid

Step 1: 6-Bromo-3-(tert-butoxycarbonylamino)-5-(trifluoromethyl)pyridine-2-carboxylic Acid To a mixture of methyl 3-[bis(tert-butoxycarbonyl) amino]-6-bromo-5-(trifluoromethyl)pyridine-2-carboxylate (247 g, 494.7 mmol) in THF (1.0 L) was added a solution of LiOH (47.2 g, 1.971 mol) in water (500 mL). The mixture was stirred at ambient temperature for 18 hours, affording a yellow slurry. The mixture was cooled with an ice-bath and slowly acidified with HCl (1000 mL of 2 M, 2.000 mol) keeping the reaction temperature <15° C. The mixture was diluted with heptane (1.5 L), mixed and the organic phase separated. The aqueous phase was extracted with heptane (500 mL). The combined organic phases were washed with brine, dried over $MgSO_4$, filtered and concentrated in vacuo. The crude oil was dissolved in heptane (600 mL), seeded and stirred at ambient temperature for 18 hours, affording a thick slurry. The slurry was diluted with cold heptane (500 mL) and the precipitate collected using a medium frit. The filter cake was washed with cold heptane and air dried for 1 hour, then in vacuo at 45° C. for 48 hours to afford 6-bromo-3-(tert-butoxycarbonylamino)-5-(trifluoromethyl) pyridine-2-carboxylic acid (158.3 g, 83%). $^1H$ NMR (400 MHz, DMSO-$d_6$) δ 10.38 (s, 1H), 9.01 (s, 1H), 1.50 (s, 9H) ppm. ESI-MS m/z calc. 383.99326, found 384.9 $(M+1)^+$; Retention time: 2.55 minutes. LCMS Method Detail: Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C.

Intermediate 3: Preparation of 2-Benzyloxy-2-(trifluoromethyl)hex-5-enoic Acid

Step 1: Ethyl 2-hydroxy-2-(trifluoromethyl)hex-5-enoate

To a solution of ethyl 3,3,3-trifluoro-2-oxo-propanoate (25.15 g, 147.87 mmol) in $Et_2O$ (270 mL) at −78° C. was added bromo(but-3-enyl)magnesium in THF (190 mL of 0.817 M, 155.23 mmol) dropwise over a period of 1.5 hours (inner temperature −72° C. to −76° C.). The mixture was stirred at −78° C. for 20 minutes. The dry ice-acetone bath was removed. The mixture was slowly warm to 5° C. over 1 hour, added to a mixture of 1 N aqueous HCl (170 mL) and crushed ice (150 g) (pH=4). The two layers were separated. The organic layer was concentrated, and the residue was combined with aqueous phase and extracted with EtOAc (2×150 mL). The combined organic phase was washed with 5% aqueous $NaHCO_3$ (50 mL) and brine (20 mL), and dried with $Na_2SO_4$. The mixture was filtered and concentrated, and co-evaporated with THF (2×40 mL) to give ethyl 2-hydroxy-2-(trifluoromethyl)hex-5-enoate (37.44 g, 96%) as colorless oil. $^1H$ NMR (300 MHz, $CDCl_3$) δ 5.77 (ddt, J=17.0, 10.4, 6.4 Hz, 1H), 5.15-4.93 (m, 2H), 4.49-4.28 (m, 2H), 3.88 (s, 1H), 2.35-2.19 (m, 1H), 2.17-1.89 (m, 3H), 1.34 (t, J=7.0 Hz, 3H) ppm. $^{19}F$ NMR (282 MHz, $CDCl_3$) δ −78.74 (s, 3F) ppm.

Step 2: Ethyl 2-benzyloxy-2-(trifluoromethyl)hex-5-enoate

To a solution of ethyl 2-hydroxy-2-(trifluoromethyl)hex-5-enoate (24.29 g, 87.6% purity, 94.070 mmol) in DMF (120 mL) at 0° C. was added NaH (60% in mineral oil, 5.64 g, 141.01 mmol) portion-wise. The mixture was stirred at 0° C. for 10 minutes. Benzyl bromide (24.13 g, 141.08 mmol) and TBAI (8.68 g, 23.500 mmol) were added. The mixture was stirred at room temperature overnight. $NH_4Cl$ (3 g, 0.6 eq) was added. The mixture was stirred for 10 minutes. 30 mL of EtOAc was added, then ice-water was added (400 g). The mixture was extracted with $CH_2Cl_2$ and the combined organic layers were concentrated. Purification by silica gel chromatography (0-20% $CH_2Cl_2$ in heptanes) provided ethyl 2-benzyloxy-2-(trifluoromethyl)hex-5-enoate (26.05 g, 88%) as pink oil. $^1H$ NMR (300 MHz, $CDCl_3$) δ 1.34 (t, J=7.2 Hz, 3H), 2.00-2.19 (m, 3H), 2.22-2.38 (m, 1H), 4.33 (q, J=7.2 Hz, 2H), 4.64 (d, J=10.6 Hz, 1H), 4.84 (d, J=10.9 Hz, 1H), 4.91-5.11 (m, 2H), 5.62-5.90 (m, 1H), 7.36 (s, 5H) ppm. $^{19}F$ NMR (282 MHz, $CDCl_3$) δ −70.5 (s, 3F) ppm. ESI-MS m/z calc. 316.12863, found 317.1 $(M+1)^+$; Retention time: 2.47 minutes. LCMS Method: Kinetex $C_{18}$ 4.6×50 mm 2.6 μM. Temp: 45° C., Flow: 2.0 mL/min, Run Time: 3 minutes. Mobile Phase: Initial 95% $H_2O$ (0.1% formic acid) and 5% acetonitrile (0.1% formic acid) linear gradient to 95% acetonitrile (0.1% formic acid) for 2.0 minutes, then held at 95% acetonitrile (0.1% formic acid) for 1.0 minute.

Step 3: 2-Benzyloxy-2-(trifluoromethyl)hex-5-enoic Acid

A solution of sodium hydroxide (7.86 g, 196.51 mmol) in water (60 mL) was added to a solution of ethyl 2-benzyloxy-2-(trifluoromethyl)hex-5-enoate (24.86 g, 78.593 mmol) in methanol (210 mL). The reaction was heated at 50° C. overnight. The reaction was concentrated to remove methanol, diluted with water (150 mL) and the carboxylate sodium salt was washed with heptane (1×100 mL). The aqueous solution was acidified to pH=2 with aqueous 3N solution of HCl. The carboxylic acid was extracted with dichloromethane (3×100 mL) and dried over sodium sulfate. The solution was filtered and concentrated to give 2-benzyloxy-2-(trifluoromethyl)hex-5-enoic acid (22.57 g, 97%) as pale yellow oil. $^1H$ NMR (300 MHz, DMSO-$d_6$) δ 14.31 (br. s., 1H), 7.55-7.20 (m, 5H), 5.93-5.70 (m, 1H), 5.17-4.91 (m, 2H), 4.85-4.68 (m, 1H), 4.67-4.55 (m, 1H), 2.32-1.94 (m, 4H) ppm. $^{19}F$ NMR (282 MHz, DMSO-$d_6$) δ −70.29 (s, 3F) ppm. ESI-MS m/z calc. 288.09732, found 287.1 (M−1); Retention time: 3.1 minutes. LCMS Method: Kinetex Polar $C_{18}$ 3.0×50 mm 2.6 μm, 6 min, 5-95% acetonitrile in $H_2O$ (0.1% formic acid) 1.2 mL/min.

Intermediate 4: Preparation of (2R)-2-benzyloxy-2-(trifluoromethyl)hex-5-enoic Acid

Step-1: (2R)-2-Benzyloxy-2-(trifluoromethyl)hex-5-enoic Acid; (R)-4-quinolyl-[(2S,4S)-5-vinylquinuclidin-2-yl]methanol To a $N_2$ purged jacketed reactor set to 20° C. was added isopropyl acetate (IPAC, 100 L, 0.173 M, 20 Vols), followed by previously melted 2-benzyloxy-2-(trifluoromethyl)hex-5-enoic acid (5.00 kg, 17.345 mol) and cinchonidine (2.553 kg, 8.67 mol) made into a slurry with minor amount of the reaction solvent. The reactor was set to ramp internal temperature to 80° C. over 1 hour, with solids going in solution upon heating to set temperature, then the solution was held at temperature for at least 10 minutes, then cooled to 70° C. held and seeded with chiral salt (50 g, 1.0% by wt). The mixture was stirred for 10 minutes, then ramped to 20° C. internal temperature over 4 hours, then held overnight at 20° C. The mixture was filtered, cake washed with isopropyl acetate (10.0 L, 2.0 vols) and dried under vacuum. The cake was then dried in vacuo (50° C., vacuum) to afford 4.7 kg of salt. The resulting solid salt was returned to the reactor by making a slurry with a portion of isopropyl acetate (94 L, 20 vol based on current salt wt), and pumped into reactor and stirred. The mixture was then heated to 80° C. internal, stirred hot slurry for at least 10 minutes, then ramped to 20° C. over 4-6 hours, then stirred overnight at 20° C. The material was then filtered and the cake washed with isopropyl acetate (9.4 L, 2.0 vol), pulled dry, cake scooped out and dried in vacuo (50° C., vacuum) to afford 3.1 kg of solid. The solid (3.1 kg) and isopropyl acetate (62 L, 20 vol based on salt solid wt) was slurried and added to a reactor, stirred under $N_2$ purge and heated to 80° C. and held at temperature at least 10 minutes, then ramped to 20° C. over 4-6 hours, then stirred overnight. The mixture was filtered, cake washed with isopropyl acetate (6.2 L, 2 vol), pulled dry, scooped out and dried in vacuo (50° C., vac) to afford 2.25 kg of solid salt. The solid (2.25 kg) and isopropyl acetate (45 L, 20 vol based on salt solid wt) was slurried and added to a reactor, stirred under $N_2$ purge and heated to 80° C., held at temperature at least 10 minutes, then ramped to 20° C. over 4-6 hours, then stirred overnight. The mixture was filtered, cake washed with isopropyl acetate (4.5 L, 2 vol), pulled dry, scooped out and dried in vacuo (50° C. to afford (2R)-2-benzyloxy-2-(trifluoromethyl)hex-5-enoic acid; (R)-4-quinolyl-[(2S,4S)-5-vinylquinuclidin-2-yl]methanol (1.886 kg, >98.0% ee) as an off-white to tan solid. Chiral purity was determined by Agilent 1200 HPLC instrument using Phenomenex Lux i-Amylose-3 column (3 μm, 150×4.6 mm) and a dual, isocratic gradient run 30% to 70% mobile phase B over 20.0 minutes. Mobile phase A=$H_2O$ (0.1% $CF_3CO_2H$). Mobile phase B=MeOH (0.1% $CF_3CO_2H$). Flow rate=1.0 mL/min, injection volume=2 μL, and column temperature=30° C., sample concentration: 1 mg/mL in 60% acetonitrile/40% water.

Step 2: (2R)-2-Benzyloxy-2-(trifluoromethyl)hex-5-enoic Acid

A suspension of (2R)-2-benzyloxy-2-(trifluoromethyl) hex-5-enoic acid; (R)-4-quinolyl-[(2S,4S)-5-vinylquinuclidin-2-yl]methanol (50 g, 87.931 mmol) in ethyl acetate (500.00 mL) was treated with an aqueous solution of hydrochloric acid (200 mL of 1 M, 200.00 mmol). After stirring for 15 minutes at room temperature, the two phases were separated. The aqueous phase was extracted twice with ethyl acetate (200 mL). The combined organic layer was washed with 1 N HCl (100 mL). The organic layer was dried over sodium sulfate, filtered and concentrated. The material was dried over high vacuum overnight to give (2R)-2-benzyloxy-2-(trifluoromethyl)hex-5-enoic acid (26.18 g, 96%) as pale brown oil. $^1$H NMR (400 MHz, $CDCl_3$) δ 7.46-7.31 (m, 5H), 5.88-5.73 (m, 1H), 5.15-4.99 (m, 2H), 4.88 (d, J=10.3 Hz, 1H), 4.70 (d, J=10.3 Hz, 1H), 2.37-2.12 (m, 4H) ppm. $^{19}$F NMR (377 MHz, $CDCl_3$) δ −71.63 (br s, 3F) ppm. ESI-MS m/z calc. 288.0973, found 287.0 $(M-1)^-$; Retention time: 2.15 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Intermediate 5: Preparation of (2R)-2-benzyloxy-2-(trifluoromethyl)hex-5-enehydrazide

Step 1: tert-Butyl N-[[(2R)-2-benzyloxy-2-(trifluoromethyl)hex-5-enoyl]amino]carbamate To a solution of (2R)-2-benzyloxy-2-(trifluoromethyl) hex-5-enoic acid (365 g, 1.266 mol) in DMF (2 L) was added HATU (612 g, 1.610 mol) and DIEA (450 mL, 2.584 mol) and the mixture was stirred at ambient temperature for 10 minutes. To the mixture was added tert-butyl N-aminocarbamate (200 g, 1.513 mol) (slight exotherm upon addition) and the mixture was stirred at ambient temperature for 16 hours. The reaction was poured into ice water (5 L). The resultant precipitate was collected by filtration and washed with water. The solid was dissolved in EtOAc (2 L) and washed with brine. The organic phase was dried over $MgSO_4$, filtered, and concentrated in vacuo. The oil was diluted with EtOAc (500 mL) followed by heptane (3 L) and stirred at ambient temperature for several hours affording a thick slurry. The slurry was diluted with additional heptane and filtered to collect fluffy white solid (343 g). The filtrate was concentrated and purification by silica gel chromatography (0-40% EtOAc/hexanes) provided tert-butyl N-[[(2R)-2-benzyloxy-2-(trifluoromethyl)hex-5-enoyl] amino]carbamate (464 g, 91%, combined with product from crystallization). ESI-MS m/z calc. 402.17664, found 303.0 $(M+1\text{-Boc})^+$; Retention time: 2.68 minutes. Final purity was determined by reversed phase UPLC using an Acquity UPLC BEH $C_{18}$ column (50×2.1 mm, 1.7 μm particle) made by Waters (pn: 186002350) and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Step 2: (2R)-2-Benzyloxy-2-(trifluoromethyl)hex-5-enehydrazide

To a solution of tert-butyl N-[[(2R)-2-benzyloxy-2-(trifluoromethyl)hex-5-enoyl]amino]carbamate (464 g, 1.153 mol) in DCM (1.25 L) and was added HCl (925 mL of 4 M, 3.700 mol) and the mixture stirred at ambient temperature for 20 hours. The mixture was concentrated in vacuo removing most of the DCM. The mixture was diluted with isopropyl acetate (1 L) and basified to pH=6 with NaOH (140 g of 50% w/w, 1.750 mol) in 1 L of ice water. The organic phase was separated and washed with 1 L of brine and the combined aqueous phases were extracted with isopropyl acetate (1 L). The combined organic phases were dried over $MgSO_4$, filtered and concentrated in vacuo affording a dark yellow oil of (2R)-2-benzyloxy-2-(trifluoromethyl)hex-5-enehydrazide (358 g, quant.). $^1$H NMR (400 MHz, $CDCl_3$) δ 8.02 (s, 1H), 7.44-7.29 (m, 5H), 5.81 (ddt, J=16.8, 10.1, 6.4 Hz, 1H), 5.13-4.93 (m, 2H), 4.75 (dd, J=10.5, 1.5 Hz, 1H), 4.61 (d, J=10.5 Hz, 1H), 3.78 (s, 2H), 2.43 (ddd, J=14.3, 11.0, 5.9 Hz, 1H), 2.26-1.95 (m, 3H) ppm. ESI-MS m/z calc. 302.1242, found 303.0 $(M+1)^+$; Retention time: 2.0 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 6: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate

Step 1: tert-Butyl N-[2-[[[(2R)-2-benzyloxy-2-(trifluoromethyl)hex-5-enoyl]amino]carbamoyl]-6-bromo-5-(trifluoromethyl)-3-pyridyl]carbamate To a mixture of 6-bromo-3-(tert-butoxycarbonylamino)-5-(trifluoromethyl)pyridine-2-carboxylic acid (304 g, 789.3 mmol) and (2R)-2-benzyloxy-2-(trifluoromethyl)hex-5-enehydrazide (270 g, 893.2 mmol) in EtOAc (2.25 L) at ambient temperature was added DIEA (425 mL, 2.440 mol). To the mixture was slowly added $T_3P$ (622 g of 50% w/w, 977.4 mmol) using an ice-water bath to keep the temperature <35° C. (temperature rose to 34° C.) and the reaction mixture was stirred at ambient temperature for 18 hours. Additional DIEA (100 mL, 574.1 mmol) and $T_3P$ (95 g, 298.6 mmol) were added and stirred at ambient temperature for 2 days. Starting material was still observed and additional $T_3P$ (252 g, 792 mmol) was added and stirred for 5 days. The reaction was quenched with the slow addition of water (2.5 L) and the mixture stirred for 30 minutes. The organic phase was separated, and the aqueous phase extracted with EtOAc (2 L). The combined organic phases were washed with brine, dried over $MgSO_4$, filtered and concentrated in vacuo. The crude product was dissolved in MTBE (300 mL) and diluted with heptane (3 L), the mixture stirred at ambient temperature for 12 hours affording a light yellow slurry. The slurry was filtered, and the resultant solid was air dried for 2 hours, then in vacuo at 40° C. for 48 hours. The filtrate was concentrated in vacuo and purified by silica gel chromatography (0-20% EtOAc/hexanes) and combined with material obtained from crystallization providing tert-butyl N-[2-[[[(2R)-2-benzyloxy-2-(trifluoromethyl)hex-5-enoyl]amino]carbamoyl]-6-bromo-5-(trifluoromethyl)-3-pyridyl]carbamate (433 g, 82%). $^1$H NMR (400 MHz, DMSO) δ 11.07 (s, 1H), 10.91 (s, 1H), 10.32 (s, 1H), 9.15 (s, 1H), 7.53-7.45 (m, 2H), 7.45-7.28 (m, 3H), 5.87 (ddt, J=17.0, 10.2, 5.1 Hz, 1H), 5.09 (dq, J=17.1, 1.3 Hz, 1H), 5.02 (dd, J=10.3, 1.9 Hz, 1H), 4.84 (q, J=11.3 Hz, 2H), 2.37-2.13 (m, 4H), 1.49 (s, 9H) ppm. ESI-MS m/z calc. 668.1069, found 669.0 $(M+1)^+$; Retention time: 3.55 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Step 2: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate To a solution of tert-butyl N-[2-[[[(2R)-2-benzyloxy-2-(trifluoromethyl)hex-5-enoyl]amino]carbamoyl]-6-bromo-5-(trifluoromethyl)-3-pyridyl]carbamate (240 g, 358.5 mmol) in anhydrous acetonitrile (1.5 L) under nitrogen was added DIEA (230 mL, 1.320 mol) and the orange solution heated to 70° C. To the mixture was added p-toluenesulfonyl chloride (80.5 g, 422.2 mmol) in 3 equal portions over 1 hour. The mixture was stirred at 70° C. for 9 hours then additional p-toluenesulfonyl chloride (6.5 g, 34.09 mmol) was added. The mixture was stirred for a total of 24 hours then allowed to cool to ambient temperature. Acetonitrile was removed in vacuo affording a dark orange oil which was diluted with EtOAc (1.5 L) and water (1.5 L). The organic phase was separated and washed with 500 mL of 1M HCl, 500 mL of brine, dried over $MgSO_4$, filtered and concentrated in vacuo. Purification by silica gel chromatography (0-20% EtOAc/hexanes) provided tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (200 g, 86%). $^1$H NMR (400 MHz, DMSO) δ 10.11 (s, 1H), 9.10 (s, 1H), 7.55-7.48 (m, 2H), 7.47-7.28 (m, 3H), 5.87 (ddt, J=16.7, 10.2, 6.4 Hz, 1H), 5.11 (dt, J=17.2, 1.7 Hz, 1H), 5.01 (dt, J=10.2, 1.5 Hz, 1H), 4.74 (d, J=10.6 Hz, 1H), 4.65 (d, J=10.6 Hz, 1H), 2.55-2.42 (m, 2H), 2.30 (qd, J=11.3, 10.3, 6.9 Hz, 2H), 1.52 (s, 9H) ppm. ESI-MS m/z calc. 650.0963, found 650.0 $(M+1)^+$; Retention time: 3.78 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 7: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

Step 1: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate To a solution of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (222 g, 340.8 mmol) in MTBE (1.333 L) was added DIPEA (65.3 mL, 374.9 mmol) followed DMAP (2.09 g, 17.11 mmol). A solution of di-tert-butyl dicarbonate (111.6 g, 511.3 mmol) in MTBE (250 mL) was added over approximately 8 minutes, and the resulting mixture was stirred for additional 30 minutes. 1 L of water was added and the layers separated. The organic layer was washed with $KHSO_4$ (886 mL of 0.5 M, 443.0 mmol), 300 mL brine, dried with $MgSO_4$ and most (>95%) of the MTBE was evaporated by rotary evaporation at 45° C., leaving a thick oil. 1.125 L of heptane was added, spun in the 45° C. rotovap bath until dissolved, then evaporated out 325 mL of solvent by rotary evaporation. The rotovap bath temp was allowed to drop to room temperature and product started crystallizing out during the evaporation. Then the flask was placed in a −20° C. freezer overnight. The resultant solid was filtered and washed with cold heptane and dried at room temperature for 3 days to give tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (240.8 g, 94%). $^1$H NMR (400 MHz, Chloroform-d) δ 7.95 (s, 1H), 7.52-7.45 (m, 2H), 7.44-7.36 (m, 2H), 7.36-7.29 (m, 1H), 5.83-5.67 (m, 1H), 5.08-5.00 (m, 1H), 5.00-4.94 (m, 1H), 4.79 (d, J=10.4 Hz, 1H), 4.64 (d, J=10.4 Hz, 1H), 2.57-2.26 (m, 3H), 2.26-2.12 (m, 1H), 1.41 (s, 18H) ppm. ESI-MS m/z calc. 750.14874, found 751.1 $(M+1)^+$; Retention time: 3.76 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Intermediate 8: Preparation of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate Step 1: tert-Butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (280 g, 372.6 mmol) was dissolved in DMSO (1.82 L) (yellow solution) and treated with cesium acetate (215 g, 1.120 mol) under stirring at room temperature. The yellow suspension was heated at 80° C. for 5 hours. The reaction mixture was cooled to room temperature and added to a stirred cold emulsion of water (5.5 L) with 1 kg ammonium chloride dissolved in it and a 1:1 mixture of MTBE and heptane (2 L) (in 20 L). The phases were separated and the organic phase washed with water (3×3 L) and with brine (1×2.5 L). The organic phase was dried with $MgSO_4$, filtered, and concentrated under reduced pressure. The resultant yellow solution was diluted with heptane (~1 L) and seeded with tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate and stirred on the rotovap at 100 mbar pressure at room temperature for 1.5 hours. The solid mass was stirred mechanically for 2 hours at room temperature, resultant thick fine suspension was filtered, washed with dry ice cold heptane and dried under vacuum at 45° C. with a nitrogen bleed for 16 hours to give tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (220 g, 85%) as an off white solid. $^1H$ NMR (400 MHz, DMSO-$d_6$) δ 13.28 (s, 1H), 8.43 (s, 1H), 7.58-7.26 (m, 5H), 5.85 (ddt, J=16.8, 10.3, 6.5 Hz, 1H), 5.10 (dq, J=17.2, 1.6 Hz, 1H), 5.01 (dq, J=10.2, 1.3 Hz, 1H), 4.76 (d, J=11.0 Hz, 1H), 4.65 (d, J=11.0 Hz, 1H), 2.55 (dd, J=9.6, 5.2 Hz, 2H), 2.23 (td, J=13.2, 10.0, 5.7 Hz, 2H), 1.27 (d, J=3.8 Hz, 18H) ppm. ESI-MS m/z calc. 688.23315, found 689.0 $(M+1)^+$; Retention time: 3.32 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

C. Preparation of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol Step 1: tert-Butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate Dissolved tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (159.3 g, 231.3 mmol) and triphenylphosphine (72.9 g, 277.9 mmol) in toluene (1 L), then added (2S)-pent-4-en-2-ol (28.7 mL, 278.9 mmol). Heated this mixture to 45° C., then added DIAD (58.3 mL, 296.1 mmol) (exotherm) slowly over 40 minutes. For the next approximately 2 hours, the mixture was cooled to room temperature. During this cooling period, after the first 10 minutes, triphenylphosphine (6.07 g, 23.14 mmol) was added. After a further 1 hour, additional triphenylphosphine (3.04 g, 11.59 mmol) was added. After a further 23 minutes, DIAD (2.24 mL, 11.57 mmol) was added. After the ~2 hour cooling to room temperature period, the mixture was cooled to 15° C., and seed crystals of DIAD-triphenylphosphine oxide complex were added which caused precipitation to occur, then added 1000 mL heptane. Stored the mixture at −20° C. for 3 days. Filtered out and discarded the precipitate and concentrated the filtrate to give a red residue/oil. Dissolved the residue in 613 mL heptane at 45° C., then cooled to 0° C., seeded with DIAD-triphenylphosphine oxide complex, stirred at 0° C. for 30 minutes, then filtered the solution. The filtrate was concentrated to a smaller volume, then loaded onto a 1.5 kg silica gel column (column volume=2400 mL, flow rate=600 mL/min). Ran a gradient of 1% to 6% EtOAc in hexanes over 32 minutes (8 column volumes), then held at 6% EtOAc in hexanes until the product finished eluting which gave tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (163.5 g, 93%). $^1H$ NMR (400 MHz, Chloroform-d) δ 7.82 (s, 1H), 7.43-7.27 (m, 5H), 5.88-5.69 (m, 2H), 5.35 (h, J=6.2 Hz, 1H), 5.16-4.94 (m, 4H), 4.81 (d, J=10.7 Hz, 1H), 4.63 (d, J=10.7 Hz, 1H), 2.58-2.15 (m, 6H), 1.42 (s, 18H), 1.36 (d, J=6.2 Hz, 3H) ppm. ESI-MS m/z calc. 756.2958, found 757.3 $(M+1)^+$; Retention time: 4.0 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 2: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z Mixture)

The following reaction was run, split equally between two, 12 L reaction flasks run in parallel. Mechanical stirring was employed, and reactions were subjected to a constant nitrogen gas purge using a coarse porosity gas dispersion tube. To each flask was added tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (54 g, 71.36 mmol in each flask) dissolved in DCE (8 L in each flask) and both flasks were strongly purged with nitrogen at room temperature. Both flasks were heated to 62° C. and Grubbs 1st Generation Catalyst (9 g, 10.94 mmol in each flask) was added to each reaction and stirred at 400 rpm while setting an internal temperature control to 75° C. with strong nitrogen purging (both reactions reached ~75° C. after approximately 20 min). After 5 hours, 15 minutes, the internal temperature control was set to 45° C. After approximately 2 hours, 2-sulfanylpyridine-3-carboxylic acid (11 g, 70.89 mmol in each flask) was added to each flask, followed by triethylamine (10 mL, 71.75 mmol in each flask). On completion of addition, the nitrogen purge was turned off and both reaction flasks were stirred at 45° C. open to air overnight. The reactions were then removed from heat and 130 g of silica gel was added to each reaction and each was stirred at room temperature. After approximately 2 hours, the green mixtures were combined and filtered over Celite then concentrated by rotary evaporation at 43° C. The obtained residue was dissolved in dichloromethane/heptane 1:1 (400 mL) and the formed orange solid was removed by filtration. The greenish mother liquor was evaporated to give 115.5 g of a green foam. Dissolved this material in 500 mL of 1:1 dichloromethane/hexanes then loaded onto a 3 kg silica gel column (column volume=4800 mL, flow rate=900 mL/min). Ran a gradient of 2% to 9% EtOAc in hexanes over 43 minutes (8 column volumes), then ran at 9% EtOAc until the product finished eluting giving 77.8 g of impure product. This material was co-evaporated with methanol (~500 mL) then diluted with methanol (200 mL) to give 234.5 g of a methanolic solution, which was halved and each half was purified by reverse phase chromatography (3.8 kg $C_{18}$ column, column volume=3300 mL, flow rate=375 mL/min, loaded as solution in methanol). Ran the column at 55% acetonitrile for ~5 minutes (0.5 column volumes), then at a gradient of 55% to 100% acetonitrile in water over ~170 minutes (19-20 column volumes), then held at 100% acetonitrile until the product and impurities finished eluting. Clean product fractions from both columns were combined and concentrated by rotary evaporation then transferred with ethanol into 5 L flask, evaporated and carefully dried (becomes a foam) to give as a mixture of olefin isomers, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (55.5 g, 53%). ESI-MS m/z calc. 728.26447, found 729.0 $(M+1)^+$; Retention time: 3.82 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 3: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (11.7 g, 16.06 mmol) was dissolved in stirring ethanol (230 mL) and cycled the flask 3 times vacuum/nitrogen and treated with 10% Pd/C (50% water wet, 2.2 g of 5% w/w, 1.034 mmol). The mixture was cycled 3 times between vacuum/nitrogen and 3 times between vacuum/hydrogen. The mixture was then stirred strongly under hydrogen (balloon) for 7.5 hours. The catalyst was removed by filtration, replaced with fresh 10% Pd/C (50% water wet, 2.2 g of 5% w/w, 1.034 mmol) and stirred vigorously under hydrogen (balloon) overnight. Then, the catalyst was removed again by filtration, the filtrate evaporated and the residue (11.3 g, 1 g set aside) was dissolved in ethanol (230 mL), charged with fresh 10% Pd/C (50% water wet, 2.2 g of 5% w/w, 1.034 mmol) and stirred vigorously under hydrogen (balloon) for 6 hours, recharged again with fresh 10% Pd/C (50% water wet, 2.2 g of 5% w/w, 1.034 mmol) and stirred vigorously under hydrogen (balloon) overnight. The catalyst was removed by filtration and the filtrate was evaporated (10 g of residue obtained). This crude material (10 g+1 g set aside above) was purified by silica gel chromatography (330 g column, liquid load in dichloromethane) with a linear gradient of 0% to 15% ethyl acetate in hexane until the product eluted followed by 15% to 100% ethyl acetate in hexane to giving, as a colorless foam, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (9.1 g, 78%). ESI-MS m/z calc. 730.2801, found 731.0 $(M+1)^+$; Retention time: 3.89 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 4: (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (8.6 g, 11.77 mmol) was dissolved in ethanol (172 mL) then the flask was cycled 3 times between vacuum/nitrogen. Treated the mixture with 10% Pd/C (50% water wet, 1.8 g of 5% w/w, 0.8457 mmol) then cycled 3 times between vacuum/nitrogen and 3 times between vacuum/hydrogen and then stirred vigorously under hydrogen (balloon) at room temperature for 18 hours. The mixture was cycled 3 times between vacuum/nitrogen, filtered over Celite, washing with ethanol, and then the filtrate was evaporated to give 7.3 g of tert-butyl N-tert-butoxycarbonyl-N-[(6R,12R)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate an off-white solid. 1H NMR and MS confirmed the expected product. CFTR modulatory activity was confirmed using a standard Ussing Chamber Assay for CFTR potentiator activity.

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound of Formula I:

(I)

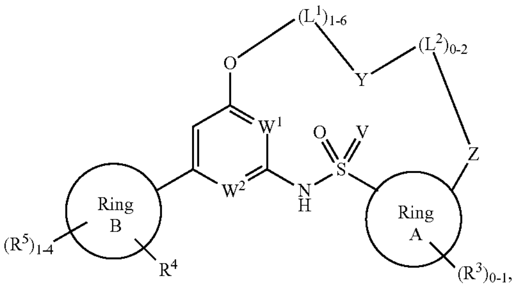

a tautomer thereof, a deuterated derivative of the compound or tautomer, or a pharmaceutically acceptable salt of any of the foregoing, wherein:

Ring A is selected from:
- $C_6$-$C_{10}$ aryl,
- $C_3$-$C_{10}$ cycloalkyl,
- 3- to 10-membered heterocyclyl, and
- 5- to 10-membered heteroaryl;

Ring B is selected from:
- $C_6$-$C_{10}$ aryl,
- $C_3$-$C_{10}$ cycloalkyl,
- 3- to 10-membered heterocyclyl, and
- 5- to 10-membered heteroaryl;

V is selected from O and NH;

$W^1$ is selected from N and CH;

$W^2$ is selected from N and CH, provided that at least one of $W^1$ and $W^2$ is N;

Y is selected from O and $C(R^{YC})_2$;

Z is selected from O, $NR^{ZN}$, and $C(R^{ZC})_2$, provided that when Y is O and $L^2$ is absent, Z is $C(R^{ZC})_2$;

each $L^1$ is independently selected from $C(R^{L1})_2$ and

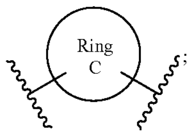

each $L^2$ is independently selected from $C(R^{L2})_2$;

Ring C is selected from $C_6$-$C_{10}$ aryl optionally substituted with 1-3 groups independently selected from:
- halogen,
- $C_1$-$C_6$ alkyl, and
- $N(R^N)_2$;

each $R^3$ is independently selected from:
- halogen,
- $C_1$-$C_6$ alkyl,
- $C_1$-$C_6$ alkoxy,
- $C_3$-$C_{10}$ cycloalkyl,
- $C_6$-$C_{10}$ aryl optionally substituted with 1-3 groups independently selected from $C_1$-$C_6$ alkyl, and
- 3- to 10-membered heterocyclyl;

$R^4$ is selected from hydrogen and $C_1$-$C_6$ alkyl;

each $R^5$ is independently selected from:
- hydrogen,
- halogen,
- hydroxyl,
- $N(R^N)_2$,
- —SO-Me,
- —CH═$C(R^{LC})_2$, wherein both $R^{LC}$ are taken together to form a $C_3$-$C_{10}$ cycloalkyl,
- $C_1$-$C_6$ alkyl optionally substituted with 1-3 groups independently selected from:
  - hydroxyl,
  - $C_1$-$C_6$ alkoxy optionally substituted with 1-3 groups independently selected from $C_1$-$C_6$ alkoxy and $C_6$-$C_{10}$ aryl,
  - $C_3$-$C_{10}$ cycloalkyl,
  - —$(O)_{0-1}$-($C_6$-$C_{10}$ aryl) optionally substituted with 1-3 groups independently selected from $C_1$-$C_6$ alkyl and $C_1$-$C_6$ alkoxy,
  - 3- to 10-membered heterocyclyl, and
  - $N(R^N)_2$,
- $C_1$-$C_6$ alkoxy optionally substituted with 1-3 groups independently selected from:
  - halogen,
  - $C_6$-$C_{10}$ aryl, and
  - $C_3$-$C_{10}$ cycloalkyl optionally substituted with 1-3 groups independently selected from $C_1$-$C_6$ fluoroalkyl,
- $C_1$-$C_6$ fluoroalkyl,
- $C_3$-$C_{10}$ cycloalkyl,
- $C_6$-$C_{10}$ aryl, and
- 3- to 10-membered heterocyclyl;

$R^{ZN}$ is selected from:
- hydrogen,
- $C_1$-$C_9$ alkyl optionally substituted with 1-3 groups independently selected from:
  - hydroxyl,
  - oxo,
  - cyano,
  - $C_1$-$C_6$ alkoxy optionally substituted with 1-3 groups independently selected from halogen and $C_1$-$C_6$ alkoxy,
  - $N(R^N)_2$,
  - $SO_2Me$,
  - $C_3$-$C_{10}$ cycloalkyl optionally substituted with 1-3 groups independently selected from:
    - hydroxyl,
    - $C_1$-$C_6$ alkyl optionally substituted with 1-3 groups independently selected from hydroxyl, oxo, $C_1$-$C_6$ alkoxy, $C_6$-$C_{10}$ aryl, and $N(R^N)_2$,
    - $C_1$-$C_6$ fluoroalkyl,
    - $C_1$-$C_6$ alkoxy,
    - COOH,
    - $N(R^N)_2$,
    - $C_6$-$C_{10}$ aryl, and
    - 3- to 10-membered heterocyclyl optionally substituted with 1-3 groups independently selected from oxo and $C_1$-$C_6$ alkyl,
  - $C_6$-$C_{10}$ aryl optionally substituted with 1-3 groups independently selected from:
    - halogen,
    - hydroxyl,
    - cyano,
    - $SiMe_3$,
    - $SO_2Me$,
    - $SF_5$,
    - $N(R^N)_2$,
    - $P(O)Me_2$,
    - —$(O)_{0-1}$-($C_3$-$C_{10}$ cycloalkyl) optionally substituted with 1-3 groups independently selected from $C_1$-$C_6$ fluoroalkyl, $C_1$-$C_6$ alkyl optionally substituted with 1-3 groups independently selected from hydroxyl, oxo, $C_1$-$C_6$ alkoxy, 5- to 10-membered heteroaryl, $SO_2Me$, and $N(R^N)_2$,
$C_1$-$C_6$ alkoxy optionally substituted with 1-3 groups independently selected from hydroxyl, oxo, $N(R^N)_2$, and Co-$C_{10}$ aryl,
$C_1$-$C_6$ fluoroalkyl,
3- to 10-membered heterocyclyl optionally substituted with 1-3 groups independently selected from $C_1$-$C_6$ alkyl,
—$(O)_{0-1}$-($C_6$-$C_{10}$ aryl), and
—$(O)_{0-1}$-(5-to 10-heteroaryl) optionally substituted with hydroxyl, oxo, $N(R^N)_2$, $C_1$-$C_6$ alkyl, $C_1$-$C_6$ alkoxy, $C_1$-$C_6$ fluoroalkyl, and $C_3$-$C_{10}$ cycloalkyl,
3- to 10-membered heterocyclyl optionally substituted with 1-4 groups independently selected from:
hydroxyl,
oxo,
$N(R^N)_2$,
$C_1$-$C_6$ alkyl optionally substituted with 1-3 groups independently selected from oxo and $C_1$-$C_6$ alkoxy,
$C_1$-$C_6$ alkoxy,
$C_1$-$C_6$ fluoroalkyl,
$C_6$-$C_{10}$ aryl optionally substituted with 1-3 groups independently selected from halogen, and
5- to 10-membered heteroaryl, and
5- to 10-membered heteroaryl optionally substituted with 1-3 groups independently selected from:
hydroxyl,
cyano,
oxo,
halogen,
B $(OH)_2$,
$N(R^N)_2$,
$C_1$-$C_6$ alkyl optionally substituted with 1-3 groups independently selected from hydroxyl, oxo, $C_1$-$C_6$ alkoxy (optionally substituted with 1-3 —$SiMe_3$), and $N(R^N)_2$,
$C_1$-$C_6$ alkoxy optionally substituted with 1-3 groups independently selected from hydroxyl, oxo, $C_1$-$C_6$ alkoxy, $N(R^N)_2$, and $C_3$-$C_{10}$ cycloalkyl,
$C_1$-$C_6$ fluoroalkyl,
—$(O)_{0-1}$-($C_3$-$C_{10}$ cycloalkyl) optionally substituted with 1-3 groups independently selected from $C_1$-$C_6$ alkyl,
—$(O)_{0-1}$-($C_6$-$C_{10}$ aryl),
—$(O)_{0-1}$-(3-to 10-membered heterocyclyl) optionally substituted with 1-4 groups independently selected from hydroxyl, oxo, halogen, cyano, $N(R^N)_2$, $C_1$-$C_6$ alkyl (optionally substituted with 1-3 groups independently selected from hydroxyl, oxo, $N(R^N)_2$, and $C_1$-$C_6$ alkoxy), $C_1$-$C_6$ alkoxy, $C_1$-$C_6$ fluoroalkyl, and 3- to 10-membered heterocyclyl (optionally substituted with 1-3 groups independently selected from $C_1$-$C_6$ fluoroalkyl), and
5- to 10-membered heteroaryl optionally substituted with 1-4 groups independently selected from $C_1$-$C_6$ alkyl and $C_3$-$C_{10}$ cycloalkyl,
$C_1$-$C_6$ fluoroalkyl,
$C_3$-$C_{10}$ cycloalkyl optionally substituted with 1-3 groups independently selected from:

hydroxyl,
oxo,
halogen,
cyano,
$N(R^N)_2$,
$C_1$-$C_6$ alkyl optionally substituted with 1-3 groups independently selected from:
hydroxyl,
oxo,
$N(R^N)_2$,
$C_1$-$C_6$ alkoxy, and
$C_6$-$C_{10}$ aryl,
$C_1$-$C_6$ alkoxy optionally substituted with 1-3 groups independently selected from halogen, oxo, $C_6$-$C_{10}$ aryl, and $N(R^N)_2$,
halogen,
$C_3$-$C_{10}$ cycloalkyl,
3- to 10-membered heterocyclyl optionally substituted with 1-3 groups independently selected from $C_1$-$C_6$ alkyl, and
5- to 10-membered heteroaryl optionally substituted with 1-3 groups independently selected from:
hydroxyl,
cyano,
oxo,
halogen,
$N(R^N)_2$,
$C_1$-$C_6$ alkyl optionally substituted with 1-3 groups independently selected from hydroxyl, oxo, $C_1$-$C_6$ alkoxy, and $N(R^N)_2$,
$C_1$-$C_6$ alkoxy optionally substituted with 1-3 groups independently selected from hydroxyl, $C_1$-$C_6$ alkoxy, $N(R^N)_2$, and $C_3$-$C_{10}$ cycloalkyl,
$C_1$-$C_6$ fluoroalkyl,
—$(O)_{0-1}$-($C_3$-$C_{10}$ cycloalkyl) optionally substituted with 1-3 groups independently selected from $C_1$-$C_6$ alkyl,
$C_6$-$C_{10}$ aryl, and
3- to 10-membered heterocyclyl optionally substituted with 1-3 groups independently selected from $C_1$-$C_6$ alkyl,
$C_6$-$C_{10}$ aryl,
3- to 10-membered heterocyclyl optionally substituted with 1-3 groups independently selected from:
oxo,
$C_1$-$C_6$ alkyl optionally substituted with 1-3 groups independently selected from:
oxo,
hydroxyl,
$N(R^N)_2$,
$C_1$-$C_6$ alkoxy optionally substituted with 1-3 groups independently selected from halogen and $C_6$-$C_{10}$ aryl, and
—$(O)_{0-1}$-($C_3$-$C_{10}$ cycloalkyl),
$C_1$-$C_6$ fluoroalkyl,
$C_3$-$C_{10}$ cycloalkyl optionally substituted with 1-3 groups independently selected from halogen, and
3- to 10-membered heterocyclyl,
5- to 10-membered heteroaryl optionally substituted with 1-3 groups independently selected from:
halogen,
$C_1$-$C_6$ alkyl optionally substituted with 1-3 groups independently selected from oxo, $C_1$-$C_6$ alkoxy, and $N(R^N)_2$, and
3- to 10-membered heterocyclyl optionally substituted with 1-3 groups independently selected from $C_1$-$C_6$ alkyl (optionally substituted with 1-3 groups selected from oxo, $C_1$-$C_6$ alkoxy, and $C_6$-$C_{10}$ aryl), and $R^F$;

each $R^{YC}$ and $R^{ZC}$ is independently selected from:

hydrogen, $C_1$-$C_6$ alkyl optionally substituted with 1-3 groups independently selected from $C_6$-$C_{10}$ aryl (optionally substituted with 1-3 groups independently selected from $C_1$-$C_6$ alkyl), $C_6$-$C_{10}$ aryl optionally substituted with 1-3 groups independently selected from $C_1$-$C_6$ alkyl, and $R^F$;

or two $R^{YC}$ are taken together to form an oxo group;

or two $R^{ZC}$ are taken together to form an oxo group;

each $R^{L1}$ is independently selected from:

hydrogen, $N(R^N)_2$, provided that two $N(R^N)_2$ are not bonded to the same carbon, $C_1$-$C_9$ alkyl optionally substituted with 1-3 groups independently selected from:

halogen, hydroxyl, oxo, $N(R^N)_2$, $C_1$-$C_6$ alkoxy optionally substituted with 1-3 groups independently selected from $C_6$-$C_{10}$ aryl, $C_3$-$C_{10}$ cycloalkyl optionally substituted with 1-3 groups independently selected from halogen and $C_1$-$C_6$ fluoroalkyl, $C_6$-$C_{10}$ aryl optionally substituted with 1-3 groups independently selected from $C_1$-$C_6$ alkyl, and 3- to 10-membered heterocyclyl optionally substituted with 1-3 groups independently selected from $C_1$-$C_6$ alkyl (optionally substituted with 1-3 groups independently selected from hydroxyl and oxo), $C_3$-$C_{10}$ cycloalkyl, $C_6$-$C_{10}$ aryl optionally substituted with 1-4 groups independently selected from:

halogen, cyano, $SiMe_3$, $POMe_2$, $C_1$-$C_7$ alkyl optionally substituted with 1-3 groups independently selected from:

hydroxyl, oxo, cyano, $SiMe_3$, $N(R^N)_2$, and $C_3$-$C_{10}$ cycloalkyl optionally substituted with 1-3 groups independently selected from $C_1$-$C_6$ fluoroalkyl, $C_1$-$C_6$ alkoxy optionally substituted with 1-3 groups independently selected from:

$C_3$-$C_{10}$ cycloalkyl optionally substituted with 1-3 groups independently selected from $C_1$-$C_6$ fluoroalkyl, and $C_1$-$C_6$ alkoxy, $C_1$-$C_6$ fluoroalkyl, $C_3$-$C_{10}$ cycloalkyl optionally substituted with 1-3 groups independently selected from $C_1$-$C_6$ alkyl and $C_1$-$C_6$ fluoroalkyl, $C_6$-$C_{10}$ aryl, 3- to 10-membered heterocyclyl optionally substituted with 1-3 groups independently selected from $C_1$-$C_6$ alkyl, and 5- to 10-membered heteroaryl, 3- to 10-membered heterocyclyl optionally substituted with 1-3 groups independently selected from:

$C_1$-$C_6$ alkyl optionally substituted with 1-3 groups independently selected from:

oxo, and $C_1$-$C_6$ alkoxy, 5- to 10-membered heteroaryl optionally substituted with 1-3 groups independently selected from:

$C_1$-$C_6$ alkyl optionally substituted with 1-3 groups independently selected from:

$C_3$-$C_{10}$ cycloalkyl optionally substituted with 1-3 groups independently selected from $C_1$-$C_6$ fluoroalkyl, and $C_6$-$C_{10}$ aryl optionally substituted with 1-3 groups independently selected from $C_1$-$C_6$ alkyl, and $R^F$;

or two $R^{L1}$ on the same carbon atom are taken together to form an oxo group;

each $R^{L2}$ is independently selected from hydrogen and $R^F$;

or two $R^{L2}$ on the same carbon atom are taken together to form an oxo group;

each $R^N$ is independently selected from:

hydrogen, $C_1$-$C_8$ alkyl optionally substituted with 1-3 groups independently selected from:

oxo, halogen, hydroxyl, $NH_2$,

NHMe, $NMe_2$, $C_1$-$C_6$ alkoxy optionally substituted with 1-3 groups independently selected from $C_6$-$C_{10}$ aryl, —$(O)_{0-1}$-($C_3$-$C_{10}$ cycloalkyl), $C_6$-$C_{10}$ aryl optionally substituted with 1-3 groups independently selected from halogen and $C_1$-$C_6$ alkyl, and 3- to 14-membered heterocyclyl optionally substituted with 1-4 groups independently selected from oxo and $C_1$-$C_6$ alkyl, and 5- to 14-membered heteroaryl optionally substituted with 1-4 groups independently selected from oxo and $C_1$-$C_6$ alkyl, $C_3$-$C_{10}$ cycloalkyl optionally substituted with 1-3 groups independently selected from:

hydroxyl, $NH_2$,

NHMe, and $C_1$-$C_6$ alkyl optionally substituted with 1-3 groups independently selected from hydroxyl, and $C_6$-$C_{10}$ aryl, and 3- to 10-membered heterocyclyl;

or two $R^N$ on the same nitrogen atom are taken together with the nitrogen to which they are bonded to form a 3- to 10-membered heterocyclyl optionally substituted with 1-3 groups selected from:

hydroxyl, oxo, cyano, $C_1$-$C_6$ alkyl optionally substituted with 1-3 groups independently selected from oxo, hydroxyl, $C_1$-$C_6$ alkoxy, and $N(R^{N2})_2$, wherein each $R^{N2}$ is independently selected from hydrogen and $C_1$-$C_6$ alkyl, $C_1$-$C_6$ alkoxy, and $C_1$-$C_6$ fluoroalkyl;

or one $R^4$ and one $R^{L1}$ are taken together to form a $C_6$-$C_8$ alkylene;

when $R^{ZN}$ is $R^F$ then at least one of $R^{YC}$, $R^{L1}$, or $R^{L2}$ is $R^F$;

when at least one of $R^{YC}$, $R^{ZC}$ $R^{L1}$, or $R^{L2}$ is $R^F$ then $R^{ZN}$ is $R^F$ or at least two of $R^{YC}$, $R^{ZC}$, $R^{L1}$, or $R^{L2}$ are $R^F$;

when $R^F$ is present, all of the $R^F$ taken together with the atoms to which they are bonded form a group selected from:

$C_3$-$C_{10}$ cycloalkyl optionally substituted with 1-3 groups independently selected from $C_1$-$C_6$ alkyl, $C_6$-$C_{10}$ aryl optionally substituted with 1-3 groups independently selected from:

halogen, $C_1$-$C_6$ alkyl, $N(R^N)_2$, and 3- to 10-membered heterocyclyl optionally substituted with 1-3 groups independently selected from hydroxyl, 3- to 11-membered heterocyclyl optionally substituted with 1-3 groups independently selected from:

oxo, $N(R^N)_2$, $C_1$-$C_9$ alkyl optionally substituted with 1-4 groups independently selected from:

oxo, halogen, hydroxyl, $N(R^N)_2$,

—$SO_2$—($C_1$-$C_6$ alkyl), $C_1$-$C_6$ alkoxy optionally substituted with 1-3 groups independently selected from halogen and $C_6$-$C_{10}$ aryl, $C_6$-$C_{10}$ aryl optionally substituted with 1-3 groups independently selected from hydroxyl, halogen, cyano, $C_1$-$C_6$ alkyl (optionally substituted with 1-3 groups independently selected from oxo and $C_1$-$C_6$ alkoxy), $C_1$-$C_6$ alkoxy (optionally substituted with 1-3 groups independently selected from $C_6$-$C_{10}$ aryl), —$(O)_{0-1}$—($C_1$-$C_6$ fluoroalkyl), and $C_6$-$C_{10}$ aryl (optionally substituted with 1-3 groups independently selected from $C_1$-$C_6$ alkoxy), —$(O)_{0-1}$-($C_3$-$C_{10}$ cycloalkyl) optionally substituted with 1-4 groups independently selected from hydroxyl, halogen, $N(R^N)_2$, $C_1$-$C_6$ alkyl (optionally substituted with 1-3 groups independently selected from oxo, hydroxyl, and $C_1$-$C_6$ alkoxy), $C_1$-$C_6$ fluoroalkyl, and $C_6$-$C_{10}$ aryl, 3- to 10-membered heterocyclyl optionally substituted with 1-3 groups independently selected from oxo, $C_1$-$C_6$ alkyl (optionally substituted with 1-3 groups independently selected from $C_6$-$C_{10}$ aryl (optionally substituted with 1-3 groups independently selected from halogens)), $C_1$-$C_6$ alkoxy, $C_3$-$C_{10}$ cycloalkyl, and $R^N$, —O-(5-to 12-membered heteroaryl) optionally substituted with 1-3 groups independently selected from $C_6$-$C_{10}$ aryl (optionally substituted with 1-3 groups independently selected from halogen) and $C_1$-$C_6$ alkyl, and 5- to 10-membered heteroaryl optionally substituted with 1-3 groups independently selected from hydroxyl, oxo, $N(R^N)_2$, $C_1$-$C_6$ alkyl (optionally substituted with 1-3 groups independently selected from cyano), $C_1$-$C_6$ alkoxy, —$(O)_{0-1}$—($C_1$-$C_6$ fluoroalkyl), —O—($C_6$-$C_{10}$ aryl), and $C_3$-$C_{10}$ cycloalkyl, $C_3$-$C_{12}$ cycloalkyl optionally substituted with 1-4 groups independently selected from halogen, $C_1$-$C_6$ alkyl, and $C_1$-$C_6$ fluoroalkyl, $C_6$-$C_{10}$ aryl, 3- to 10-membered heterocyclyl, and 5- to 10-membered heteroaryl optionally substituted with 1-3 groups independently selected from $C_1$-$C_6$ alkoxy and $C_1$-$C_6$ fluoroalkyl, and 5- to 12-membered heteroaryl optionally substituted with 1-3 groups independently selected from $C_1$-$C_6$ alkyl and $C_1$-$C_6$ fluoroalkyl.

2. The compound, tautomer, deuterated derivative, or pharmaceutically acceptable salt according to claim 1, selected from compounds of Formula Ia:

(Ia)

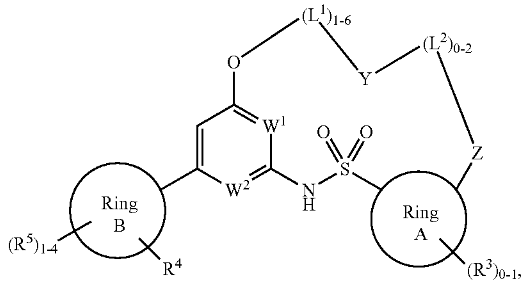

3. The compound, tautomer, deuterated derivative, or pharmaceutically acceptable salt according to claim 1, selected from compounds of Formula IIa:

(IIa)

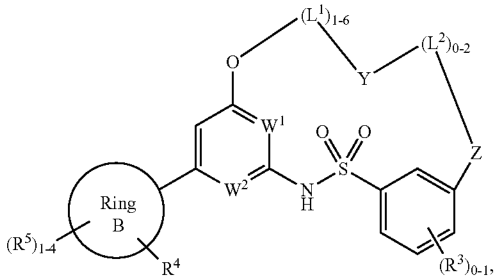

4. The compound, tautomer, deuterated derivative, or pharmaceutically acceptable salt according to claim 1, selected from compounds of Formula IIb:

(IIb)

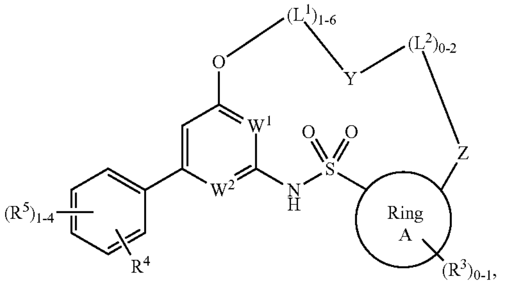

5. The compound, tautomer, deuterated derivative, or pharmaceutically acceptable salt according to claim 1, selected from compounds of Formula III:

(III)

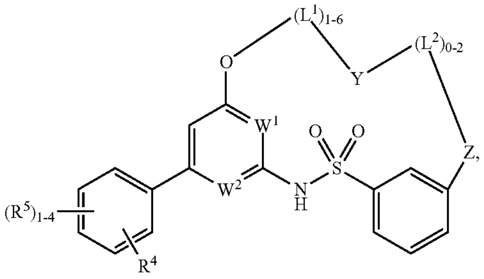

6. The compound, tautomer, deuterated derivative, or pharmaceutically acceptable salt according to claim 1, selected from compounds of Formula IV:

(IV)

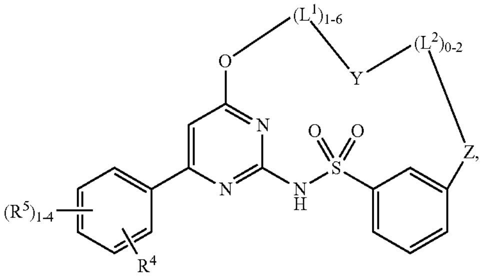

7. The compound, tautomer, deuterated derivative, or pharmaceutically acceptable salt according to claim 1, selected from compounds of Formula V:

(V)

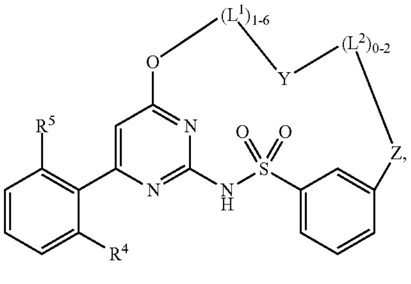

8. The compound, tautomer, deuterated derivative, or pharmaceutically acceptable salt according to claim 1, selected from compounds of Formula VI:

(VI)

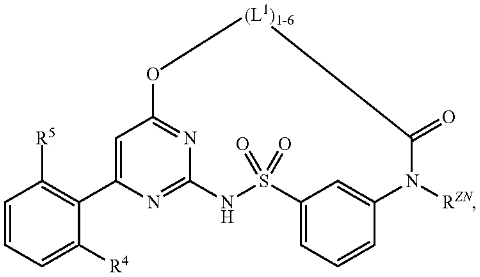

9. The compound, tautomer, deuterated derivative, or pharmaceutically acceptable salt according to claim 1, selected from:

1

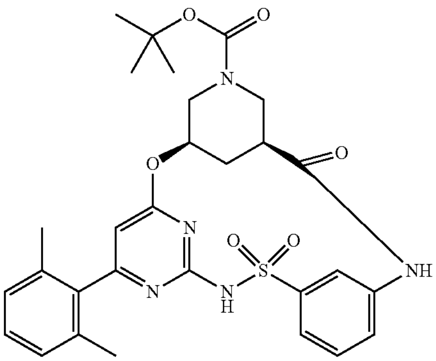

2

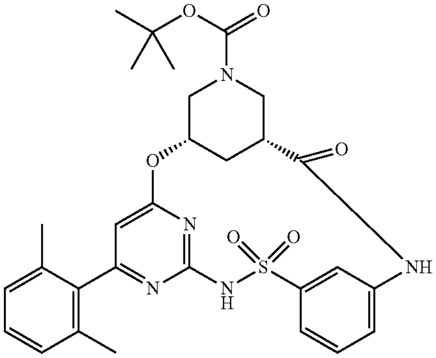

3

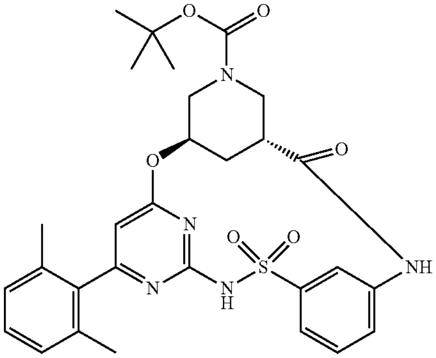

-continued
4
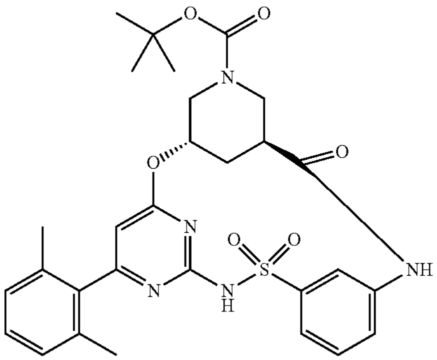
5
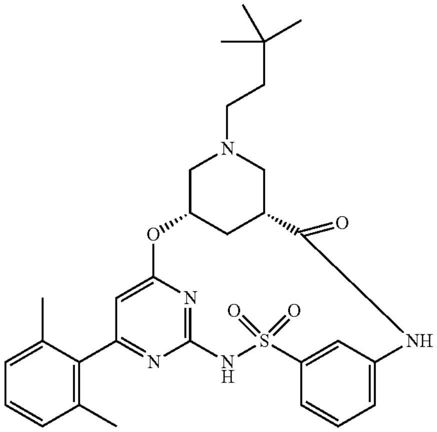
6
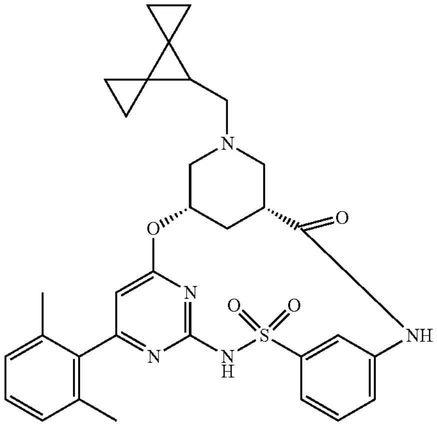
7
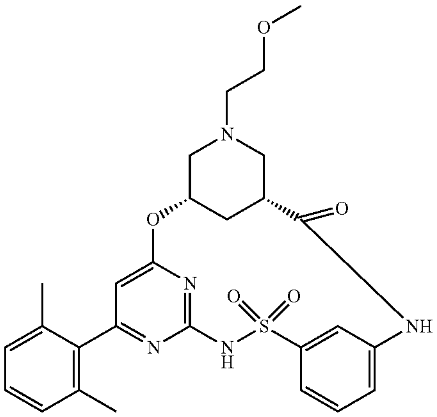
-continued
8
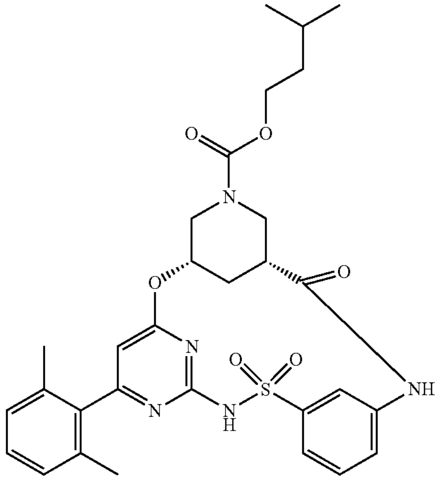
9
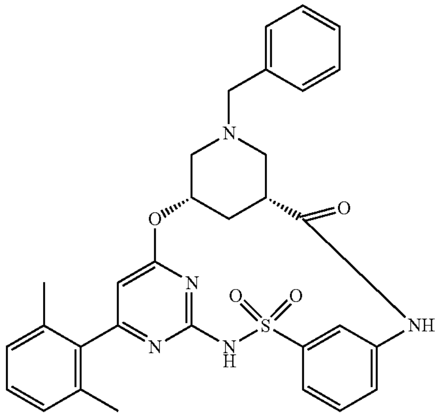
10
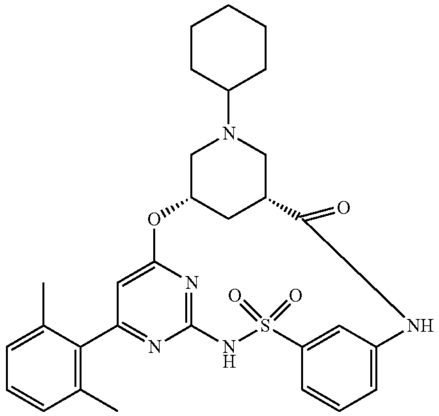

11
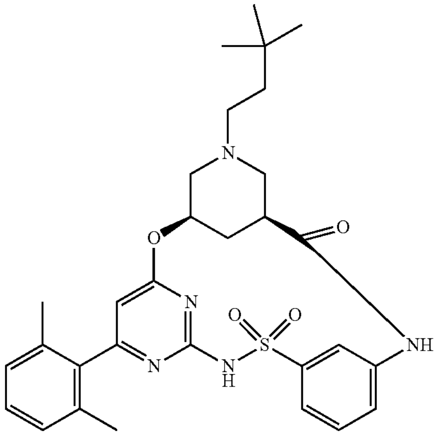
12
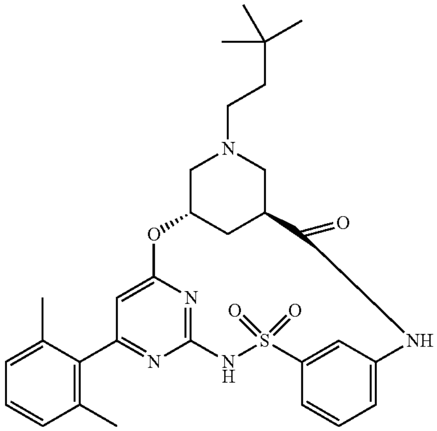
13
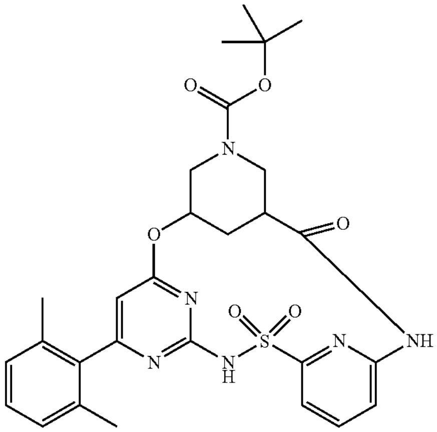
14
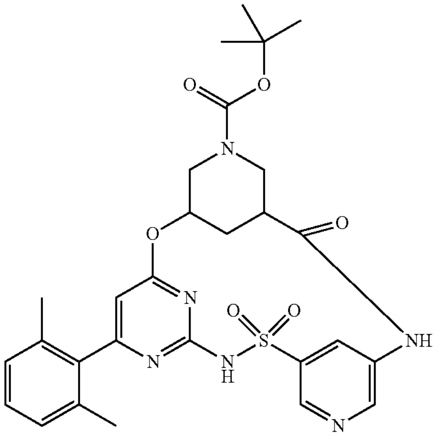
15
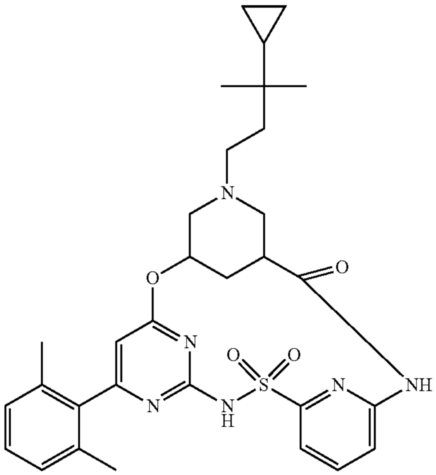
16
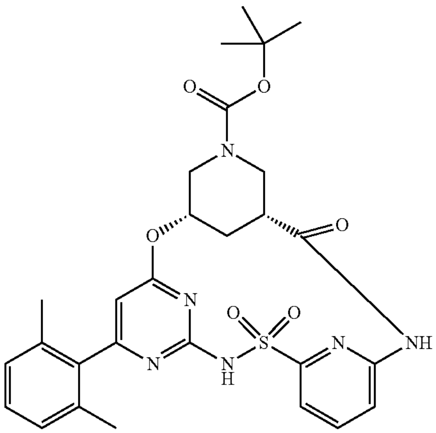

-continued
17
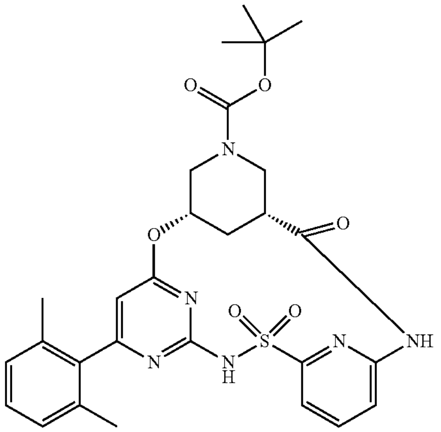
18
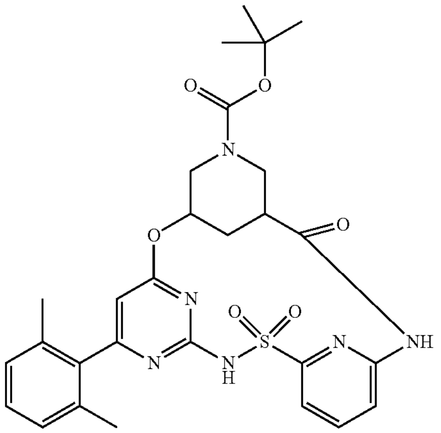
19
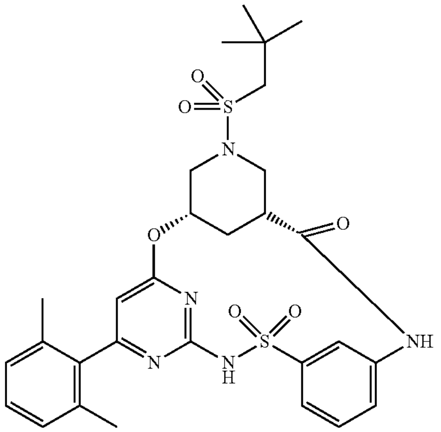
-continued
20
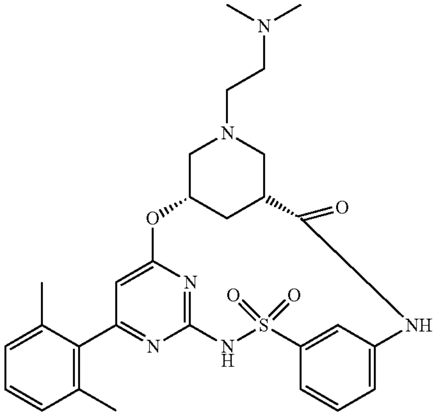
21
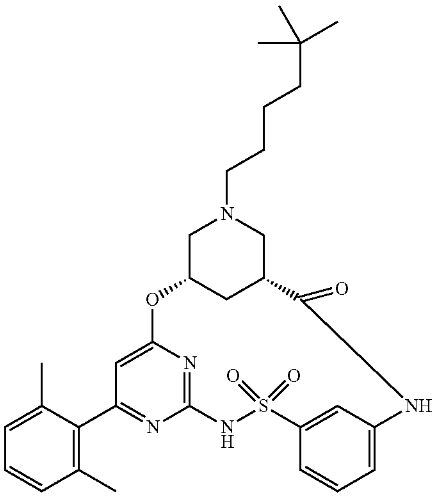
22
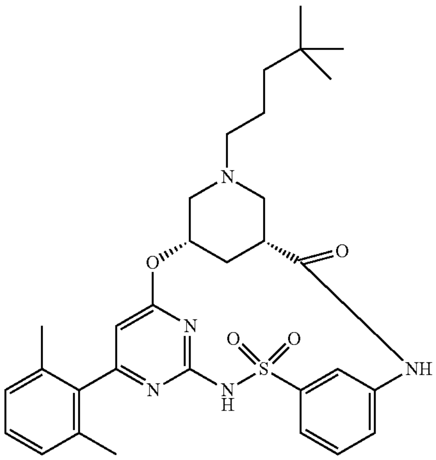

23
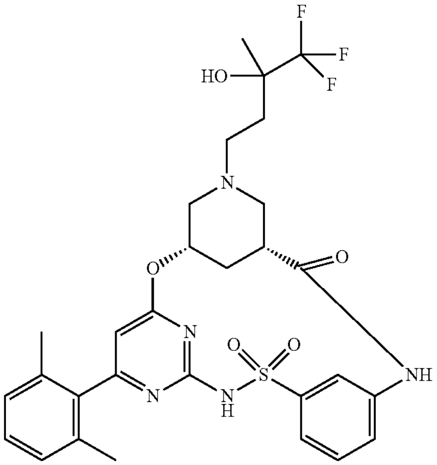
24
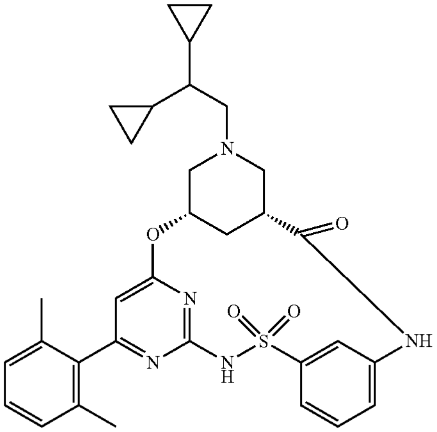
25
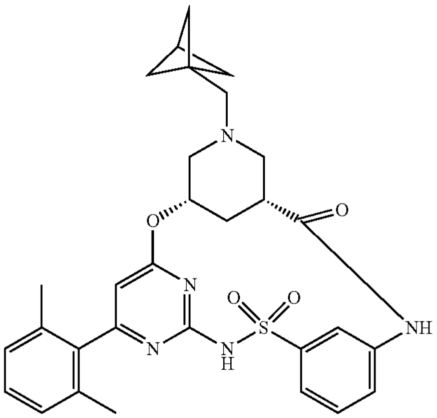
26
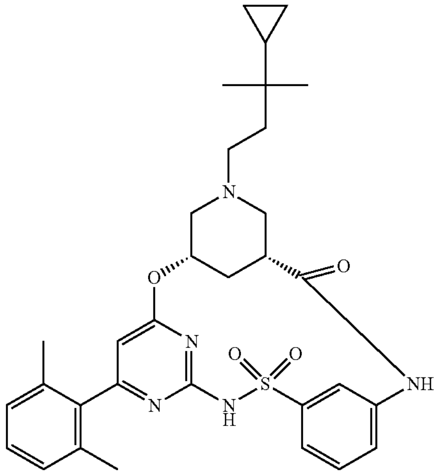
27
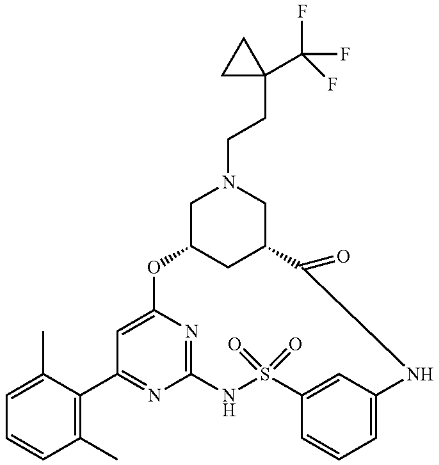
28
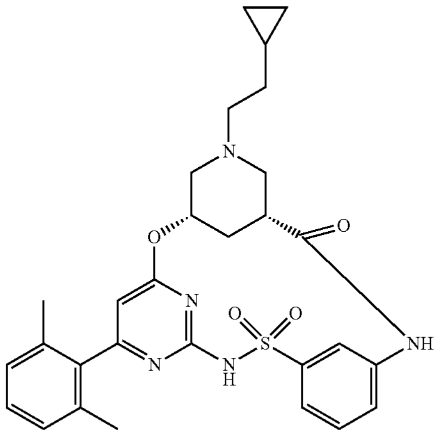

-continued
29
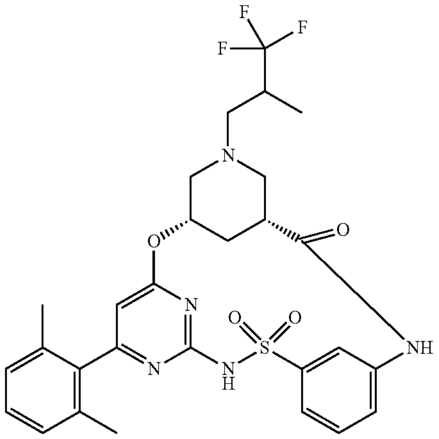
30
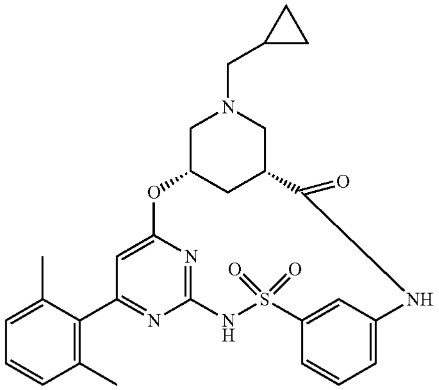
31
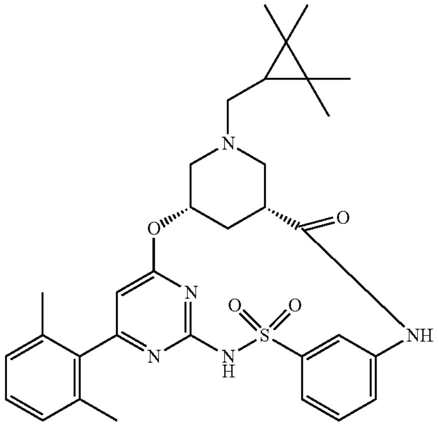
32
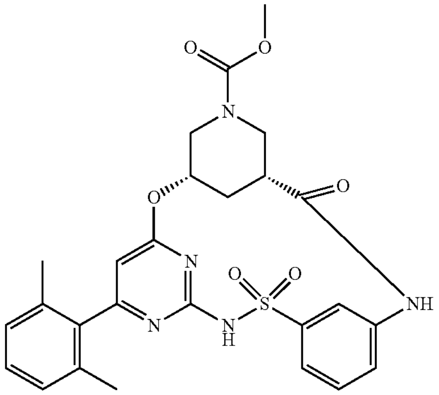
-continued
33
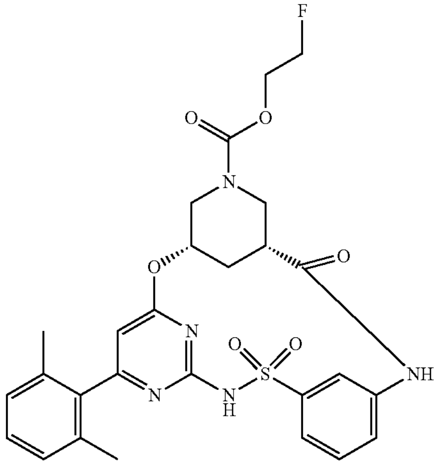
34
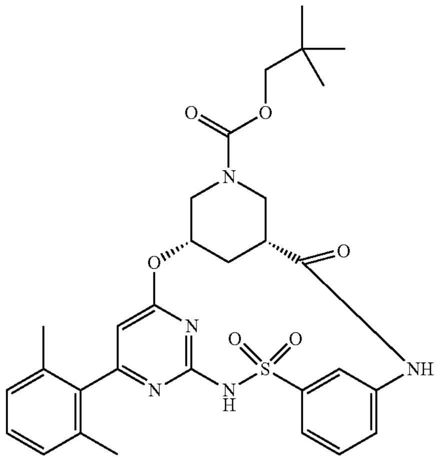
35
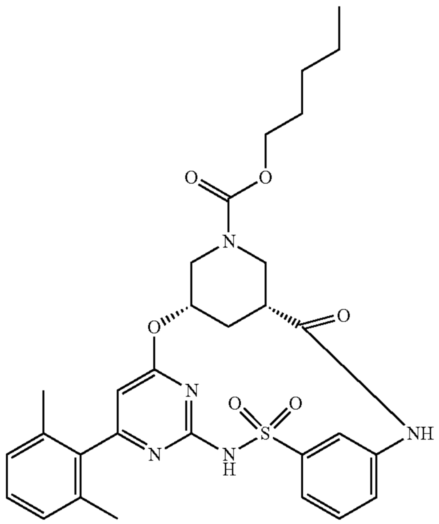

-continued
36
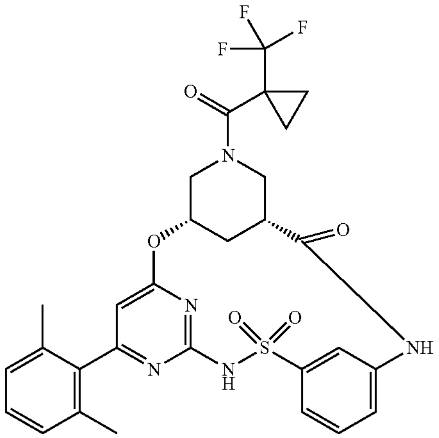
37
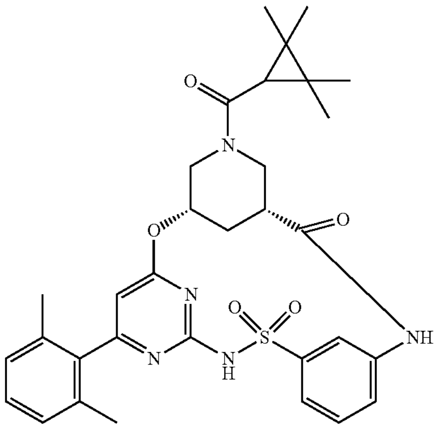
38
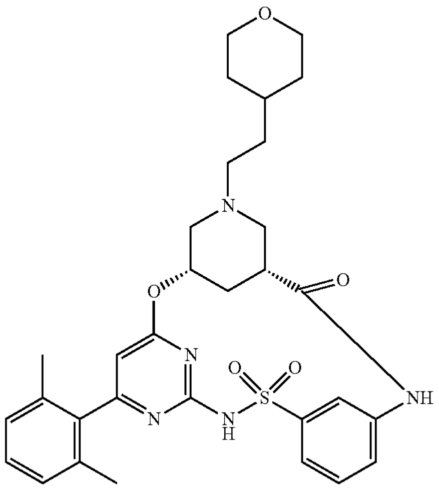
-continued
39
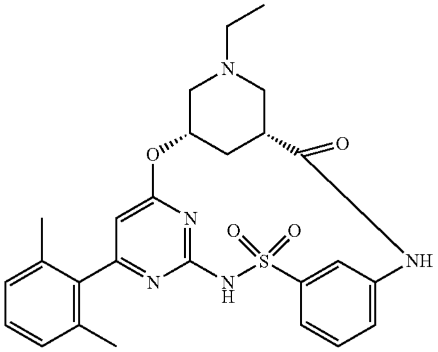
40
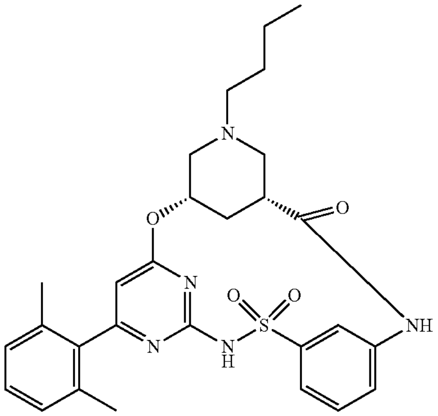
41
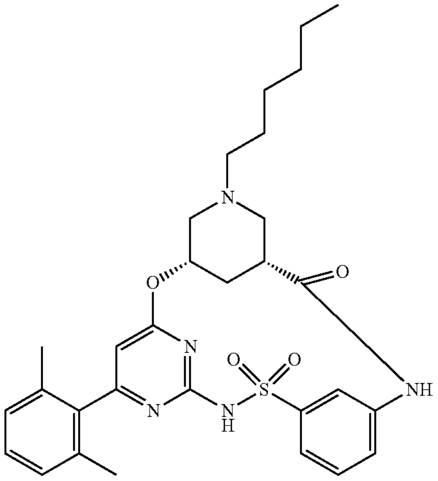

-continued
42
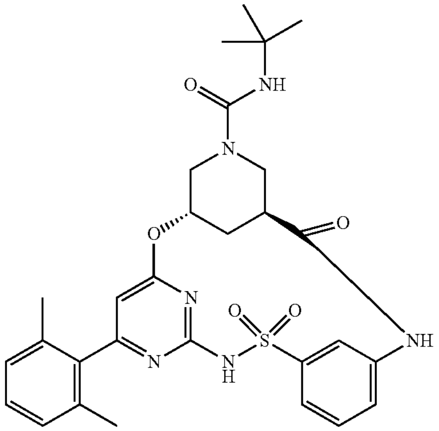
43
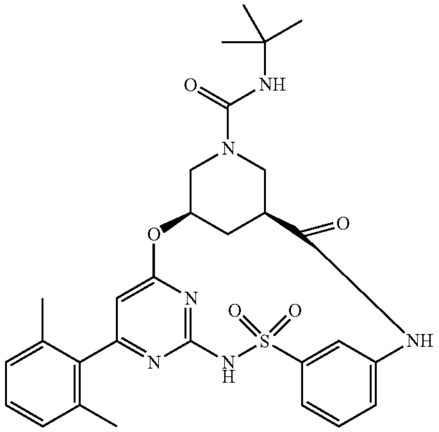
44
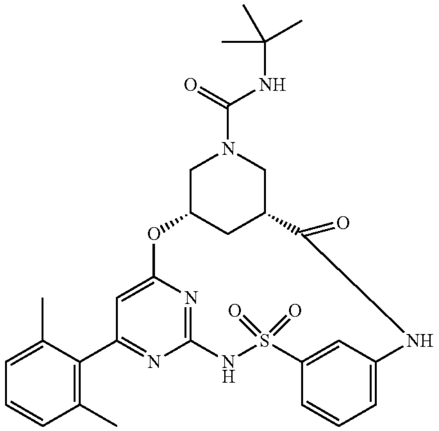
-continued
45
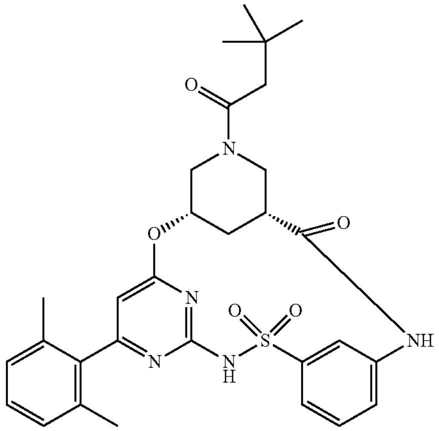
46
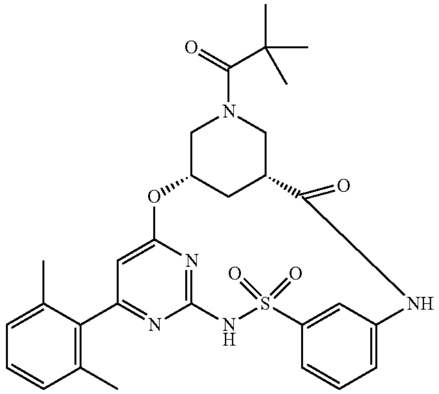
47
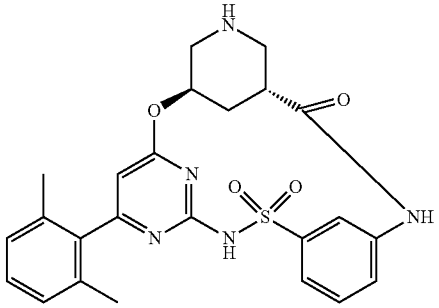
48
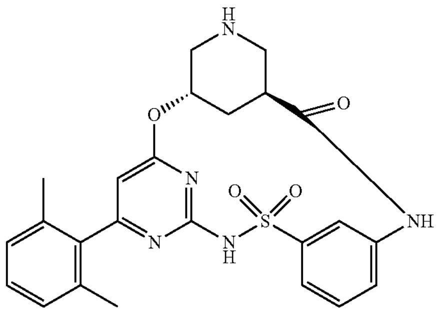

-continued
49
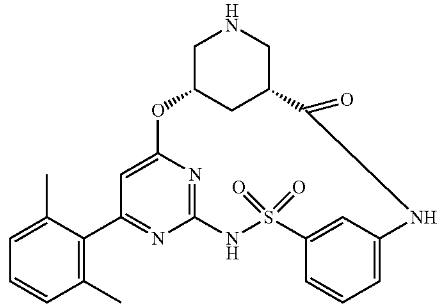
50
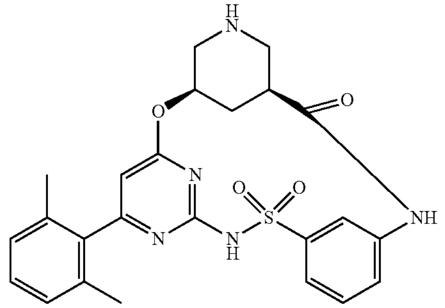
51
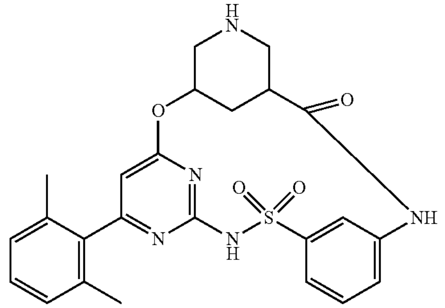
52
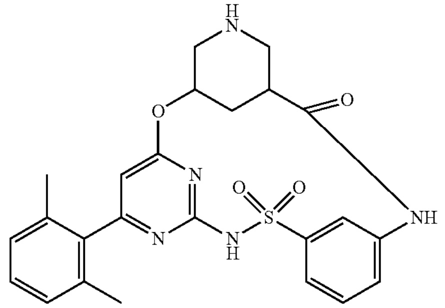
53
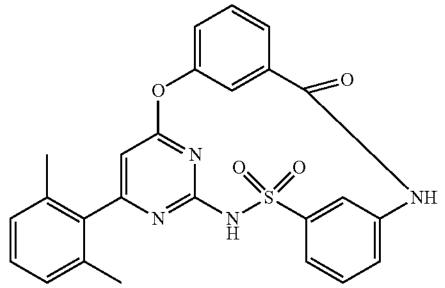
-continued
54
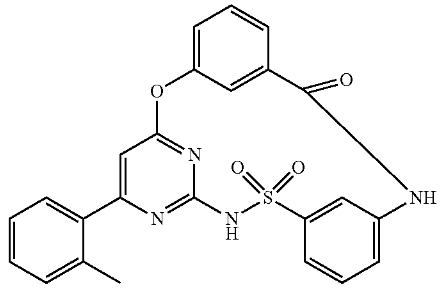
55
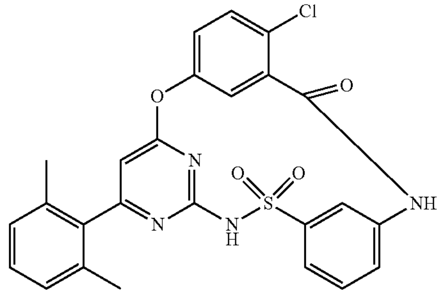
56
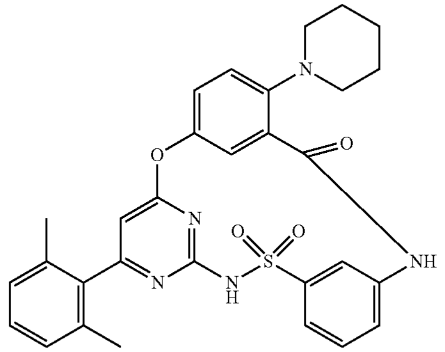
57
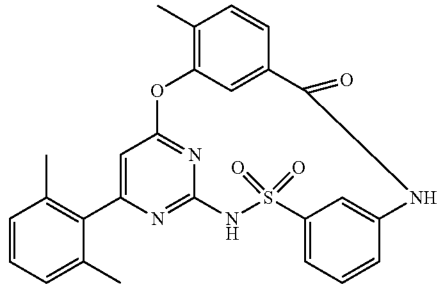
58
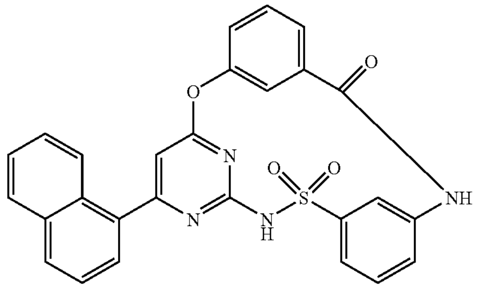

-continued
59
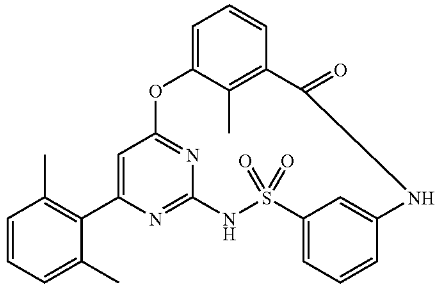
60
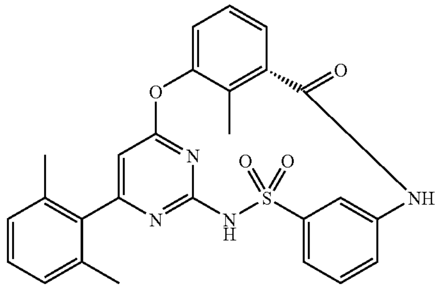
61
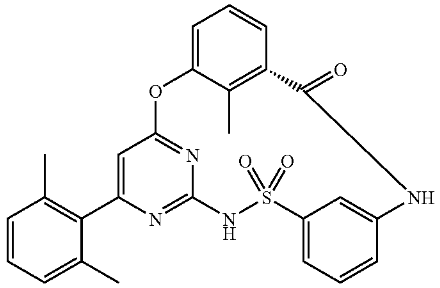
62
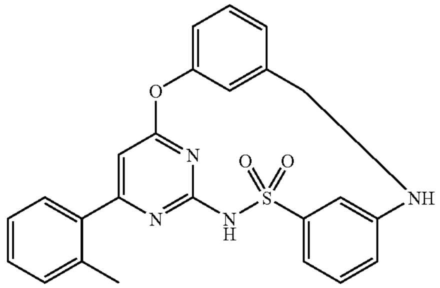
63
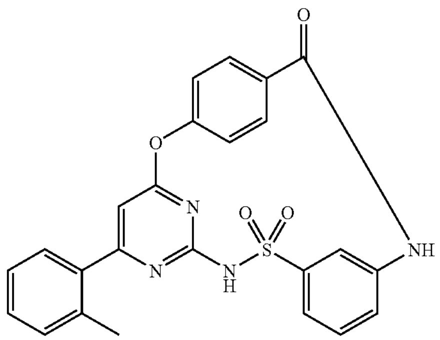
-continued
65
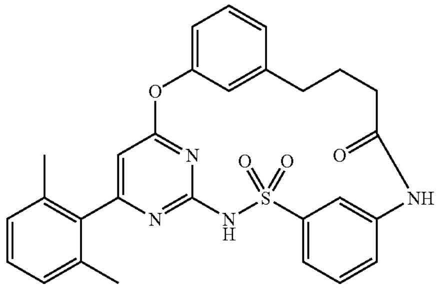
66
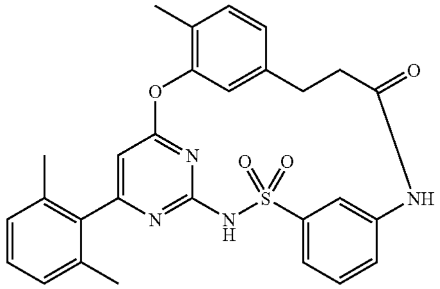
67
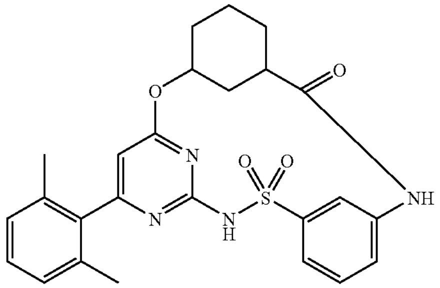
68
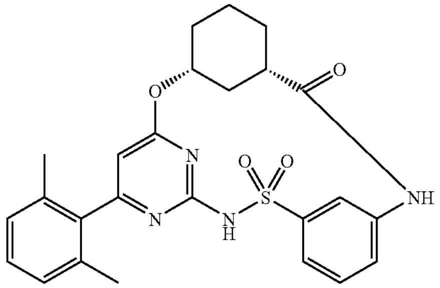
68
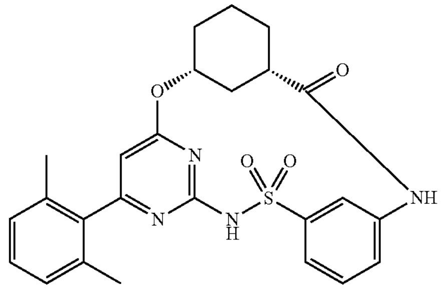

-continued
69
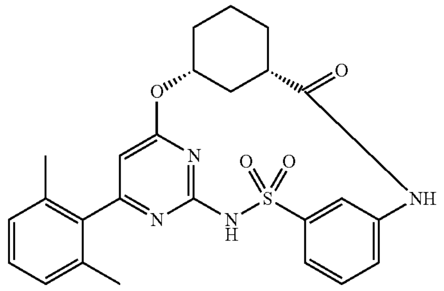
70
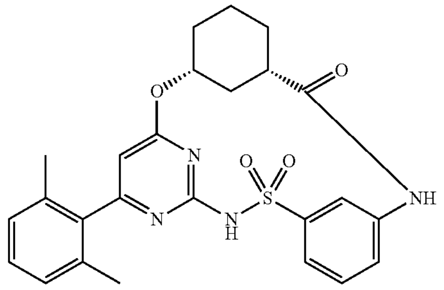
71
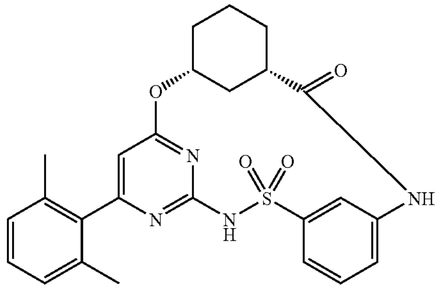
72
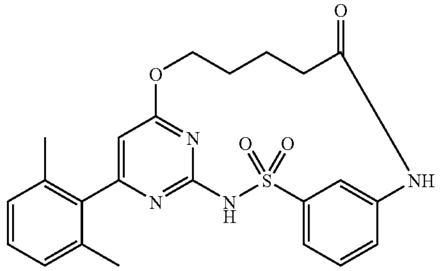
73
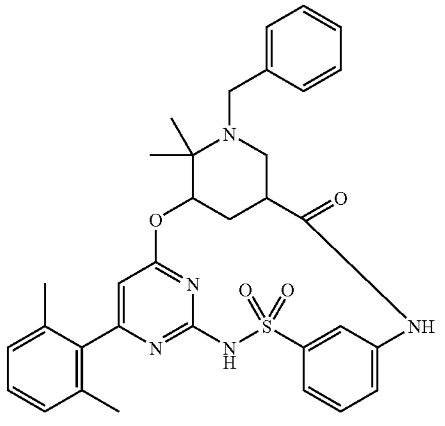
-continued
74
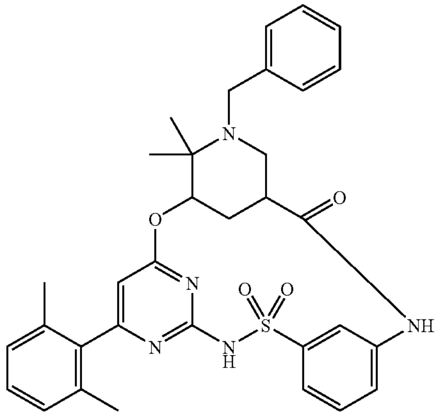
75
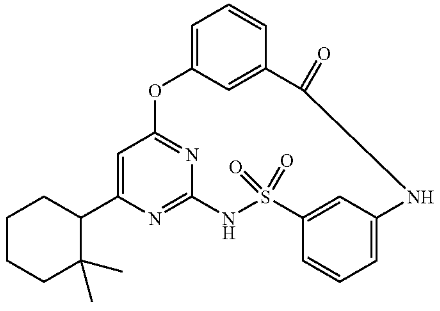
76
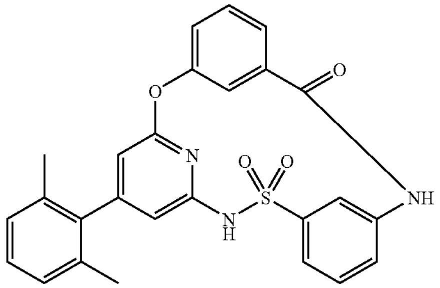
77
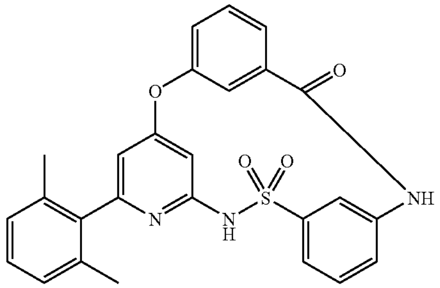

-continued
78
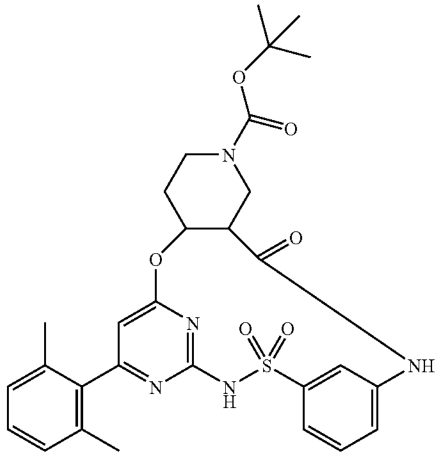
79
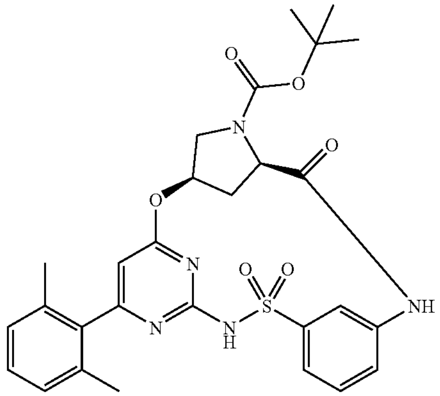
80
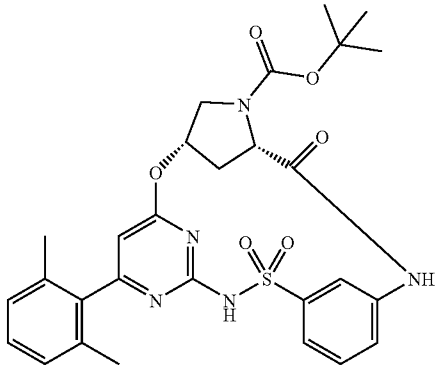
81
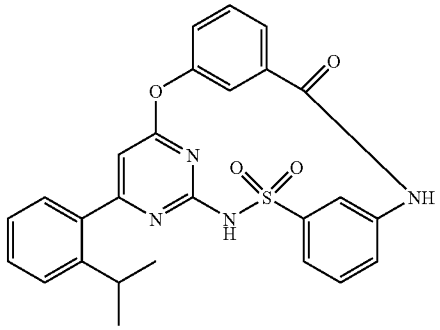
-continued
82
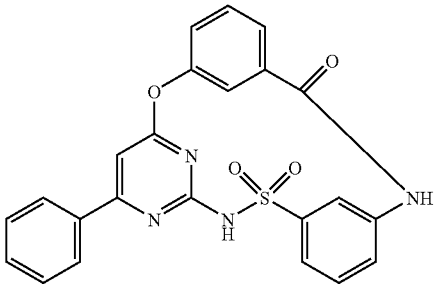
83
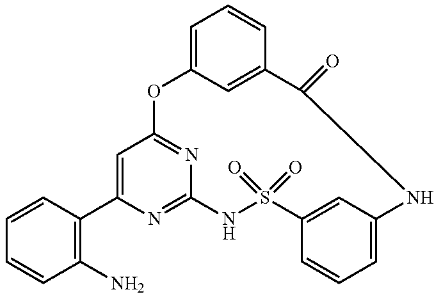
84
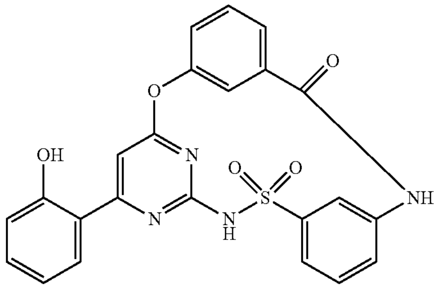
85
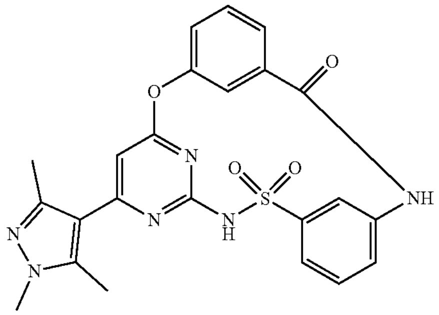
86
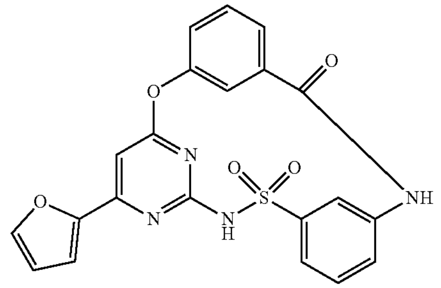

87
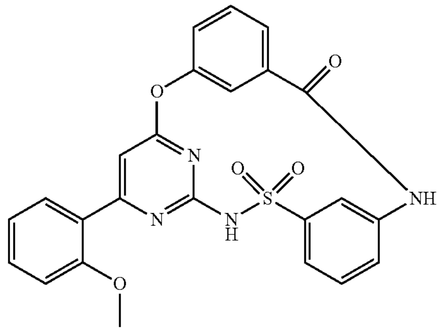
88
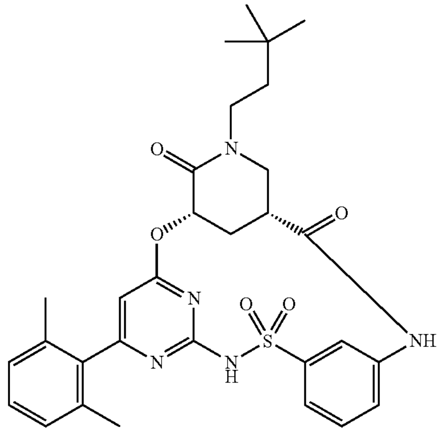
89
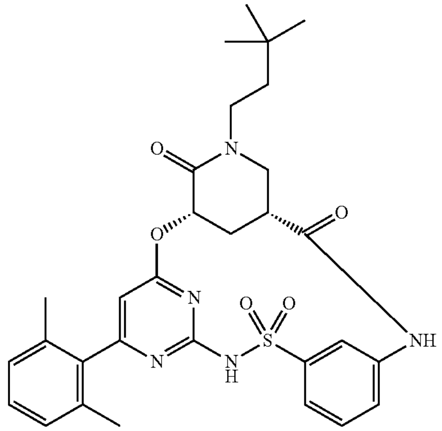
90
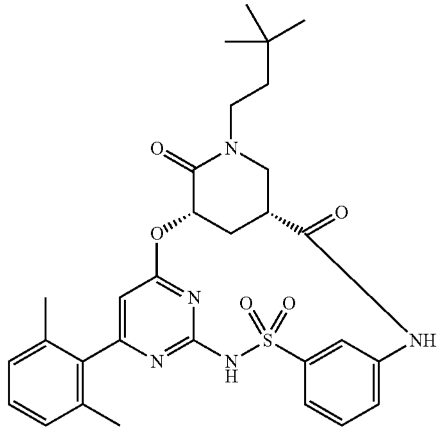
91
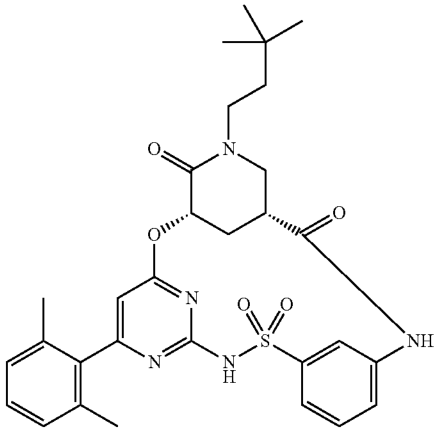
92
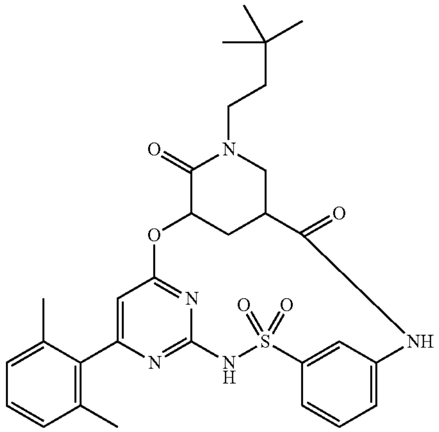
93
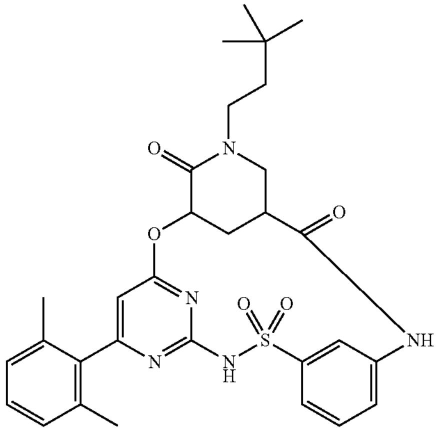
94
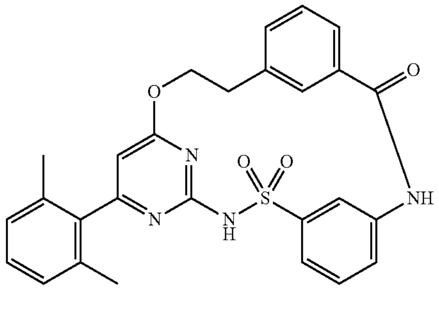

-continued
95
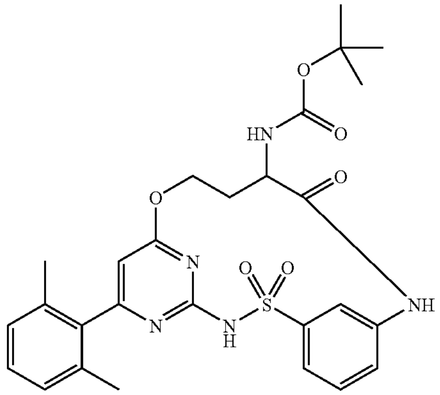
96
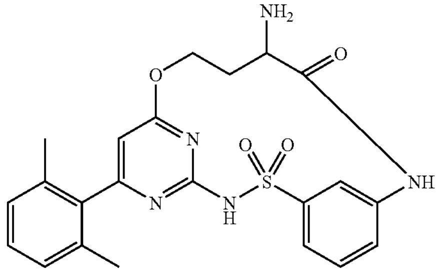
97
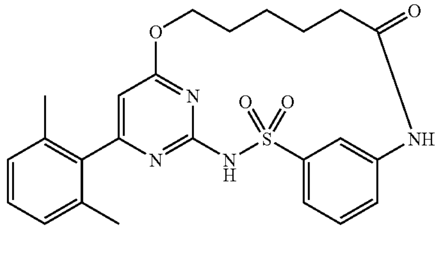
98
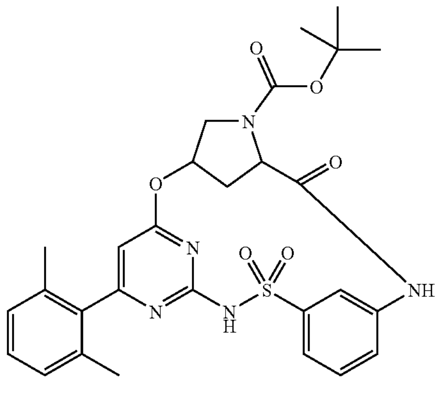
-continued
99
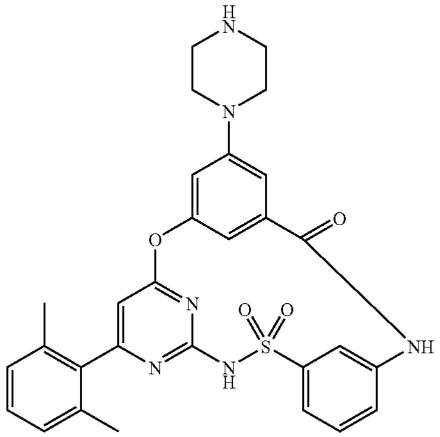
100
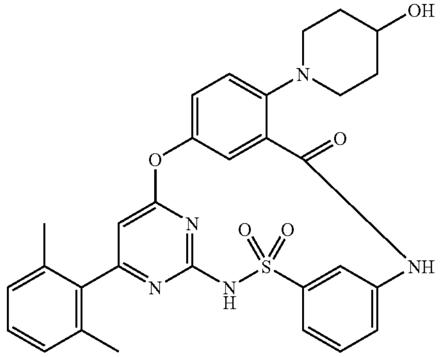
101
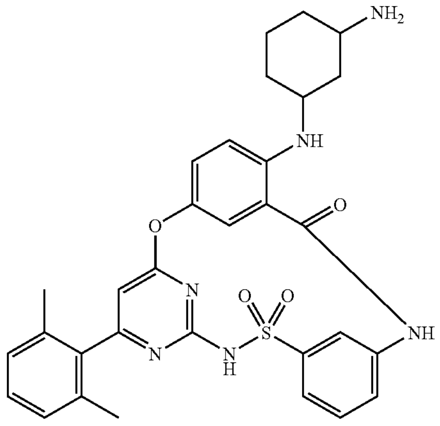
102
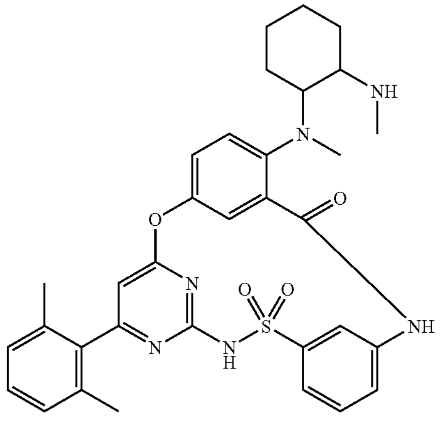

-continued
103
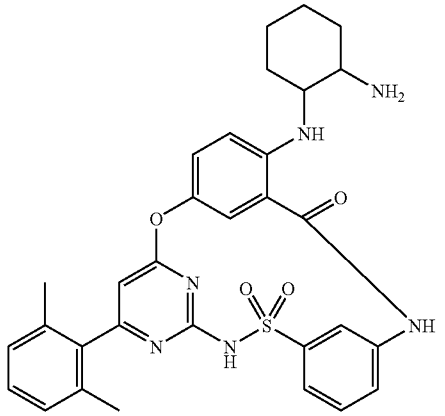
104
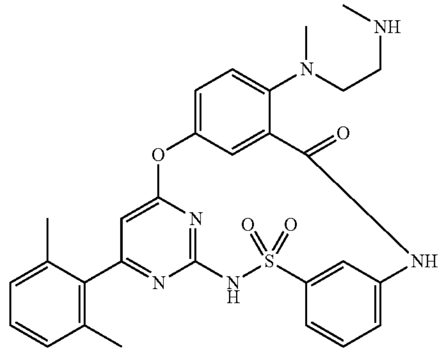
105
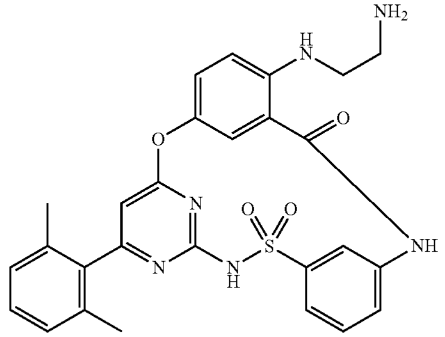
106
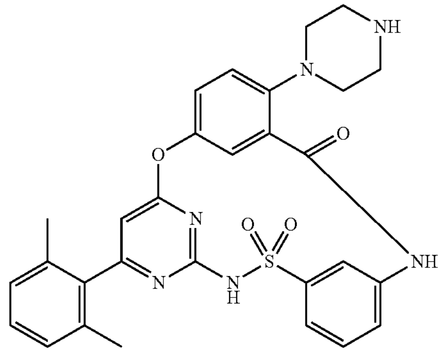
-continued
107
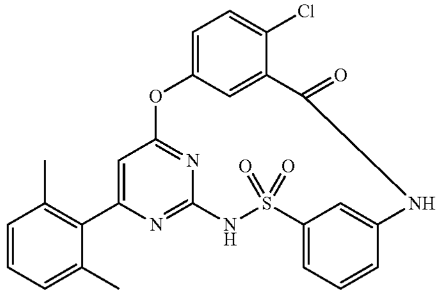
108
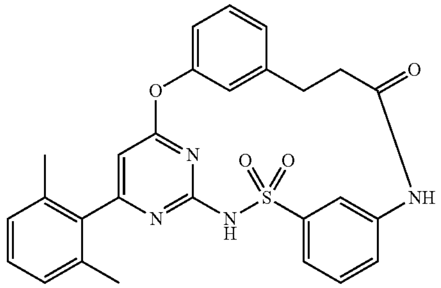
109
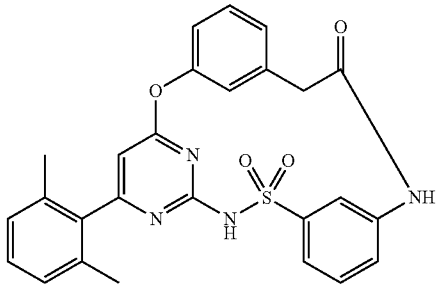
110
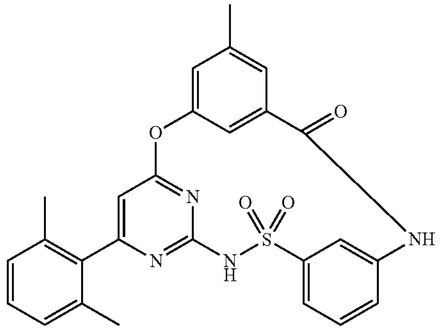
111
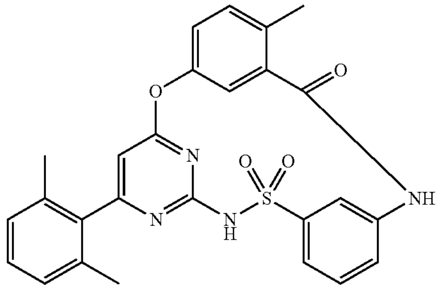

-continued
113
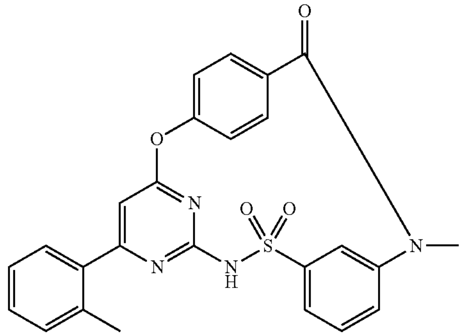
115
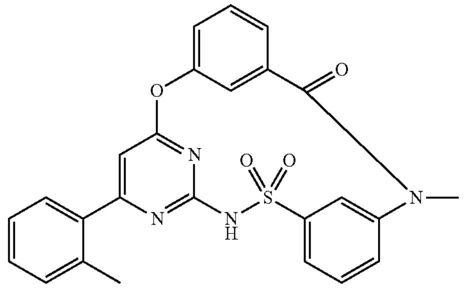
116
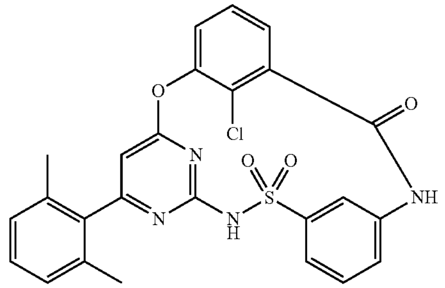
117
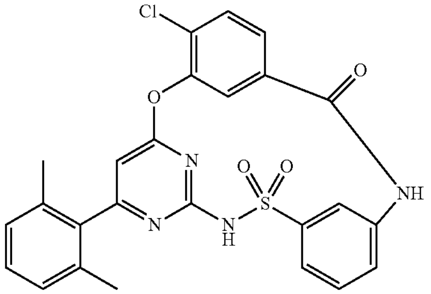
118
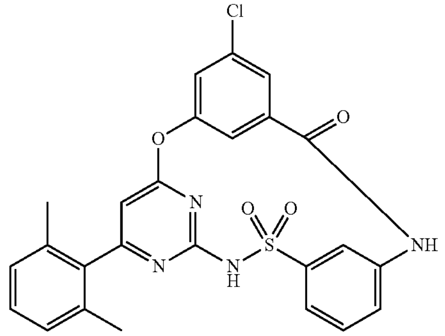
-continued
119
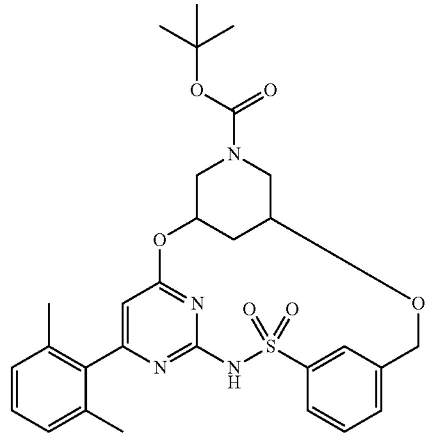
120
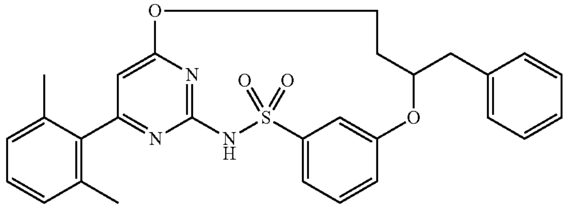
121
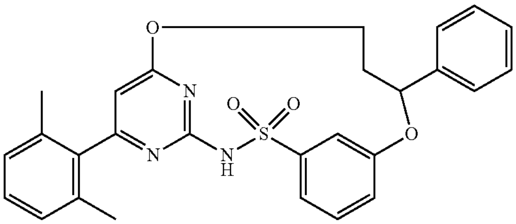
122
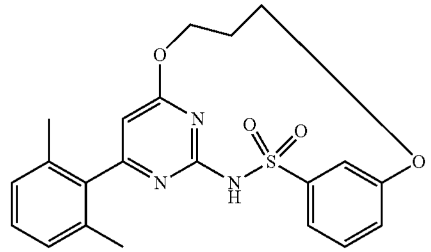
123
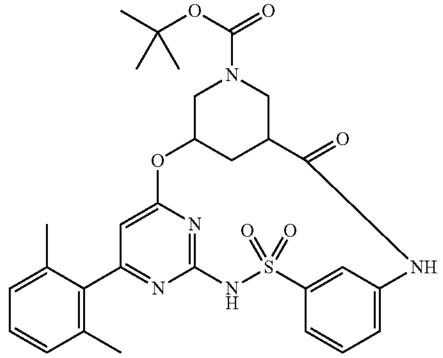

-continued

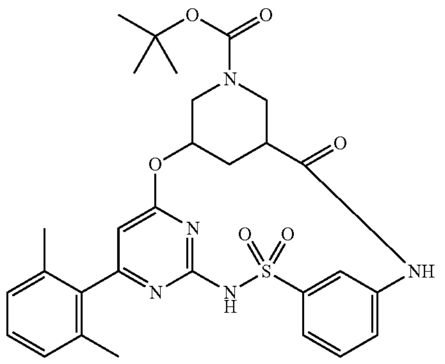

124 tautomers thereof, deuterated derivatives of the compounds and tautomers, and pharmaceutically acceptable salts of the compounds, tautomers, and deuterated derivatives.

10. A pharmaceutical composition comprising the compound, tautomer, deuterated derivative, or pharmaceutically acceptable salt according to claim 1, and a pharmaceutically acceptable carrier.

11. The pharmaceutical composition of claim 10, further comprising one or more additional therapeutic agents.

12. The pharmaceutical composition of claim 11, wherein the one or more additional therapeutic agents are selected from one or more CFTR modulators.

13. The pharmaceutical composition of claim 12, wherein the one or more CFTR modulators is (are) selected from tezacaftor, ivacaftor, deutivacaftor, lumacaftor, (6R,12R)-17-amino-12-methyl-6,15-bis (trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

14. A method of treating cystic fibrosis comprising administering to a patient in need thereof the compound, tautomer, deuterated derivative, or pharmaceutically acceptable salt according to claim 1.

15. The method of claim 14, further comprising administering to the patient one or more additional therapeutic agents prior to, concurrent with, or subsequent to the compound, tautomer, deuterated derivative, or pharmaceutically acceptable salt.

16. The method of claim 15, wherein the one or more additional therapeutic agents are selected from one or more additional CFTR modulators.

17. The method of claim 16, wherein the one or more additional CFTR modulators is (are) selected from tezacaftor, ivacaftor, deutivacaftor, lumacaftor, (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, and deuterated derivatives and pharmaceutically acceptable salts of any of the foregoing.

* * * * *